(12) United States Patent
Govindarajan et al.

(10) Patent No.: US 8,825,411 B2
(45) Date of Patent: Sep. 2, 2014

(54) DESIGN, SYNTHESIS AND ASSEMBLY OF SYNTHETIC NUCLEIC ACIDS

(75) Inventors: Sridhar Govindarajan, Redwood City, CA (US); Jeremy S. Minshull, Los Altos, CA (US); Jon E. Ness, Redwood City, CA (US)

(73) Assignee: DNA Twopointo, Inc., Menlo Park, CA (US)

( * ) Notice: Subject to any disclaimer, the term of this patent is extended or adjusted under 35 U.S.C. 154(b) by 2144 days.

(21) Appl. No.: 11/579,704

(22) PCT Filed: May 4, 2005

(86) PCT No.: PCT/US2005/015593
§ 371 (c)(1),
(2), (4) Date: Feb. 27, 2009

(87) PCT Pub. No.: WO2005/115102
PCT Pub. Date: Dec. 8, 2005

(65) Prior Publication Data
US 2008/0300842 A1 Dec. 4, 2008

Related U.S. Application Data

(60) Provisional application No. 60/567,460, filed on May 4, 2004, provisional application No. 60/666,909, filed on Mar. 31, 2005.

(51) Int. Cl.
| | | |
|---|---|---|
| G06F 19/00 | (2011.01) | |
| G06G 7/48 | (2006.01) | |
| C40B 30/00 | (2006.01) | |
| C12N 15/10 | (2006.01) | |
| C12Q 1/68 | (2006.01) | |
| G06F 19/20 | (2011.01) | |

(52) U.S. Cl.
CPC .......... *C12N 15/1027* (2013.01); *C12Q 1/6806* (2013.01); *G06F 19/20* (2013.01); *C12N 15/1089* (2013.01)
USPC ................... 702/19; 435/6.1; 506/23; 506/24

(58) Field of Classification Search
None
See application file for complete search history.

(56) References Cited

U.S. PATENT DOCUMENTS 6,506,602 B1 * 1/2003 Stemmer .......................... 506/1

FOREIGN PATENT DOCUMENTS

WO    WO 02/081490 A2    10/2002

OTHER PUBLICATIONS

EPO, Supplementary European Search Report dated Mar. 11, 2011 for Application No. EP 05 78 0055.

* cited by examiner

*Primary Examiner* — Lori A Clow
(74) *Attorney, Agent, or Firm* — Morgan, Lewis & Bockius LLP

(57) ABSTRACT

Methods of synthesizing oligonucleotides with high coupling efficiency (>99.5%) are provided. Methods for purification of synthetic oligonucleotides are also provided. Instrumentation configurations for oligonucleotide synthesis are also provided. Methods of designing and synthesizing polynucleotides are also provided. Polynucleotide design is optimized for subsequent assembly from shorter oligonucleotides. Modifications of phosphoramidite chemistry to improve the subsequent assembly of polynucleotides are provided. The design process also incorporates codon biases into polynucleotides that favor expression in defined hosts. Design and assembly methods are also provided for the efficient synthesis of sets of polynucleotide variants. Software to automate the design and assembly process is also provided.

36 Claims, 93 Drawing Sheets

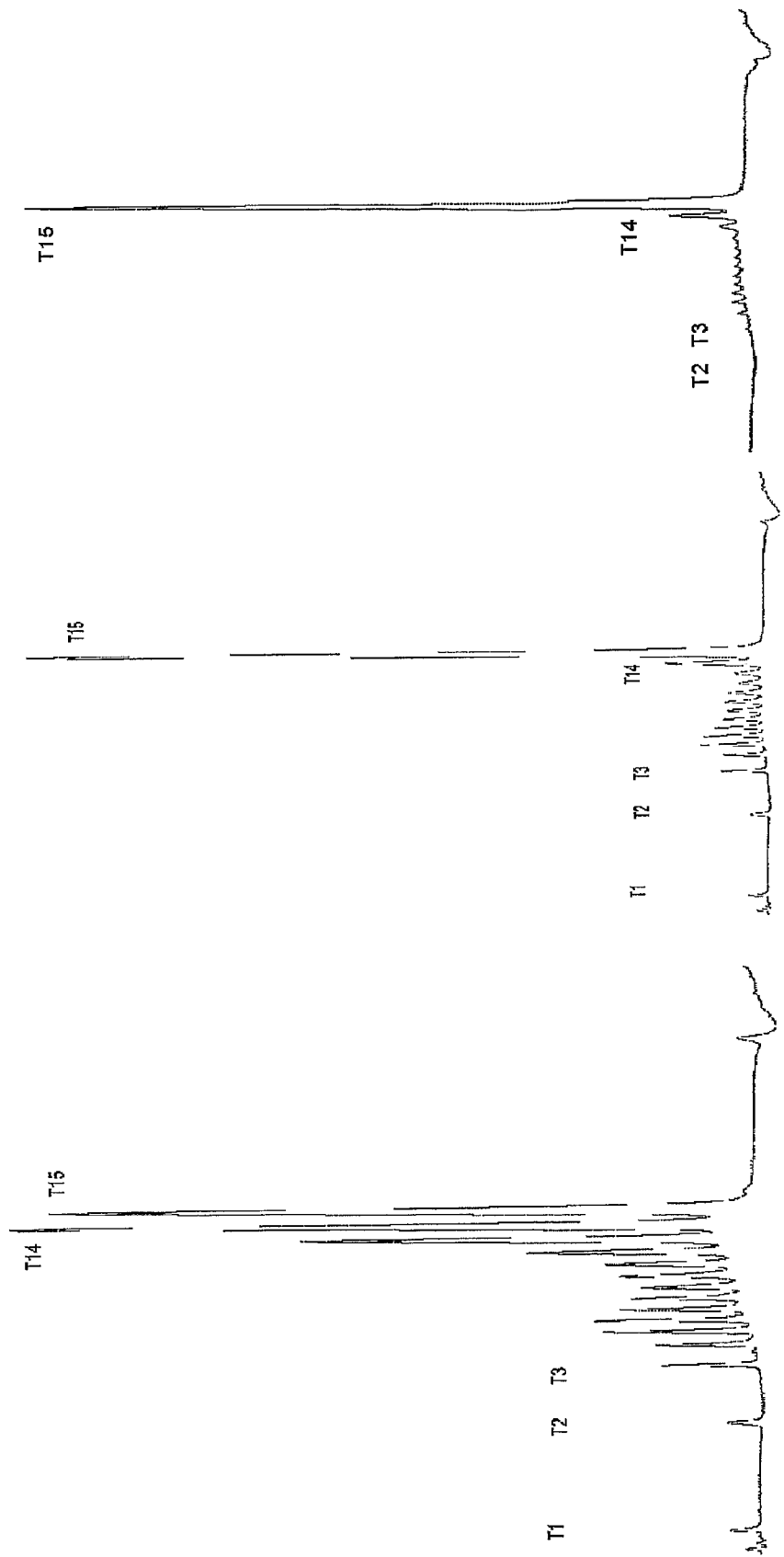

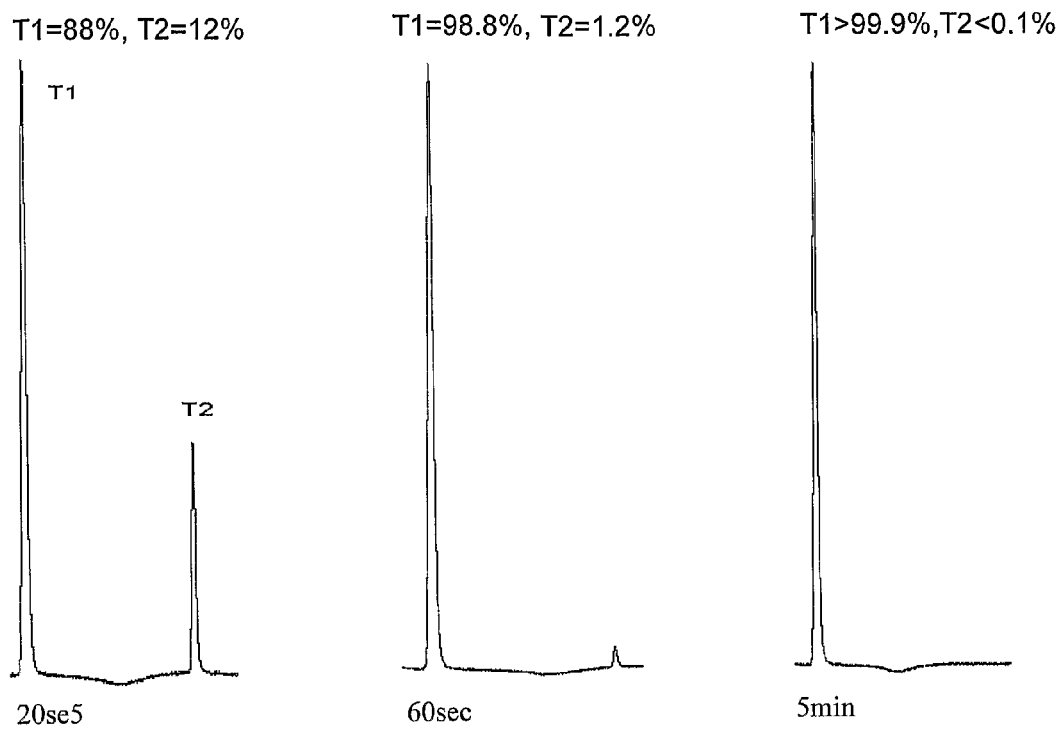
Figure 8A
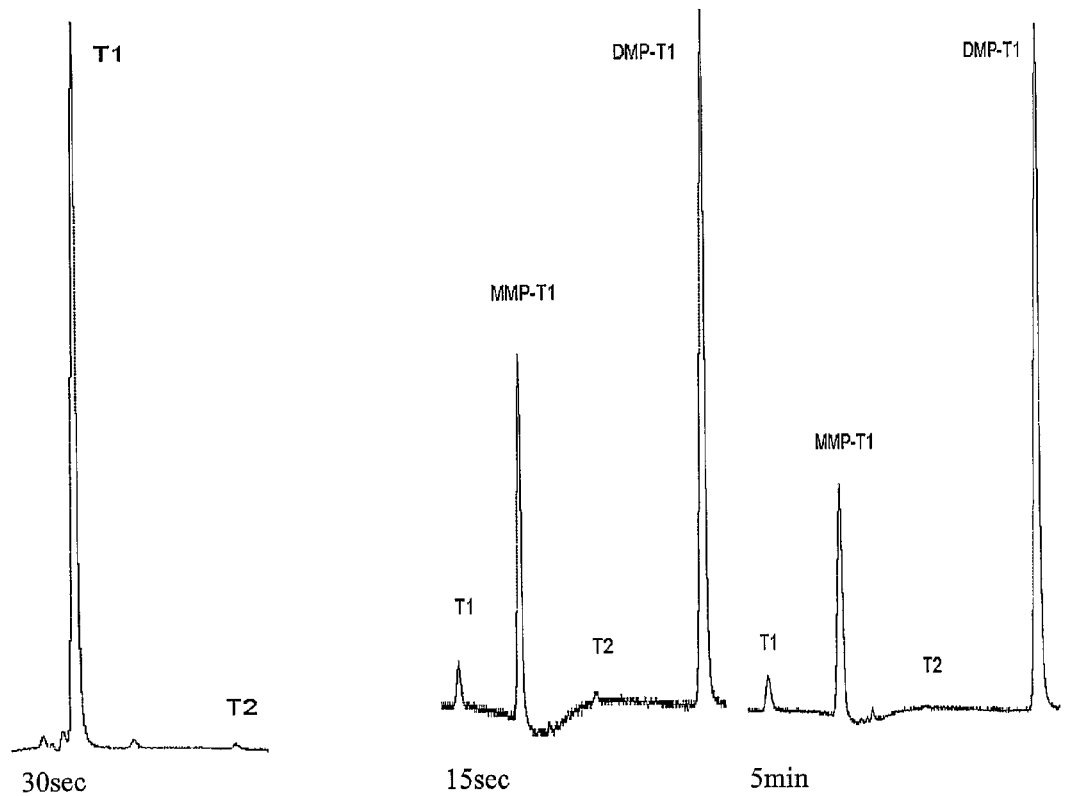
Figure 8B
Figure 8C 77.2%
99.1%

77.8%
99.2%

65.4%   RCE (15 seconds)
97.1%   RCE (1 minute)

50.4%
93.8%

95.6%
100%

100%   RCE (15 seconds)
100%   RCE (1 minute)

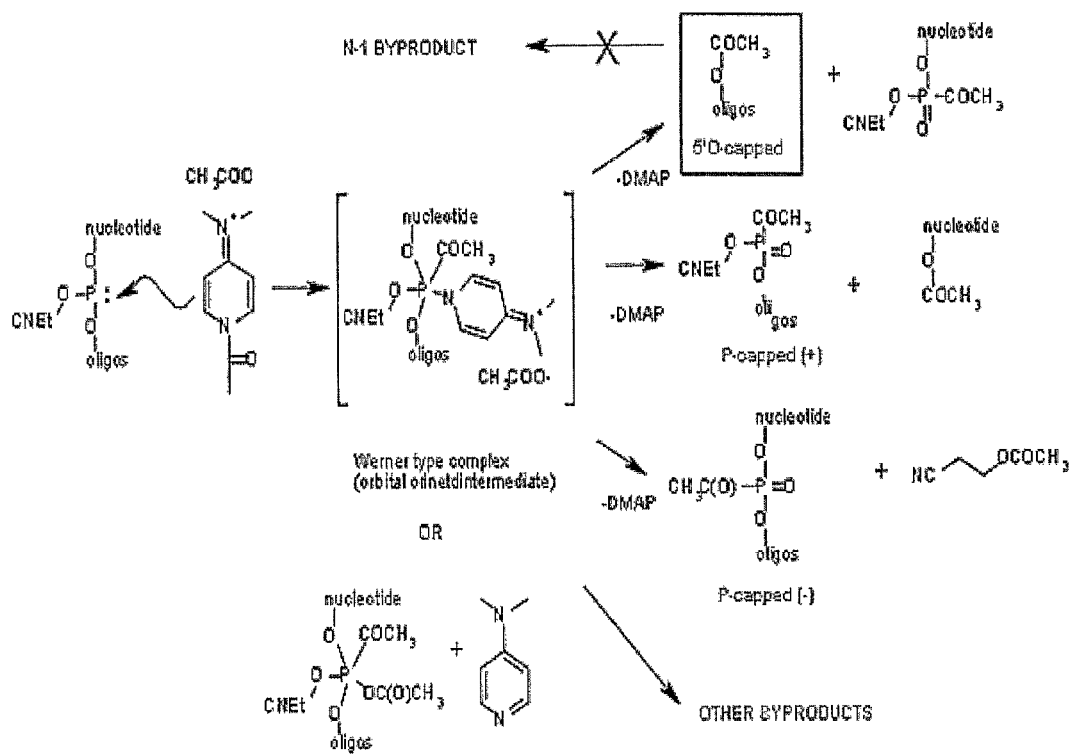
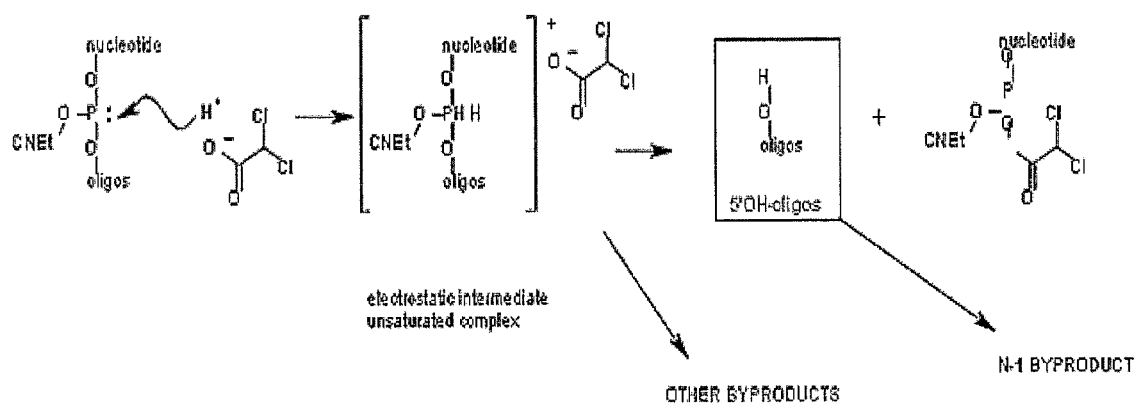
Figure 11
Prior art

Coupling cycles

0.5-1 min detrytilation by 3% dichloroacetic acid at 25'C (or below room temperature)

0.5-1 min coupling promoted by 0.4M tetrazole (4,5-Dicyanoimidazole can be used to avoid possible nozzle plugging problem [Glen_Research, 2004 #193])

0.5-1 min guanidine regeneration & pre-capping by acetic anhydride - N-methyl imidazole [Eadie, 1987 #154]

1-2 min oxidation by freshly prepared 0.1M iodine in THF : 2,6-lutidine : water = 4 : 1 : 1

1 min P(III)-O cleavage and final capping by acetic anhydride – dimethylaminopyridine (DNA2.0)

Cleavage of depurinated oligos on solid support [Kwiatkowski, 1996 #35]

3-6h cleavage from solid support and deprotection of basic labile groups by gas ammonia (55'C, 60psi) [Boal, 1996 #155]

3-6h digestion of "trityl-off" residues by 0.1U PDE-II at pH=7

Final purification and detrytilation of pool of 96 oligos on C-18 cartridge

Figure 13

| Amino Acid | Codon | Frequency |
|---|---|---|
| Gly | GGG | 0.04 |
| Gly | GGA | 0.02 |
| Gly | GGT | 0.51 |
| Gly | GGC | 0.43 |
| Glu | GAG | 0.25 |
| Glu | GAA | 0.75 |
| Asp | GAT | 0.46 |
| Asp | GAC | 0.54 |
| Val | GTG | 0.27 |
| Val | GTA | 0.20 |
| Val | GTT | 0.40 |
| Val | GTC | 0.13 |
| Ala | GCG | 0.32 |
| Ala | GCA | 0.24 |
| Ala | GCT | 0.28 |
| Ala | GCC | 0.16 |
| Arg | AGG | 0.00 |
| Arg | AGA | 0.01 |
| Ser | AGT | 0.04 |
| Ser | AGC | 0.24 |
| Lys | AAG | 0.21 |
| Lys | AAA | 0.79 |
| Asn | AAT | 0.17 |
| Asn | AAC | 0.83 |
| Met | ATG | 1.00 |
| Ile | ATA | 0.01 |
| Ile | ATT | 0.33 |
| Ile | ATC | 0.66 |
| Thr | ACG | 0.13 |
| Thr | ACA | 0.04 |
| Thr | ACT | 0.29 |
| Thr | ACC | 0.54 |
| Trp | TGG | 1.00 |
| End | TGA | 0.29 |
| Cys | TGT | 0.39 |
| Cys | TGC | 0.61 |
| End | TAG | 0.08 |
| End | TAA | 0.63 |
| Tyr | TAT | 0.35 |
| Tyr | TAC | 0.65 |
| Leu | TTG | 0.05 |
| Leu | TTA | 0.03 |
| Phe | TTT | 0.29 |
| Phe | TTC | 0.71 |
| Ser | TCG | 0.07 |
| Ser | TCA | 0.05 |
| Ser | TCT | 0.33 |
| Ser | TCC | 0.27 |
| Arg | CGG | 0.01 |
| Arg | CGA | 0.01 |
| Arg | CGT | 0.64 |
| Arg | CGC | 0.33 |
| Gln | CAG | 0.81 |
| Gln | CAA | 0.19 |
| His | CAT | 0.30 |
| His | CAC | 0.70 |
| Leu | CTG | 0.77 |
| Leu | CTA | 0.01 |
| Leu | CTT | 0.06 |
| Leu | CTC | 0.08 |
| Pro | CCG | 0.72 |
| Pro | CCA | 0.15 |
| Pro | CCT | 0.11 |
| Pro | CCC | 0.02 |

Figure 22

| Amino Acid | Codon | Frequency |
|---|---|---|
| Gly | GGG | 0.25 |
| Gly | GGA | 0.25 |
| Gly | GGT | 0.16 |
| Gly | GGC | 0.34 |
| Glu | GAG | 0.58 |
| Glu | GAA | 0.42 |
| Asp | GAT | 0.46 |
| Asp | GAC | 0.54 |
| Val | GTG | 0.46 |
| Val | GTA | 0.12 |
| Val | GTT | 0.18 |
| Val | GTC | 0.24 |
| Ala | GCG | 0.11 |
| Ala | GCA | 0.23 |
| Ala | GCT | 0.26 |
| Ala | GCC | 0.40 |
| Arg | AGG | 0.20 |
| Arg | AGA | 0.20 |
| Ser | AGT | 0.15 |
| Ser | AGC | 0.24 |
| Lys | AAG | 0.57 |
| Lys | AAA | 0.43 |
| Asn | AAT | 0.46 |
| Asn | AAC | 0.54 |
| Met | ATG | 1.00 |
| Ile | ATA | 0.17 |
| Ile | ATT | 0.35 |
| Ile | ATC | 0.48 |
| Thr | ACG | 0.11 |
| Thr | ACA | 0.28 |
| Thr | ACT | 0.24 |
| Thr | ACC | 0.36 |
| Trp | TGG | 1.00 |
| End | TGA | 0.54 |
| Cys | TGT | 0.45 |
| Cys | TGC | 0.55 |
| End | TAG | 0.20 |
| End | TAA | 0.26 |
| Tyr | TAT | 0.44 |
| Tyr | TAC | 0.56 |
| Leu | TTG | 0.13 |
| Leu | TTA | 0.07 |
| Phe | TTT | 0.45 |
| Phe | TTC | 0.55 |
| Ser | TCG | 0.06 |
| Ser | TCA | 0.15 |
| Ser | TCT | 0.18 |
| Ser | TCC | 0.22 |
| Arg | CGG | 0.21 |
| Arg | CGA | 0.11 |
| Arg | CGT | 0.08 |
| Arg | CGC | 0.19 |
| Gln | CAG | 0.74 |
| Gln | CAA | 0.26 |
| His | CAT | 0.41 |
| His | CAC | 0.59 |
| Leu | CTG | 0.40 |
| Leu | CTA | 0.08 |
| Leu | CTT | 0.13 |
| Leu | CTC | 0.20 |
| Pro | CCG | 0.11 |
| Pro | CCA | 0.27 |
| Pro | CCT | 0.28 |
| Pro | CCC | 0.33 |

Figure 23

| Codon | AmAcid | Frequency |
|---|---|---|
| AAA | Lys | 0.610000 |
| AAC | Asn | 0.685000 |
| AAG | Lys | 0.390000 |
| AAT | Asn | 0.315000 |
| ACA | Thr | 0.000000 |
| ACC | Thr | 0.540000 |
| ACG | Thr | 0.140000 |
| ACT | Thr | 0.320000 |
| AGA | Arg | 0.000000 |
| AGC | Ser | 0.270000 |
| AGG | Arg | 0.000000 |
| AGT | Ser | 0.000000 |
| ATA | Ile | 0.000000 |
| ATC | Ile | 0.630000 |
| ATG | Met | 1.000000 |
| ATT | Ile | 0.370000 |
| CAA | Gln | 0.225000 |
| CAC | His | 0.645000 |
| CAG | Gln | 0.775000 |
| CAT | His | 0.355000 |
| CCA | Pro | 0.260000 |
| CCC | Pro | 0.000000 |
| CCG | Pro | 0.510000 |
| CCT | Pro | 0.230000 |
| CGA | Arg | 0.000000 |
| CGC | Arg | 0.420000 |
| CGG | Arg | 0.000000 |
| CGT | Arg | 0.580000 |
| CTA | Leu | 0.000000 |
| CTC | Leu | 0.150000 |
| CTG | Leu | 0.640000 |
| CTT | Leu | 0.110000 |
| GAA | Glu | 0.585000 |
| GAC | Asp | 0.540000 |
| GAG | Glu | 0.415000 |
| GAT | Asp | 0.460000 |
| GCA | Ala | 0.235000 |
| GCC | Ala | 0.280000 |
| GCG | Ala | 0.215000 |
| GCT | Ala | 0.270000 |
| GGA | Gly | 0.000000 |
| GGC | Gly | 0.530000 |
| GGG | Gly | 0.000000 |
| GGT | Gly | 0.470000 |
| GTA | Val | 0.160000 |
| GTC | Val | 0.185000 |
| GTG | Val | 0.365000 |
| GTT | Val | 0.290000 |
| TAA | End | 0.445000 |
| TAC | Tyr | 0.605000 |
| TAG | End | 0.140000 |
| TAT | Tyr | 0.395000 |
| TCA | Ser | 0.110000 |
| TCC | Ser | 0.270000 |
| TCG | Ser | 0.070000 |
| TCT | Ser | 0.280000 |
| TGA | End | 0.415000 |
| TGC | Cys | 0.580000 |
| TGG | Trp | 1.000000 |
| TGT | Cys | 0.420000 |
| TTA | Leu | 0.000000 |
| TTC | Phe | 0.630000 |
| TTG | Leu | 0.100000 |
| TTT | Phe | 0.370000 |

Figure 24

| Amino Acid | Codon | Frequency |
|---|---|---|
| Gly | GGG | 0.23 |
| Gly | GGA | 0.26 |
| Gly | GGT | 0.18 |
| Gly | GGC | 0.33 |
| Glu | GAG | 0.60 |
| Glu | GAA | 0.40 |
| Asp | GAT | 0.44 |
| Asp | GAC | 0.56 |
| Val | GTG | 0.47 |
| Val | GTA | 0.12 |
| Val | GTT | 0.17 |
| Val | GTC | 0.25 |
| Ala | GCG | 0.10 |
| Ala | GCA | 0.23 |
| Ala | GCT | 0.29 |
| Ala | GCC | 0.38 |
| Arg | AGG | 0.21 |
| Arg | AGA | 0.21 |
| Ser | AGT | 0.15 |
| Ser | AGC | 0.24 |
| Lys | AAG | 0.61 |
| Lys | AAA | 0.39 |
| Asn | AAT | 0.43 |
| Asn | AAC | 0.57 |
| Met | ATG | 1.00 |
| Ile | ATA | 0.15 |
| Ile | ATT | 0.34 |
| Ile | ATC | 0.51 |
| Thr | ACG | 0.11 |
| Thr | ACA | 0.29 |
| Thr | ACT | 0.25 |
| Thr | ACC | 0.35 |
| Trp | TGG | 1.00 |
| End | TGA | 0.51 |
| Cys | TGT | 0.47 |
| Cys | TGC | 0.53 |
| End | TAG | 0.23 |
| End | TAA | 0.26 |
| Tyr | TAT | 0.42 |
| Tyr | TAC | 0.58 |
| Leu | TTG | 0.13 |
| Leu | TTA | 0.06 |
| Phe | TTT | 0.43 |
| Phe | TTC | 0.57 |
| Ser | TCG | 0.05 |
| Ser | TCA | 0.14 |
| Ser | TCT | 0.19 |
| Ser | TCC | 0.22 |
| Arg | CGG | 0.19 |
| Arg | CGA | 0.12 |
| Arg | CGT | 0.09 |
| Arg | CGC | 0.18 |
| Gln | CAG | 0.75 |
| Gln | CAA | 0.25 |
| His | CAT | 0.40 |
| His | CAC | 0.60 |
| Leu | CTG | 0.40 |
| Leu | CTA | 0.08 |
| Leu | CTT | 0.13 |
| Leu | CTC | 0.20 |
| Pro | CCG | 0.11 |
| Pro | CCA | 0.28 |
| Pro | CCT | 0.30 |
| Pro | CCC | 0.31 |

Figure 25

| 1  | Denature | 96°C       | 2min     |
|----|----------|------------|----------|
| 2  | Denature | 96°C       | 30sec    |
| 3  | Anneal   | 40°C -72°C | 30sec    |
| 4  | Extend   | 72°C       | 15sec    |
| 5  | Goto     | step 2     | 11 times |
| 6  | Denature | 96°C       | 30sec    |
| 7  | Anneal   | 40°C -72°C | 30sec    |
| 8  | Extend   | 72°C       | 30sec    |
| 9  | Goto     | step 6     | 11 times |
| 10 | Extend   | 72°C       | 1min     |
| 11 |          | 4°C        | forever  |
| 12 | End      |            |          |

Figure 32

| 1  | Denature | 96°C       | 2min    |
|----|----------|------------|---------|
| 2  | Denature | 96°C       | 30sec   |
| 3  | Anneal   | 40°C -72°C | 30sec   |
| 4  | Extend   | 72°C       | 15sec   |
| 5  | Goto     | step 2     | 7 times |
| 6  | Denature | 96°C       | 30sec   |
| 7  | Anneal   | 40°C -72°C | 30sec   |
| 8  | Extend   | 72°C       | 30sec   |
| 9  | Goto     | step 6     | 7 times |
| 10 | Denature | 96°C       | 30sec   |
| 11 | Anneal   | 40°C -72°C | 30sec   |
| 12 | Extend   | 72°C       | 45sec   |
| 13 | Goto     | step 10    | 7 times |
| 14 | Extend   | 72°C       | 1min    |
| 15 |          | 4°C        | forever |
| 16 | End      |            |         |

Figure 33

| 1  | Denature | 96°C       | 2min    |
|----|----------|------------|---------|
| 2  | Denature | 96°C       | 30sec   |
| 3  | Anneal   | 40°C -72°C | 30sec   |
| 4  | Extend   | 72°C       | 15sec   |
| 5  | Goto     | step 2     | 7 times |
| 6  | Denature | 96°C       | 30sec   |
| 7  | Anneal   | 40°C -72°C | 30sec   |
| 8  | Extend   | 72°C       | 30sec   |
| 9  | Goto     | step 6     | 7 times |
| 10 | Denature | 96°C       | 30sec   |
| 11 | Anneal   | 40°C -72°C | 30sec   |
| 12 | Extend   | 72°C       | 45sec   |
| 13 | Goto     | step 10    | 7 times |
| 14 | Extend   | 72°C       | 1min    |
| 15 |          | 4°C        | forever |
| 16 | End      |            |         |

Figure 34

| | | | |
|---|---|---|---|
| 1 | Denature | 96°C | 2min |
| 2 | Denature | 96°C | 30sec |
| 3 | Anneal | 40°C -72°C | 30sec |
| 4 | Extend | 72°C | 15sec |
| 5 | Goto | step 2 | 3 times |
| 6 | Denature | 96°C | 30sec |
| 7 | Anneal | 40°C -72°C | 30sec |
| 8 | Extend | 72°C | 30sec |
| 9 | Goto | step 6 | 3 times |
| 10 | Denature | 96°C | 30sec |
| 11 | Anneal | 40°C -72°C | 30sec |
| 12 | Extend | 72°C | 45sec |
| 13 | Goto | step 10 | 3 times |
| 14 | Denature | 96°C | 30sec |
| 15 | Anneal | 40°C -72°C | 30sec |
| 16 | Extend | 72°C | 60sec |
| 17 | Goto | step 14 | 3 times |
| 18 | Denature | 96°C | 30sec |
| 19 | Anneal | 40°C -72°C | 30sec |
| 20 | Extend | 72°C | 75sec |
| 21 | Goto | step 18 | 3 times |
| 22 | Denature | 96°C | 30sec |
| 23 | Anneal | 40°C -72°C | 30sec |
| 24 | Extend | 72°C | 90sec |
| 25 | Goto | step 22 | 3 times |
| 26 | Extend | 72°C | 1min |
| 27 | | 4°C | forever |
| 28 | End | | |

Figure 35

| | | | |
|---|---|---|---|
| 1 | Denature | 96°C | 2min |
| 2 | Denature | 96°C | 30sec |
| 3 | Anneal | 40°C -72°C | 30sec |
| 4 | Extend | 72°C | 15sec |
| 5 | Goto | step 2 | 2 times |
| 6 | Denature | 96°C | 30sec |
| 7 | Anneal | 40°C -72°C | 30sec |
| 8 | Extend | 72°C | 30sec |
| 9 | Goto | step 6 | 2 times |
| 10 | Denature | 96°C | 30sec |
| 11 | Anneal | 40°C -72°C | 30sec |
| 12 | Extend | 72°C | 45sec |
| 13 | Goto | step 10 | 2 times |
| 14 | Denature | 96°C | 30sec |
| 15 | Anneal | 40°C -72°C | 30sec |
| 16 | Extend | 72°C | 60sec |
| 17 | Goto | step 14 | 2 times |
| 18 | Denature | 96°C | 30sec |
| 19 | Anneal | 40°C -72°C | 30sec |
| 20 | Extend | 72°C | 75sec |
| 21 | Goto | step 18 | 2 times |
| 22 | Denature | 96°C | 30sec |
| 23 | Anneal | 40°C -72°C | 30sec |
| 24 | Extend | 72°C | 90sec |
| 25 | Goto | step 22 | 2 times |
| 26 | Denature | 96°C | 30sec |
| 27 | Anneal | 40°C -72°C | 30sec |
| 28 | Extend | 72°C | 105sec |
| 29 | Goto | step 26 | 2 times |
| 30 | Denature | 96°C | 30sec |
| 31 | Anneal | 40°C -72°C | 30sec |
| 32 | Extend | 72°C | 120sec |
| 33 | Goto | step 30 | 2 times |
| 34 | Extend | 72°C | 1min |
| 35 | | 4°C | forever |
| 36 | End | | |

Figure 36

3bp overlap, 5' overhang
target sequence: 5'-$N_{-9}N_{-8}N_{-7}N_{-6}N_{-5}N_{-4}N_{-3}N_{-2}N_{-1}\mathbf{N_A N_B N_C}N_{+1}N_{+2}N_{+3}N_{+4}N_{+5}N_{+6}N_{+7}N_{+8}N_{+9}$-3'

<u>7 base recognition site</u>
                              *SapI:* GCTCTTC (5x digestion, 95% ligation, 95% recut)
5' segment end: 5'-$N_{-9}N_{-8}N_{-7}N_{-6}N_{-5}N_{-4}N_{-3}N_{-2}N_{-1}\mathbf{N_A N_B N_C}N_{+1}$GAAGAGC-3' (SEQ ID NO: 1)
3' segment end: 5'-GCTCTTC$N_{-1}\mathbf{N_A N_B N_C}N_{+1}N_{+2}N_{+3}N_{+4}N_{+5}N_{+6}N_{+7}N_{+8}N_{+9}$-3' (SEQ ID NO: 2)

<u>6 base recognition site</u>
                              *EarI:* CTCTTC (2x digestion, 95% ligation, 95% recut)
5' segment end: 5'-$N_{-9}N_{-8}N_{-7}N_{-6}N_{-5}N_{-4}N_{-3}N_{-2}N_{-1}\mathbf{N_A N_B N_C}N_{+1}$GAAGAG-3' (SEQ ID NO: 3)
3' segment end: 5'-CTCTTC$N_{-1}\mathbf{N_A N_B N_C}N_{+1}N_{+2}N_{+3}N_{+4}N_{+5}N_{+6}N_{+7}N_{+8}N_{+9}$-3' (SEQ ID NO: 4)

4bp overlap, 5' overhang
target sequence: 5'-$N_{-9}N_{-8}N_{-7}N_{-6}N_{-5}N_{-4}N_{-3}N_{-2}N_{-1}\mathbf{N_A N_B N_C N_D}N_{+1}N_{+2}N_{+3}N_{+4}N_{+5}N_{+6}N_{+7}N_{+8}N_{+9}$-3'

6 base recognition site
                         *BbsI:* GAAGAC (10x digestion, 95% ligation, 95% recut)
5' segment end: 5'-$N_{-9}N_{-8}N_{-7}N_{-6}N_{-5}N_{-4}N_{-3}N_{-2}N_{-1}\mathbf{N_A N_B N_C N_D}N_{+1}N_{+2}$GTCTTC-3' (SEQ ID NO: 5)
3' segment end: 5'-GAAGAC$N_{-2}N_{-1}\mathbf{N_A N_B N_C N_D}N_{+1}N_{+2}N_{+3}N_{+4}N_{+5}N_{+6}N_{+7}N_{+8}N_{+9}$-3' (SEQ ID NO: 6)

*BsaI:* GGTCTC (10x digestion, 95% ligation, 95% recut)
5' segment end: 5'-$N_{-9}N_{-8}N_{-7}N_{-6}N_{-5}N_{-4}N_{-3}N_{-2}N_{-1}\mathbf{N_A N_B N_C N_D}N_{+1}$GAGACC-3' (SEQ ID NO: 7)
3' segment end: 5'-GGTCTC$N_{-1}\mathbf{N_A N_B N_C N_D}N_{+1}N_{+2}N_{+3}N_{+4}N_{+5}N_{+6}N_{+7}N_{+8}N_{+9}$-3' (SEQ ID NO: 8)

*BsmBI:* CGTCTC (2x digestion, 95% ligation, 95% recut)
5' segment end: 5'-$N_{-9}N_{-8}N_{-7}N_{-6}N_{-5}N_{-4}N_{-3}N_{-2}N_{-1}\mathbf{N_A N_B N_C N_D}N_{+1}$GAGACG-3' (SEQ ID NO: 9)
3' segment end: 5'-CGTCTC$N_{-1}\mathbf{N_A N_B N_C N_D}N_{+1}N_{+2}N_{+3}N_{+4}N_{+5}N_{+6}N_{+7}N_{+8}N_{+9}$-3' (SEQ ID NO: 10)

*BspMI:* ACCTGC (5x digestion, 95% ligation, 95% recut)
5' segment end: 5'-$N_{-9}N_{-8}N_{-7}N_{-6}N_{-5}N_{-4}N_{-3}N_{-2}N_{-1}\mathbf{N_A N_B N_C N_D}N_{+1}N_{+2}N_{+3}N_{+4}$GCAGGT-3' (SEQ ID NO: 11)
3' segment end: 5'-ACCTGC$N_{-4}N_{-3}N_{-2}N_{-1}\mathbf{N_A N_B N_C N_D}N_{+1}N_{+2}N_{+3}N_{+4}N_{+5}N_{+6}N_{+7}N_{+8}N_{+9}$-3' (SEQ ID NO: 12)

Figure 41A

5 base recognition site
BbvI: GCAGC (2x digestion, 95% ligation, 95% recut)

5' segment end: 5'-$N_{-9}N_{-8}N_{-7}N_{-6}N_{-5}N_{-4}N_{-3}N_{-2}N_{-1}\mathbf{N_A N_B N_C N_D}N_{+1}N_{+2}N_{+3}N_{+4}N_{+5}N_{+6}N_{+7}N_{+8}$GCTGC-3' (SEQ ID NO: 13)

3' segment end: 5'-GCAGC$N_{-8}N_{-7}N_{-6}N_{-5}N_{-4}N_{-3}N_{-2}N_{-1}\mathbf{N_A N_B N_C N_D}N_{+1}N_{+2}N_{+3}N_{+4}N_{+5}N_{+6}N_{+7}N_{+8}N_{+9}$-3' (SEQ ID NO: 14)

BsmAI: GTCTC (5x digestion, 95% ligation, 95% recut)

5' segment end: 5'-$N_{-9}N_{-8}N_{-7}N_{-6}N_{-5}N_{-4}N_{-3}N_{-2}N_{-1}\mathbf{N_A N_B N_C N_D}N_{+1}$GAGAC-3' (SEQ ID NO: 15)
3' segment end: 5'-GTCTC$N_{-1}\mathbf{N_A N_B N_C N_D}N_{+1}N_{+2}N_{+3}N_{+4}N_{+5}N_{+6}N_{+7}N_{+8}N_{+9}$-3' (SEQ ID NO: 16)

BsmFI: GGGAC (10x digestion, 95% ligation, 95% recut)

5' segment end: 5'-$N_{-10}N_{-9}N_{-8}N_{-7}N_{-6}N_{-5}N_{-4}N_{-3}N_{-2}N_{-1}\mathbf{N_A N_B N_C N_D}N_{+1}N_{+2}N_{+3}N_{+4}N_{+5}N_{+6}N_{+7}N_{+8}N_{+9}N_{+10}$GTCCC-3' (SEQ ID NO: 17)

3' segment end: 5'-GGGAC$N_{-10}N_{-9}N_{-8}N_{-7}N_{-6}N_{-5}N_{-4}N_{-3}N_{-2}N_{-1}\mathbf{N_A N_B N_C N_D}N_{+1}N_{+2}N_{+3}N_{+4}N_{+5}N_{+6}N_{+7}N_{+8}N_{+9}N_{+10}$-3' (SEQ ID NO: 18)

BspBI

5' segment end: 5'-$N_{-9}N_{-8}N_{-7}N_{-6}N_{-5}N_{-4}N_{-3}N_{-2}N_{-1}\mathbf{N_A N_B N_C N_D}N_{+1}$GAGACG-3' (SEQ ID NO: 19)
3' segment end: 5'-CGTCTC$N_{-1}\mathbf{N_A N_B N_C N_D}N_{+1}N_{+2}N_{+3}N_{+4}N_{+5}N_{+6}N_{+7}N_{+8}N_{+9}$-3' (SEQ ID NO: 20)

FokI: GGATG (5x digestion, 95% ligation, 95% recut)

5' segment end: 5'-$N_{-9}N_{-8}N_{-7}N_{-6}N_{-5}N_{-4}N_{-3}N_{-2}N_{-1}\mathbf{N_A N_B N_C N_D}N_{+1}N_{+2}N_{+3}N_{+4}N_{+5}N_{+6}N_{+7}N_{+8}N_{+9}$CATCC-3' (SEQ ID NO: 21)

3' segment end: 5'-GGATG$N_{-9}N_{-8}N_{-7}N_{-6}N_{-5}N_{-4}N_{-3}N_{-2}N_{-1}\mathbf{N_A N_B N_C N_D}N_{+1}N_{+2}N_{+3}N_{+4}N_{+5}N_{+6}N_{+7}N_{+8}N_{+9}$-3' (SEQ ID NO: 22)

SfaNI: GCATC (2x digestion, 95% ligation, 95% recut)

5' segment end: 5'-$N_{-9}N_{-8}N_{-7}N_{-6}N_{-5}N_{-4}N_{-3}N_{-2}N_{-1}\mathbf{N_A N_B N_C N_D}N_{+1}N_{+2}N_{+3}N_{+4}N_{+5}$GATGC-3' (SEQ ID NO: 23)
3' segment end: 5'-GCATC$N_{-5}N_{-4}N_{-3}N_{-2}N_{-1}\mathbf{N_A N_B N_C N_D}N_{+1}N_{+2}N_{+3}N_{+4}N_{+5}N_{+6}N_{+7}N_{+8}N_{+9}$-3' (SEQ ID NO: 24)

Figure 41B

5bp overlap, 5' overhang
target sequence: 5'-$N_{-9}N_{-8}N_{-7}N_{-6}N_{-5}N_{-4}N_{-3}N_{-2}N_{-1}\mathbf{N_A N_B N_C N_D N_E}N_{+1}N_{+2}N_{+3}N_{+4}N_{+5}N_{+6}N_{+7}N_{+8}N_{+9}$-3'

5 base recognition site
*HgaI:* GACGC (5x digestion, 95% ligation, 95% recut)

5' segment end: 5'-$N_{-9}N_{-8}N_{-7}N_{-6}N_{-5}N_{-4}N_{-3}N_{-2}N_{-1}\mathbf{N_A N_B N_C N_D N_E}N_{+1}N_{+2}N_{+3}N_{+4}N_{+5}$GCGTC-3' (SEQ ID NO: 25)

3' segment end: 5'-GACGC$N_{-5}N_{-4}N_{-3}N_{-2}N_{-1}\mathbf{N_A N_B N_C N_D N_E}N_{+1}N_{+2}N_{+3}N_{+4}N_{+5}N_{+6}N_{+7}N_{+8}N_{+9}$-3' (SEQ ID NO: 26)

3' OVERHANG
1bp overlap, 3' overhang
target sequence: 5'-$N_{-9}N_{-8}N_{-7}N_{-6}N_{-5}N_{-4}N_{-3}N_{-2}N_{-1}\mathbf{N_A}N_{+1}N_{+2}N_{+3}N_{+4}N_{+5}N_{+6}N_{+7}N_{+8}N_{+9}$-3'

<u>6 base recognition site</u>
*BmrI:* ACTGGG (2x digestion, 75% ligation, 95% recut)
5' segment end: 5'-$N_{-10}N_{-9}N_{-8}N_{-7}N_{-6}N_{-5}N_{-4}N_{-3}N_{-2}N_{-1}\mathbf{N_A}N_{+1}N_{+2}N_{+3}N_{+4}$CCCAGT-3' (SEQ ID NO: 27)
3' segment end: 5'-ACTGGG$N_{-4}N_{-3}N_{-2}N_{-1}\mathbf{N_A}N_{+1}N_{+2}N_{+3}N_{+4}N_{+5}N_{+6}N_{+7}N_{+8}N_{+9}N_{+10}$-3' (SEQ ID NO: 28)

2bp overlap, 3' overhang

6 base recognition site
*BpmI:* CTGGAG (5x digestion, 95% ligation, 95% recut)

5' segment end:
5'-$N_{-9}N_{-8}N_{-7}N_{-6}N_{-5}N_{-4}N_{-3}N_{-2}N_{-1}\mathbf{N_A N_B}N_{+1}N_{+2}N_{+3}N_{+4}N_{+5}N_{+6}N_{+7}N_{+8}N_{+9}N_{+10}N_{+11}N_{+12}N_{+13}N_{+14}$CTCCAG-3' (SEQ ID NO: 29)

3' segment end:
5'-CTGGAG$N_{-14}N_{-13}N_{-12}N_{-11}N_{-10}N_{-9}N_{-8}N_{-7}N_{-6}N_{-5}N_{-4}N_{-3}N_{-2}N_{-1}\mathbf{N_A N_B}N_{+1}N_{+2}N_{+3}N_{+4}N_{+5}N_{+6}N_{+7}N_{+8}N_{+9}N_{+10}$-3' (SEQ ID NO: 30)

*BseRI:* GAGGAG (4x digestion, 95% ligation, 95% recut)

5' segment end: 5'-$N_{-9}N_{-8}N_{-7}N_{-6}N_{-5}N_{-4}N_{-3}N_{-2}N_{-1}\mathbf{N_A N_B}N_{+1}N_{+2}N_{+3}N_{+4}N_{+5}N_{+6}N_{+7}N_{+8}$CTCCAG-3' (SEQ ID NO: 31)
3' segment end: 5'-CTGGAG$N_{-8}N_{-7}N_{-6}N_{-5}N_{-4}N_{-3}N_{-2}N_{-1}\mathbf{N_A N_B}N_{+1}N_{+2}N_{+3}N_{+4}N_{+5}N_{+6}N_{+7}N_{+8}N_{+9}N_{+10}$-3' (SEQ ID NO: 32)

*BsmI:* GAATGC (10x digestion, 95% ligation, 95% recut) Note: $N_A N_B$ must be CG
5' segment end: 5'-$N_{-9}N_{-8}N_{-7}N_{-6}N_{-5}N_{-4}N_{-3}N_{-2}N_{-1}\mathbf{N_A}$GCATTC-3' (SEQ ID NO: 33)
3' segment end: 5'-GAATGC$\mathbf{N_B}N_{+1}N_{+2}N_{+3}N_{+4}N_{+5}N_{+6}N_{+7}N_{+8}N_{+9}N_{+10}$-3' (SEQ ID NO: 34)

*BsrI:* ACTGG (4x digestion, 95% ligation, 95% recut) Note: $N_A N_B$ must be GC
5' segment end: 5'-$N_{-9}N_{-8}N_{-7}N_{-6}N_{-5}N_{-4}N_{-3}N_{-2}N_{-1}\mathbf{N_A}$CCAGT-3' (SEQ ID NO: 35)
3' segment end: 5'-ACTGG$\mathbf{N_B}N_{+1}N_{+2}N_{+3}N_{+4}N_{+5}N_{+6}N_{+7}N_{+8}N_{+9}N_{+10}$-3' (SEQ ID NO: 36)

*BsrDI:* GCAATG (10x digestion, 95% ligation, 95% recut)
5' segment end: 5'-$N_{-9}N_{-8}N_{-7}N_{-6}N_{-5}N_{-4}N_{-3}N_{-2}N_{-1}\mathbf{N_A N_B}$CATTGC-3' (SEQ ID NO: 37)
3' segment end: 5'-GCAATG$\mathbf{N_A N_B}N_{+1}N_{+2}N_{+3}N_{+4}N_{+5}N_{+6}N_{+7}N_{+8}N_{+9}N_{+10}$-3' (SEQ ID NO: 38)

Figure 41C

| | | | |
|---|---|---|---|
| 1 | Denature | 95°C | 30sec |
| 2 | Denature | 95°C | 30sec |
| 3 | Anneal | 48°C -70°C | 30sec |
| 4 | Extend | 70°C | 60sec |
| 5 | Goto | step 2 | 39 times |
| 6 | | 4°C | forever |
| 7 | End | | |

Figure 43

```
gaggaagcggaaggcgagagtagggaactgccaggcatcaaactaagcagaaggcccctgacggatggcc
tttttgcgtttctacaaactctttctgtgttgtaaaacgacggccagtcttaagctcgggcctcaaataa
tgattttagatatcgccatccagctgatattccctatagtgcatggtcatagctgtttcctggcagctct
ggcccgtgtctcaaaatctctgatgttacattgtacaagataaaataatatcatcatgaacaataaaact
gtctgcttacataaacagtaatacaaggggtgttatgagccatattcaacgggaaacgtcgaggccgcga
ttaaattccaacatggatgctgatttatatgggtataaatgggctcgcgataatgtcgggcaatcaggtg
cgacaatctatcgcttgtatgggaagcccgatgcgccagagttgtttctgaaacatggcaaaggtagcgt
tgccaatgatgttacagatgagatggtcagactaaactggctgacggaatttatgccacttccgaccatc
aagcatttatccgtactcctgatgatgcatggttactcaccactgcgatccccggaaaaacagcgttcc
aggtattagaagaatatcctgattcaggtgaaaatattgttgatgcgctggcagtgttcctgcgccggtt
gcactcgattcctgtttgtaattgtccttttaacagcgatcgcgtatttcgcctcgctcaggcgaatca
cgaatgaataacggtttggttgatgcgagtgattttgatgacgagcgtaatggctggcctgttgaacaag
tctggaaagaaatgcataaacttttgccattctcaccggattcagtcgtcactcatggtgatttctcact
tgataaccttattttttgacgaggggaaattaataggttgtattgatgttggacgagtcggaatcgcagac
cgataccaggatcttgccatcctatggaactgcctcggtgagttttctccttcattacagaaacggcttt
ttcaaaaatatggtattgataatcctgatatgaataaattgcagtttcatttgatgctcgatgagttttt
ctaatcagaattggttaattggttgtaacactggcagagcattacgctgacttgacgggacggcgcaagc
tcatgaccaaaatcccttaacgtgagttacgcgcgcgtcgttccactgagcgtcagaccccgtagaaaag
atcaaaggatcttcttgagatccttttttttctgcgcgtaatctgctgcttgcaaacaaaaaaaccaccgc
taccagcggtggtttgtttgccggatcaagagctaccaactctttttccgaaggtaactggcttcagcag
agcgcagataccaaatactgttcttctagtgtagccgtagttagcccaccacttcaagaactctgtagca
ccgcctacatacctcgctctgctaatcctgttaccagtggctgctgccagtggcgataagtcgtgtctta
ccgggttggactcaagacgatagttaccggataaggcgcagcggtcgggctgaacggggggttcgtgcac
acagcccagcttggagcgaacgacctacaccgaactgagatacctacagcgtgagctatgagaaagcgcc
acgcttcccgaagggagaaaggcggacaggtatccggtaagcggcagggtcggaacaggagagcgcacga
gggagcttccaggggaaacgcctggtatctttatagtcctgtcgggtttcgccacctctgacttgagcg
tcgatttttgtgatgctcgtcaggggggcggagccatggaaaaacgccagcaacgcggcctttttacgg
ttcctggccttttgctggccttttgctcacatgttctttcctgcgttatcccctgattctgtggataacc
gtattaccgcctttgagtgagctgataccgctcgccgcagccgaacgaccgagcgcagcgagtcagtgag
c (SEQ ID NO: 39)
```

Figure 46

```
gaggaagcggaaggcgagagtagggaactgccaggcatcaaactaagcagaaggcccctgacggatggcc
tttttgcgtttctacaaactctttctgtgttgtaaaacgacggccagtcttaagctcgggccccaaataa
tgatttatttgactgatagtgacctgttcgttgcaacacattgatgagcaatgcttttttataatgcc
aactttgtacaaaaagctgaacgagaaacgtaaaatgatataaatatcaatatattaaattagattttg
cataaaaaacagactacataatactgtaaaacacaacatatccagtcactatgaatcaactacttagatg
gtattagtgacctgtagtcgaccgacgacgtttccaaatgttcttcgggtgatgctgccaacttagtcgac
cgacagccttccaaatgttcttctcaaacggaatcgtcgtatccagcctactcgctattgtcctcaatgc
cgtattaaatcataaaaagaaataagaaaaagaggtgcgagcctcttttttgtgtgacaaaataaaaaca
tctacctattcatatacgctagtgtcatagtcctgaaaatcatctgcatcaagaacaatttcacaactct
tatacttttctcttacaagtcgttcggcttcatctggattttcagcctctatacttactaaacgtgataa
agtttctgtaatttctactgtatcgacctgcagactggctgtgtataagggagcctgacatttatattcc
ccagaacatcaggttaatggcgttttgatgtcattttcgcggtggctgagatcagccacttcttcccg
ataacggagaccggcacactggccatatcggtggtcatcatgcgccagctttcatcccgatatgcacca
ccgggtaaagttcacgggagactttatctgacagcagacgtgcactggccaggggatcaccatccgtcg
cccgggcgtgtcaataatatcactctgtacatccacaaacagacgataacggctctctcttttataggtg
taaaccttaaactgcatttcaccagcccctgttctcgtcagcaaaagagccgttcatttcaataaaccgg
gcgacctcagccatcccttcctgattttccgctttccagcgttcggcacgcagacgacgggcttcattct
gcatggttgtgcttaccagaccggagatattgacatcatatatgccttgagcaactgatagctgtcgctg
tcaactgtcactgtaatacgctgcttcatagcatacctcttttgacatacttcgggtatacatatcagt
atatattcttataccgcaaaaatcagcgcgcaaatacgcatactgttatctggcttttagtaagccggat
ccacgcggcgtttacgccccgcctgccactcatcgcagtactgttgtaattcattaagcattctgccga
catggaagccatcacagacggcatgatgaacctgaatcgccagcggcatcagcaccttgtcgccttgcgt
ataatatttgccatggtgaaaacggggcgaagaagttgtccatattggccacgtttaaatcaaaactg
gtgaaactcacccaggggattggctggacgaaacatattctcaatacccctttaggcgaaaataggcca
ggttttcaccgtaacacgccacatcttgcaatatatgtgtagaaactgccggaaatcgtcgtggtattc
actccagagcgatgaaaacgtttcagtttgctcatggaaaacggtgtaacaagggtgaacactatcccat
atcaccagctcaccgtctttcattgccatacggaattccggatgagcattcatcaggcgggcaagaatgt
gaataaaggccggataaaacttgtgcttatttttctttacggtctttaaaaaggccgtaatatccagctg
aacggtctggttataggtacattgagcaactgactgaaatgcctcaaaatgttctttacgatgccattgg
gatatatcaacggtggtatatccagtgatttttttctccattttagcttccttagctcctgaaaatctcg
ataactcaaaaaatacgcccggtagtgatcttatttcattatggtgaaagttggaacctcttacgtgccg
atcaacgtctcattttcgccaaaagttggcccagggcttcccggtatcaacagggacaccaggatttatt
tattctgcgaagtgatcttccgtcacaggtatttattcggcgcaaagtgcgtcgggtgatgctgccaact
tagtcgactacaggtcactaataccatctaagtagttgattcatagtgactggatatgttgtgttttaca
gtattatgtagtctgttttttatgcaaaatcaatttaatatattgatatttatatcattttacgtttct
cgttcagctttcttgtacaaagttggcattataagaaagcattgcttatcaatttgttgcaacgaacagg
tcactatcagtcaaaataaaatcattatttgccatccagctgatatccctataggtcatagctgtttcc
tggcagctctggcccgtgtctcaaaatctctgatgttacattgtacaagataaaataatatcatcatgaa
caataaaactgtctgcttacataaacagtaatacaaggggtgttatgagccatattcaacgggaaacgtc
gaggccgcgattaaattccaacatggatgctgatttatatgggtataaatgggctcgcgataatgtcggg
caatcaggtgcgacaatctatcgcttgtatgggaagcccgatgcgccagagttgtttctgaaacatggca
aaggtagcgttgccaatgatgttacagatgagatggtcagactaaactggctgacggaatttatgccact
tccgaccatcaagcattttatccgtactcctgatgatgcatggttactcaccactgcgatccccggaaaa
acagcgttccaggtattagaagaatatcctgattcaggtgaaaatattgttgatgcgctggcagtgttcc
tgcgccggttgcactcgattcctgtttgtaattgtccttttaacagcgatcgcgtatttcgcctcgctca
ggcgcaatcacgaatgaataacggtttggttgatgcgagtgattttgatgacgagcgtaatggctggcct
gttgaacaagtctggaaagaaatgcataaacttttgccattctcaccggattcagtcgtcactcatggtg
atttctcacttgataaccttatttttgacgaggggaaattaataggttgtattgatgttggacgagtcgg
aatcgcagaccgataccaggatcttgccatcctatggaactgcctcggtgagttttctccttcattacag
aaacggctttttcaaaaatatggtattgataatcctgatatgaataaattgcagtttcatttgatgctcg
atgagttttctaatcagaattggttaattggttgtaacactggcagagcattacgctgacttgacggga
cggcgcaagctcatgaccaaaatcccttaacgtgagttacgcgcgcgtcgttccactgagcgtcagaccc
cgtagaaagatcaaaggatcttcttgagatcctttttttctgcgcgtaatctgctgcttgcaaacaaaa
aaaccaccgctaccagcggtggtttgtttgccggatcaagagctaccaactctttttccgaaggtaactg
gcttcagcagagcgcagataccaaatactgttcttctagtgtagccgtagttagcccaccacttcaagaa
ctctgtagcaccgcctacatacctcgctctgctaatcctgttaccagtggctgctgccagtggcgataag
tcgtgtcttaccgggttggactcaagacgatagttaccggataaggcgcagcggtcgggctgaacggggg
gttcgtgcacacagcccagcttggagcgaacgacctacaccgaactgagatacctacagcgtgagctatg
agaaagcgccacgcttcccgaagggagaaaggcggacaggtatccggtaagcggcagggtcggaacagga
gagcgcacgagggagcttccaggggggaaacgcctggtatctttatagtcctgtcgggtttcgccacctcg
acttgagcgtcgatttttgtgatgctcgtcaggggggcggagcctatggaaaaacgccagcaacgcggcc
tttttacggttcctggccttttgctggccttttgctcacatgttctttcctgcgttatcccctgattctg
tggataaccgtattaccgcctttgagtgagctgataccgctcgccgcagccgaacgaccgagcgcagcga
gtcagtgagc  (SEQ ID NO: 40)
```

Figure 47

```
gaggaagcggaaggcgagagtagggaactgccaggcatcaaactaagcagaaggcccctgacggatggcc
tttttgcgtttctacaaactctttctgtgttgtaaaacgacggccagtcttaagctcgggcctcaaataa
tgattttagattaacggtctccttttctcgagcggataaatgtgagcggataacattgacattgtgagcg
gataacaagatactgagcacatcagcaggacgcactgaccgcgggatcccggtgcagaaaataaggagga
aaaaaaaatgagcaaaggtgaagaactgttcaccggcgttgtgccaattctggttgagctggatggtgac
gtgaatggccacaaattttccgtgtctggtgaaggcgagggtgatgctacttatggcaaactgactctga
aactgatctgtaccaccggcaaactgcctgttccgtggccaactctggtcactactctgggttacggcct
gatgtgttttgcgcgttacccggatcacatgaaacagcatgacttcttcaaatctgccatgccggaaggc
tatgtccaagaacgtacgatctttttcaaggacgacggcaactataaaacccgtgccgaagttaaattcg
agggtgacaccctggttaaccgcatcgaactgaaaggcattgacttcaaagaggacggcaacattctggg
tcacaagctggaatacaactacaactcccacaacgtttacattactgctgacaagcagaaaaaacggcatc
aaagcaaacttcaagatccgtcacaacattgaagatggtggcgtacagctggcagatcactaccagcaga
acactccaatcggtgatggccagtactgctgccagataaccattacctgtcctaccagagcaaactgtc
taaagacccgaacgaaaaacgtgaccacatggtactgctggaatttgttaccgcggcaggcattacccac
ggtatggacgaactgtataaataaccccagagaccgttaatcgccatccagctgatattccctatagtgc
atggtcatagctgtttcctggcagctctggccgtgtctcaaaatctctgatgttacattgtacaagata
aaataatatcatcatgaacaataaaactgtctgcttacataaacagtaatacaaggggtgttatgagcca
tattcaacgggaaacgtcgaggccgcgattaaattccaacatggatgctgatttatatgggtataaatgg
gctcgcgataatgtcgggcaatcaggtgcgacaatctatcgcttgtatgggaagcccgatgcgccagagt
tgtttctgaaacatggcaaaggtagcgttgccaatgatgttacagatgagatggtcagactaaactggct
gacggaatttatgccacttccgaccatcaagcattttatccgtactcctgatgatgcatggttactcacc
actgcgatccccggaaaaacagcgttccaggtattagaagaatatcctgattcaggtgaaaatattgttg
atgcgctggcagtgttcctgcgccggttgcactcgattcctgtttgtaattgtccttttaacagcgatcg
cgtatttcgcctcgctcaggcgcaatcacgaatgaataacggtttggttgatgcgagtgattttgatgac
gagcgtaatggctggcctgttgaacaagtctggaaagaaatgcataaacttttgccattctcaccggatt
cagtcgtcactcatggtgatttctcacttgataaccttattttgacgaggggaaattaataggttgtat
tgatgttggacgagtcggaatcgcagaccgataccaggatcttgccatcctatggaactgcctcggtgag
ttttctccttcattacagaaacggcttttttcaaaaatatggtattgataatcctgatatgaataaattgc
agtttcatttgatgctcgatgagttttttctaatcagaattggttaattggttgtaacactggcagagcat
tacgctgacttgacgggacggcgcaagctcatgaccaaaatcccttaacgtgagttacgcgcgcgtcgtt
ccactgagcgtcagaccccgtagaaaagatcaaaggatcttcttgagatcctttttttctgcgcgtaatc
tgctgcttgcaaacaaaaaaaccaccgctaccagcggtggtttgtttgccggatcaagagctaccaactc
tttttccgaaggtaactggcttcagcagagcgcagataccaaatactgttcttctagtgtagccgtagtt
agcccaccacttcaagaactctgtagcaccgcctacatacctcgctctgctaatcctgttaccagtggct
gctgccagtggcgataagtcgtgtcttaccgggttggactcaagacgatagttaccggataaggcgcagc
ggtcgggctgaacggggggttcgtgcacacagcccagcttggagcgaacgacctacaccgaactgagata
cctacagcgtgagctatgagaaagcgccacgcttcccgaagggagaaaggcggacaggtatccggtaagc
ggcagggtcggaacaggagagcgcacgagggagcttccaggggaaacgcctggtatctttatagtcctg
tcgggtttcgccacctctgacttgagcgtcgatttttgtgatgctcgtcaggggggcggagcctatggaa
aaacgccagcaacgcggcctttttacggttcctggccttttgctggccttttgctcacatgttctttcct
gcgttatcccctgattctgtggataaccgtattaccgcctttgagtgagctgataccgctcgccgcagcc
gaacgaccgagcgcagcgagtcagtgagc    (SEQ ID NO: 43)
```

Figure 48

CYP52A17
    1 atgatcg_agcagctgc_tggaatactggtacgtggttgtgcctgttctgtatattatcaaa
   61 cagctgctggcgtacactaaaacgcgtgtcctgatgaagaaactgggcgcagcgccggtg
  121 actaacaaactgtacgataacgctttcggcatcgtaaatggttggaaagccctgcagttt
  181 aagaaagagggtcgtgcgcaagaatataatgactataaattcgatcattctaagaacccg
  241 agcgtgggtacttatgtgtctatcctgttcggtactcgcatcgtggtaactaaagaccca
  301 gaaaacatcaaagcaatcctggcgacgcaattcggcgacttctctctgggtaaacgtcac
  361 acgctgttcaaacctctgctgggcgatggcatttttcaccctggatggtgaaggttggaaa
  421 cattcccgtgcgatgctgcgtccgcagtttgcgcgtgaacaggttgcgcacgttacgtct
  481 ctggagccgcacttccagctgctgaagaaacatatcctgaaacacaaaggcgagtatttc
  541 gatatccaggagctgttcttccgtttcaccgtagattccgctaccgaatttctgttcggt
  601 gaatctgttcatagcctgaaagatgaaagcatcggcatcaaccaggatgacatcgacttc
  661 gctggtcgcaaggatttcgcagaatccttcaataaagctcaggaatatctggcgatccgt
  721 actctggtgcaaactttctattggctggttaacaataaagagtttcgcgactgtaccaaa
  781 tccgttcataaattcactaactactacgttcagaaagctctggatgcatccccggaagaa
  841 ctggaaaagcagtccggttacgttttcctgtacgaactggtgaaacagactcgtgacccg
  901 aacgtcctgcgtgaccagtctctgaacatcctgctggccggccgtgacactaccgctggc
  961 ctgctgtccttcgcggtcttcgagctggccgtcatccggaaatctgggccaaactgcgt
 1021 gaagaaatcgaacagcaattcggcctgggtgaggactcccgtgttgaagaaatcactttc
 1081 gaatctctgaaacgttgcgaatatctgaaagcattcctgaacgaaacgctgcgtatctac
 1141 ccgtccgttccgcgcaacttccgcattgctaccaagaacacgaccctgccgcgtggcggt
 1201 ggcagcgacggcacctctccgatcctgattcaaaagggtgaagcagtatcctacggtatt
 1261 aactccacccacctggacccggtatactacggtccggacgcggcagaatttcgtccagag
 1321 cgctggttttgaaccgtctaccaagaagctgggttgggcttatctgccgttcaacggcggc
 1381 cctcgtatctgtctgggtcagcagtttgccctgaccgaggcaggctacgttctggttcgc
 1441 ctggtccaagaatttttctcacgtacgtagcgacccggacgaagtttacccgccgaagcgc
 1501 ctgaccaacctgactatgtgcctgcaagatggcgctatcgtcaaatttgattaataa
     (SEQ ID NO: 47)

CYP52A No Palindrome
    1 atgatcgaacaactgctggaatactggtacgtggttgtgcctgttctgtatattatcaaa
   61 cagctgctggcgtacactaaaacgcgtgtcctgatgaagaaactgggcgcagcgccggtg
  121 actaacaaactgtacgataacgctttcggcatcgtaaatggttggaaagccctgcagttt
  181 aagaaagagggtcgtgcgcaagaatataacgactataaattcgatcattctaagaacccg
  241 agcgtgggtacttatgtgtctatcctgttcggtactcgcatcgtggtaactaaagaccca
  301 gaaaacatcaaagcaatcctggcgacgcaattcggcgacttctctctgggtaaacgtcac
  361 acgctgttcaaacctctgctgggcgatggcatttttcaccctggatggtgaaggttggaaa
  421 cattcccgtgcgatgctgcgtccgcagtttgcgcgtgaacaggttgcgcacgttacgtct
  481 ctggagccgcacttccagctgctgaagaaacatatcctgaaacacaaaggcgagtatttc
  541 gatatccaggagctgttcttccgtttcaccgtagattccgctaccgaatttctgttcggt
  601 gaatctgttcatagcctgaaagatgaaagcatcggcatcaaccaggatgacatcgacttc
  661 gctggtcgcaaggatttcgcagaatccttcaataaagctcaggaatatctggcgatccgt
  721 actctggtgcaaactttctattggctggttaacaataaagagtttcgcgactgtaccaaa
  781 tccgttcataaattcactaactactacgttcagaaagctctggatgcatccccggaagaa
  841 ctggaaaagcagtccggttacgttttcctgtacgaactggtgaaacagactcgtgacccg
  901 aacgtcctgcgtgaccagtctctgaacatcctgctggccggccgtgacactaccgctggc
  961 ctgctgtccttcgcggtcttcgagctggccgtcatccggaaatctgggccaaactgcgt
 1021 gaagaaatcgaacagcaattcggcctgggtgaggactcccgtgttgaagaaatcactttc
 1081 gaatctctgaaacgttgcgaatatctgaaagcattcctgaacgaaacgctgcgtatctac
 1141 ccgtccgttccgcgcaacttccgcattgctaccaagaacacgaccctgccgcgtggcggt
 1201 ggcagcgacggcacctctccgatcctgattcaaaagggtgaagcagtatcctacggtatt
 1261 aactccacccacctggacccggtatactacggtccggacgcggcagaatttcgtccagag
 1321 cgctggttttgaaccgtctaccaagaagctgggttgggcttatctgccgttcaacggcggc
 1381 cctcgtatctgtctgggtcagcagtttgccctgaccgaggcaggctacgttctggttcgc
 1441 ctggtccaagaatttttctcacgtacgtagcgacccggacgaagtttacccgccgaagcgc
 1501 ctgaccaacctgactatgtgcctgcaagatggcgctatcgtcaaatttgattaataa
     SEQ ID NO: 48)

Figure 52

SEQUENCE LISTING

<160> NUMBER OF SEQ ID NOS: 158

<210> SEQ ID NO 1
<211> LENGTH: 23
<212> TYPE: DNA
<213> ORGANISM: Artificial Sequence
<220> FEATURE:
<223> OTHER INFORMATION: Synthetic Nucleotide
<220> FEATURE:
<221> NAME/KEY: misc_feature
<222> LOCATION: 1, 2, 3, 4, 5, 6, 7, 8, 9, 10, 12, 14, 16
<223> OTHER INFORMATION: n = A,T,C or G

<400> SEQUENCE: 1
nnnnnnnnnn anbncngaag agc                                        23

<210> SEQ ID NO 2
<211> LENGTH: 23
<212> TYPE: DNA
<213> ORGANISM: Artificial Sequence
<220> FEATURE:
<223> OTHER INFORMATION: Synthetuc Nucleotide
<220> FEATURE:
<221> NAME/KEY: misc_feature
<222> LOCATION: 8, 9, 11, 13, 15, 16, 17, 18, 19, 20, 21, 22, 23
<223> OTHER INFORMATION: n = A,T,C or G

<400> SEQUENCE: 2
gctcttcnna nbncnnnnnn nnn                                        23

<210> SEQ ID NO 3
<211> LENGTH: 22
<212> TYPE: DNA
<213> ORGANISM: Artificial Sequence
<220> FEATURE:
<223> OTHER INFORMATION: Synthetic Nucleotide
<220> FEATURE:
<221> NAME/KEY: misc_feature
<222> LOCATION: 1, 2, 3, 4, 5, 6, 7, 8, 9, 10, 12, 14, 16
<223> OTHER INFORMATION: n = A,T,C or G

<400> SEQUENCE: 3
nnnnnnnnnn anbncngaag ag                                         22

<210> SEQ ID NO 4
<211> LENGTH: 22
<212> TYPE: DNA
<213> ORGANISM: Artificial Sequence
<220> FEATURE:
<223> OTHER INFORMATION: Synthetic Nucleotide
<220> FEATURE:
<221> NAME/KEY: misc_feature
<222> LOCATION: 7, 8, 10, 12, 14, 15, 16, 17, 18, 19, 20, 21, 22
<223> OTHER INFORMATION: n = A,T,C or G

<400> SEQUENCE: 4
ctcttcnnan bncnnnnnnn nn                                         22

<210> SEQ ID NO 5
<211> LENGTH: 25
<212> TYPE: DNA
<213> ORGANISM: Artificial Sequence
<220> FEATURE:
<223> OTHER INFORMATION: Synthetic Nucleotide
<220> FEATURE:
<221> NAME/KEY: misc_feature
<222> LOCATION: 1, 2, 3, 4, 5, 6, 7, 8, 9, 10, 12, 14, 16, 18, 19
<223> OTHER INFORMATION: n = A,T,C or G

<400> SEQUENCE: 5
nnnnnnnnnn anbncndnng tcttc                                    25

<210> SEQ ID NO 6
<211> LENGTH: 25
<212> TYPE: DNA
<213> ORGANISM: Artificial Sequence
<220> FEATURE:
<223> OTHER INFORMATION: Synthetic Nucleotide
<220> FEATURE:
<221> NAME/KEY: misc_feature
<222> LOCATION: 7, 8, 9, 11, 13, 15, 17, 18, 19, 20, 21, 22, 23, 24, 25
<223> OTHER INFORMATION: n = A,T,C or G

<400> SEQUENCE: 6
gaagacnnna nbncndnnnn nnnnn                                    25

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12, 14, 16, 18
<223> OTHER INFORMATION: n = A,T,C or G

<400> SEQUENCE: 7
nnnnnnnnnn anbncndnga gacc                                     24

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 10, 12, 14, 16, 17, 18, 19, 20, 21, 22, 23, 24
<223> OTHER INFORMATION: n = A,T,C or G

<400> SEQUENCE: 8
ggtctcnnan bncndnnnnn nnnn                                     24

<210> SEQ ID NO 9
<211> LENGTH: 24
<212> TYPE: DNA
<213> ORGANISM: Artificial Sequence
<220> FEATURE:
<223> OTHER INFORMATION: Synthetic Nucleotide
<220> FEATURE:
<221> NAME/KEY: misc_feature
<222> LOCATION: 1, 2, 3, 4, 5, 6, 7, 8, 9, 10, 12, 14, 16, 18
<223> OTHER INFORMATION: n = A,T,C or G

<400> SEQUENCE: 9
nnnnnnnnnn anbncndnga gacg                                     24

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 10, 12, 14, 16, 17, 18, 19, 20, 21, 22, 23, 24
<223> OTHER INFORMATION: n = A,T,C or G

<400> SEQUENCE: 10
cgtctcnnan bncndnnnnn nnnn                                    24

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12, 14, 16, 18, 19, 20,
      21
<223> OTHER INFORMATION: n = A,T,C or G

<400> SEQUENCE: 11
nnnnnnnnnn anbncndnnn ngcaggt                                 27

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 9, 10, 11, 13, 15, 17, 19, 20, 21, 22, 23, 24, 25,
      26, 27
<223> OTHER INFORMATION: n = A,T,C or G

<400> SEQUENCE: 12
acctgcnnnn nanbncndnn nnnnnnn                                 27

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12, 14, 16, 18, 19, 20,
      21, 22, 23, 24, 25
<223> OTHER INFORMATION: n = A,T,C or G

<400> SEQUENCE: 13
nnnnnnnnnn anbncndnnn nnnnngctgc                              30

<210> SEQ ID NO 14
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 6, 7, 8, 9, 10, 11, 12, 13, 14, 16, 18, 20, 22, 23, 24,
      25, 26, 27, 28, 29, 30
<223> OTHER INFORMATION: n = A,T,C or G

<400> SEQUENCE: 14
gcagcnnnnn nnnnanbncn dnnnnnnnnn                              30

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide

```
<220> FEATURE:
<221> NAME/KEY: misc_feature
<222> LOCATION: 1, 2, 3, 4, 5, 6, 7, 8, 9, 10, 12, 14, 16, 18
<223> OTHER INFORMATION: n = A,T,C or G

<400> SEQUENCE: 15
nnnnnnnnnn anbncndnga gac                                              23

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 6, 7, 9, 11, 13, 15, 16, 17, 18, 19, 20, 21, 22, 23
<223> OTHER INFORMATION: n = A,T,C or G

<400> SEQUENCE: 16
gtctcnnanb ncndnnnnnn nnn                                              23

<210> SEQ ID NO 17
<211> LENGTH: 33
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 11, 13, 15, 17, 19, 20,
      21, 22, 23, 24, 25, 26, 27, 28
<223> OTHER INFORMATION: n = A,T,C or G

<400> SEQUENCE: 17
nnnnnnnnnn nanbncndnn nnnnnnngt ccc                                    33

<210> SEQ ID NO 18
<211> LENGTH: 33
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 6, 7, 8, 9, 10, 11, 12, 13, 14, 15, 16, 18, 20, 22, 24,
      25, 26, 27, 28, 29, 30, 31, 32, 33
<223> OTHER INFORMATION: n = A,T,C or G

<400> SEQUENCE: 18
gggacnnnnn nnnnnnanbn cndnnnnnnn nnn                                   33

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12, 14, 16, 18
<223> OTHER INFORMATION: n = A,T,C or G

<400> SEQUENCE: 19
nnnnnnnnnn anbncndnga gacg                                             24

<210> SEQ ID NO 20
<211> LENGTH: 24
<212> TYPE: DNA
```

```
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 10, 12, 14, 16, 17, 18, 19, 20, 21, 22, 23, 24
<223> OTHER INFORMATION: n = A,T,C or G

<400> SEQUENCE: 20
cgtctcnnan bncndnnnnn nnnn                                              24

<210> SEQ ID NO 21
<211> LENGTH: 31
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12, 14, 16, 18, 19, 20,
      21, 22, 23, 24, 25, 26
<223> OTHER INFORMATION: n = A,T,C or G

<400> SEQUENCE: 21
nnnnnnnnnn anbncndnnn nnnnnncatc c                                      31

<210> SEQ ID NO 22
<211> LENGTH: 31
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 6, 7, 8, 9, 10, 11, 12, 13, 14, 15, 17, 19, 21, 23, 24,
      25, 26, 27, 28, 29, 30, 31
<223> OTHER INFORMATION: n = A,T,C or G

<400> SEQUENCE: 22
ggatgnnnnn nnnnnanbnc ndnnnnnnnn n                                      31

<210> SEQ ID NO 23
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12, 14, 16, 18, 19, 20,
      21, 22
<223> OTHER INFORMATION: n = A,T,C or G

<400> SEQUENCE: 23
nnnnnnnnnn anbncndnnn nngatgc                                           27

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 6, 7, 8, 9, 10, 11, 13, 15, 17, 19, 20, 21, 22, 23, 24,
      25, 26, 27
<223> OTHER INFORMATION: n = A,T,C or G

<400> SEQUENCE: 24
gcatcnnnnn nanbncndnn nnnnnnn                                           27
```

<210> SEQ ID NO 25
<211> LENGTH: 28
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12, 14, 16, 18, 19, 20,
      21, 22, 23
<223> OTHER INFORMATION: n = A,T,C or G

<400> SEQUENCE: 25
nnnnnnnnnn anbncndnnn nnngcgtc                                      28

<210> SEQ ID NO 26
<211> LENGTH: 28
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 6, 7, 8, 9, 10, 11, 13, 15, 17, 19, 20, 21, 22, 23, 24,
      25, 26, 27, 28
<223> OTHER INFORMATION: n = A,T,C or G

<400> SEQUENCE: 26
gacgcnnnnn nanbncndnn nnnnnnnn                                      28

<210> SEQ ID NO 27
<211> LENGTH: 22
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 11, 13, 14, 15, 16
<223> OTHER INFORMATION: n = A,T,C or G

<400> SEQUENCE: 27
nnnnnnnnnn nannnnccca gt                                            22

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 9, 10, 11, 13, 14, 15, 16, 17, 18, 19, 20, 21, 22
<223> OTHER INFORMATION: n = A,T,C or G

<400> SEQUENCE: 28
actgggnnnn nannnnnnnn nn                                            22

<210> SEQ ID NO 29
<211> LENGTH: 33
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12, 14, 15, 16, 17, 18,
      19, 20, 21, 22, 23, 24, 25, 26, 27
<223> OTHER INFORMATION: n = A,T,C or G

```
<400> SEQUENCE: 29
nnnnnnnnnn anbnnnnnnn nnnnnnnctc cag                            33

<210> SEQ ID NO 30
<211> LENGTH: 34
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 9, 10, 11, 12, 13, 14, 15, 16, 17, 18, 19, 20, 21,
      23, 25, 26, 27, 28, 29, 30, 31, 32, 33, 34
<223> OTHER INFORMATION: n = A,T,C or G

<400> SEQUENCE: 30
ctggagnnnn nnnnnnnnnn nanbnnnnnn nnnn                           34

<210> SEQ ID NO 31
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12, 14, 15, 16, 17, 18,
      19, 20, 21
<223> OTHER INFORMATION: n = A,T,C or G

<400> SEQUENCE: 31
nnnnnnnnnn anbnnnnnnn nctccag                                   27

<210> SEQ ID NO 32
<211> LENGTH: 28
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 8, 9, 10, 11, 12, 13, 14, 15, 17, 19, 20, 21, 22, 23,
      24, 25, 26, 27, 28
<223> OTHER INFORMATION: n = A,T,C or G

<400> SEQUENCE: 32
ctggagnnnn nnnnnanbnn nnnnnnnn                                  28

<210> SEQ ID NO 33
<211> LENGTH: 17
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10
<223> OTHER INFORMATION: n = A,T,C or G

<400> SEQUENCE: 33
nnnnnnnnnn agcattc                                              17

<210> SEQ ID NO 34
<211> LENGTH: 18
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: misc_feature
<222> LOCATION: 7, 9, 10, 11, 12, 13, 14, 15, 16, 17, 18
<223> OTHER INFORMATION: n = A,T,C or G

<400> SEQUENCE: 34
gaatgcnbnn nnnnnnnn                                                    18

<210> SEQ ID NO 35
<211> LENGTH: 16
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10
<223> OTHER INFORMATION: n = A,T,C or G

<400> SEQUENCE: 35
nnnnnnnnnn accagt                                                      16

<210> SEQ ID NO 36
<211> LENGTH: 17
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 6, 8, 9, 10, 11, 12, 13, 14, 15, 16, 17
<223> OTHER INFORMATION: n = A,T,C or G

<400> SEQUENCE: 36
actggnbnnn nnnnnnn                                                     17

<210> SEQ ID NO 37
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1, 2, 3, 4, 5, 6, 7, 8, 9, 10, 12
<223> OTHER INFORMATION: n = A,T,C or G

<400> SEQUENCE: 37
nnnnnnnnnn anbcattgc                                                   19

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 7, 9, 11, 12, 13, 14, 15, 16, 17, 18, 19, 20
<223> OTHER INFORMATION: n = A,T,C or G

<400> SEQUENCE: 38
gcaatgnanb nnnnnnnnnn                                                  20

<210> SEQ ID NO 39
<211> LENGTH: 2031
<212> TYPE: DNA
<213> ORGANISM: Artificial Sequence
<220> FEATURE:
```

<223> OTHER INFORMATION: Vector 1

<400> SEQUENCE: 39

```
gaggaagcgg aaggcgagag tagggaactg ccaggcatca aactaagcag aaggcccctg      60
acggatggcc tttttgcgtt tctacaaact ctttctgtgt tgtaaaacga cggccagtct     120
taagctcggg cctcaaataa tgattttaga tatcgccatc cagctgatat tccctatagt     180
gcatggtcat agctgtttcc tggcagctct ggcccgtgtc tcaaaatctc tgatgttaca     240
ttgtacaaga taaataata tcatcatgaa caataaaact gtctgcttac ataaacagta      300
atacaagggg tgttatgagc catattcaac gggaaacgtc gaggccgcga ttaaattcca     360
acatggatgc tgatttatat gggtataaat gggctcgcga taatgtcggg caatcaggtg     420
cgacaatcta tcgcttgtat gggaagcccg atgcgccaga gttgtttctg aaacatggca     480
aaggtagcgt tgccaatgat gttacagatg agatggtcag actaaactgg ctgacggaat     540
ttatgccact tccgaccatc aagcatttta tccgtactcc tgatgatgca tggttactca     600
ccactgcgat ccccggaaaa acagcgttcc aggtattaga agaatatcct gattcaggtg     660
aaaatattgt tgatgcgctg gcagtgttcc tgcgccggtt gcactcgatt cctgtttgta     720
attgtccttt taacagcgat cgcgtatttc gcctcgctca ggcgcaatca cgaatgaata     780
acggtttggt tgatgcgagt gattttgatg acgagcgtaa tggctggcct gttgaacaag     840
tctggaaaga aatgcataaa cttttgccat tctcaccgga ttcagtcgtc actcatggtg     900
atttctcact tgataacctt attttgacg aggggaaatt aataggttgt attgatgttg     960
gacgagtcgg aatcgcagac cgataccagg atcttgccat cctatggaac tgcctcggtg    1020
agttttctcc ttcattacag aaacggcttt tcaaaaata tggtattgat aatcctgata    1080
tgaataaatt gcagtttcat ttgatgctcg atgagttttt ctaatcagaa ttggttaatt    1140
ggttgtaaca ctggcagagc attacgctga cttgacggga cggcgcaagc tcatgaccaa    1200
aatcccttaa cgtgagttac gcgcgcgtcg ttccactgag cgtcagaccc cgtagaaaag    1260
atcaaaggat cttcttgaga tcctttttt ctgcgcgtaa tctgctgctt gcaaacaaaa    1320
aaaccaccgc taccagcggt ggtttgtttg ccggatcaag agctaccaac tcttttccg    1380
aaggtaactg gcttcagcag agcgcagata ccaaatactg ttcttctagt gtagccgtag    1440
ttagcccacc acttcaagaa ctctgtagca ccgcctacat acctcgctct gctaatcctg    1500
ttaccagtgg ctgctgccag tggcgataag tcgtgtctta ccgggttgga ctcaagacga    1560
tagttaccgg ataaggcgca gcggtcgggc tgaacggggg gttcgtgcac acagcccagc    1620
ttggagcgaa cgacctacac cgaactgaga tacctacagc gtgagctatg agaaagcgcc    1680
acgcttcccg aagggagaaa ggcggacagg tatccggtaa gcggcagggt cggaacagga    1740
gagcgcacga gggagcttcc agggggaaac gcctggtatc tttatagtcc tgtcgggttt    1800
cgccacctct gacttgagcg tcgatttttg tgatgctcgt caggggggcg gagcctatgg    1860
aaaaacgcca gcaacgcggc ctttttacgg ttcctggcct tttgctggcc ttttgctcac    1920
atgttctttc ctgcgttatc ccctgattct gtggataacc gtattaccgc ctttgagtga    1980
gctgataccg ctcgccgcag ccgaacgacc gagcgcagcg agtcagtgag c             2031
```

<210> SEQ ID NO 40
<211> LENGTH: 4420
<212> TYPE: DNA
<213> ORGANISM: Artificial Sequence
<220> FEATURE:
<223> OTHER INFORMATION: Vector

<400> SEQUENCE: 40

```
gaggaagcgg aaggcgagag tagggaactg ccaggcatca aactaagcag aaggcccctg     60
acggatggcc ttttgcgtt tctacaaact ctttctgtgt tgtaaaacga cggccagtct    120
taagctcggg ccccaaataa tgattttatt ttgactgata gtgacctgtt cgttgcaaca    180
cattgatgag caatgctttt ttataatgcc aactttgtac aaaaaagctg aacgagaaac    240
gtaaaatgat ataaatatca atatattaaa ttagattttg cataaaaaac agactacata    300
atactgtaaa acacaacata tccagtcact atgaatcaac tacttagatg gtattagtga    360
cctgtagtcg accgacagcc ttccaaatgt tcttcgggtg atgctgccaa cttagtcgac    420
cgacagcctt ccaaatgttc ttctcaaacg gaatcgtcgt atccagccta ctcgctattg    480
tcctcaatgc cgtattaaat cataaaaaga aataagaaaa agaggtgcga gcctcttttt    540
tgtgtgacaa aataaaaaca tctacctatt catatacgct agtgtcatag tcctgaaaat    600
catctgcatc aagaacaatt tcacaactct tatacttttc tcttacaagt cgttcggctt    660
catctggatt ttcagcctct atacttacta aacgtgataa agtttctgta atttctactg    720
tatcgacctg cagactggct gtgtataagg gagcctgaca tttatattcc ccagaacatc    780
aggttaatgg cgttttgat gtcattttcg cggtggctga gatcagccac ttcttccccg    840
ataacggaga ccggcacact ggccatatcg gtggtcatca tgcgccagct ttcatccccg    900
atatgcacca ccgggtaaag ttcacgggag actttatctg acagcagacg tgcactggcc    960
agggggatca ccatccgtcg cccgggcgtg tcaataatat cactctgtac atccacaaac   1020
agacgataac ggctctctct tttataggtg taaaccttaa actgcatttc accagcccct   1080
gttctcgtca gcaaaagagc cgttcatttc aataaaccgg gcgacctcag ccatcccttc   1140
ctgattttcc gctttccagc gttcggcacg cagacgacgg gcttcattct gcatggttgt   1200
gcttaccaga ccggagatat tgacatcata tatgccttga gcaactgata gctgtcgctg   1260
tcaactgtca ctgtaatacg ctgcttcata gcatacctct ttttgacata cttcgggtat   1320
acatatcagt atatattctt ataccgcaaa aatcagcgcg caaatacgca tactgttatc   1380
tggcttttag taagccggat ccacgcggcg tttacgcccc gccctgccac tcatcgcagt   1440
actgttgtaa ttcattaagc attctgccga catggaagcc atcacagacg gcatgatgaa   1500
cctgaatcgc cagcggcatc agcaccttgt cgccttgcgt ataatatttg cccatggtga   1560
aaacgggggc gaagaagttg tccatattgg ccacgtttaa atcaaaactg gtgaaactca   1620
cccagggatt ggctgagacg aaaaacatat tctcaataaa ccctttaggg aaataggcca   1680
ggttttcacc gtaacacgcc acatcttgcg aatatatgtg tagaaactgc cggaaatcgt   1740
cgtggtattc actccagagc gatgaaaacg tttcagtttg ctcatggaaa acggtgtaac   1800
aagggtgaac actatcccat atccagct caccgtcttt cattgccata cggaattccg   1860
gatgagcatt catcaggcgg gcaagaatgt gaataaaggc cggataaaac ttgtgcttat   1920
ttttctttac ggtctttaaa aaggccgtaa tatccagctg aacggtctgg ttataggtac   1980
attgagcaac tgactgaaat gcctcaaaat gttctttacg atgccattgg gatatatcaa   2040
cggtggtata tccagtgatt ttttctcca ttttagcttc cttagctcct gaaaatctcg   2100
ataactcaaa aaatacgccc ggtagtgatc ttatttcatt atggtgaaag ttggaacctc   2160
ttacgtgccg atcaacgtct cattttcgcc aaaagttggc ccagggcttc ccggtatcaa   2220
cagggacacc aggatttatt tattctgcga agtgatcttc cgtcacaggt atttattcgg   2280
```

-continued

```
cgcaaagtgc gtcgggtgat gctgccaact tagtcgacta caggtcacta ataccatcta    2340
agtagttgat tcatagtgac tggatatgtt gtgttttaca gtattatgta gtctgttttt    2400
tatgcaaaat ctaatttaat atattgatat ttatatcatt ttacgtttct cgttcagctt    2460
tcttgtacaa agttggcatt ataagaaagc attgcttatc aatttgttgc aacgaacagg    2520
tcactatcag tcaaaataaa atcattattt gccatccagc tgatatcccc tataggtcat    2580
agctgtttcc tggcagctct ggcccgtgtc tcaaaatctc tgatgttaca ttgtacaaga    2640
taaaataata tcatcatgaa caataaaact gtctgcttac ataaacagta atacaagggg    2700
tgttatgagc catattcaac gggaaacgtc gaggccgcga ttaaattcca acatggatgc    2760
tgatttatat gggtataaat gggctcgcga taatgtcggg caatcaggtg cgacaatcta    2820
tcgcttgtat gggaagcccg atgcgccaga gttgtttctg aaacatggca aaggtagcgt    2880
tgccaatgat gttacagatg agatggtcag actaaactgg ctgacggaat ttatgccact    2940
tccgaccatc aagcatttta tccgtactcc tgatgatgca tggttactca ccactgcgat    3000
ccccggaaaa acagcgttcc aggtattaga agaatatcct gattcaggtg aaaatattgt    3060
tgatgcgctg gcagtgttcc tgcgccggtt gcactcgatt cctgtttgta attgtccttt    3120
taacagcgat cgcgtatttc gcctcgctca ggcgcaatca cgaatgaata cggtttggt     3180
tgatgcgagt gattttgatg acgagcgtaa tggctggcct gttgaacaag tctggaaaga    3240
aatgcataaa cttttgccat tctcaccgga ttcagtcgtc actcatgtga tttctcact     3300
tgataacctt attttgacg aggggaaatt aataggttgt attgatgttg gacgagtcgg    3360
aatcgcagac cgataccagg atcttgccat cctatggaac tgcctcggtg agttttctcc    3420
ttcattacag aaacggcttt ttcaaaaata tggtattgat aatcctgata tgaataaatt    3480
gcagtttcat ttgatgctcg atgagttttt ctaatcagaa ttggttaatt ggttgtaaca    3540
ctggcagagc attacgctga cttgacggga cggcgcaagc tcatgaccaa aatcccttaa    3600
cgtgagttac gcgcgcgtcg ttccactgag cgtcagaccc cgtagaaaag atcaaaggat    3660
cttcttgaga tcctttttt ctgcgcgtaa tctgctgctt gcaaacaaaa aaaccaccgc    3720
taccagcggt ggtttgtttg ccggatcaag agctaccaac tctttttccg aaggtaactg    3780
gcttcagcag agcgcagata ccaaatactg ttcttctagt gtagccgtag ttagcccacc    3840
acttcaagaa ctctgtagca ccgcctacat acctcgctct gctaatcctg ttaccagtgg    3900
ctgctgccag tggcgataag tcgtgtctta ccgggttgga ctcaagacga tagttaccgg    3960
ataaggcgca gcggtcgggc tgaacggggg gttcgtgcac acagcccagc ttggagcgaa    4020
cgacctacac cgaactgaga tacctacagc gtgagctatg agaaagcgcc acgcttcccg    4080
aagggagaaa ggcggacagg tatccggtaa gcggcagggt cggaacagga gagcgcacga    4140
gggagcttcc agggggaaac gcctggtatc tttatagtcc tgtcgggttt cgccacctcg    4200
acttgagcgt cgatttttgt gatgctcgtc aggggggcgg agcctatgga aaaacgccag    4260
caacgcggcc ttttacggtt cctggccctt tgctggcctt ttgctcaca tgttctttcc     4320
tgcgttatcc cctgattctg tggataaccg tattaccgcc tttgagtgag ctgataccgc    4380
tcgccgcagc cgaacgaccg agcgcagcga gtcagtgagc                           4420
```

<210> SEQ ID NO 41
<211> LENGTH: 29
<212> TYPE: DNA
<213> ORGANISM: Artificial Sequence
<220> FEATURE:
<223> OTHER INFORMATION: Syn thetic Nucleotide

<400> SEQUENCE: 41 gggacaagt ttgtacaaaa aagcaggct                                        29

<210> SEQ ID NO 42
<211> LENGTH: 29
<212> TYPE: DNA
<213> ORGANISM: Artificial Sequence
<220> FEATURE:
<223> OTHER INFORMATION: Synthetic Nucleotide

<400> SEQUENCE: 42
acccagcttt cttgtacaaa gtggtcccc                                       29

<210> SEQ ID NO 43
<211> LENGTH: 2899
<212> TYPE: DNA
<213> ORGANISM: Artificial Sequence
<220> FEATURE:
<223> OTHER INFORMATION: Vector

<400> SEQUENCE: 43

| | | |
|---|---|---|
| gaggaagcgg aaggcgagag tagggaactg ccaggcatca aactaagcag aaggcccctg | 60 |
| acggatggcc ttttttgcgtt tctacaaact ctttctgtgt tgtaaaacga cggccagtct | 120 |
| taagctcggg cctcaaataa tgattttaga ttaacggtct ccttttctcg agcggataaa | 180 |
| tgtgagcgga taacattgac attgtgagcg ataacaaga tactgagcac atcagcagga | 240 |
| cgcactgacc gcgggatccc ggtgcagaaa ataaggagga aaaaaaatg agcaaaggtg | 300 |
| aagaactgtt caccggcgtt gtgccaattc tggttgagct ggatggtgac gtgaatggcc | 360 |
| acaaattttc cgtgtctggt gaaggcgagg gtgatgctac ttatggcaaa ctgactctga | 420 |
| aactgatctg taccaccggc aaactgcctg ttccgtggcc aactctggtc actactctgg | 480 |
| gttacggcct gatgtgtttt gcgcgttacc cggatcacat gaaacagcat gacttcttca | 540 |
| aatctgccat gccggaaggc tatgtccaag aacgtacgat cttttttcaag gacgacggca | 600 |
| actataaaac ccgtgccgaa gttaaattcg agggtgacac cctggttaac cgcatcgaac | 660 |
| tgaaaggcat tgacttcaaa gaggacggca acattctggg tcacaagctg gaatacaact | 720 |
| acaactccca caacgtttac attactgctg acaagcagaa aaacggcatc aaagcaaact | 780 |
| tcaagatccg tcacaacatt gaagatggtg gcgtacagct ggcagatcac taccagcaga | 840 |
| acactccaat cggtgatggc ccagtactgc tgccagataa ccattacctg tcctaccaga | 900 |
| gcaaactgtc taaagacccg aacgaaaaac gtgaccacat ggtactgctg gaatttgtta | 960 |
| ccgcggcagg cattacccac ggtatggacg aactgtataa ataaccccag agaccgttaa | 1020 |
| tcgccatcca gctgatattc cctatagtgc atggtcatag ctgtttcctg gcagctctgg | 1080 |
| cccgtgtctc aaaatctctg atgttacatt gtacaagata aaataatatc atcatgaaca | 1140 |
| ataaaactgt ctgcttacat aaacagtaat acaaggggtg ttatgagcca tattcaacgg | 1200 |
| gaaacgtcga ggccgcgatt aaattccaac atggatgctg atttatatgg gtataaatgg | 1260 |
| gctcgcgata atgtcgggca atcaggtgcg acaatctatc gcttgtatgg gaagcccgat | 1320 |
| gcgccagagt tgtttctgaa acatggcaaa ggtagcgttg ccaatgatgt tacagatgag | 1380 |
| atggtcagac taaactggct gacggaattt atgccacttc cgaccatcaa gcattttatc | 1440 |
| cgtactcctg atgatgcatg gttactcacc actgcgatcc ccggaaaaac agcgttccag | 1500 |
| gtattagaag aatatcctga ttcaggtgaa aatattgttg atgcgctggc agtgttcctg | 1560 |

```
cgccggttgc actcgattcc tgtttgtaat tgtccttta acagcgatcg cgtatttcgc   1620
ctcgctcagg cgcaatcacg aatgaataac ggtttggttg atgcgagtga ttttgatgac   1680
gagcgtaatg ctggcctgt tgaacaagtc tggaaagaaa tgcataaact tttgccattc   1740
tcaccggatt cagtcgtcac tcatggtgat ttctcacttg ataaccttat ttttgacgag   1800
gggaaattaa taggttgtat tgatgttgga cgagtcggaa tcgcagaccg ataccaggat   1860
cttgccatcc tatggaactg cctcggtgag ttttctcctt cattacagaa acggctttt    1920 caaaaatatg gtattgataa tcctgatatg aataaattgc agtttcattt gatgctcgat   1980 gagttttct aatcagaatt ggttaattgg ttgtaacact ggcagagcat acgctgact    2040 tgacgggacg gcgcaagctc atgaccaaaa tcccttaacg tgagttacgc gcgcgtcgtt   2100
ccactgagcg tcagacccg tagaaaagat caaaggatct tcttgagatc ctttttttct   2160
gcgcgtaatc tgctgcttgc aaacaaaaaa accaccgcta ccagcggtgg tttgtttgcc   2220
ggatcaagag ctaccaactc tttttccgaa ggtaactggc ttcagcagag cgcagatacc   2280
aaatactgtt cttctagtgt agccgtagtt agcccaccac ttcaagaact ctgtagcacc   2340
gcctacatac ctcgctctgc taatcctgtt accagtggct gctgccagtg gcgataagtc   2400
gtgtcttacc gggttggact caagacgata gttaccggat aaggcgcagc ggtcgggctg   2460 aacgggggt tcgtgcacac agcccagctt ggagcgaacg acctacaccg aactgagata   2520
cctacagcgt gagctatgag aaagcgccac gcttcccgaa gggagaaagg cggacaggta   2580
tccggtaagc ggcagggtcg aacaggaga gcgcacgagg gagcttccag ggggaaacgc   2640
ctggtatctt tatagtcctg tcgggtttcg ccacctctga cttgagcgtc gattttgtg    2700 atgctcgtca gggggggcgga gcctatggaa aaacgccagc aacgcggcct ttttacggtt   2760
cctggccttt tgctggcctt tgctcacat gttctttcct gcgttatccc ctgattctgt    2820
ggataaccgt attaccgcct ttgagtgagc tgataccgct cgccgcagcc gaacgaccga   2880
gcgcagcgag tcagtgagc                                               2899
```

<210> SEQ ID NO 44
<211> LENGTH: 39
<212> TYPE: DNA
<213> ORGANISM: Artificial Sequence
<220> FEATURE:
<223> OTHER INFORMATION: Synthetic Nucleotide
<220> FEATURE:
<221> NAME/KEY: misc_feature
<222> LOCATION: 15, 16, 17, 18, 19, 20, 21, 22, 23, 24, 25
<223> OTHER INFORMATION: n = A,T,C or G

<400> SEQUENCE: 44

```
aacggtctcc ttttnnnnnn nnnnnccca gagaccgtt                            39
```

<210> SEQ ID NO 45
<211> LENGTH: 11
<212> TYPE: DNA
<213> ORGANISM: Artificial Sequence
<220> FEATURE:
<223> OTHER INFORMATION: Oligonucleotide

<400> SEQUENCE: 45

```
ggtctccttt t                                                         11
```

<210> SEQ ID NO 46
<211> LENGTH: 11
<212> TYPE: DNA
<213> ORGANISM: Artificial Sequence -continued

```
<220> FEATURE:
<223> OTHER INFORMATION: Oligonucleotide

<400> SEQUENCE: 46 cccagagac c                                                          11

<210> SEQ ID NO 47
<211> LENGTH: 1556
<212> TYPE: DNA
<213> ORGANISM: Artificial Sequence
<220> FEATURE:
<223> OTHER INFORMATION: Vector

<400> SEQUENCE: 47
atgatcgagc agctgctgga atactggtac gtggttgtgc ctgttctgta tattatcaaa      60
cagctgctgg cgtacactaa aacgcgtgtc ctgatgaaga aactgggcgc agcgccggtg     120
actaacaaac tgtacgataa cgctttcggc atcgtaaatg gttggaaagc cctgcagttt     180
aagaaagagg gtcgtgcgca agaatataac gactataaat tcgatcattc taagaacccg     240
agcgtgggta cttatgtgtc tatcctgttc ggtactcgca tcgtggtaac taagacccca     300
gaaaacatca agcaatcct ggcgacgcaa ttcggcgact tctctctggg taaacgtcac     360
acgctgttca aacctctgct gggcgatggc attttcaccc tggatggtga aggttggaaa     420
cattcccgtg cgatgctgcg tccgcagttt gcgcgtgaac aggttgcgca cgttacgtct     480
ctggagccgc acttccagct gctgaagaaa catatcctga acacaaagg cgagtatttc     540 gatatccagg agctgttctt ccgtttcacc gtagattccg ctaccgaatt tctgttcggt     600
gaatctgttc atagcctgaa agatgaaagc atcggcatca accaggatga catcgacttc     660
gctggtcgca aggatttcgc agaatccttc aataaagctc aggaatatct ggcgatccgt     720
actctggtgc aaacttttcta ttggctggtt aacaataaag agtttcgcga ctgtaccaaa     780
tccgttcata aattcactaa ctactacgtt cagaaagctc tggatgcatc cccggaagaa     840
ctggaaaagc agtccggtta cgttttcctg tacgaactgg tgaaacagac tcgtgacccg     900
aacgtcctgc gtgaccagtc tctgaacatc ctgctggccg gccgtgacac taccgctggc     960
ctgctgtcct tcgcggtctt cgagctggcc cgtcatccgg aaatctgggc caaactgcgt    1020
gaagaaatcg aacagcaatt cggcctgggt gaggactccc gtgttgaaga aatcactttc    1080
gaatctctga acgttgcga atatctgaaa gcattcctga cgaaacgct gcgtatctac     1140 ccgtccgttc cgcgcaactt ccgcattgct accaagaaca cgaccctgcc gcgtggcggt    1200
ggcagcgacg gcacctctcc gatcctgatt caaaagggtg aagcagtatc ctacggtatt    1260
aactccaccc acctggaccg gtatactacg gtccggacgc ggcagaattt cgtccagagc    1320
gctggtttga accgtctacc aagaagctgg gttgggctta tctgccgttc aacggcggcc    1380
ctcgtatctg tctgggtcag cagtttgccc tgaccgaggc aggctacgtt ctggttcgcc    1440
tggtccaaga atttctctcac gtacgtagcg acccggacga agtttacccg ccgaagcgcc    1500
tgaccaacct gactatgtgc ctgcaagatg gcgctatcgt caaatttgat taataa        1556

<210> SEQ ID NO 48
<211> LENGTH: 1557
<212> TYPE: DNA
<213> ORGANISM: Artificial Sequence
<220> FEATURE:
<223> OTHER INFORMATION: Vector

<400> SEQUENCE: 48
```

| | |
|---|---:|
| atgatcgaac aactgctgga atactggtac gtggttgtgc ctgttctgta tattatcaaa | 60 |
| cagctgctgg cgtacactaa aacgcgtgtc ctgatgaaga aactgggcgc agcgccggtg | 120 |
| actaacaaac tgtacgataa cgctttcggc atcgtaaatg gttggaaagc cctgcagttt | 180 |
| aagaaagagg gtcgtgcgca agaatataac gactataaat tcgatcattc taagaacccg | 240 |
| agcgtgggta cttatgtgtc tatcctgttc ggtactcgca tcgtggtaac taagacccca | 300 |
| gaaaacatca aagcaatcct ggcgacgcaa ttcggcgact ctctctctggg taaacgtcac | 360 |
| acgctgttca aacctctgct gggcgatggc attttcaccc tggatggtga aggttggaaa | 420 |
| cattcccgtg cgatgctgcg tccgcagttt gcgcgtgaac aggttgcgca cgttacgtct | 480 |
| ctggagccgc acttccagct gctgaagaaa catatcctga acacaaagg cgagtatttc | 540 |
| gatatccagg agctgttctt ccgtttcacc gtagattccg ctaccgaatt tctgttcggt | 600 |
| gaatctgttc atagcctgaa agatgaaagc atcggcatca accaggatga catcgacttc | 660 |
| gctggtcgca aggatttcgc agaatccttc aataaagctc aggaatatct ggcgatccgt | 720 |
| actctggtgc aaacttttcta ttggctggtt aacaataaag agtttcgcga ctgtaccaaa | 780 |
| tccgttcata aattcactaa ctactacgtt cagaaagctc tggatgcatc cccggaagaa | 840 |
| ctggaaaagc agtccggtta cgttttcctg tacgaactgg tgaaacagac tcgtgacccg | 900 |
| aacgtcctgc gtgaccagtc tctgaacatc ctgctggccg ccgtgacac taccgctggc | 960 |
| ctgctgtcct tcgcggtctt cgagctggcc cgtcatccgg aaatctgggc caaactgcgt | 1020 |
| gaagaaatcg aacagcaatt cggcctgggt gaggactccc gtgttgaaga aatcactttc | 1080 |
| gaatctctga acgttgcga atatctgaaa gcattcctga cgaaacgct gcgtatctac | 1140 |
| ccgtccgttc cgcgcaactt ccgcattgct accaagaaca cgaccctgcc gcgtggcggt | 1200 |
| ggcagcgacg gcacctctcc gatcctgatt caaaagggtg aagcagtatc ctacggtatt | 1260 |
| aactccaccc acctggaccc ggtatactac ggtccggacg cggcagaatt tcgtccagag | 1320 |
| cgctggtttg aaccgtctac caagaagctg ggttgggctt atctgccgtt caacggcggc | 1380 |
| cctcgtatct gtctgggtca gcagtttgcc ctgaccgagg caggctacgt tctggttcgc | 1440 |
| ctggtccaag aattttctca cgtacgtagc gacccggacg aagtttaccc gccgaagcgc | 1500 |
| ctgaccaacc tgactatgtg cctgcaagat ggcgctatcg tcaaatttga ttaataa | 1557 |

<210> SEQ ID NO 49
<211> LENGTH: 1574
<212> TYPE: DNA
<213> ORGANISM: Artificial Sequence
<220> FEATURE:
<223> OTHER INFORMATION: Polynucleotide

<400> SEQUENCE: 49

| | |
|---|---:|
| tgctggggaa aagtaaacac acacaggcgc actcgagaac agatgagttc tttggacgag | 60 |
| gatgaagagg acttcgaaat gctggacacg gagaacctcc agtttatggg gaagaagatg | 120 |
| tttggcaaac aggccggcga agacgagagt gatgattttg ctataggggg tagcaccccg | 180 |
| accaataaac tgaaatttta tccatatgcg aacaacaaat tgacaagagc tacggggacc | 240 |
| ttgaacctgt cattaagtaa tgcagctttg tcagaggcta actccaaatt tcttgggaaa | 300 |
| attgaagaag aggaagaaga ggaggaagaa ggcaaggatg aggaaagcgt ggatgctcgt | 360 |
| attaaaaggt ggtctccgtt ccatgaaaat gaaagtgtta ctactcctat tgcaaaagaa | 420 |
| gctgcgaaaa aaacgaacag tcctattgct ctcaaacaat ggaaccagcg atggtttccg | 480 |
| aaaaatgatg ctcgcactga aaatacatcc tcatcctctt catatagcgt cgctaaacct | 540 |

```
aaccaatcag cctttacgtc ttcgggcctc gtatctaaaa tgtctatgga cacttcgtta    600
taccctgcga aattgaggat accagaaaca ccagtgaaaa atcacccctt agtggaggga    660
agagaccata agcatgtcca cctttcgagt tcgaaaaatg catcgtcttc tctaagtgtt    720 tccccttttaa atttttgttga agacaataat ttacaagaag acctttttatt ttcagattct   780 ccgtcttcga aagctttacc ttccatccat gtaccaacca tagacgcatc cccactgagc    840
gaggcaaaat atcatgcaca tgatcgtcac aataaccaga caaacatcct gtctcccact    900
aatagcttgg ttaccaacag ctctccacaa acattgcatt ctaacaagtt caaaaaaatc    960
aaaagagcaa ggaattcggt tattttgaaa aatagagagc taacaaacag tttacaacaa    1020
ttcaaagatg atttatacgg cacggacgag aatttcccac ctccaatcat aatatcaagt    1080
catcattcaa ctagaaagaa ccctcaacct tatcaatttc gtggacgcta tgacaatgac    1140
gctgacgaag agatctccac tccaacaaga cgaaaatcta ttattggggc agcatctcaa    1200
acacatagaa aaagcagacc attgtcactc tcctctgcca tcgtgacaaa cacaacaagt    1260
gcagagacgc attccatatc ttccaccgat tcttcgccgt taaattccaa aaggcgtcta    1320
atctcttcaa ataagttatc agcaaatcca gattcccatc ttttcgaaaa atttacgaat    1380
gtgcattcca ttggtaaagg ccagttttcc acggtctacc aggttacgtt tgcccaaaca    1440
aacaaaaagt atgcaatcaa agccattaaa ccaaacaaat ataattcctt gaaacgcata    1500
ttactggaaa ttaaaatact aaacgaggta acaaaccaaa ttaccatgga tcaagaaggg    1560
aaggaataca tcat                                                     1574
```

<210> SEQ ID NO 50
<211> LENGTH: 17
<212> TYPE: DNA
<213> ORGANISM: Artificial Sequence
<220> FEATURE:
<223> OTHER INFORMATION: Oligonucleotide

<400> SEQUENCE: 50
gaagaagagg aagaaga                                                  17

<210> SEQ ID NO 51
<211> LENGTH: 17
<212> TYPE: DNA
<213> ORGANISM: Artificial Sequence
<220> FEATURE:
<223> OTHER INFORMATION: Oligonucleotide

<400> SEQUENCE: 51
gaagaagagg aggaaga                                                  17

<210> SEQ ID NO 52
<211> LENGTH: 16
<212> TYPE: DNA
<213> ORGANISM: Artificial Sequence
<220> FEATURE:
<223> OTHER INFORMATION: Oligonucleotide

<400> SEQUENCE: 52
gaagaggagg aagaag                                                   16

<210> SEQ ID NO 53
<211> LENGTH: 369
<212> TYPE: PRT
<213> ORGANISM: Artificial Sequence
<220> FEATURE:

<223> OTHER INFORMATION: Proteinase K

<400> SEQUENCE: 53

```
Ala Pro Ala Val Glu Gln Arg Ser Glu Ala Ala Pro Leu Ile Glu Ala
 1               5                  10                  15
Arg Gly Glu Met Val Ala Asn Lys Tyr Ile Val Lys Phe Lys Glu Gly
             20                  25                  30
Ser Ala Leu Ser Ala Leu Asp Ala Ala Met Glu Lys Ile Ser Gly Lys
         35                  40                  45
Pro Asp His Val Tyr Lys Asn Val Phe Ser Gly Phe Ala Ala Thr Leu
     50                  55                  60
Asp Glu Asn Met Val Arg Val Leu Arg Ala His Pro Asp Val Glu Tyr
 65                  70                  75                  80
Ile Glu Gln Asp Ala Val Val Thr Ile Asn Ala Ala Gln Thr Asn Ala
                 85                  90                  95
Pro Trp Gly Leu Ala Arg Ile Ser Ser Thr Ser Pro Gly Thr Ser Thr
            100                 105                 110
Tyr Tyr Tyr Asp Glu Ser Ala Gly Gln Gly Ser Cys Val Tyr Val Ile
        115                 120                 125
Asp Thr Gly Ile Glu Ala Ser His Pro Glu Phe Glu Gly Arg Ala Gln
130                 135                 140
Met Val Lys Thr Tyr Tyr Tyr Ser Ser Arg Asp Gly Asn Gly His Gly
145                 150                 155                 160
Thr His Cys Ala Gly Thr Val Gly Ser Arg Thr Tyr Gly Val Ala Lys
                165                 170                 175
Lys Thr Gln Leu Phe Gly Val Lys Val Leu Asp Asp Asn Gly Ser Gly
            180                 185                 190
Gln Tyr Ser Thr Ile Ile Ala Gly Met Asp Phe Val Ala Ser Asp Lys
        195                 200                 205
Asn Asn Arg Asn Cys Pro Lys Gly Val Val Ala Ser Leu Ser Leu Gly
    210                 215                 220
Gly Gly Tyr Ser Ser Ser Val Asn Ser Ala Ala Ala Arg Leu Gln Ser
225                 230                 235                 240
Ser Gly Val Met Val Ala Val Ala Ala Gly Asn Asn Asn Ala Asp Ala
                245                 250                 255
Arg Asn Tyr Ser Pro Ala Ser Glu Pro Ser Val Cys Thr Val Gly Ala
            260                 265                 270
Ser Asp Arg Tyr Asp Arg Arg Ser Ser Phe Ser Asn Tyr Gly Ser Val
        275                 280                 285
Leu Asp Ile Phe Gly Pro Gly Thr Ser Ile Leu Ser Thr Trp Ile Gly
    290                 295                 300
Gly Ser Thr Arg Ser Ile Ser Gly Thr Ser Met Ala Thr Pro His Val
305                 310                 315                 320
Ala Gly Leu Ala Ala Tyr Leu Met Thr Leu Gly Lys Thr Thr Ala Ala
                325                 330                 335
Ser Ala Cys Arg Tyr Ile Ala Asp Thr Ala Asn Lys Gly Asp Leu Ser
            340                 345                 350
Asn Ile Pro Phe Gly Thr Val Asn Leu Leu Ala Tyr Asn Asn Tyr Gln
        355                 360                 365
Ala
```

<210> SEQ ID NO 54
<211> LENGTH: 1107
<212> TYPE: DNA

<213> ORGANISM: Artificial Sequence
<220> FEATURE:
<223> OTHER INFORMATION: Coding for Proteinase K

<400> SEQUENCE: 54

```
gctccggcag ttgaacagcg ttctgaagcg gcgccgctga tcgaggcgcg tggtgagatg    60
gttgctaaca atacattgt gaaattcaag gagggctctg ctctgtctgc actggacgcc   120
gcaatggaaa agatcagcgg caagccggac cacgtgtaca aaaacgtgtt ttccggtttc   180
gccgctactc tggatgaaaa tatggttcgt gttctgcgtg cgcacccgga tgtagaatat   240
atcgaacagg atgcagtcgt aaccatcaat gctgctcaga ccaatgcgcc gtggggtctg   300
gcacgtattt cttctacctc cccgggtacc agcacctatt attacgacga aagcgccggc   360
cagggctctt gcgtttacgt tattgacacc ggcatcgaag cttctcatcc agaattcgag   420
ggtcgtgcgc agatggtgaa aacctactac tactcctctc gcgatggcaa cggtcatggc   480
acgcattgcg caggcacggt aggctcccgt acgtacggtg ttgcaaaaaa aacccagctg   540
ttcggcgtta aagtgctgga cgataacggt tctggtcagt actccaccat catcgcaggt   600
atggacttcg tagcgtccga caaaaacaac cgtaactgtc cgaaaggcgt cgttgcgagc   660
ctgagcctgg gtggtggcta ttcttcctcc gtgaactctg gcggcccg cctgcagagc   720
tctggtgtaa tggttgcagt agccgcaggc aacaacaacg ctgatgcacg taactactct   780
ccggcttccg aaccatctgt gtgtaccgtg ggtgcatccg atcgttacga ccgccgtagc   840
tcttttttcta actacggctc cgtgctggac attttcggcc cgggtacttc tattctgtct   900
acttggatcg gcggttctac ccgcagcatc agcggtactt ctatggcgac cccgcacgtg   960
gcaggcctgg cggcttatct gatgactctg ggtaaaacca ccgcggcgag cgcgtgtcgt  1020
tacatcgcgg atactgctaa caaaggtgac ctgtctaaca tccctttcgg taccgtcaac  1080
ctgctggcat acaacaacta ccaagcg                                      1107
```

<210> SEQ ID NO 55
<211> LENGTH: 12
<212> TYPE: DNA
<213> ORGANISM: Artificial Sequence
<220> FEATURE:
<223> OTHER INFORMATION: Nucleotide

<400> SEQUENCE: 55

```
agcggcgccg ct                                                         12
```

<210> SEQ ID NO 56
<211> LENGTH: 12
<212> TYPE: DNA
<213> ORGANISM: Artificial Sequence
<220> FEATURE:
<223> OTHER INFORMATION: Nucleotide

<400> SEQUENCE: 56

```
ccgtacgtac gg                                                         12
```

<210> SEQ ID NO 57
<211> LENGTH: 1107
<212> TYPE: DNA
<213> ORGANISM: Artificial Sequence
<220> FEATURE:
<223> OTHER INFORMATION: Coding for Proteinase K

<400> SEQUENCE: 57

```
gctccagcgg ttgaacagcg cagcgaggcc gcaccgctga tcgaagcccg tggtgaaatg    60
```

```
gtggcaaaca aatacattgt caagttcaaa gaaggttccg cgctgagcgc tctggatgct      120
gcaatggaaa aaatctccgg taaaccggac cacgtatata aaaatgtctt ttctggcttc      180
gcggctactc tggatgagaa catggttcgt gtgctgcgtg cgcatccgga tgttgaatac      240
attgaacagg acgcagttgt aacgattaac gctgcccaaa ctaacgcgcc atggggcctg      300
gcccgcatta gctccacctc cccaggtact ccacttatt  actacgacga atccgcaggt      360
cagggttcct gcgtatatgt tatcgacacc ggtatcgaag cgtcccaccc ggaatttgag      420
ggtcgtgcgc aaatggtgaa gacctactac tactcttccc gtgacggtaa cggtcacggt      480
acccactgtg cgggtactgt aggtagccgt acctatggtg ttgccaaaaa aacccagctg      540
tttggcgtta aagtgctgga tgataatggc tccggtcagt actccaccat catcgctggc      600
atggactttg tcgcaagcga caaaaacaac cgcaactgcc cgaaaggtgt tgtggcttct      660
ctgtccctgg gtggtggcta tagctcctct gtgaactctg cggcagcgcg tctgcaatcc      720
tccggcgtga tggtcgcggt tgccgcaggt aacaacaacg cggatgcgcg caactactct      780
cctgcatccg aaccgtccgt ttgtactgtt ggtgcgtctg accgttacga ccgtcgttct      840
tctttctcca actacggttc tgtactggac atcttcggtc ctggcacctc catcctgtct      900
acgtggattg gcggtagcac ccgtagcatc tctggtacta gcatggctac cccgcacgta      960
gcaggcctgg cggcatatct gatgacgctg ggcaagacta ccgcggctag cgcttgccgt     1020
tacatcgcgg ataccgcgaa caaaggcgac ctgtctaaca tcccgttcgg caccgtgaac     1080
ctgctggcat acaacaacta tcaggcg                                         1107
```

<210> SEQ ID NO 58  
<211> LENGTH: 18  
<212> TYPE: DNA  
<213> ORGANISM: Artificial Sequence  
<220> FEATURE:  
<223> OTHER INFORMATION: RNA Stem Loop Structure

<400> SEQUENCE: 58

```
tttgtcgcaa gcgacaaa                                                     18
```

<210> SEQ ID NO 59  
<211> LENGTH: 1107  
<212> TYPE: DNA  
<213> ORGANISM: Artificial Sequence  
<220> FEATURE:  
<223> OTHER INFORMATION: Polynucleotide

<400> SEQUENCE: 59

```
gcgccggcag tagaacagcg ttctgaagca gcaccgctga tcgaagctcg cggcgaaatg       60
gtagcgaaca aatatattgt aaaattcaaa gaaggctctg cactgtctgc gctggatgct      120
gcgatggaga aaatctctgg taaaccggat cacgtataca agaacgtttt ttctggcttc      180
gctgcaacgc tggatgaaaa catggtgcgt gtactgcgtg cgcacccgga tgtggagtac      240
atcgaacagg acgcagttgt gaccatcaac gcggcgcaga ctaacgctcc gtggggcctg      300
gctcgcatct cttccacctc cccgggcact ccacctact  actatgatga gtctgctggt      360
cagggtagct gtgtttacgt tatcgatacg ggcatcgaag cttcccaccc ggaattcgaa      420
ggccgtgcgc agatggtgaa aacctattac tattcttctc gtgatggcaa tggccacggc      480
acccactgcg ccggcaccgt tggttctcgc acctacggtg tggcaaagaa aacccagctg      540
ttcggtgtga aggttctgga cgataacggt tccggccagt actccactat catcgccggc      600
```

```
atggacttcg ttgcctccga caaaaataac cgtaattgcc cgaaaggtgt tgttgcttcc    660
ctgagcctgg gtggcggtta ttccagctct gtgaactctg cagccgctcg cctgcagtcc    720
tctggcgtta tggtagccgt cgcggctggt aacaacaacg cggatgcacg caattactcc    780
ccggcctccg aaccttctgt ctgtaccgtt ggcgctagcg accgttatga tcgtcgctct    840
agcttctcta actatggttc cgtactggat atcttcggcc cgggtacctc tattctgtcc    900
acttggattg cggctctac ccgctctatc tccggtacct ctatggccac gccgcatgtc    960
gcaggcctgg cagcttacct gatgactctg ggtaaaacta ccgcggcctc cgcttgccgc   1020
tacattgccg acactgctaa caaaggcgac ctgagcaaca ttccattcgg caccgttaac   1080
ctgctggcct acaacaatta ccaggca                                        1107
```

<210> SEQ ID NO 60
<211> LENGTH: 419
<212> TYPE: PRT
<213> ORGANISM: Artificial Sequence
<220> FEATURE:
<223> OTHER INFORMATION: Polypeptide

<400> SEQUENCE: 60

```
Met Ala Gln His Asp Glu Ala Gln Gln Asn Ala Phe Tyr Gln Val Leu
 1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro Lys Ala Asp Ala Gln Asn Asn Phe
    50                  55                  60

Asn Lys Asp Gln Gln Ser Ala Phe Tyr Glu Ile Leu Asn Met Pro Asn
 65                  70                  75                  80

Leu Asn Glu Ala Gln Arg Asn Gly Phe Ile Gln Ser Leu Lys Asp Asp
                85                  90                  95

Pro Ser Gln Ser Thr Asn Val Leu Gly Glu Ala Lys Lys Leu Asn Glu
           100                 105                 110

Ser Gln Ala Pro Lys Asp Asn Asn Phe Asn Lys Glu Gln Gln Asn Ala
       115                 120                 125

Phe Tyr Glu Ile Leu Asn Met Pro Asn Leu Asn Glu Glu Gln Arg Asn
   130                 135                 140

Gly Phe Ile Gln Ser Leu Lys Asp Asp Pro Ser Gln Ser Ala Asn Leu
145                 150                 155                 160

Leu Ser Glu Ala Lys Lys Leu Asn Glu Ser Gln Ala Pro Lys Asp Asn
               165                 170                 175

Lys Phe Asn Lys Glu Gln Gln Asn Ala Phe Tyr Glu Ile Leu His Leu
           180                 185                 190

Pro Asn Leu Asn Glu Glu Gln Arg Asn Gly Phe Ile Gln Ser Leu Lys
       195                 200                 205

Asp Asp Pro Ser Gln Ser Ala Asn Leu Leu Ala Glu Ala Lys Lys Leu
   210                 215                 220

Asn Asp Ala Gln Ala Pro Lys Asp Asn Lys Phe Asn Lys Glu Gln Gln
225                 230                 235                 240

Asn Ala Phe Tyr Glu Ile Leu His Leu Pro Asn Leu Thr Glu Glu Gln
               245                 250                 255

Arg Asn Gly Phe Ile Gln Ser Leu Lys Asp Asp Pro Ser Val Ser Lys
           260                 265                 270
```

```
Glu Ile Leu Ala Glu Ala Lys Lys Leu Asn Asp Ala Gln Ala Pro Lys
            275                 280                 285

Glu Glu Asp Asn Asn Lys Pro Gly Lys Glu Asp Asn Asn Lys Pro Gly
        290                 295                 300

Lys Glu Asp Asn Asn Lys Pro Gly Lys Glu Asp Asn Asn Lys Pro Gly
305                 310                 315                 320

Lys Glu Asp Asn Asn Lys Pro Gly Lys Glu Asp Asn Asn Lys Pro Gly
            325                 330                 335

Lys Glu Asp Gly Asn Lys Pro Gly Lys Glu Asp Asn Lys Lys Pro Gly
            340                 345                 350

Lys Glu Asp Gly Asn Lys Pro Gly Lys Glu Asp Asn Lys Lys Pro Gly
            355                 360                 365

Lys Glu Asp Gly Asn Lys Pro Gly Lys Glu Asp Gly Asn Lys Pro Gly
            370                 375                 380

Lys Glu Asp Gly Asn Gly Val His Val Val Lys Pro Gly Asp Thr Val
385                 390                 395                 400

Asn Asp Ile Ala Lys Ala Asn Gly Thr Thr Ala Asp Lys Ile Ala Ala
            405                 410                 415

Asp Asn Lys

<210> SEQ ID NO 61
<211> LENGTH: 175
<212> TYPE: PRT
<213> ORGANISM: Artificial Sequence
<220> FEATURE:
<223> OTHER INFORMATION: Polypeptide

<400> SEQUENCE: 61

Met Ala Gln His Asp Glu Ala Gln Gln Asn Ala Phe Tyr Gln Val Leu
  1               5                  10                  15

Asn Met Pro Asn Leu Asn Ala Asp Gln Arg Asn Gly Phe Ile Gln Ser
                 20                  25                  30

Leu Lys Asp Asp Pro Ser Gln Ser Ala Asn Val Leu Gly Glu Ala Gln
             35                  40                  45

Lys Leu Asn Asp Ser Gln Ala Pro Lys Ala Asp Ala Gln Asn Asn Phe
 50                  55                  60

Asn Lys Asp Gln Gln Ser Ala Phe Tyr Glu Ile Leu Asn Met Pro Asn
 65                  70                  75                  80

Leu Asn Glu Ala Gln Arg Asn Gly Phe Ile Gln Ser Leu Lys Asp Asp
                 85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
            115                 120                 125

Ala Phe Tyr Glu Ile Leu Asn Met Pro Asn Leu Asn Glu Glu Gln Arg
            130                 135                 140

Asn Gly Phe Ile Gln Ser Leu Lys Asp Asp Pro Ser Gln Ser Ala Asn
145                 150                 155                 160

Leu Leu Ser Glu Ala Lys Lys Leu Asn Glu Ser Gln Ala Pro Lys
                165                 170                 175

<210> SEQ ID NO 62
<211> LENGTH: 136
<212> TYPE: PRT
<213> ORGANISM: Artificial Sequence
<220> FEATURE:
<223> OTHER INFORMATION: Polypeptide
```

<400> SEQUENCE: 62

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Asp Asn Lys Phe Asn Lys
50                  55                  60

Glu Gln Gln Asn Ala Phe Tyr Glu Ile Leu His Leu Pro Asn Leu Thr
65                  70                  75                  80

Glu Glu Gln Arg Asn Gly Phe Ile Gln Ser Leu Lys Asp Asp Pro Ser
                85                  90                  95

Val Ser Lys Glu Ile Leu Ala Glu Ala Lys Lys Leu Asn Asp Ala Gln
            100                 105                 110

Ala Pro Lys Glu Glu Asp Asn Asn Lys Pro Gly Lys Glu Asp Asn Asn
        115                 120                 125

Lys Pro Gly Lys Glu Asp Asn Asn
    130                 135

<210> SEQ ID NO 63
<211> LENGTH: 110
<212> TYPE: PRT
<213> ORGANISM: Artificial Sequence
<220> FEATURE:
<223> OTHER INFORMATION: Oligonucleotide

<400> SEQUENCE: 63

Lys Pro Gly Lys Glu Asp Asn Asn Lys Pro Gly Lys Glu Asp Asn Asn
1               5                   10                  15

Lys Pro Gly Lys Glu Asp Asn Asn Lys Pro Gly Lys Glu Asp Gly Asn
            20                  25                  30

Lys Pro Gly Lys Glu Asp Asn Lys Pro Gly Lys Glu Asp Gly Asn
        35                  40                  45

Lys Pro Gly Lys Glu Asp Asn Lys Pro Gly Lys Glu Asp Gly Asn
50                  55                  60

Lys Pro Gly Lys Glu Asp Gly Asn Lys Pro Gly Lys Glu Asp Gly Asn
65                  70                  75                  80

Gly Val His Val Val Lys Pro Gly Asp Thr Val Asn Asp Ile Ala Lys
                85                  90                  95

Ala Asn Gly Thr Thr Ala Asp Lys Ile Ala Ala Asp Asn Lys
            100                 105                 110

<210> SEQ ID NO 64
<211> LENGTH: 548
<212> TYPE: DNA
<213> ORGANISM: Artificial Sequence
<220> FEATURE:
<223> OTHER INFORMATION: Vector

<400> SEQUENCE: 64 ggtacccgg taacgcgtat ggcgcaacat gacgaagctc agcagaacgc tttttaccag      60
gtactgaaca tgccgaacct gaacgcggat cagcgcaacg gtttcatcca gagcctgaaa    120 gacgacccctt tcagtccgc aaacgttctg gcgaggctc agaaactgaa cgacagccag    180
gccccaaaag cagatgctca gcaaaataac ttcaacaagg accagcagag cgcattctac    240

```
gaaatcctga acatgccaaa tctgaacgaa gctcaacgca acggcttcat tcagtctctg    300
aaagacgatc cgtcccagtc cactaacgtt ctgggtgaag ctaagaagct gaacgaatcc    360
caggcaccaa aagcagacaa caacttcaac aaagagcagc agaacgcttt ctatgaaatc    420
ttgaacatgc ctaacctgaa tgaagaacag cgtaacggct tcatccagtc tctgaaggac    480
gaccctagcc agtctgctaa cctgctgtcc gaagcaaaaa aactgaacga gtcccaggct    540
ccaaaagc                                                              548

<210> SEQ ID NO 65
<211> LENGTH: 407
<212> TYPE: DNA
<213> ORGANISM: Artificial Sequence
<220> FEATURE:
<223> OTHER INFORMATION: Synthetic Nucleotide

<400> SEQUENCE: 65
ggataacaaa ttcaacaagg agcagcagaa cgcattctac gaaatcctgc acctgccgaa     60
cctgaacgaa gaacagcgta acggtttcat ccaatccctg aaagacgatc cttcccagtc    120
cgcaaatctg ctggcagaag caaagaaact gaacgacgca caggcaccga aggctgacaa    180
caagttcaac aaagagcagc agaatgcctt ctacgagatt ctgcatctgc caaacctgac    240
tgaggagcag cgcaacggtt tcattcagtc cctgaaggac gacccaagcg tcagcaagga    300
aatcctggct gaggcgaaaa aactgaacga tgcacaggct ccgaaggaag aagacaacaa    360
taaacctggt aaagaagata taataagcc tggcaaggaa gataaca              407

<210> SEQ ID NO 66
<211> LENGTH: 363
<212> TYPE: DNA
<213> ORGANISM: Artificial Sequence
<220> FEATURE:
<223> OTHER INFORMATION: Synthetic Nucleotide

<400> SEQUENCE: 66
acaagccggg caaggaggac aacaataaac cggcaaagga ggataataac aagcctggta     60
aggaagacaa caacaaacca ggcaaagaag atggcaacaa gccgggtaag gaggataata    120 aaaaccagg caaggaagac ggcaacaaac ctggcaagga ggataacaaa aagccaggca    180
aggaggatgg taataaaccg ggcaaagaag acggcaacaa gcctggtaaa gaagacggta    240
acggtgtaca cgtcgttaaa cctggtgaca ccgtgaacga catcgctaag gctaatggca    300
ccacggcaga caagattgca gcggacaata aattagctga taaataagga tccgcggaag    360
ctt                                                                   363

<210> SEQ ID NO 67
<211> LENGTH: 29
<212> TYPE: DNA
<213> ORGANISM: Artificial Sequence
<220> FEATURE:
<223> OTHER INFORMATION: Oligonucleotide

<400> SEQUENCE: 67
ggggacaagt ttgtacaaaa aagcaggct                                       29

<210> SEQ ID NO 68
<211> LENGTH: 29
<212> TYPE: DNA
<213> ORGANISM: Artificial Sequence
<220> FEATURE:
<223> OTHER INFORMATION: Oligonucleotide
```

<400> SEQUENCE: 68
acccagcttt cttgtacaaa gtggtcccc                                    29

<210> SEQ ID NO 69
<211> LENGTH: 615
<212> TYPE: DNA
<213> ORGANISM: Artificial Sequence
<220> FEATURE:
<223> OTHER INFORMATION: Synthetic Polynucleotide

<400> SEQUENCE: 69
ggggacaagt tgtacaaaa aagcaggctg gtaccccggt aacgcgtatg gcgcaacatg      60
acgaagctca gcagaacgct ttttaccagg tactgaacat gccgaacctg aacgcggatc     120
agcgcaacgg tttcatccag agcctgaaag acgacccttc tcagtccgca aacgttctgg     180
gcgaggctca gaaactgaac gacagccagg ccccaaaagc agatgctcag caaaataact     240
tcaacaagga ccagcagagc gcattctacg aaatcctgaa catgccaaat ctgaacgaag     300
ctcaacgcaa cggcttcatt cagtctctga agacgatccc gtcccagtcc actaacgttc     360
tgggtgaagc taagaagctg aacgaatccc aggcaccaaa agcagacaac aacttcaaca     420
aagagcagca gaacgctttc tatgaaatct tgaacatgcc taacctgaat gaagaacagc     480
gtaacggctt catccagtct ctgaaggacg accctagcca gtctgctaac ctgctgtccg     540
aagcaaaaaa actgaacgag tcccaggctc aaaagcgga gagaccaccc agctttcttg     600
tacaaagtgg tcccc                                                   615

<210> SEQ ID NO 70
<211> LENGTH: 483
<212> TYPE: DNA
<213> ORGANISM: Artificial Sequence
<220> FEATURE:
<223> OTHER INFORMATION: Synthetic Polynucleotide

<400> SEQUENCE: 70
ggggacaagt tgtacaaaa aagcaggctg gtctcagcgg ataacaaatt caacaaggag      60
cagcagaacg cattctacga aatcctgcac ctgccgaacc tgaacgaaga cagcgtaac     120 ggtttcatcc aatccctgaa agacgatcct tcccagtccg caaatctgct ggcagaagca     180
aagaaactga cgacgcaca ggcaccgaag gctgacaaca gttcaacaa agagcagcag      240 aatgccttct acgagattct gcatctgcca aacctgactg aggagcagcg caacggtttc     300
attcagtccc tgaaggacga cccaagcgtc agcaaggaaa tcctggctga ggcgaaaaaa     360
ctgaacgatg cacaggctcc gaaggaagaa gacaacaata aacctggtaa agaagataat     420
aataagcctg gcaaggaaga taacaacaga gaccacccag ctttcttgta caaagtggtc     480
ccc                                                                483

<210> SEQ ID NO 71
<211> LENGTH: 430
<212> TYPE: DNA
<213> ORGANISM: Artificial Sequence
<220> FEATURE:
<223> OTHER INFORMATION: Synthetic Polynucleotide

<400> SEQUENCE: 71
ggggacaagt tgtacaaaa aagcaggctg gtctcacaac aagccgggca aggaggacaa      60
caataaaccg ggcaaagagg ataataacaa gcctggtaag gaagacaaca acaaaccagg     120

```
caaagaagat ggcaacaagc cgggtaagga ggataataaa aaaccaggca aggaagacgg      180
caacaaacct ggcaaggagg ataacaaaaa gccaggcaag gaggatggta ataaaccggg      240
caaagaagac ggcaacaagc ctggtaaaga agacggtaac ggtgtacacg tcgttaaacc      300
tggtgacacc gtgaacgaca tcgctaaggc taatggcacc acggcagaca agattgcagc      360
ggacaataaa ttagctgata ataaggatcg cgcggaagct tacccagctt tcttgtacaa      420
agtggtcccc                                                            430
```

```
<210> SEQ ID NO 72
<211> LENGTH: 43
<212> TYPE: DNA
<213> ORGANISM: Artificial Sequence
<220> FEATURE:
<223> OTHER INFORMATION: Oligonucleotide

<400> SEQUENCE: 72
ggggacaagt ttgtacaaaa aagcaggctg gtctcacaac aag                       43

<210> SEQ ID NO 73
<211> LENGTH: 49
<212> TYPE: DNA
<213> ORGANISM: Artificial Sequence
<220> FEATURE:
<223> OTHER INFORMATION: Oligonucleotide

<400> SEQUENCE: 73
gacaacaata aaccgggcaa agaggataat aacaagcctg gtaaggaag                 49

<210> SEQ ID NO 74
<211> LENGTH: 58
<212> TYPE: DNA
<213> ORGANISM: Artificial Sequence
<220> FEATURE:
<223> OTHER INFORMATION: Oligonucleotide

<400> SEQUENCE: 74
acaacaacaa accaggcaaa gaagatggca caagccggg taaggaggat aataaaaa        58

<210> SEQ ID NO 75
<211> LENGTH: 50
<212> TYPE: DNA
<213> ORGANISM: Artificial Sequence
<220> FEATURE:
<223> OTHER INFORMATION: Oligonucleotide

<400> SEQUENCE: 75
accaggcaag gaagacggca acaaacctgg caaggaggat aacaaaaagc                50

<210> SEQ ID NO 76
<211> LENGTH: 54
<212> TYPE: DNA
<213> ORGANISM: Artificial Sequence
<220> FEATURE:
<223> OTHER INFORMATION: Oligonucleotide

<400> SEQUENCE: 76
caggcaagga ggatggtaat aaaccgggca agaagacgg caacaagcct ggta            54

<210> SEQ ID NO 77
<211> LENGTH: 49
<212> TYPE: DNA
<213> ORGANISM: Artificial Sequence
<220> FEATURE:
<223> OTHER INFORMATION: Oligonucleotide
```

<400> SEQUENCE: 77
aagaagacgg taacggtgta cacgtcgtta aacctggtga caccgtgaa    49

<210> SEQ ID NO 78
<211> LENGTH: 60
<212> TYPE: DNA
<213> ORGANISM: Artificial Sequence
<220> FEATURE:
<223> OTHER INFORMATION: Oligonucleotide

<400> SEQUENCE: 78
cgacatcgct aaggctaatg gcaccacggc agacaagatt gcagcggaca ataaattagc    60

<210> SEQ ID NO 79
<211> LENGTH: 53
<212> TYPE: DNA
<213> ORGANISM: Artificial Sequence
<220> FEATURE:
<223> OTHER INFORMATION: Oligonucleotide

<400> SEQUENCE: 79
ataaataagg atccgcggaa gcttacccag ctttcttgta caaagtggtc ccc    53

<210> SEQ ID NO 80
<211> LENGTH: 60
<212> TYPE: DNA
<213> ORGANISM: Artificial Sequence
<220> FEATURE:
<223> OTHER INFORMATION: Oligonucleotide

<400> SEQUENCE: 80
tttgcccggt ttattgttgt cctccttgcc cggcttgttg tgagaccagc ctgcttttt    60

<210> SEQ ID NO 81
<211> LENGTH: 52
<212> TYPE: DNA
<213> ORGANISM: Artificial Sequence
<220> FEATURE:
<223> OTHER INFORMATION: Oligonucleotide

<400> SEQUENCE: 81
cttctttgcc tggtttgttg ttgtcttcct taccaggctt gttattatcc tc    52

<210> SEQ ID NO 82
<211> LENGTH: 61
<212> TYPE: DNA
<213> ORGANISM: Artificial Sequence
<220> FEATURE:
<223> OTHER INFORMATION: Oligonucleotide

<400> SEQUENCE: 82
ggtttgttgc cgtcttcctt gcctggtttt ttattatcct ccttacccgg cttgttgcca    60
t    61

<210> SEQ ID NO 83
<211> LENGTH: 41
<212> TYPE: DNA
<213> ORGANISM: Artificial Sequence
<220> FEATURE:
<223> OTHER INFORMATION: Oligonucleotide

<400> SEQUENCE: 83
taccatcctc cttgcctggc tttttgttat cctccttgcc a    41

<210> SEQ ID NO 84
<211> LENGTH: 57
<212> TYPE: DNA
<213> ORGANISM: Artificial Sequence
<220> FEATURE:
<223> OTHER INFORMATION: Oligonucleotide

<400> SEQUENCE: 84
gtacaccgtt accgtcttct ttaccaggct tgttgccgtc ttctttgccc ggtttat      57

<210> SEQ ID NO 85
<211> LENGTH: 55
<212> TYPE: DNA
<213> ORGANISM: Artificial Sequence
<220> FEATURE:
<223> OTHER INFORMATION: Oligonucleotide

<400> SEQUENCE: 85
gtggtgccat tagccttagc gatgtcgttc acggtgtcac caggtttaac gacgt        55

<210> SEQ ID NO 86
<211> LENGTH: 60
<212> TYPE: DNA
<213> ORGANISM: Artificial Sequence
<220> FEATURE:
<223> OTHER INFORMATION: Oligonucleotide

<400> SEQUENCE: 86
taagcttccg cggatcctta tttatcagct aatttattgt ccgctgcaat cttgtctgcc   60

<210> SEQ ID NO 87
<211> LENGTH: 28
<212> TYPE: DNA
<213> ORGANISM: Artificial Sequence
<220> FEATURE:
<223> OTHER INFORMATION: Oligonucleotide

<400> SEQUENCE: 87
ggggaccact ttgtacaaga aagctggg                                      28

<210> SEQ ID NO 88
<211> LENGTH: 1306
<212> TYPE: DNA
<213> ORGANISM: Artificial Sequence
<220> FEATURE:
<223> OTHER INFORMATION: Synthetic Polynucleotide

<400> SEQUENCE: 88
ccggtaacgc gtatggcgca acatgacgaa gctcagcaga acgctttta ccaggtactg    60 aacatgccga acctgaacgc ggatcagcgc aacggtttca tccagagcct gaaagacgac   120
ccttctcagt ccgcaaacgt tctgggcgag gctcagaaac tgaacgacag ccaggcccca   180
aaagcagatg ctcagcaaaa taacttcaac aaggaccagc agagcgcatt ctacgaaatc   240
ctgaacatgc caaatctgaa cgaagctcaa cgcaacggct tcattcagtc tctgaaagac   300
gatccgtccc agtccactaa cgttctgggt gaagctaaga gctgaacga atcccaggca    360 ccaaaagcag acaacaactt caacaaagag cagcagaacg ctttctatga atcttgaac    420 atgcctaacc tgaatgaaga acagcgtaac ggcttcatcc agtctctgaa ggacgaccct   480
agccagtctg ctaacctgct gtccgaagca aaaaaactga acgagtccca ggctccaaaa   540
gcggataaca aattcaacaa ggagcagcag aacgcattct acgaaatcct gcacctgccg   600
aacctgaacg aagaacagcg taacggtttc atccaatccc tgaaagacga tccttcccag   660

```
tccgcaaatc tgctggcaga agcaaagaaa ctgaacgacg cacaggcacc gaaggctgac      720
aacaagttca acaaagagca gcagaatgcc ttctacgaga ttctgcatct gccaaacctg      780
actgaggagc agcgcaacgg tttcattcag tccctgaagg acgacccaag cgtcagcaag      840
gaaatcctgg ctgaggcgaa aaaactgaac gatgcacagg ctccgaagga agaagacaac      900
aataaacctg gtaaagaaga taataataag cctggcaagg aagataacaa caagccgggc      960
aaggaggaca caataaaacc gggcaaagag gataataaca agcctggtaa ggaagacaac     1020
aacaaaccag gcaaagaaga tggcaacaag ccgggtaagg aggataataa aaaaccaggc     1080
aaggaagacg gcaacaaacc tggcaaggag gataacaaaa agccaggcaa ggaggatggt     1140
aataaaccgg gcaaagaaga cggcaacaag cctggtaaag aagacggtaa cggtgtacac     1200
gtcgttaaac tggtgacac cgtgaacgac atcgctaagg ctaatggcac cacggcagac     1260
aagattgcag cggacaataa attagctgat aaataaggat ccgcgg                    1306
```

<210> SEQ ID NO 89
<211> LENGTH: 369
<212> TYPE: PRT
<213> ORGANISM: Artificial Sequence
<220> FEATURE:
<223> OTHER INFORMATION: T7 Endonuclease

<400> SEQUENCE: 89

```
Ala Pro Ala Val Glu Gln Arg Ser Glu Ala Ala Pro Leu Ile Glu Ala
 1               5                  10                  15

Arg Gly Glu Met Val Ala Asn Lys Tyr Ile Val Lys Phe Lys Glu Gly
            20                  25                  30

Ser Ala Leu Ser Ala Leu Asp Ala Ala Met Glu Lys Ile Ser Gly Lys
        35                  40                  45

Pro Asp His Val Tyr Lys Asn Val Phe Ser Gly Phe Ala Ala Thr Leu
    50                  55                  60

Asp Glu Asn Met Val Arg Val Leu Arg Ala His Pro Asp Val Glu Tyr
65                  70                  75                  80

Ile Glu Gln Asp Ala Val Val Thr Ile Asn Ala Ala Gln Thr Asn Ala
                85                  90                  95

Pro Trp Gly Leu Ala Arg Ile Ser Ser Thr Ser Pro Gly Thr Ser Thr
            100                 105                 110

Tyr Tyr Tyr Asp Glu Ser Ala Gly Gln Gly Ser Cys Val Tyr Val Ile
        115                 120                 125

Asp Thr Gly Ile Glu Ala Ser His Pro Glu Phe Glu Gly Arg Ala Gln
    130                 135                 140

Met Val Lys Thr Tyr Tyr Tyr Ser Ser Arg Asp Gly Asn Gly His Gly
145                 150                 155                 160

Thr His Cys Ala Gly Thr Val Gly Ser Arg Thr Tyr Gly Val Ala Lys
                165                 170                 175

Lys Thr Gln Leu Phe Gly Val Lys Val Leu Asp Asp Asn Gly Ser Gly
            180                 185                 190

Gln Tyr Ser Thr Ile Ile Ala Gly Met Asp Phe Val Ala Ser Asp Lys
        195                 200                 205

Asn Asn Arg Asn Cys Pro Lys Gly Val Val Ala Ser Leu Ser Leu Gly
    210                 215                 220

Gly Gly Tyr Ser Ser Ser Val Asn Ser Ala Ala Arg Leu Gln Ser
225                 230                 235                 240

Ser Gly Val Met Val Ala Val Ala Ala Gly Asn Asn Asn Ala Asp Ala
```

```
                    245                 250                 255
Arg Asn Tyr Ser Pro Ala Ser Glu Pro Ser Val Cys Thr Val Gly Ala
                260                 265                 270

Ser Asp Arg Tyr Asp Arg Arg Ser Phe Ser Asn Tyr Gly Ser Val
            275                 280                 285

Leu Asp Ile Phe Ala Pro Gly Thr Ser Ile Leu Ser Thr Trp Ile Gly
        290                 295                 300

Gly Ser Thr Arg Ser Ile Ser Gly Thr Ser Met Ala Thr Pro His Val
305                 310                 315                 320

Ala Gly Leu Ala Ala Tyr Leu Met Thr Leu Gly Lys Thr Thr Ala Ala
                325                 330                 335

Ser Ala Cys Arg Tyr Ile Ala Asp Thr Ala Asn Lys Gly Asp Leu Ser
                340                 345                 350

Asn Ile Pro Phe Gly Thr Val Asn Leu Leu Ala Tyr Asn Asn Tyr Gln
            355                 360                 365

Ala

<210> SEQ ID NO 90
<211> LENGTH: 1107
<212> TYPE: DNA
<213> ORGANISM: Artificial Sequence
<220> FEATURE:
<223> OTHER INFORMATION: Synthetic Polynucleotde

<400> SEQUENCE: 90
gcaccggccg ttgaacagcg ttctgaagca gctcctctga ttgaggcacg tggtgaaatg      60
gtagcaaaca agtacatcgt gaagttcaag gagggttctg ctctgtctgc tctggatgct     120
gctatggaaa agatctctgg caagcctgat cacgtctata agaacgtgtt cagcggtttc     180
gcagcaactc tggacgagaa catggtccgt gtactgcgtg ctcatccaga cgttgaatac     240
atcgaacagg acgctgtggt tactatcaac gcggcacaga ctaacgcacc ttggggtctg     300
gcacgtattt cttctacttc cccgggtacg tctacttact actacgacga gtctgccggt     360
caaggttctt gcgtttacgt gatcgatacg ggcatcgagg cttctcatcc tgagtttgaa     420
ggccgtgcac aaatggtgaa gacctactac tactcttccc gtgacggtaa tggtcacggt     480
actcattgcg caggtactgt tggtagccgt acctacggtg ttgctaagaa acgcaactg      540 ttcggcgtta aagtgctgga cgacaacggt tctggtcagt actccaccat tatcgcgggt     600
atggatttcg tagcgagcga taaaaacaac cgcaactgcc cgaaaggtgt tgtggcttct     660
ctgtctctgg gtggtggtta ctcctcttct gttaacagcg cagctgcacg tctgcaatct     720
tccggtgtca tggtcgcagt agcagctggt aacaataacg ctgatgcacg caactactct     780
cctgctagcg agccttctgt ttgcaccgtg ggtgcatctg atcgttatga tcgtcgtagc     840
tccttcagca actatggttc cgtcctggat atcttcgcgc tggtacttc atcctgtct      900 acctggattg gcgtagcac tcgttccatt tccggtacga gcatggctac tccacatgtt     960
gctggtctgg cagcatacct gatgaccctg ggtaagacca ctgctgcatc cgcttgtcgt    1020
tacatcgcgg atactgcgaa caaaggcgat ctgtctaaca tcccgttcgg caccgttaat    1080
ctgctggcat acaacaacta tcaggct                                         1107

<210> SEQ ID NO 91
<211> LENGTH: 30
<212> TYPE: DNA
<213> ORGANISM: Artificial Sequence
<220> FEATURE:
```

<223> OTHER INFORMATION: Oligonucleotide

<400> SEQUENCE: 91
taacaggagg aattaaccat gaaaaaactg                              30

<210> SEQ ID NO 92
<211> LENGTH: 29
<212> TYPE: DNA
<213> ORGANISM: Artificial Sequence
<220> FEATURE:
<223> OTHER INFORMATION: Oligonucleotide

<400> SEQUENCE: 92
taatctgtat caggctgaaa atcttctct                               29

<210> SEQ ID NO 93
<211> LENGTH: 36
<212> TYPE: DNA
<213> ORGANISM: Artificial Sequence
<220> FEATURE:
<223> OTHER INFORMATION: Oligonucleotide

<400> SEQUENCE: 93
taacaggagg aattaaccat gaaaaaactg ctgttc                       36

<210> SEQ ID NO 94
<211> LENGTH: 41
<212> TYPE: DNA
<213> ORGANISM: Artificial Sequence
<220> FEATURE:
<223> OTHER INFORMATION: Oligonucleotide

<400> SEQUENCE: 94
aagtacatcg tgaagttcaa ggagggttct gctctgtctg c                 41

<210> SEQ ID NO 95
<211> LENGTH: 43
<212> TYPE: DNA
<213> ORGANISM: Artificial Sequence
<220> FEATURE:
<223> OTHER INFORMATION: Oligonucleotide

<400> SEQUENCE: 95
cgttgaatac atcgaacagg acgctgtggt tactatcaac gcg               43

<210> SEQ ID NO 96
<211> LENGTH: 38
<212> TYPE: DNA
<213> ORGANISM: Artificial Sequence
<220> FEATURE:
<223> OTHER INFORMATION: Oligonucleotide

<400> SEQUENCE: 96
ggcatcgagg cttctcatcc tgagtttgaa ggccgtgc                     38

<210> SEQ ID NO 97
<211> LENGTH: 41
<212> TYPE: DNA
<213> ORGANISM: Artificial Sequence
<220> FEATURE:
<223> OTHER INFORMATION: Oligonucleotide

<400> SEQUENCE: 97
ttaaagtgct ggacgacaac ggttctggtc agtactccac c                 41

```
<210> SEQ ID NO 98
<211> LENGTH: 37
<212> TYPE: DNA
<213> ORGANISM: Artificial Sequence
<220> FEATURE:
<223> OTHER INFORMATION: Oligonucleotide

<400> SEQUENCE: 98
cgtctgcaat cttccggtgt catggtcgca gtagcag                                37

<210> SEQ ID NO 99
<211> LENGTH: 43
<212> TYPE: DNA
<213> ORGANISM: Artificial Sequence
<220> FEATURE:
<223> OTHER INFORMATION: Oligonucleotide

<400> SEQUENCE: 99
cgttacatcg cggatactgc gaacaaaggc gatctgtcta aca                         43

<210> SEQ ID NO 100
<211> LENGTH: 42
<212> TYPE: DNA
<213> ORGANISM: Artificial Sequence
<220> FEATURE:
<223> OTHER INFORMATION: Oligonucleotide

<400> SEQUENCE: 100
ccaccagcgg aatcgcgaac agcagttttt tcatggttaa tt                          42

<210> SEQ ID NO 101
<211> LENGTH: 39
<212> TYPE: DNA
<213> ORGANISM: Artificial Sequence
<220> FEATURE:
<223> OTHER INFORMATION: Oligonucleotide

<400> SEQUENCE: 101
ttttccatag cagcatccag agcagacaga gcagaaccc                              39

<210> SEQ ID NO 102
<211> LENGTH: 39
<212> TYPE: DNA
<213> ORGANISM: Artificial Sequence
<220> FEATURE:
<223> OTHER INFORMATION: Oligonucleotide

<400> SEQUENCE: 102
aggtgcgtta gtctgtgccg cgttgatagt aaccacagc                              39

<210> SEQ ID NO 103
<211> LENGTH: 44
<212> TYPE: DNA
<213> ORGANISM: Artificial Sequence
<220> FEATURE:
<223> OTHER INFORMATION: Oligonucleotide

<400> SEQUENCE: 103
gtagtagtag gtcttccacca tttgtgcacg gccttcaaac tcag                       44

<210> SEQ ID NO 104
<211> LENGTH: 42
<212> TYPE: DNA
<213> ORGANISM: Artificial Sequence
<220> FEATURE:
<223> OTHER INFORMATION: Oligonucleotide
```

<400> SEQUENCE: 104
cgaaatccat acccgcgata atggtggagt actgaccaga ac            42

<210> SEQ ID NO 105
<211> LENGTH: 41
<212> TYPE: DNA
<213> ORGANISM: Artificial Sequence
<220> FEATURE:
<223> OTHER INFORMATION: Oligonucleotide

<400> SEQUENCE: 105
gcatcagcgt tattgttacc agctgctact gcgaccatga c             41

<210> SEQ ID NO 106
<211> LENGTH: 42
<212> TYPE: DNA
<213> ORGANISM: Artificial Sequence
<220> FEATURE:
<223> OTHER INFORMATION: Oligonucleotide

<400> SEQUENCE: 106
acgagtgcta ccgccaatcc aggtagacag gatagaagta cc            42

<210> SEQ ID NO 107
<211> LENGTH: 38
<212> TYPE: DNA
<213> ORGANISM: Artificial Sequence
<220> FEATURE:
<223> OTHER INFORMATION: Oligonucleotide

<400> SEQUENCE: 107
cggtgccgaa cgggatgtta gacagatcgc ctttgttc                 38

<210> SEQ ID NO 108
<211> LENGTH: 36
<212> TYPE: DNA
<213> ORGANISM: Artificial Sequence
<220> FEATURE:
<223> OTHER INFORMATION: Oligonucleotide

<400> SEQUENCE: 108
gcgattccgc tggtggtgcc gttctatagc catagc                   36

<210> SEQ ID NO 109
<211> LENGTH: 41
<212> TYPE: DNA
<213> ORGANISM: Artificial Sequence
<220> FEATURE:
<223> OTHER INFORMATION: Oligonucleotide

<400> SEQUENCE: 109
tctggatgct gctatggaaa agatctctgg caagcctgat c             41

<210> SEQ ID NO 110
<211> LENGTH: 35
<212> TYPE: DNA
<213> ORGANISM: Artificial Sequence
<220> FEATURE:
<223> OTHER INFORMATION: Oligonucleotide

<400> SEQUENCE: 110
gcacagacta acgcaccttg gggtctggca cgtat                    35

<210> SEQ ID NO 111
<211> LENGTH: 45

<210> SEQ ID NO 111
<211> LENGTH: 45 (implied)
<212> TYPE: DNA
<213> ORGANISM: Artificial Sequence
<220> FEATURE:
<223> OTHER INFORMATION: Oligonucleotide

<400> SEQUENCE: 111
acaaatggtg aagacctact actactcttc ccgtgacggt aatgg                45

<210> SEQ ID NO 112
<211> LENGTH: 44
<212> TYPE: DNA
<213> ORGANISM: Artificial Sequence
<220> FEATURE:
<223> OTHER INFORMATION: Oligonucleotide

<400> SEQUENCE: 112
attatcgcgg gtatggattt cgtagcgagc gataaaaaca accg                 44

<210> SEQ ID NO 113
<211> LENGTH: 41
<212> TYPE: DNA
<213> ORGANISM: Artificial Sequence
<220> FEATURE:
<223> OTHER INFORMATION: Oligonucleotide

<400> SEQUENCE: 113
ctggtaacaa taacgctgat gcacgcaact actctcctgc t                    41

<210> SEQ ID NO 114
<211> LENGTH: 37
<212> TYPE: DNA
<213> ORGANISM: Artificial Sequence
<220> FEATURE:
<223> OTHER INFORMATION: Oligonucleotide

<400> SEQUENCE: 114
attggcggta gcactcgttc catttccggt acgagca                         37

<210> SEQ ID NO 115
<211> LENGTH: 38
<212> TYPE: DNA
<213> ORGANISM: Artificial Sequence
<220> FEATURE:
<223> OTHER INFORMATION: Oligonucleotide

<400> SEQUENCE: 115
tcccgttcgg caccgttaat ctgctggcat acaacaac                        38

<210> SEQ ID NO 116
<211> LENGTH: 35
<212> TYPE: DNA
<213> ORGANISM: Artificial Sequence
<220> FEATURE:
<223> OTHER INFORMATION: Oligonucleotide

<400> SEQUENCE: 116
ggccggtgcc atggtgctat ggctatagaa cggca                           35

<210> SEQ ID NO 117
<211> LENGTH: 43
<212> TYPE: DNA
<213> ORGANISM: Artificial Sequence
<220> FEATURE:
<223> OTHER INFORMATION: Oligonucleotide

<400> SEQUENCE: 117
gctgaacacg ttcttataga cgtgatcagg cttgccagag atc                    43

<210> SEQ ID NO 118
<211> LENGTH: 36
<212> TYPE: DNA
<213> ORGANISM: Artificial Sequence
<220> FEATURE:
<223> OTHER INFORMATION: Oligonucleotide

<400> SEQUENCE: 118
acccggggaa gtagaagaaa tacgtgccag acccca                            36

<210> SEQ ID NO 119
<211> LENGTH: 38
<212> TYPE: DNA
<213> ORGANISM: Artificial Sequence
<220> FEATURE:
<223> OTHER INFORMATION: Oligonucleotide

<400> SEQUENCE: 119
gcgcaatgag taccgtgacc attaccgtca cgggaaga                          38

<210> SEQ ID NO 120
<211> LENGTH: 40
<212> TYPE: DNA
<213> ORGANISM: Artificial Sequence
<220> FEATURE:
<223> OTHER INFORMATION: Oligonucleotide

<400> SEQUENCE: 120
acacctttcg ggcagttgcg gttgttttta tcgctcgcta                        40

<210> SEQ ID NO 121
<211> LENGTH: 37
<212> TYPE: DNA
<213> ORGANISM: Artificial Sequence
<220> FEATURE:
<223> OTHER INFORMATION: Oligonucleotide

<400> SEQUENCE: 121
gcaaacagaa ggctcgctag caggagagta gttgcgt                           37

<210> SEQ ID NO 122
<211> LENGTH: 38
<212> TYPE: DNA
<213> ORGANISM: Artificial Sequence
<220> FEATURE:
<223> OTHER INFORMATION: Oligonucleotide

<400> SEQUENCE: 122
gcaacatgtg gagtagccat gctcgtaccg gaaatgga                          38

<210> SEQ ID NO 123
<211> LENGTH: 43
<212> TYPE: DNA
<213> ORGANISM: Artificial Sequence
<220> FEATURE:
<223> OTHER INFORMATION: Oligonucleotide

<400> SEQUENCE: 123
tgatggtcga cagcctgata gttgttgtat gccagcagat taa                    43

<210> SEQ ID NO 124
<211> LENGTH: 35
<212> TYPE: DNA
<213> ORGANISM: Artificial Sequence

```
<220> FEATURE:
<223> OTHER INFORMATION: Oligonucleotide

<400> SEQUENCE: 124
accatggcac cggccgttga acagcgttct gaagc                           35

<210> SEQ ID NO 125
<211> LENGTH: 42
<212> TYPE: DNA
<213> ORGANISM: Artificial Sequence
<220> FEATURE:
<223> OTHER INFORMATION: Oligonucleotide

<400> SEQUENCE: 125
acgtctataa gaacgtgttc agcggtttcg cagcaactct gg                   42

<210> SEQ ID NO 126
<211> LENGTH: 42
<212> TYPE: DNA
<213> ORGANISM: Artificial Sequence
<220> FEATURE:
<223> OTHER INFORMATION: Oligonucleotide

<400> SEQUENCE: 126
ttcttctact tccccgggta cgtctactta ctactacgac ga                   42

<210> SEQ ID NO 127
<211> LENGTH: 37
<212> TYPE: DNA
<213> ORGANISM: Artificial Sequence
<220> FEATURE:
<223> OTHER INFORMATION: Oligonucleotide

<400> SEQUENCE: 127
tcacggtact cattgcgcag gtactgttgg tagccgt                         37

<210> SEQ ID NO 128
<211> LENGTH: 38
<212> TYPE: DNA
<213> ORGANISM: Artificial Sequence
<220> FEATURE:
<223> OTHER INFORMATION: Oligonucleotide

<400> SEQUENCE: 128
caactgcccg aaaggtgttg tggcttctct gtctctgg                        38

<210> SEQ ID NO 129
<211> LENGTH: 35
<212> TYPE: DNA
<213> ORGANISM: Artificial Sequence
<220> FEATURE:
<223> OTHER INFORMATION: Oligonucleotide

<400> SEQUENCE: 129
agcgagcctt ctgtttgcac cgtgggtgca tctga                           35

<210> SEQ ID NO 130
<211> LENGTH: 37
<212> TYPE: DNA
<213> ORGANISM: Artificial Sequence
<220> FEATURE:
<223> OTHER INFORMATION: Oligonucleotide

<400> SEQUENCE: 130
tggctactcc acatgttgct ggtctggcag catacct                         37
```

<210> SEQ ID NO 131
<211> LENGTH: 46
<212> TYPE: DNA
<213> ORGANISM: Artificial Sequence
<220> FEATURE:
<223> OTHER INFORMATION: Oligonucleotide

<400> SEQUENCE: 131
tatcaggctg tcgaccatca tcatcatcat cattgagttt aaacgg         46

<210> SEQ ID NO 132
<211> LENGTH: 39
<212> TYPE: DNA
<213> ORGANISM: Artificial Sequence
<220> FEATURE:
<223> OTHER INFORMATION: Oligonucleotide

<400> SEQUENCE: 132
tgcctcaatc agaggagctg cttcagaacg ctgttcaac         39

<210> SEQ ID NO 133
<211> LENGTH: 38
<212> TYPE: DNA
<213> ORGANISM: Artificial Sequence
<220> FEATURE:
<223> OTHER INFORMATION: Ologonucleotide

<400> SEQUENCE: 133
acacggacca tgttctcgtc cagagttgct gcgaaacc         38

<210> SEQ ID NO 134
<211> LENGTH: 41
<212> TYPE: DNA
<213> ORGANISM: Artificial Sequence
<220> FEATURE:
<223> OTHER INFORMATION: Oligonucleotide

<400> SEQUENCE: 134
gaaccttgac cggcagactc gtcgtagtag taagtagacg t         41

<210> SEQ ID NO 135
<211> LENGTH: 40
<212> TYPE: DNA
<213> ORGANISM: Artificial Sequence
<220> FEATURE:
<223> OTHER INFORMATION: Oligonucleotide

<400> SEQUENCE: 135
tttcttagca acaccgtagg tacggctacc aacagtacct         40

<210> SEQ ID NO 136
<211> LENGTH: 41
<212> TYPE: DNA
<213> ORGANISM: Artificial Sequence
<220> FEATURE:
<223> OTHER INFORMATION: Oligonucleotide

<400> SEQUENCE: 136
cagaagagga gtaaccacca cccagagaca gagaagccac a         41

<210> SEQ ID NO 137
<211> LENGTH: 38
<212> TYPE: DNA
<213> ORGANISM: Artificial Sequence
<220> FEATURE:
<223> OTHER INFORMATION: Oligonucleotide

<400> SEQUENCE: 137
gagctacgac gatcataacg atcagatgca cccacggt        38

<210> SEQ ID NO 138
<211> LENGTH: 38
<212> TYPE: DNA
<213> ORGANISM: Artificial Sequence
<220> FEATURE:
<223> OTHER INFORMATION: Oligonucleotide

<400> SEQUENCE: 138
tggtcttacc cagggtcatc aggtatgctg ccagacca        38

<210> SEQ ID NO 139
<211> LENGTH: 45
<212> TYPE: DNA
<213> ORGANISM: Artificial Sequence
<220> FEATURE:
<223> OTHER INFORMATION: Oligonucleotide

<400> SEQUENCE: 139
aaaacagcca agctggagac cgtttaaact caatgatgat gatga        45

<210> SEQ ID NO 140
<211> LENGTH: 40
<212> TYPE: DNA
<213> ORGANISM: Artificial Sequence
<220> FEATURE:
<223> OTHER INFORMATION: Oligonucleotide

<400> SEQUENCE: 140
agctcctctg attgaggcac gtggtgaaat ggtagcaaac        40

<210> SEQ ID NO 141
<211> LENGTH: 37
<212> TYPE: DNA
<213> ORGANISM: Artificial Sequence
<220> FEATURE:
<223> OTHER INFORMATION: Oligonucleotide

<400> SEQUENCE: 141
acgagaacat ggtccgtgta ctgcgtgctc atccaga        37

<210> SEQ ID NO 142
<211> LENGTH: 40
<212> TYPE: DNA
<213> ORGANISM: Artificial Sequence
<220> FEATURE:
<223> OTHER INFORMATION: Oligonucleotide

<400> SEQUENCE: 142
gtctgccggt caaggttctt gcgtttacgt gatcgatacg        40

<210> SEQ ID NO 143
<211> LENGTH: 37
<212> TYPE: DNA
<213> ORGANISM: Artificial Sequence
<220> FEATURE:
<223> OTHER INFORMATION: Oligonucleotide

<400> SEQUENCE: 143
acctacggtg ttgctaagaa aacgcaactg ttcggcg        37

<210> SEQ ID NO 144

```
<211> LENGTH: 38
<212> TYPE: DNA
<213> ORGANISM: Artificial Sequence
<220> FEATURE:
<223> OTHER INFORMATION: Oligonucleotide

<400> SEQUENCE: 144
gtggtggtta ctcctcttct gttaacagcg cagctgca                              38

<210> SEQ ID NO 145
<211> LENGTH: 42
<212> TYPE: DNA
<213> ORGANISM: Artificial Sequence
<220> FEATURE:
<223> OTHER INFORMATION: Oligonucleotide

<400> SEQUENCE: 145
tcgttatgat cgtcgtagct ccttcagcaa ctatggttcc gt                         42

<210> SEQ ID NO 146
<211> LENGTH: 37
<212> TYPE: DNA
<213> ORGANISM: Artificial Sequence
<220> FEATURE:
<223> OTHER INFORMATION: Oligonucleotide

<400> SEQUENCE: 146
gatgaccctg ggtaagacca ctgctgcatc cgcttgt                               37

<210> SEQ ID NO 147
<211> LENGTH: 41
<212> TYPE: DNA
<213> ORGANISM: Artificial Sequence
<220> FEATURE:
<223> OTHER INFORMATION: Oligonucleotide

<400> SEQUENCE: 147
tctccagctt ggctgttttg gcggatgaga gaagattttc a                          41

<210> SEQ ID NO 148
<211> LENGTH: 43
<212> TYPE: DNA
<213> ORGANISM: Artificial Sequence
<220> FEATURE:
<223> OTHER INFORMATION: Oligonucleotide

<400> SEQUENCE: 148
cctggatatc ttcgcgcctg gtacttctat cctgtctacc tgg                        43

<210> SEQ ID NO 149
<211> LENGTH: 44
<212> TYPE: DNA
<213> ORGANISM: Artificial Sequence
<220> FEATURE:
<223> OTHER INFORMATION: Oligonucleotide

<400> SEQUENCE: 149
tccttgaact tcacgatgta cttgtttgct accatttcac cacg                       44

<210> SEQ ID NO 150
<211> LENGTH: 40
<212> TYPE: DNA
<213> ORGANISM: Artificial Sequence
<220> FEATURE:
<223> OTHER INFORMATION: Oligonucleotide

<400> SEQUENCE: 150
```
gtcctgttcg atgtattcaa cgtctggatg agcacgcagt 40

<210> SEQ ID NO 151
<211> LENGTH: 41
<212> TYPE: DNA
<213> ORGANISM: Artificial Sequence
<220> FEATURE:
<223> OTHER INFORMATION: Oligonucleotide

<400> SEQUENCE: 151
gatgagaagc ctcgatgccc gtatcgatca cgtaaacgca a 41

<210> SEQ ID NO 152
<211> LENGTH: 37
<212> TYPE: DNA
<213> ORGANISM: Artificial Sequence
<220> FEATURE:
<223> OTHER INFORMATION: Oligonucleotide

<400> SEQUENCE: 152
cgttgtcgtc cagcacttta acgccgaaca gttgcgt 37

<210> SEQ ID NO 153
<211> LENGTH: 35
<212> TYPE: DNA
<213> ORGANISM: Artificial Sequence
<220> FEATURE:
<223> OTHER INFORMATION: Oligonucleotide

<400> SEQUENCE: 153
accggaagat tgcagacgtg cagctgcgct gttaa 35

<210> SEQ ID NO 154
<211> LENGTH: 37
<212> TYPE: DNA
<213> ORGANISM: Artificial Sequence
<220> FEATURE:
<223> OTHER INFORMATION: Oligonucleotide

<400> SEQUENCE: 154
gcagtatccg cgatgtaacg acaagcggat gcagcag 37

<210> SEQ ID NO 155
<211> LENGTH: 37
<212> TYPE: DNA
<213> ORGANISM: Artificial Sequence
<220> FEATURE:
<223> OTHER INFORMATION: Oligonucleotide

<400> SEQUENCE: 155
taatctgtat caggctgaaa atcttctctc atccgcc 37

<210> SEQ ID NO 156
<211> LENGTH: 40
<212> TYPE: DNA
<213> ORGANISM: Artificial Sequence
<220> FEATURE:
<223> OTHER INFORMATION: Oligonucleotide

<400> SEQUENCE: 156
aggcgcgaag atatccagga cggaaccata gttgctgaag        40

<210> SEQ ID NO 157
<211> LENGTH: 1382
<212> TYPE: DNA
<213> ORGANISM: Artificial Sequence
<220> FEATURE:
<223> OTHER INFORMATION: Synthetic Polynucleotide

<400> SEQUENCE: 157
cggggacaag tttgtacaaa aaagcaggct gctcttcgcc tgctggctgg taatcgccag        60
caggcctttt tatttggggg agagggaagt catgaaaaaa ctaacctttg aaattcgatc       120
tccaccacat cagctctgaa gcaacgtaaa aaaacccgcc ccggcgggtt tttttatacc       180
cgtagtatcc ccacttatct acaatagctg tccttaatta aggttgaata aataaaaaca       240
gccgttgcca gaaagaggca cggctgtttt tattttctag tgagaccggg accagtttat       300
taagcgccag tgctatgacg accttctgcg cgctcgtact gttcgacaat ggtgtaatct       360
tcgttgtgag aagtgatgtc cagcttgatg tcagttttgt aagcgccgg cagttgcaca        420
ggttttttg ccatgtacgt agttttacc tctgcgtcgt agtgaccacc gtccttcagc         480
ttcaggcgca tttaatttc gcccttcagg gcaccatctt ccgggtacat acgctcagtg        540
gacgcttccc aacccatcgt cttttttctgc attacaggac cgtcagacgg aagttagta      600
ccgcgcagct tcactttgta gatgaactcg ccgtcttgca ggctagagtc ttgggtcaca       660
gtcaccacac caccgtcctc gaagttcata acacgttccc atttgaaacc ttccgggaaa      720
gacagtttca ggtaatccgg aatatccgcc gggtgtttaa cgtacgcctt agagccatac       780
tggaactgag ggctcagaat atcccatgca aaaggcagtg ggccaccttt ggtcactttc       840
agtttcgcgg tctgagtacc ctcgtaagga cggccttcac cttcaccctc gatttcaaat       900
tcgtggccat ttacagagcc ctccatacgc actttgaagc gcatgaactc cttgattaca       960
tcttcagagg aggccatttt ttttttcctcc ttattttctc aagcctaggt ctgtgtgaaa     1020
ttgttatccg ctcacaattg aatctatcat aattgtgagc gctcacaatt gtaaaggtta     1080
gatccgctaa tcttatggat aaaaatgcta tgttcccccc ggggggatat caacaggagt     1140
ccaagcgacc ggtggttgca tgtctagcta gctagaacag gactagtcct gagtaatagt     1200
caaaagcctc cggtcggagg cttttgactt tctgaaatgt aatcacactg gctcaccttc     1260
gggtgggcct ttctgcgttt ataagaagga aaaagcggc cgcaaaagga aaaattatt       1320
cgtatagcat acattatacg aagttataag cttacccagc tttcttgtac aaagtggtcc     1380
cc                                                                    1382

<210> SEQ ID NO 158
<211> LENGTH: 21
<212> TYPE: DNA
<213> ORGANISM: Artificial Sequence
<220> FEATURE:
<223> OTHER INFORMATION: RNA Stem Loop Structure

<400> SEQUENCE: 158
ccgtgacggt aacggtcacg g        21

DESIGN, SYNTHESIS AND ASSEMBLY OF SYNTHETIC NUCLEIC ACIDS

CROSS-REFERENCES TO RELATED APPLICATIONS

This application claims priority to U.S. Patent Application No. 60/567,460 filed on May 4, 2004, which is hereby incorporated in its entirety by reference. This application also claims priority to U.S. Patent Application No. 60/666,909, filed Mar. 31, 2005, entitled "High Fidelity Low Cost Synthesis of Oligonucleotides," which is hereby incorporated by reference in its entirety.

STATEMENT AS TO RIGHTS TO INVENTIONS MADE UNDER FEDERALLY SPONSORED RESEARCH AND DEVELOPMENT

The research described in this application was funded in part by NIH grant R43 HG003507 from NHGR1.

1. FIELD OF THE INVENTION

This invention relates to methods for designing and synthesizing nucleic acids.

2. BACKGROUND OF THE INVENTION

Several methods have been described for the synthesis of oligonucleotides using phosphoramidite chemistry, which are now capable of achieving nucleotide coupling efficiencies of 99%. The primary markets for commercial oligonucleotide synthesis are synthesis of oligonucleotide arrays for genomic and expression applications, and for use as PCR primers, for which such efficiencies are adequate. Since 1990 there has been little work done improving oligonucleotide chemistries to increase coupling efficiencies, the focus has instead been on increasing throughput with existing chemistries. Increased coupling efficiencies would provide a significant benefit to growing applications such as synthesis of long polynucleotides by assembly of oligonucleotides, accurate detection of single nucleotide polymorphisms in individuals and populations, the manufacture of high quality microarray chips for use in clinical diagnostics, haplotyping, real-time polymerase chain reaction, small inhibitory RNAs (siRNAs) used for validation of drug targets, expression array production, and chip-based sequencing. There is therefore a need in the art for synthetic processes that reduce synthesis errors and increase oligonucleotide coupling efficiencies.

Several methods have been described for the synthesis of larger polynucleotides by the assembly of oligonucleotides, using combinations of ligation, polymerase chain reaction and ligase chain reaction. See, for example, Hayden et al., 1988, DNA 7, 571-7; Ciccarelli et al., 1991, Nucleic Acids Res 19, 6007-13; Jayaraman et al., 1991, Proc Natl Acad Sci USA 88, 4084-8; Jayaraman et al., 1992, Biotechniques 12: 392-8; Graham et al., 1993, Nucleic Acids Res 21: 4923-8; Kobayashi et al., 1997, Biotechniques 23: 500-3; Au et al., 1998, Biochem Biophys Res Commun. 248: 200-203; Hoover et al., 2002, Nucleic Acids Res 30: e43, each of which is hereby incorporated by reference in its entirety. The assembly of polynucleotides from oligonucleotides is an error-prone process. Errors arise from the chemical synthesis of oligonucleotides, and the enzymatic processes used to assemble these oligonucleotides into longer polynucleotides. These errors increase the cost and time taken to synthesize polynucleotides. There is therefore a need in the art for synthetic processes that reduce synthesis errors and synthesis time.

3. SUMMARY OF THE INVENTION

Methods of synthesizing oligonucleotides with high coupling efficiency (>99.5%) are provided. Methods for purification of synthetic oligonucleotides are also described. Instrumentation configurations for oligonucleotide synthesis are also described. Methods of designing and synthesizing polynucleotides are also provided. Polynucleotide design is optimized for subsequent assembly from shorter oligonucleotides. Modifications of phosphoramidite chemistry to improve the subsequent assembly of polynucleotides are described. The design process also incorporates codon biases into polynucleotides that favor expression in defined hosts. Design and assembly methods are also described for the efficient synthesis of sets of polynucleotide variants. Software to automate the design and assembly process is also described.

One aspect of the invention provides a method of designing a polynucleotide. The method comprises selecting an initial polynucleotide sequence that codes for a polypeptide, where a codon frequency in the initial polynucleotide sequence is determined by a codon bias table and modifying an initial codon choice in the initial polynucleotide sequence in accordance with a design criterion, thereby constructing a final polynucleotide sequence that codes for the polypeptide. In some embodiments, the design criterion comprises one or more of:

(i) exclusion of a restriction site sequence in said initial polynucleotide sequence;

(ii) incorporation of a restriction site sequence in said initial polynucleotide sequence;

(iii) a designation of a target G+C content in the initial polynucleotide sequence;

(iv) an allowable length of a sub-sequence that can be exactly repeated within either strand of the initial polynucleotide sequence;

(v) an allowable annealing temperature of any sub-sequence to any other sub-sequence within either strand of the initial polynucleotide sequence;

(vi) exclusion of a hairpin turn in the initial polynucleotide sequence;

(vii) exclusion of a repeat element in the initial polynucleotide sequence;

(viii) exclusion of a ribosome binding site in the initial polynucleotide sequence;

(ix) exclusion of a polyadenylation signal in the initial polynucleotide sequence;

(x) exclusion of a splice site in the initial polynucleotide sequence;

(xi) exclusion of an open reading frame in each possible 5' reading frame in the initial polynucleotide sequence;

(xii) exclusion of a polynucleotide sequence that facilitates RNA degradation in the initial polynucleotide sequence;

(xiii) exclusion of an RNA polymerase termination signal in the initial polynucleotide sequence;

(xiv) exclusion of a transcriptional promoter in the initial polynucleotide sequence;

(xv) exclusion of an immunostimulatory sequence in the initial polynucleotide sequence;

(xvi) incorporation of an immunostimulatory sequence in the initial polynucleotide sequence;

(xvii) exclusion of an RNA methylation signal in the initial polynucleotide sequence;

(xviii) exclusion of a selenocysteine incorporation signal in the initial polynucleotide sequence;

(xix) exclusion of an RNA editing sequence in the initial polynucleotide sequence;

(xx) exclusion of an RNAi-targeted sequence in the initial polynucleotide sequence; and/or (xxi) exclusion of an inverted repeat within the first 45 nucleotides encoding said synthetic polypeptide in the initial polynucleotide sequence.

In some embodiments, the design criterion comprises reduced sequence identity to a reference polynucleotide, and modification of the initial codon choice in the initial polynucleotide in accordance with the design criterion comprises altering a codon choice in the initial polynucleotide sequence to reduce sequence identity to the reference polynucleotide. In some embodiments, the design criterion comprises increased sequence identity to a reference polynucleotide, and the modification of the initial codon choice in the initial polynucleotide in accordance with the design criterion comprises altering a codon choice in the initial polynucleotide sequence to increase sequence identity to the reference polynucleotide.

Another aspect of the present invention provides a computer program product for use in conjunction with a computer system, the computer program product comprising a computer readable storage medium and a computer program mechanism embedded therein. The computer program mechanism comprising (a) instructions for selecting an initial polynucleotide sequence that codes for a polypeptide, where a codon frequency in the initial polynucleotide sequence is determined by a codon bias table; and (b) instructions for modifying an initial codon choice in the initial polynucleotide sequence in accordance with a design criterion, thereby constructing a final polynucleotide sequence that codes for the polypeptide. Still another aspect of the invention provides a computer system comprising a central processing unit and a memory, coupled to the central processing unit, the memory storing the aforementioned computer program product.

4. BRIEF DESCRIPTION OF THE FIGURES

FIG. 1 illustrates a flowchart showing the standard coupling process for oligonucleotide synthesis in accordance with the prior art. See also, Gait, 1984, Practical approach series, xiii, 217). Minor modifications have also been described in Matteucci & Caruthers, 1981, J Am Chem Soc. 103, 3185-3191; Pon et al., 1985, Tetrahedron Lett. 26, 2525-2528; Adams et al., 1983, J Am Chem Soc 105, 661-663; McBride et al., 1986; J Am Chem Soc 108, 2040-2048; Letsinger et al., 1984, Tetrahedron 40, 137-143; Hayakawa et al., 1990, J Am Chem Soc 112, 1691-1696; and Hayakawa & Kataoka., 1998, J Am Chem Soc 120, 12395-12401.

FIGS. 2A-2C illustrate the effect of a capping procedure on the distribution of truncated oligomers. (A) Expected distribution of oligonucleotide products with and without capping. (B) HPLC trace showing the observed distribution of oligonucleotide products without capping. (C) Proposed explanation for failures in elongation: oligonucleotide packing produces populations that grow as desired (202A and 202E), are trapped by neighboring chains (202B) or protected by neighboring trityl groups (202D) resulting in n−1, n−2, n−3 etc. byproducts, or nonoxidized (202C) that will generate n−1 byproducts.

FIGS. 3A-3D illustrate the stability of the trityl protection group. Samples of 5NO-dimethoxytrityl-bisthymydyllthymidine were incubated at 25° C. for 60 hours in 0.5M phosphate buffer at the pH indicated, then analyzed by HPLC. Protected oligonucleotides are indicated as the DMTr-T3 peak to the right of each trace, loss of protection is seen as an increase in height of the T3 peak towards the left of each trace. (A) start, (B) pH 7.0, (C) pH 6.0, (D) pH 5.0.

FIGS. 4A-4F illustrate optimization of phosphodiesterase cleavage of non-tritylated oligonucleotides. A total of 1 nmol of $dT_{20}$ (QIAgen) in 10 μl of 0.5M phosphate buffer was treated for sixteen hours with calf spleen phosphodiesterase II (Sigma cat #P9041) and analyzed by HPLC. (A) undigested, (B) 0.01 U enzyme 25° C., pH 7.0, (C) 0.01 U enzyme 37° C., pH 7.0, (D) 0.01 U enzyme 25° C., pH 6.0, (E) 0.01 U enzyme 25° C., pH 5.0, and (F) 0.1 U enzyme 25° C., pH 7.0. Undigested 20mer is the large peak to the right of trace A. Completely digested monomer is the large peak to the left of traces B-F.

FIGS. 5A-5C illustrate phosphodiesterase-II-assisted oligonucleotide purification. An oligomer of $dT_{15}$ was synthesized on CPG 2000 Å without capping, treated with phosphodiesterase and analyzed by HPLC. (A) ~80 nmol of fully deprotected $dT_{15}$ on 2 mg CPG treated with 1 U enzyme for 30 hours at 37° C. prior to cleavage, (B) ~40 nmol of $dT_{15}$ cleaved from 1 mg CPG untreated with phosphodiesterase, (C) ~10 nmol of trityl protected $dT_{15}$ from the same synthesis as trace B, cleaved from 1 mg CPG and treated with 0.1 U enzyme for 16 hours at 25° C. Following cleavage, the enzyme was denaturated by heating to 65° C. for 30 minutes, the oligomer detritylated by acetic acid for 2 hours and neutralized with 10 M ammonia. Undigested 15mer is the large peak to the right of each trace. Truncated oligomers are labeled.

FIGS. 6A-6C illustrate HPLC purification of tritylated oligonucleotides. 9mer oligodeoxythymidine was synthesized under standard conditions without capping (6A), (6B) with $Ac_2O$-DMAP capping before oxidation (0.1M THF:L:W=4:1:1) and (6C) with $Ac_2O$-DMAP capping after oxidation (0.1M THF:L:W=4:1:1). Oligonucleotides were cleaved without detritylation and HPLC purified on a XTerra MS-C18. Untritylated oligonucleotides (traces A in 6A, 6B and 6C) were separated from full-length tritlated oligonucleotides (traces B in 6A, 6B and 6C) which were eluted after 8 min of washing with 0.1% TFA. Oligonucleotides were then detritylated and analyzed by HPLC. The full-length 9mer is the large peak to the right of traces B.

FIGS. 7A-7H illustrate two classes of chain elongation failures. Tetramers of homo-thymidine (A, B), homo-cytidine (C, D), homo-adenine (E, F) and homo-guanine (G, H) were synthesized without capping on a CPG support and cleaved without detritylation. HPLC was then used to separate the tritylated (the large peak to the right of traces A, C, E and G) from the non-tritylated oligomers (the small peak to the left of traces A, C, E and G), or to separate tritylated trimer (the small peak to the right of traces B, D, F and H) from tritylated tetramer (the large peak to the left of traces B, D, F and H).

FIGS. 8A-8C illustrate comparison of capping reagents. A single CPG-linked thymidine was capped with (A) acetic anhydride/NMI (B) $Pac_2O$/NMI or (C) DMPA for the times indicated. Incomplete capping was measured by coupling a second thymidine. Capped (T1, the large peak to the left of traces in A and B) and dimer (T2, produced from uncapped chains) peaks were separated by HPLC.

FIGS. 9A-F illustrate efficiency of capping after fifteen seconds and after one minute. A first CPG-supported thymidine was capped for fifteen seconds with (A) N-MI:Lut:THF=1:1.5:7, (B) N-MI:Lut:THF=1.5:1.5:7 (C) N-MI:Lut:DIOX=1.5:1.5:7, (D) N-I:Lut:DMA=1.5:1.5:7, (E) N-MI:Lut:TOL=1.5:1.5:7, (F) DMAP:Lut:DMA=1.5:1.5:7 (N-MI=N-methylimidazole; Lut=2,6-lutidine;

THF=tetrahydrafuran; DIOX=dioxane; DMA=dimethylacetamide; and DMAP=N,N-dimethylaminopyridine). The base was then coupled to a second thymidine which reacted at the unprotected positions. Oligonucleotides were detritylated, cleaved from the support and analyzed by HPLC. Relative Capping Efficiency (RCE) was calculated as the ratio of T1 to T2. RCE after fifteen seconds was (A) 77.2%, (B) 77.8%, (C) 65.4%, (D) 50.4%, (E) 95.6%, and (F) 100%. RCE after one minute was (A) 99.1%, B) 99.2%, (C) 97.1%, (D) 93.8%, (E) 100%, and (F) 100%.

FIGS. 10A-F illustrate comparison of oxidation conditions. A single CPG-linked thymidine was coupled to a second thymidine and oxidized with 0.1M iodine, in THF:2,6-lutidine:Water 40:10:1 in accordance with Gait, 1984, *Practical Approach Series*, xiii, 217, for (A) five seconds, (B) twenty seconds, (C) one minute, (D) ten minutes or (E) with 0.1M iodine in THF:2,6-lutidine:water 40:10:1 for 15 seconds or (F) 0.08M iodine in THF: 2,6-lutidine:Water 4:1:1 for 15 seconds. The dimer was then detritylated, cleaved from CPG and analyzed by HPLC. The T2 peak (to the right of each trace) corresponds to completely oxidized chains, the T1 peak (to the left of each trace) corresponds to incomplete oxidation followed by bond cleavage upon detritylation.

FIG. 11 illustrate products resulting from incomplete chain oxidation in accordance with the prior art.

FIGS. 12A-G compare oxidation reagents. A single CPG-linked thymidine was coupled to a second thymidine and oxidized for fifteen seconds with (A) no oxidizer; (B) 0.08M iodine in THF:2,6-lutidine:water=4:1:1 (stored for three months at 25° C., no precipitation as described by Pon, 1987, Nucleic Acids Res 15, 7203; (C) freshly prepared 1.25M iodine in THF:2,6-lutidine:water 4:1:1; (D) 1M t-butyl hydroperoxide (TBHP)/toluene (stored at 25° C. for three months in a dark glass bottle as described in Hayakawa et al., 1986, Tetrahedron Lett 27, 4191-4194; (E) $CCl_4$ oxidation as described in Padiya and Salunkhe, 1998, J Chem Research, 804; two month old solutions A and B were mixed immediately before use; (F) 3.3M TBHP/toluene stored at 25° C. for three months in a dark glass bottle; and (G) ten minute oxidation with iodine aqueous solution (same as B). The dimer was then detritylated, cleaved from CPG and analyzed by HPLC. The T2 peak (to the right of each trace) corresponds to completely oxidized chains, the T1 peak (to the left of each trace) corresponds to incomplete oxidation followed by bond cleavage upon detritylation.

FIG. 13 illustrates a modified oligonucleotide synthesis procedure. See Eadie & Davidson, 1987, Nucleic Acids Res 15, 8333-49; Boal et al., 1996; Nucleic Acids Res 24, 3115; and Kwiatkowski et al., 1996, Nucleic Acids Res 24, 4632-4638.

FIGS. 14A-14F illustrate a comparison of efficiency of standard and modified coupling protocols. HPLC chromatograms of (14A) high quality dT20, (14B) low quality dT20, (14C) gel-purified dT20 (from ABRF NARG 2000-2001 DNA synthesis studies that covered 20 DNA synthesis core facilities and 30 DNA synthesizers, (14D) dT10 purchased from QIAgen, (14E) dT9, and (14F) dT16 synthesized using a modified protocol.

FIGS. 15A-15O illustrate quartz surface reorganization in which 7 mm quartz rods were broken and kept under vacuum (15A)-(15F) or in air (15G)-(15L) before measuring the surface wettability with a 2 μl water drop. Broken glass vacuum: (15A) 0 h (0N), (15B) 0.5 h (48N), (15C) 2 h (58N), (15D), 5 h (61N), (15E) 17 h (64N), and (15F) 48 h (69N). Broken glass atmosphere: (15G) 0 h, (15H) 2 h, (15I) 24 h, (15J) 32 h, (15K) 75 h, (15L) old surface (87'). Freshly polished glass rod: (15M) 220 mesh, (15N) 600 mesh. (15O). Quantification of (15A) through (15F) was by measuring the contact angle between the water and the surface.

FIGS. 16A-16O illustrates activation of glass surfaces. All silanoyl groups were removed by heating a freshly broken quartz rod in a vacuum at 125° C. for 1 hour. The rod was then treated with (16A)-(16B) 10M Ammonium hydroxide (16A) start, (16B) after 24 hours; (16C)-(16D) 10M HCl (16C) start, (16D) after 24 hours; (16E)-(16F) trifluoroacetic acid (E) start, (F) after 24 hours; (G)-(I) 65% nitric acid, (G) start, (H) after 1 hour, (16I) after 24 hours; (16J)-(16K) 50% w/v sodium hydroxide; (16J) start, (16K) after 24 hours; (16L)-(16M) sodium fluoride, (16L) start, (16M) after 24 hours. Cleavage of Si—O—Si bonds was assessed by measuring changes in the contact angle of a two 111 water drop.

FIGS. 17A-17J illustrate derivatization of rod surfaces. (17A) The sides of the rods are protected with trimethylsilane (TMS) while the ends are derivatized with aminopropylsilane (APS). The polished surfaces of quartz rods were activated using 50% w/v sodium hydroxide for 11 minutes at 25° C. followed by 5 minutes with concentrated nitric acid before treatment with (17B)-(17E) trimethylsilane (17B) start, (17C) 6 seconds, (17D) 12 seconds, (17E) 60 seconds; (17F)-(17I) aminopropylsilane from a freshly opened bottle (17F) 1 minute, (17G) 5 minutes, (17H) 10 minutes, (17I) 20 minutes, or (17J) aminopropylsilane from an old bottle. Hydrophobicity was assessed by measuring changes in the contact angle of a two μl water drop.

FIGS. 18A-18B illustrate the loading of APS and first nucleotide. The loading of dimethoxytritylthymidine onto derivatized glass surfaces was measured by comparison to the curve "peak area—concentration". (A) Loading was measured on surfaces derivatized by exposure to 1% aminopropylsilane (APS) in EtOH for different times. (B) Loading was measured on surfaces derivatized with aminopropylsilane for eight minutes then loaded.

FIGS. 19A-19F illustrate single and twelve channel devices for oligonucleotide synthesis: (19A) a single channel CPG reaction vessel, (19B) twelve-pin activated glass rods, (19C) rods in prototype reactor, (19D) removing a microtiter plate from reactor (19E) illustrates the use of a humidity sensor to ensure water-free conditions. Cleavage from glass rods was carried out in gaseous ammonia at 55° C. inside an autoclave (19F).

FIGS. 20A-20C illustrate oligonucleotide synthesis on different supports. A polythymidine 9mer was synthesized, cleaved, detritylated and analyzed by HPLC. (20A) Synthesis on derivatized quartz rod with capping prior to oxidation. (20B) synthesis on derivatized quartz rod following the modified protocol shown in FIG. 13. (20C) Synthesis on CPG in parallel with the synthesis in (20B).

FIG. 21. A schematic representation of the assembly of oligonucleotides into a polynucleotide. Oligonucleotides are represented by arrows pointing from 5' to 3'. In this example the polynucleotide is assembled from sixteen oligonucleotides, eight for each strand. Each oligonucleotide is labeled: those that comprise the top strand of the polynucleotide with one capital letter, those that comprise the bottom strand with two lower case letters. These letters indicate the two top strand oligonucleotides to which the bottom strand is complementary. In this representation the oligonucleotides are shown precisely abutting one another, that is the 3'-most base of each oligonucleotide is the base following the 5'-most base of the preceding oligonucleotide, so that the consecutive sequences of the top strand oligonucleotides are identical to the top strand of the polynucleotide sequence. Similarly the consecutive sequences of the bottom strand oligonucleotides are identical to the bottom strand of the polynucleotide sequence. Other oligonucleotide arrangements are also possible: the oligonucleotides may not precisely abut one another. In one case there could be a gap between two adjacent oligonucleotides which is "covered" by the sequence in the complementary oligonucleotide. In another case there could be overlap between two adjacent oligonucleotides. In this scheme and in the text of this application the term "correct annealing partner" refers to oligonucleotides whose annealing will result in the subsequent synthesis of the desired polynucleotide. In this figure for example, the correct annealing partners for oligonucleotide B are oligonucleotide ab and oligonucleotide bc. The term "incorrect annealing partner" refers to oligonucleotides whose annealing will not result in the subsequent synthesis of the desired polynucleotide. In this figure, for example, the incorrect annealing partners for oligonucleotide B are all oligonucleotides other than oligonucleotide ab and oligonucleotide bc.

FIG. 22 illustrates the frequency of codon usage in *Escherichia coli* class II (highly expressed) genes. The table shows the three letter amino acid code, a three nucleotide codon that encodes that amino acid, and the frequency with which that codon appears in highly expressed *Escherichia coli* genes.

FIG. 23 illustrates a table reflecting the bias of codon usage in human (*Homo sapiens*) genes. The table shows the three letter amino acid code, a three nucleotide codon that encodes that amino acid, and the frequency with which that codon appears in human genes.

FIG. 24 illustrates a table reflecting a combination of the biases of codon usage in human (*Homo sapiens*) genes and *Escherichia coli* class II (highly expressed) genes. The table was constructed from those shown in FIGS. 23 and 24 as follows. Any codon that occurred with a frequency of less than 0.05 in either human or highly expressed *Escherichia coli* genes was eliminated by setting its frequency in the new table to zero. For example the codon TTA encodes Leu with a frequency of 0.07 in human genes, but only 0.03 in highly expressed *E. coli* genes, so its frequency in the hybrid table is set to 0. The remaining non-zero codon frequencies were calculated by averaging the values in the two organisms, for example the codon TTT encodes Phe with a frequency of 0.29 in highly expressed *E. coli* genes and a frequency of 0.45 in human genes so its value is set to the average of these values, 0.37, in the hybrid table. This calculation will yield frequencies that do not sum to 1 for amino acids for which one or more codon has been eliminated because it fell below the threshold (in this case Thr, Arg, Ser, Ile, Pro, Leu and Gly). For these amino acids, the frequencies have been normalized by dividing the frequency for each codon by the sum of the codon frequencies for that amino acid.

FIG. 25 illustrates a table reflecting the bias of codon usage in mouse (*Mus musculus*) genes. The table shows the three letter amino acid code, a three nucleotide codon that encodes that amino acid, and the frequency with which that codon appears in mouse genes.

Figure 26:
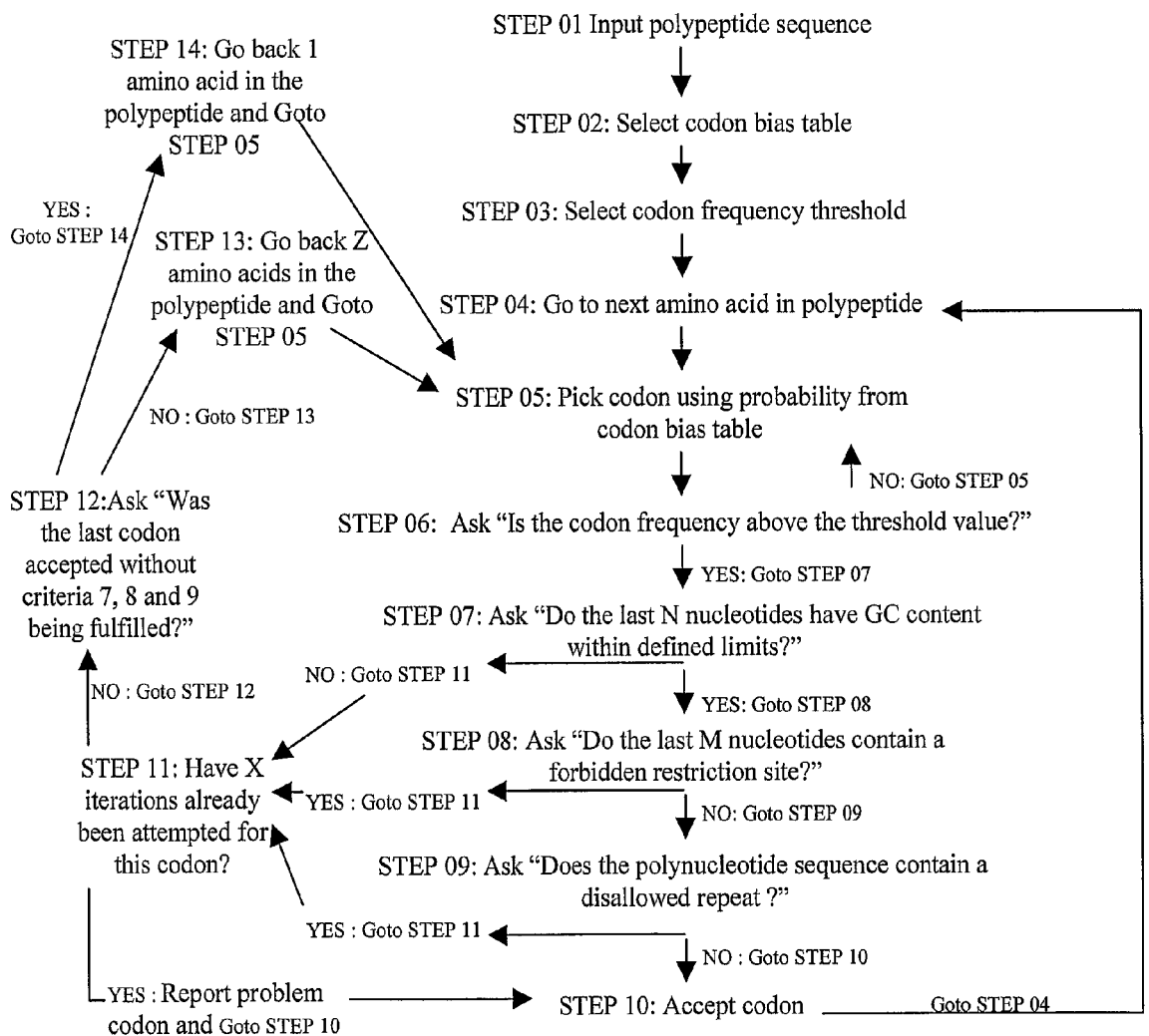

FIG. 26 illustrates an automated process for designing a polynucleotide to encode a provided polypeptide sequence, incorporating functional and synthetic constraints. The steps in the process are: (01) input a polypeptide sequence for which an encoding polynucleotide is desired; (02) select a codon bias table that reflects the distribution of codons found in genes, or a class of genes (e.g. highly expressed genes) in one or more expression organisms; (03) select a threshold frequency (codons that are used with a frequency below this threshold will be rejected from the design); (04) select the next amino acid in the polypeptide; (05) select a codon that encodes the amino acid, by using the codon bias table to provide the probability of selection; (06) ensure that the selected codon is above the threshold (if it is not return to 05, otherwise proceed to 07); (07) check that the last N nucleotides have a GC content within defined limits, the number of nucleotides (N) and the GC content are both parameters that can be varied in the method. If this criterion is not satisfied proceed to 11, otherwise proceed to 08; (08) check that the last M nucleotides of sequence do not contain a forbidden restriction site, the number of nucleotides (M) and the list of sites to be avoided are both parameters that can be varied in the method. If the sequence does contain a forbidden site proceed to 11. Otherwise proceed to 09; (09) check whether the entire polynucleotide sequence contains a disallowed repeat. The parameters for repeats may be varied in the method. If the sequence does contain a disallowed repeat proceed to 11. Otherwise proceed to 10; (10) accept the codon and proceed to 04; (11-14) if any of the criteria from steps 07, 08 or 09 are not met, the method requires that the process move back some length of sequence (Z amino acids, where Z is preferably between 2 and 20 amino acids, more preferably between 5 and 10 amino acids) in the polypeptide, delete the codons that were selected for those amino acids and reselect those codons (Steps 11 and 12). Because the codons are selected probabilistically, different iterations of the process will produce different sequences that still fulfill the functional codon bias criteria. This process is repeated X number of times, where X is preferably less than 10,000, and more preferably less than 1,000. If X iterations are repeated without meeting all of the desired criteria, a report is generated describing the failure, the codon is accepted, and the process proceeds to the next amino acid. This is to prevent the method from becoming trapped in an endless loop if no solutions are available. The report will then allow manual adjustment of the constraints to obtain an acceptable solution (such as reducing the threshold for a single position or relaxing the repeat or GC content requirement).

Figure 27:
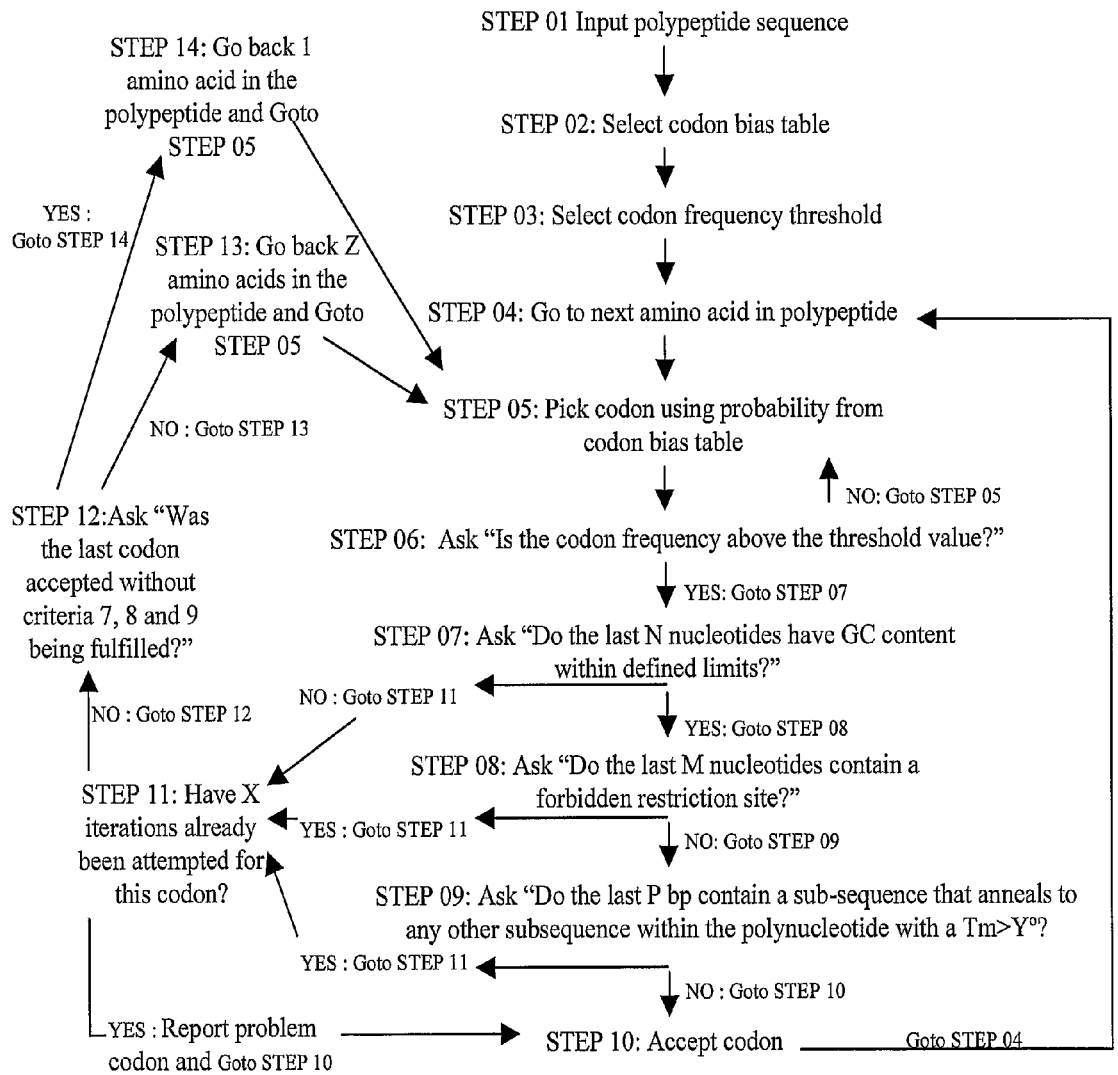

FIG. 27 illustrates an automated process for designing a polynucleotide to encode a provided polypeptide sequence, incorporating functional and synthetic constraints. The steps in the process are (01) input a polypeptide sequence for which an encoding polynucleotide is desired; (02) select a codon bias table that reflects the distribution of codons found in genes, or a class of genes (e.g. highly expressed genes) in one or more expression organisms; (03) select a threshold frequency. Codons that are used with a frequency below this threshold will be rejected from the design. (04) Select the next amino acid in the polypeptide. (05) Select a codon that encodes the amino acid, by using the codon bias table to provide the probability of selection. (06) Ensure that the selected codon is above the threshold. If it is not return to 05. Otherwise proceed to 07. (07) Check that the last N nucleotides have a GC content within defined limits. The number of nucleotides (N) and the GC content are both parameters that can be varied in the method. If this criterion is not satisfied proceed to 11. Otherwise proceed to 08. (08) Check that the last M nucleotides of sequence do not contain a forbidden restriction site. The number of nucleotides (M) and the list of sites to be avoided are both parameters that can be varied in the method. If the sequence does contain a forbidden site proceed to 11. Otherwise proceed to 09. (09) Check whether the last P nucleotides contain a subsequence that will anneal to any subsequence in the polynucleotide (or its reverse complement) with a calculated Tm of >Y° C. The number of nucleotides (P) and the annealing temperature are both parameters that can be varied in the method. If the sequence does contain a forbidden subsequence proceed to 11. Otherwise proceed to 10. (10) Accept the codon and proceed to 04.

(11-14) If any of the criteria from steps 07, 08 or 09 are not met, the move back some length of sequence (Z amino acids, where Z is preferably between 2 and 20 amino acids, more preferably between 5 and 10 amino acids) in the polypeptide, delete the codons that were selected for those amino acids and reselect those codons (Steps 11 and 12). Because the codons are selected probabilistically, different iterations of the process will produce different sequences that still fulfill the functional codon bias criteria. This process is repeated X number of times, where X is preferably less than 10,000, more preferably less than 1,000. If X iterations are repeated without meeting all of the desired criteria, a report is generated describing the failure, the codon is accepted, and the process proceeds to the next amino acid. This is to prevent the method from becoming trapped in an endless loop if no solutions are available. The report will then allow manual adjustment of the constraints to obtain an acceptable solution (such as reducing the threshold for a single position or relaxing the repeat or GC content requirement).

Figure 28:
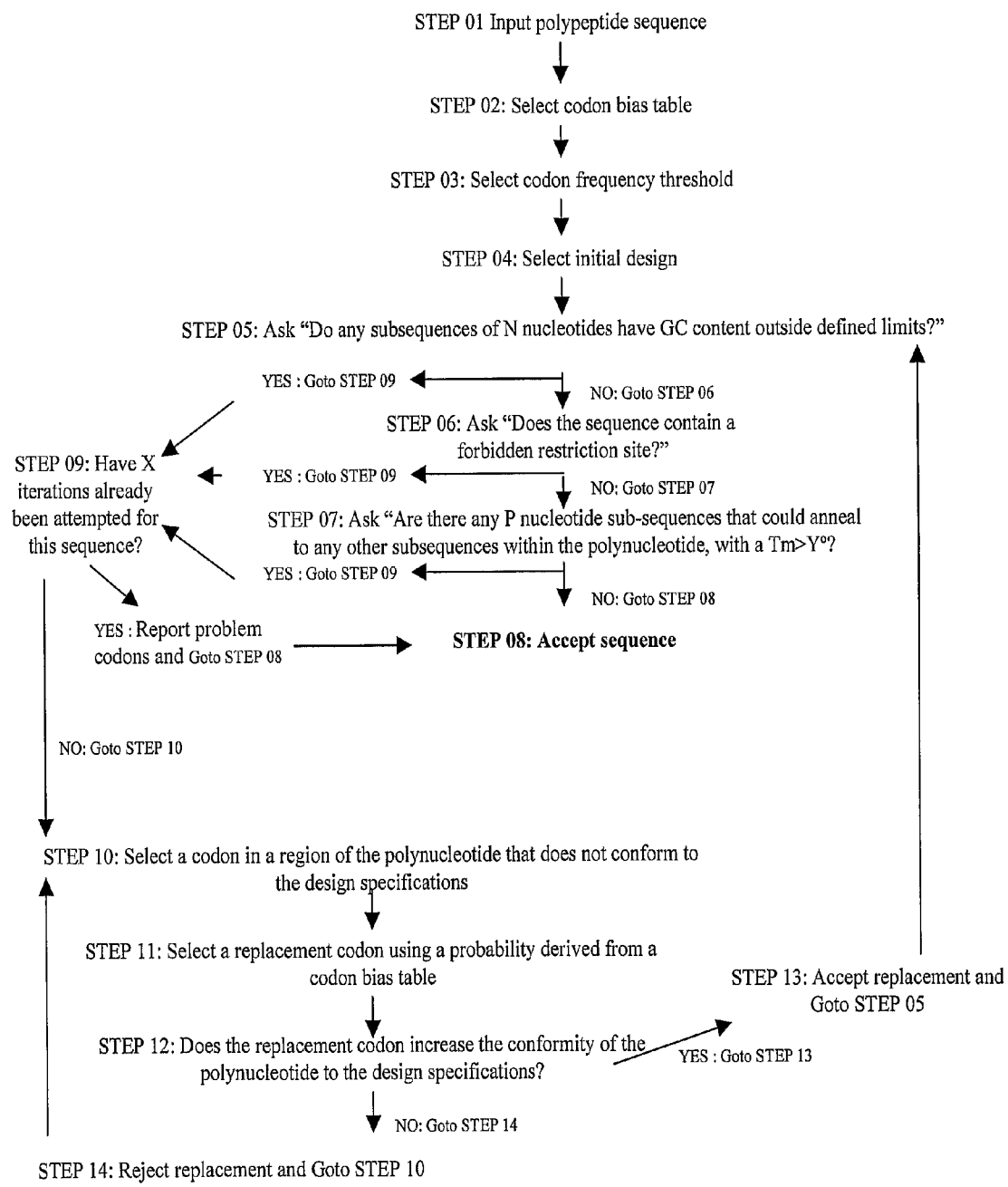

FIG. 28 illustrates an automatable process for modifying a designed polynucleotide to alter some properties (such as restriction sites, GC content and repeated subsequences) while retaining others (such as overall codon bias). (01) input a polypeptide sequence for which an encoding polynucleotide is desired; (02) select a codon bias table that reflects the distribution of codons found in genes, or a class of genes (e.g. highly expressed genes) in one or more expression organisms; (03) select a threshold frequency. Codons that are used with a frequency below this threshold will be rejected from the design. (04) Select an initial sequence design. This may be accomplished by using a method disclosed herein, or by selecting codons using a codon bias table but without applying any additional constraints. (05) identify whether any subsequence of N nucleotides has a GC content outside defined limits. The number of nucleotides (N) and the GC content are both parameters that can be varied in the method. If there are any such subsequences, proceed to 10. Otherwise proceed to 06. (06) Identify whether the polynucleotide contains any forbidden restriction sites. The list of sites to be avoided is a parameter that can be varied in the method. If the sequence does contain a forbidden site proceed to 10. Otherwise proceed to 07. (07) Check whether the polynucleotide contains any subsequences that will anneal to any subsequence in the polynucleotide (or its reverse complement) with a calculated Tm of >Y° C. The length of such subsequences is preferably between 6 and 40 nucleotides, more preferably between 8 and 30 nucleotides and even more preferably between 10 and 25 nucleotides. The size of the subsequence and the annealing temperature are both parameters that can be varied in the method. If the sequence does contain a forbidden subsequence proceed to 10. Otherwise proceed to 08. (08) Accept the sequence. (09-14) If the design fails any of the criteria from steps 05, 06 or 07, the method selects one codon in one of the regions that does not conform to the design specifications, and replaces it using another codon selected probabilistically from a codon bias table. The new polynucleotide sequence is then assessed to see whether it more closely conforms to the design specifications than the sequence before the replacement. If it does, the replacement is accepted, if not it is rejected.

Figure 29:
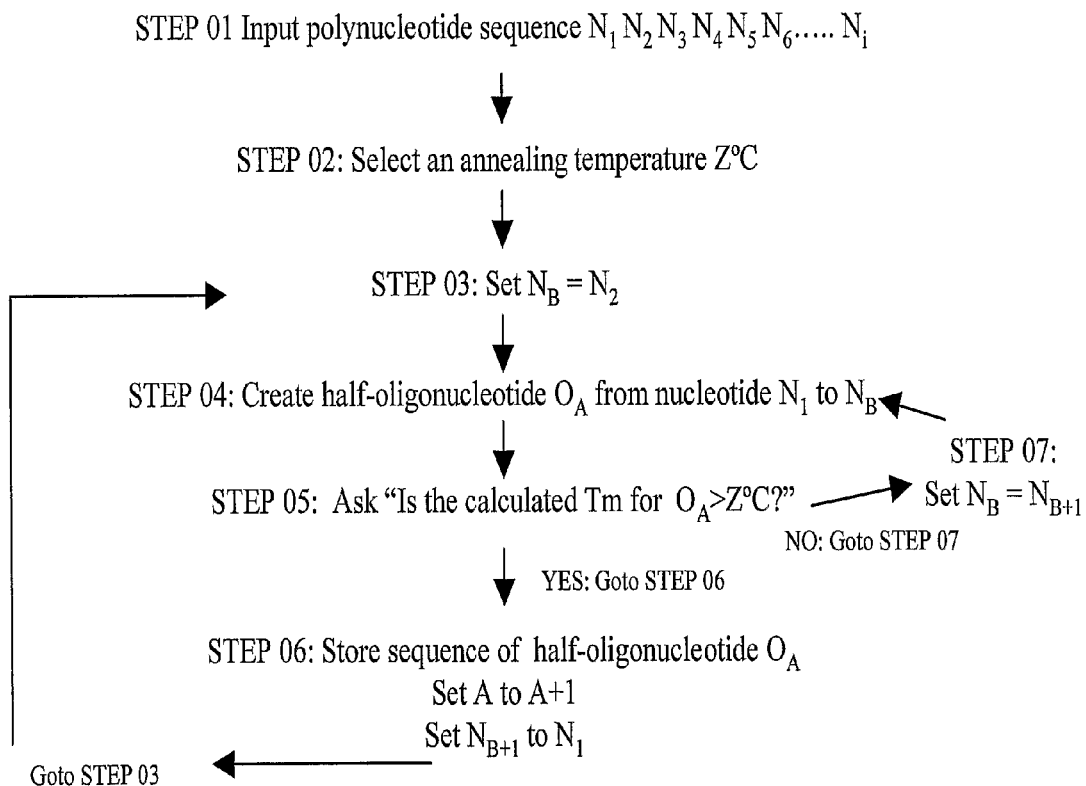

FIG. 29 illustrates an automatable process for designing a set of half-oligonucleotides as a basis for an oligonucleotide set for assembly into a polynucleotide. The half-oligonucleotides are designed to have a very close range of calculated annealing temperatures. (01) Input a polynucleotide sequence. (02) Select an annealing temperature Z° C., where Z is preferably between 40° C. and 80° C., more preferably between 50° C. and 76° C., even more preferably between 60° C. and 74° C. (04, 05 and 07) Starting at the first position in the polynucleotide, begin adding nucleotides until a subsequence is obtained with an annealing temperature greater than the set annealing temperature. (06) Define the subsequence as one "half oligonucleotide". Repeat the process by resetting the start of a new half oligonucleotide (OA, with A set to A+1) to the first nucleotide following the just completed half oligonucleotide (set NB+1 to N1). The process continues until the entire polynucleotide has been divided into half-oligonucleotides.

Figure 30:
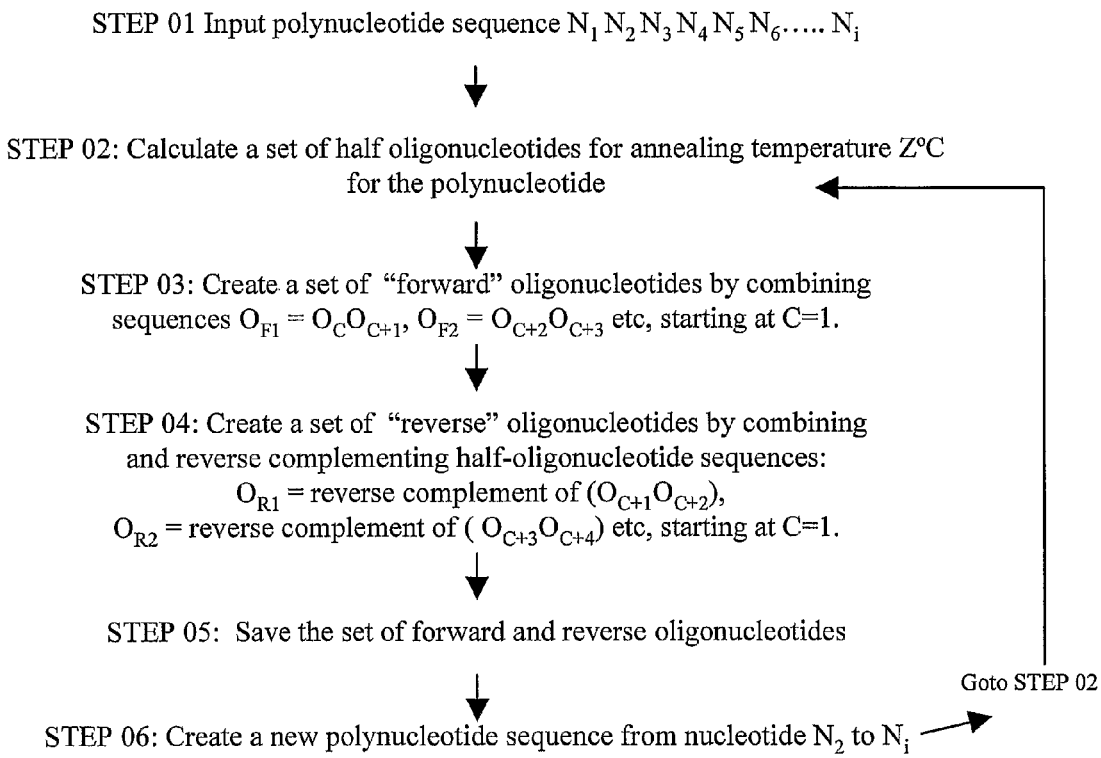

FIG. 30 illustrates an automatable process for combining pairs of half-oligonucleotides to design an oligonucleotide set for assembly into a polynucleotide. This process can be encoded into a computer program. This process produces a set of oligonucleotide designs, each with a tight range of annealing temperatures. (01) input a polynucleotide sequence. (02) Calculate a set of half oligonucleotides. For example, by using the process shown schematically in FIG. 29. (03) Create a set of forward oligonucleotides by combining the first with second, the third with the fourth, the fifth with the sixth half oligonucleotides and so on. (04) Create a set of reverse oligonucleotides by combining the second with the third, the fourth with the fifth, the sixth with the seventh half oligonucleotides and so on. Each of these sequences should then be reverse complemented to provide the set of reverse oligonucleotides. (05) The forward and reverse set of oligonucleotides are then saved. (06) A new set of forward and reverse oligonucleotides are then created, with the starting point for the first half-oligonucleotide advanced by 1 nucleotide from the previous set. This process is repeated until the starting position is the first nucleotide of OF2 from the first set. A set of oligonucleotides starting from this position would be identical to the first set, except that OF1 would be missing.

Figure 31:
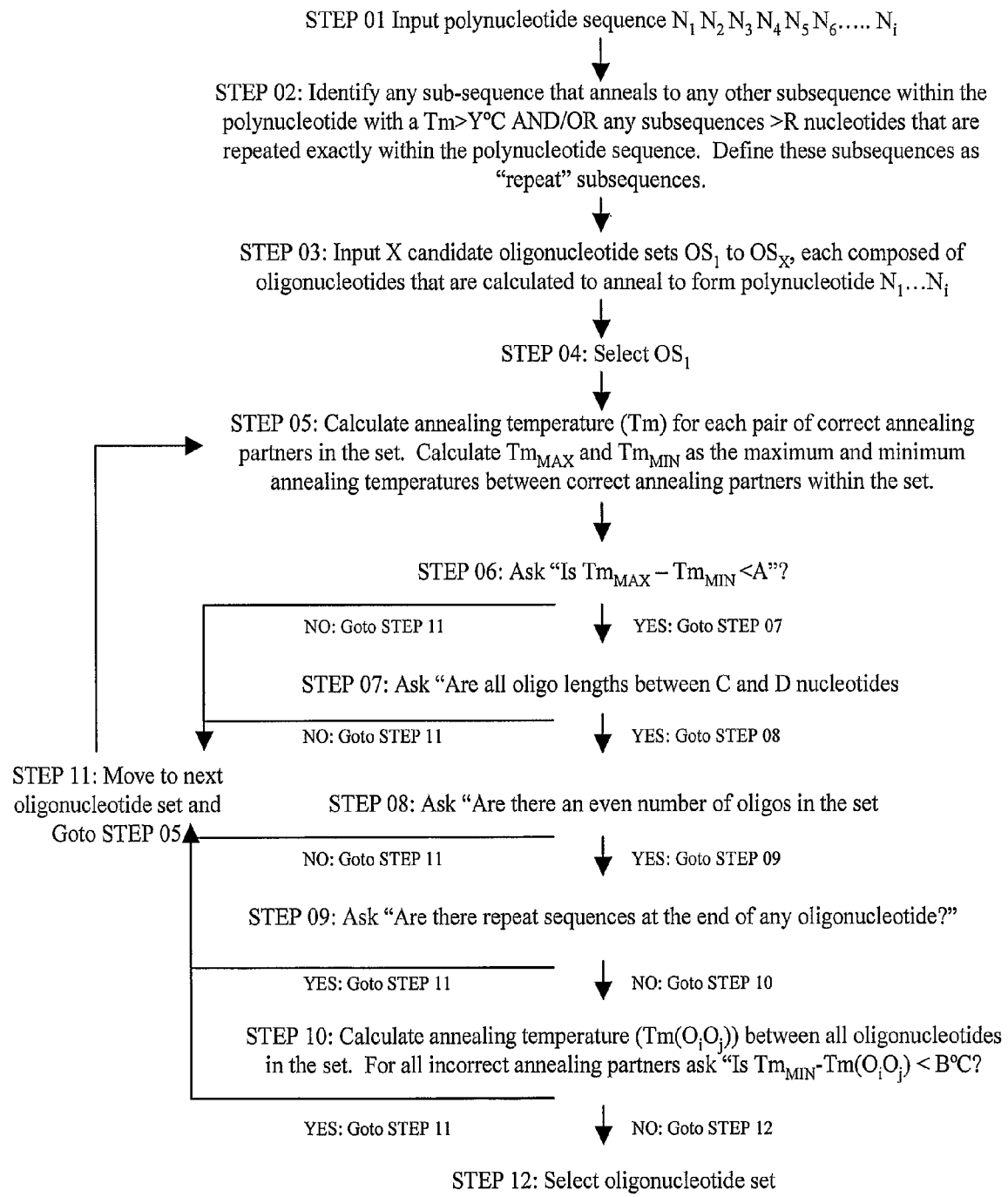

FIG. 31 illustrates an automatable process for selecting an oligonucleotide set suitable for assembly into a polynucleotide. (01) Input a polynucleotide sequence. (02) Identify and flag any subsequences that are repetitive defined either by annealing properties with other parts of the polynucleotide, or by sequence matches. The annealing temperature and the length of sequence match are both parameters that can be varied in the method. (03) Input candidate oligonucleotide sets. Such sets can be produced by many methods, including for example by the methods shown in FIGS. 29 and 30. (04) Select one of the candidate sets. (05) Calculate the annealing temperatures for all of the correct annealing partners in the oligonucleotide set. Calculate the highest and lowest annealing temperatures within the set. (06) Determine whether the range of annealing temperatures for the correct annealing partners within the set is smaller than some specified value (A). If yes, proceed to 07. If no, proceed to 11. The annealing temperature range is a parameter that can be varied in the method. (07) Determine whether the range of oligonucleotide lengths within the set is between two specified values (C and D). If yes, proceed to 08. If no, proceed to 11. The lower and upper limits are parameters that can be varied in the method. (08) Determine whether there are an even number of oligonucleotides in the set. If yes, proceed to 09. If no, proceed to 11. (09) Determine whether there are repeat sequences (flagged in O2) at the end of any oligonucleotide. If no, proceed to 10. If yes, proceed to 11. (10) Determine whether any pair of incorrect annealing partners have an annealing temperature closer than a defined value (B) to the lowest annealing temperature between correct annealing partners. The value (B) is a parameter that can be varied in the method. If yes, proceed to 11. If no, proceed to 12. (11) If the set fails based on any of the criteria described, a new set of oligonucleotides may be selected and tested. If all sets fail, the adjustable parameters may be altered until an oligonucleotide set is identified that fulfills the relaxed selection criteria. (12) If a set passes all selection criteria, it is accepted.

FIG. 32 illustrates a PCR protocol for assembly of a gene of length <500 bp. The exact annealing temperature depends upon the calculated annealing temperatures of the correct annealing partners in the oligonucleotide set. For example, if the calculated annealing temperatures are in the range from 62° C. to 65° C., the PCR annealing temperature should be between 58° C. and 65° C.

FIG. 33 illustrates a PCR protocol for assembly of a gene of length 500-750 bp. The exact annealing temperature depends upon the calculated annealing temperatures of the correct annealing partners in the oligonucleotide set. For example, if the calculated annealing temperatures are in the range form 62° C. to 65° C., the PCR annealing temperature should be between 58° C. and 65° C.

FIG. 34 illustrates a PCR protocol for assembly of a gene of length 750-1,000 bp. The exact annealing temperature depends upon the calculated annealing temperatures of the correct annealing partners in the oligonucleotide set. For example, if the calculated annealing temperatures are in the range form 62° C. to 65° C., the PCR annealing temperature should be between 58° C. and 65° C.

FIG. 35 illustrates a PCR protocol for assembly of a gene of length 1,000-1,500 bp. The exact annealing temperature depends upon the calculated annealing temperatures of the correct annealing partners in the oligonucleotide set. For example, if the calculated annealing temperatures are in the range form 62° C. to 65° C., the PCR annealing temperature should be between 58° C. and 65° C.

FIG. 36 illustrates a PCR protocol for assembly of a gene of length 1,500-2,000 bp. The exact annealing temperature depends upon the calculated annealing temperatures of the correct annealing partners in the oligonucleotide set. For example, if the calculated annealing temperatures are in the range form 62° C. to 65° C., the PCR annealing temperature should be between 58° C. and 65° C.

Figure 37:
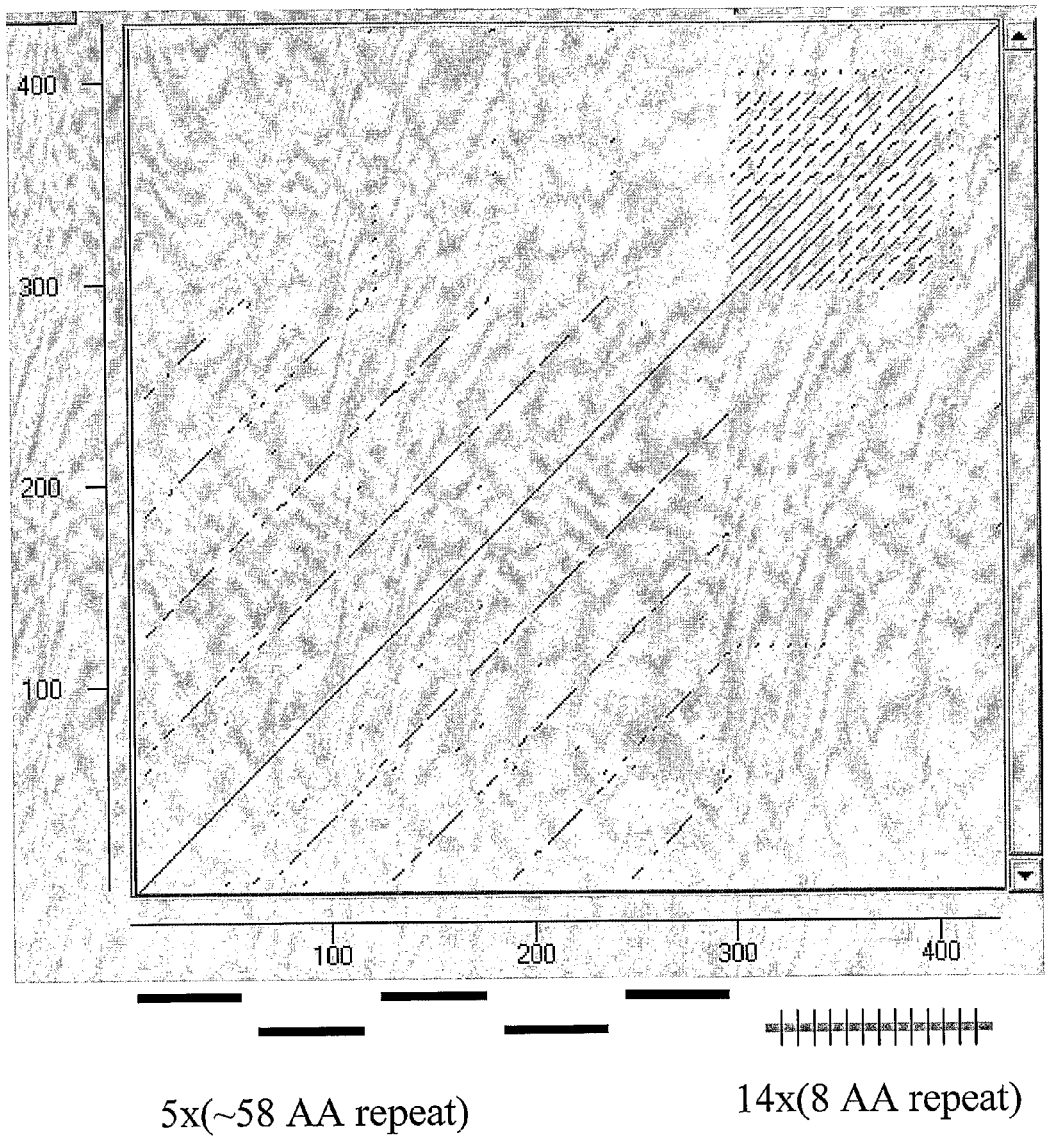

FIG. 37 illustrates a dot-plot representation of repetitive sequence elements within a polypeptide. The same sequence is represented on the vertical and horizontal axes. The entire sequence was scanned using all consecutive overlapping 3 amino acid sequence elements. Dots and lines off the diagonal indicate repeated sequence elements within the polynucleotide.

Figure 38:
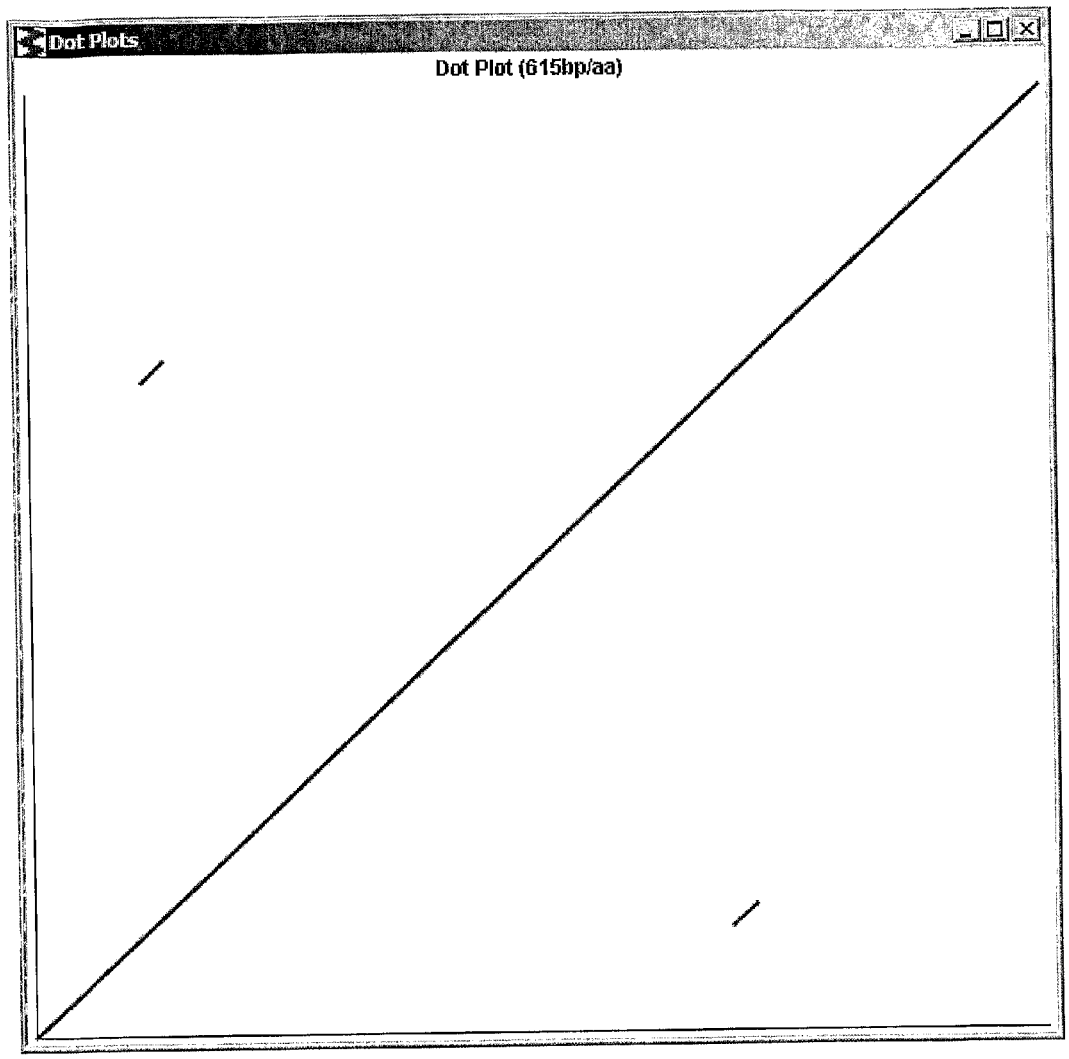

FIG. 38 illustrates a dot-plot representation of repetitive sequence elements within Part 1 of the polynucleotide shown in FIG. 37. The same sequence is represented on the vertical and horizontal axes. The entire sequence was scanned using all consecutive overlapping 12 base pair sequence elements. Dots and lines off the diagonal indicate repeated sequence elements within the polynucleotide.

Figure 39:
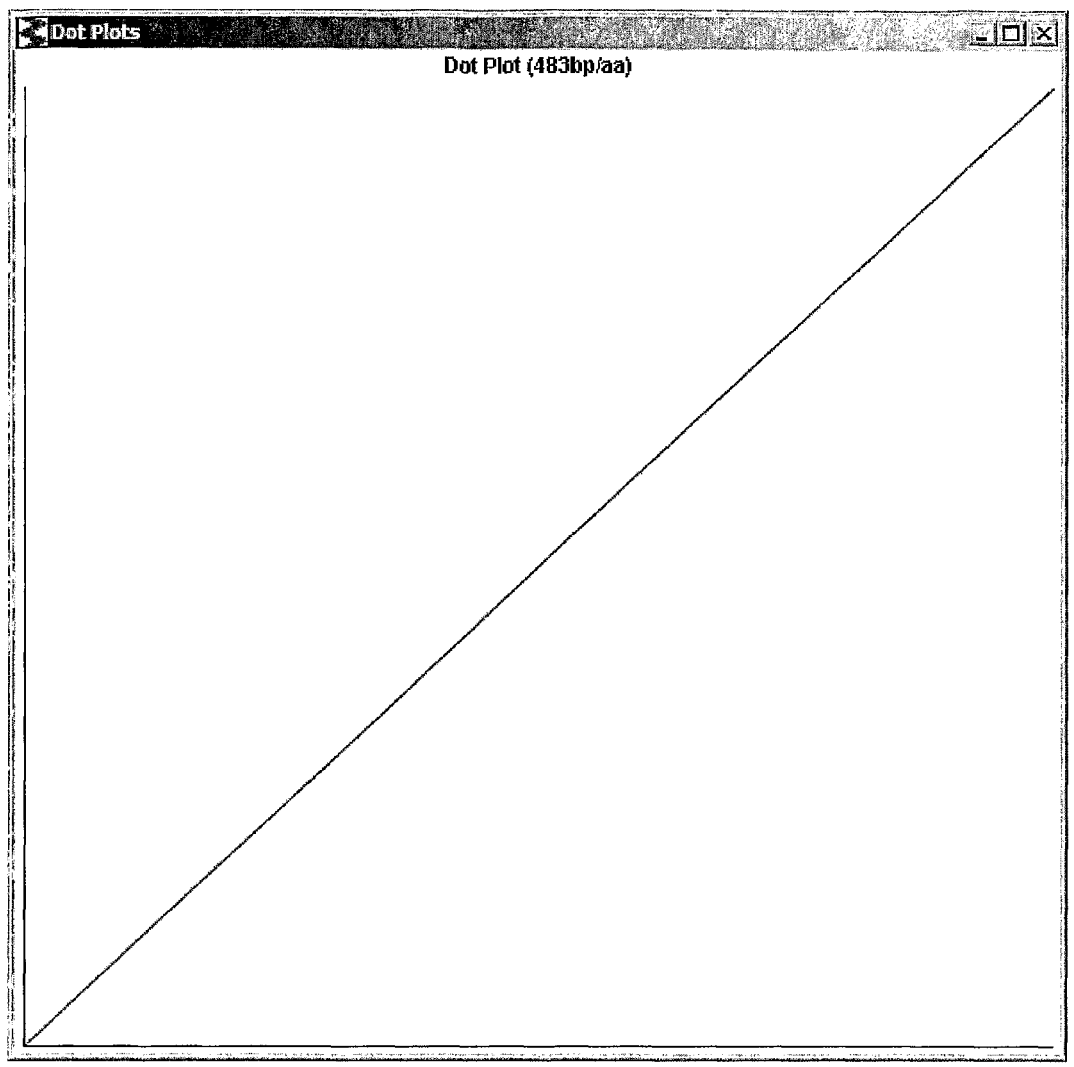

FIG. 39 illustrates a dot-plot representation of repetitive sequence elements within Part 2 of the polynucleotide shown in FIG. 37. The same sequence is represented on the vertical and horizontal axes. The entire sequence was scanned using all consecutive overlapping 12 base pair sequence elements. Dots and lines off the diagonal indicate repeated sequence elements within the polynucleotide.

Figure 40:
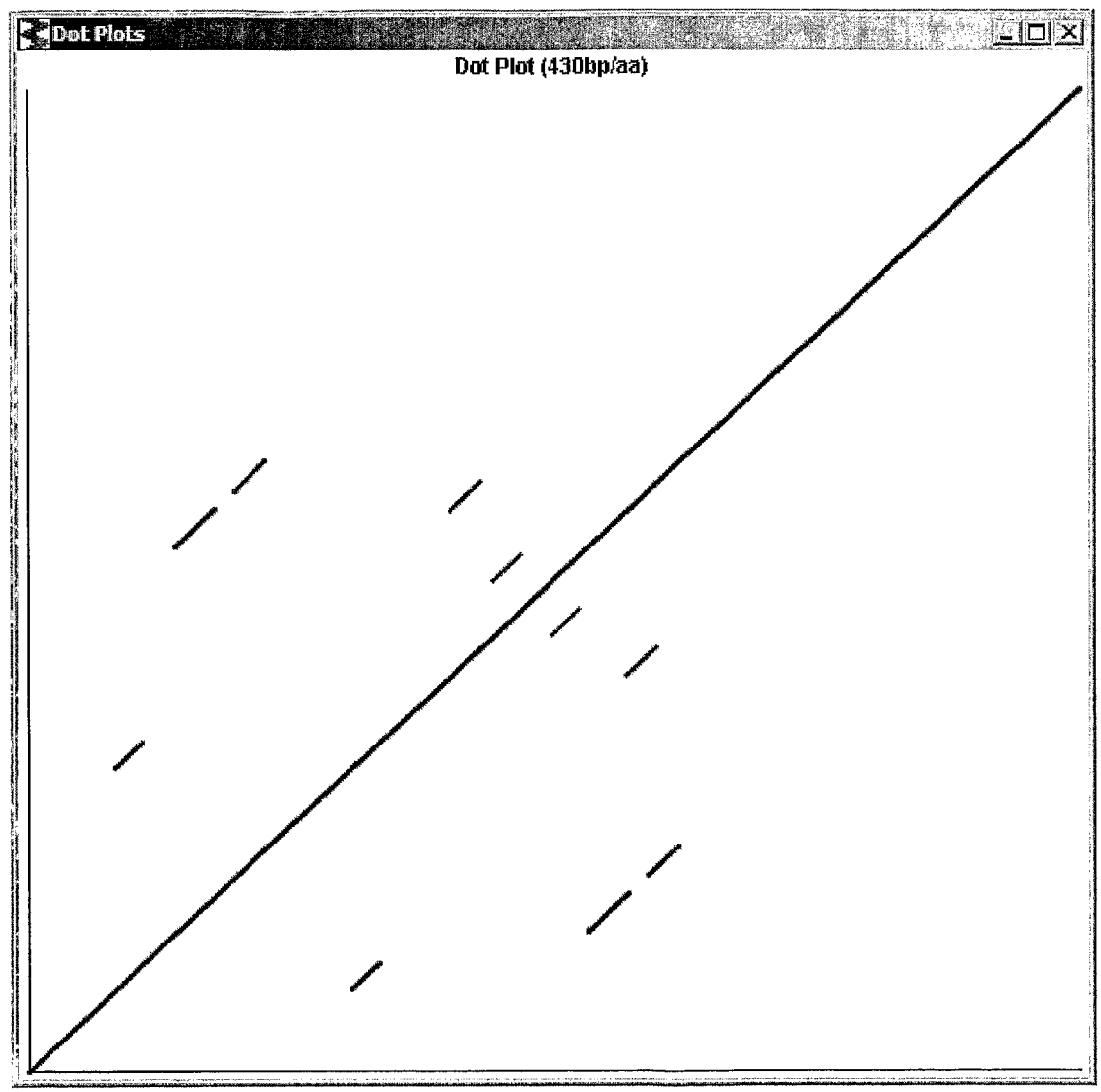

FIG. 40 illustrates a dot-plot representation of repetitive sequence elements within Part 3 of the polynucleotide shown in FIG. 37. The same sequence is represented on the vertical and horizontal axes. The entire sequence was scanned using all consecutive overlapping 12 base pair sequence elements. Dots and lines off the diagonal indicate repeated sequence elements within the polynucleotide.

FIG. 41 illustrates type IIS restriction sites useful for joining sections of a polynucleotide. The figure shows different type IIs restriction enzymes that may be used to generate compatible sticky ends useful for subsequent ligation of two or more DNA fragments. The targeted overhangs resulting from digestion are indicated in bold letters with alphabetic subscripts (e.g. $N_A N_B$ etc). Other nucleotides within the polynucleotide sequence are indicated with numerical subscripts, negative numbers indicating that the bases are before (i.e. 5' of) the targeted ligation overhang, positive numbers indicating that the bases are after (i.e. 3' of) the targeted ligation overhang. The figure shows a general scheme by which compatible ends may be generated in synthetic DNA segments, by adding the indicated sequences to the 3' end of the intended 5' segment, and to the 5' end of the intended 3' segment. Providing the same kind of overhang is produced (i.e. the same number of bases and either 3' or 5'), different restriction enzymes may be used to digest the different fragments.

Figure 42:
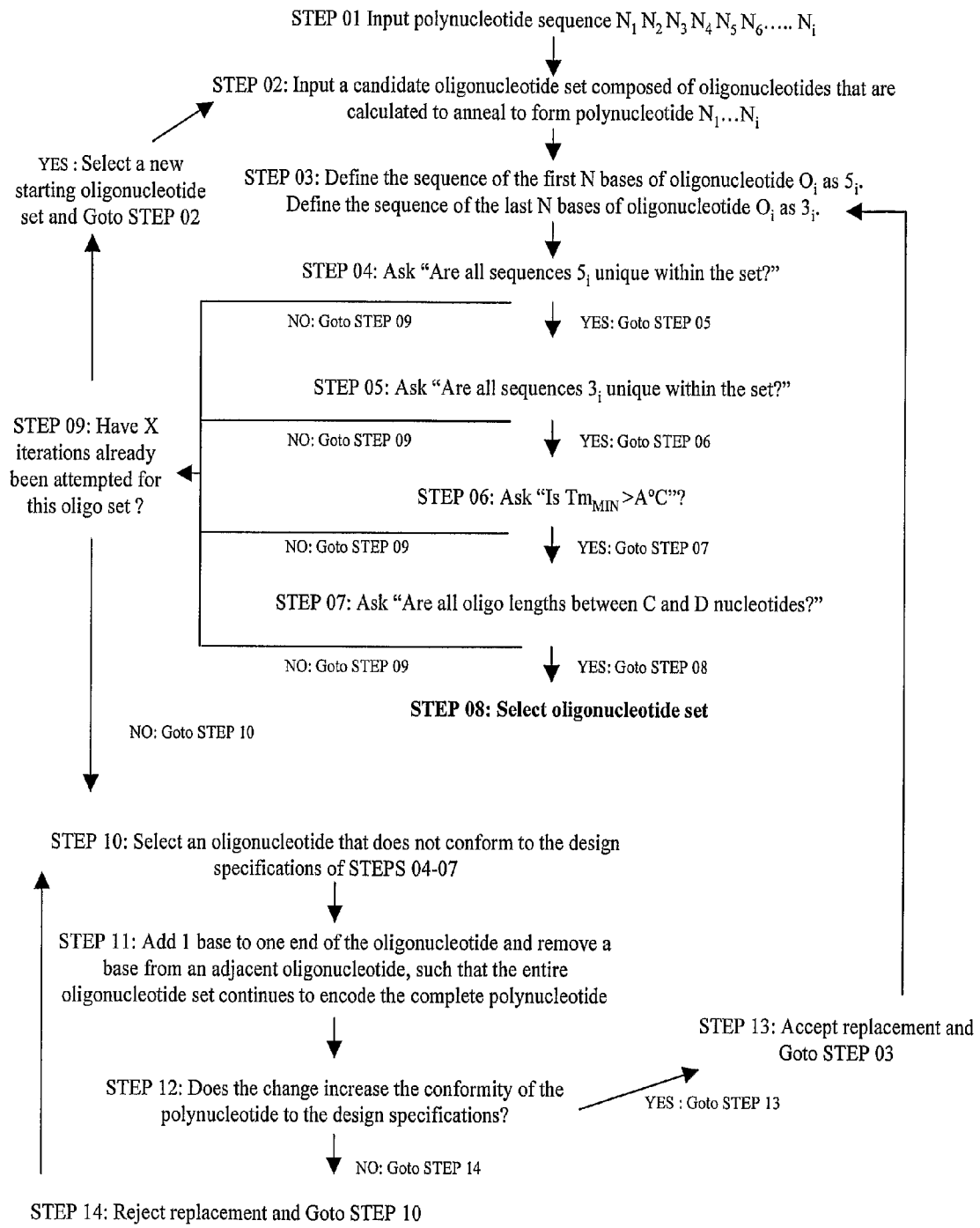

FIG. 42 illustrates an automatable process for selecting an oligonucleotide set suitable for assembly into a polynucleotide using ligation- or ligation chain reaction-based methods. This process can be encoded into a computer program. (01) Input a polynucleotide sequence. (02) Input a candidate set of oligonucleotides. Such sets can be produced by many methods, including for example by the methods shown in FIGS. 29 and 30. (03) For ligation-based assembly methods, the most important sequence recognition occurs at the ends of the sequence. Sequence designs that minimize incorrect ligation are thus those that minimize sequence similarities at the end of the oligonucleotides. This step defines the sequences at the ends. The length of this sequence is a parameter that can be varied within the method. (04) Determine whether the 5' ends of all the oligos are unique. If yes, proceed to 05. If no, proceed to 09. (05) Determine whether the 3' ends of all the oligos are unique. If yes, proceed to 06. If no, proceed to 09. (06) Determine whether the minimum annealing temperatures for the correct annealing partners within the set is greater than some specified temperature (A). If yes, proceed to 07. If no, proceed to 09. The annealing temperature range is a parameter that can be varied in the method. (07) Determine whether the range of oligonucleotide lengths within the set is between two specified values (C and D). If yes, proceed to 08. If no, proceed to 11. The lower and upper oligonucleotide lengths are parameters that can be varied in the method. (08) Accept the design. (09) Count the number of attempts to modify the oligonucleotide set (X). This number is a parameter that can be varied in the method. If the number of attempts exceeds the set number, choose a new set of oligonucleotides and proceed to 02. If the number of attempts does not exceed X, proceed to 10. (10-14) If the design fails any of the criteria from steps 04, 05, 06 or 07, the method selects one oligonucleotide that does not conform to the design specifications, and moves the boundary between it and an adjacent oligonucleotide. The new oligonucleotide set is then assessed to see whether it more closely conforms to the design specifications than the set before the replacement. If it does, the replacement is accepted, if not it is rejected.

FIG. 43 illustrates the thermocycling protocol for assembly of a gene by ligation using a thermostable DNA ligase. The exact annealing temperature depends upon the calculated annealing temperatures of the correct annealing partners in the oligonucleotide set. For example, if the calculated annealing temperatures are in the range from 62° C. to 65° C., the PCR annealing temperature should be between 58° C. and 65° C.

Figure 44:
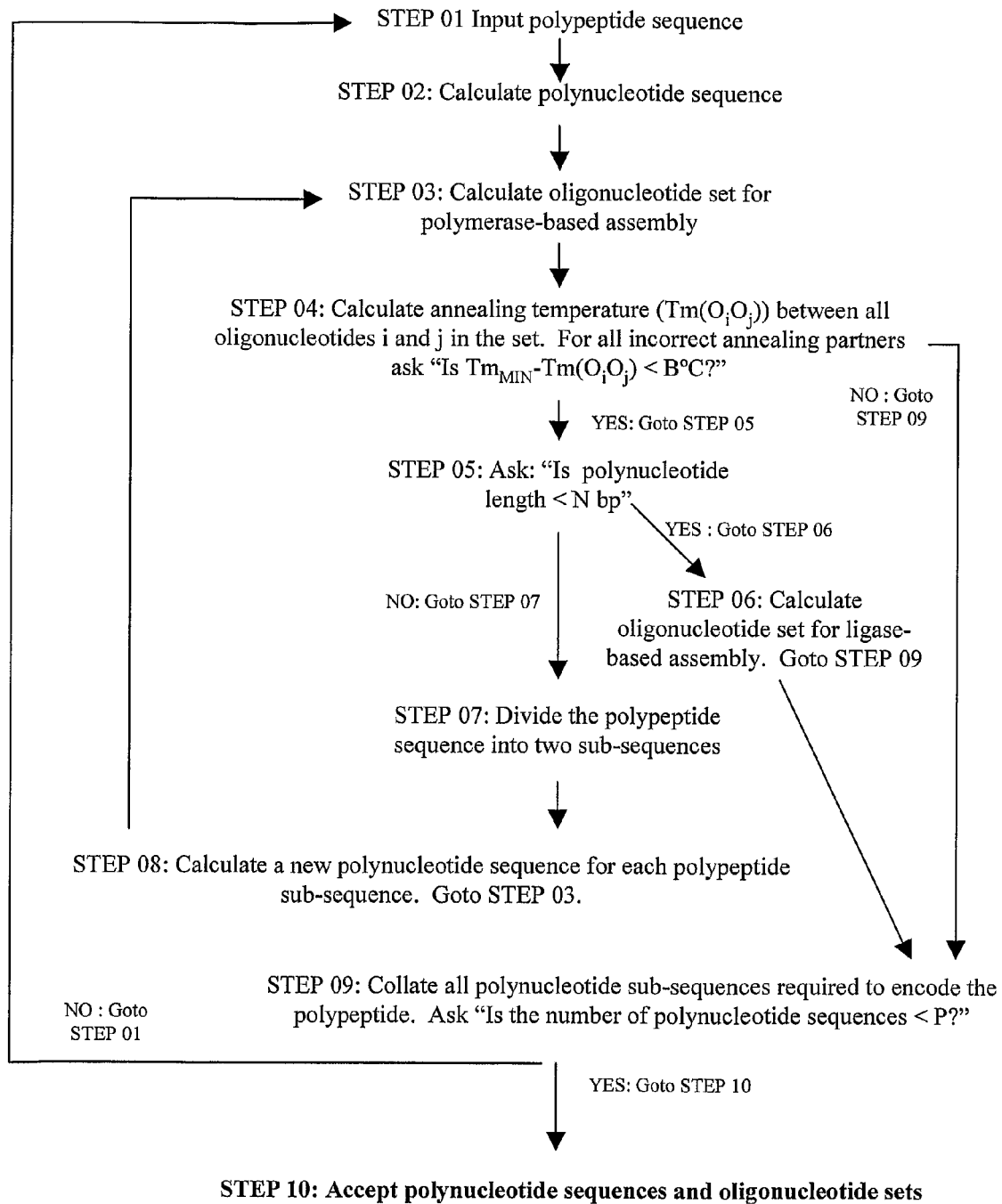

FIG. 44 illustrates an automatable process for designing a polynucleotide in parts. This process can be encoded into a computer program. (01) Input a polypeptide sequence. (02) Calculate a polynucleotide sequence that encodes the polypeptide. Processes such as those shown in FIG. 26, 27 or 28 are possible ways of calculating the polynucleotide. Varying the parameters within these methods will result in different polynucleotides. (03) Calculate an oligonucleotide set that will assemble into the calculated polynucleotide. Processes such as those shown in FIGS. 29, 30 and 31 are possible ways of calculating the oligonucleotide sets. Varying the parameters within these methods will result in different oligonucleotide sets. (04) Determine whether any pair of incorrect annealing partners have an annealing temperature closer than a defined value (B) to the lowest annealing temperature between correct annealing partners. The aim of this step is to determine whether there are oligonucleotides that are likely to present a problem by annealing to incorrect partners during the assembly process. The value B is a parameter that can be varied in the method. If no, proceed to 09. If yes, proceed to 05. (05) Determine whether the length of the polynucleotide is less than N base pairs long. The value N is a parameter that can be varied in the method. If yes, then further division is undesirable, and the design criteria should be changed to allow ligase-based assembly instead of polymerase-based assembly, so proceed to 06. If no, proceed to 07. (06) Calculate an oligonucleotide set to assemble into the polynucleotide using a ligase-based method. One example of such a method is the process shown in FIG. 26. (07) Divide the polypeptide into two sub-sequences. There are many different ways to divide the polypeptide. For example it can be divided between two residues such that the division separates two incorrect annealing partners with high annealing temperatures within the oligonucleotide set. The polypeptide can also be divided randomly. (08) For each part of the polypeptide design a polynucleotide segment to encode it. Many methods are available for design of polynucleotide encoding a specific polypeptide sequence, including those shown in FIGS. 26, 27 and 28. Each polynucleotide may also include restriction sites useful in joining the polynucleotide segments together; for example the type IIs restriction sites shown in FIG. 40 may be added to the ends of the sequence in order to produce a complementary overlap between polynucleotide segments. In addition a recombinase-recognition sequence may be added to the end of each polynucleotide segment to facilitate independent cloning of each polynucleotide segment by a recombinase-based method. Since steps 03 to 08 are iterative, the original polypeptide may be divided into more than 2 sub-sequences. It is important to ensure that the resultant polynucleotide segments can be joined, for example by overlap extension or restriction digestion and ligation, to form a single polynucleotide. Return to 03. (09) Count the number of polynucleotides. If the number is <P accept the design. If the number is >P reject the design and return to 01. Because the design methods are probabilistic, a repeat of the process will yield a different solution that may conform to the design criteria. The value P is a parameter that can vary within the method.

Figure 45:
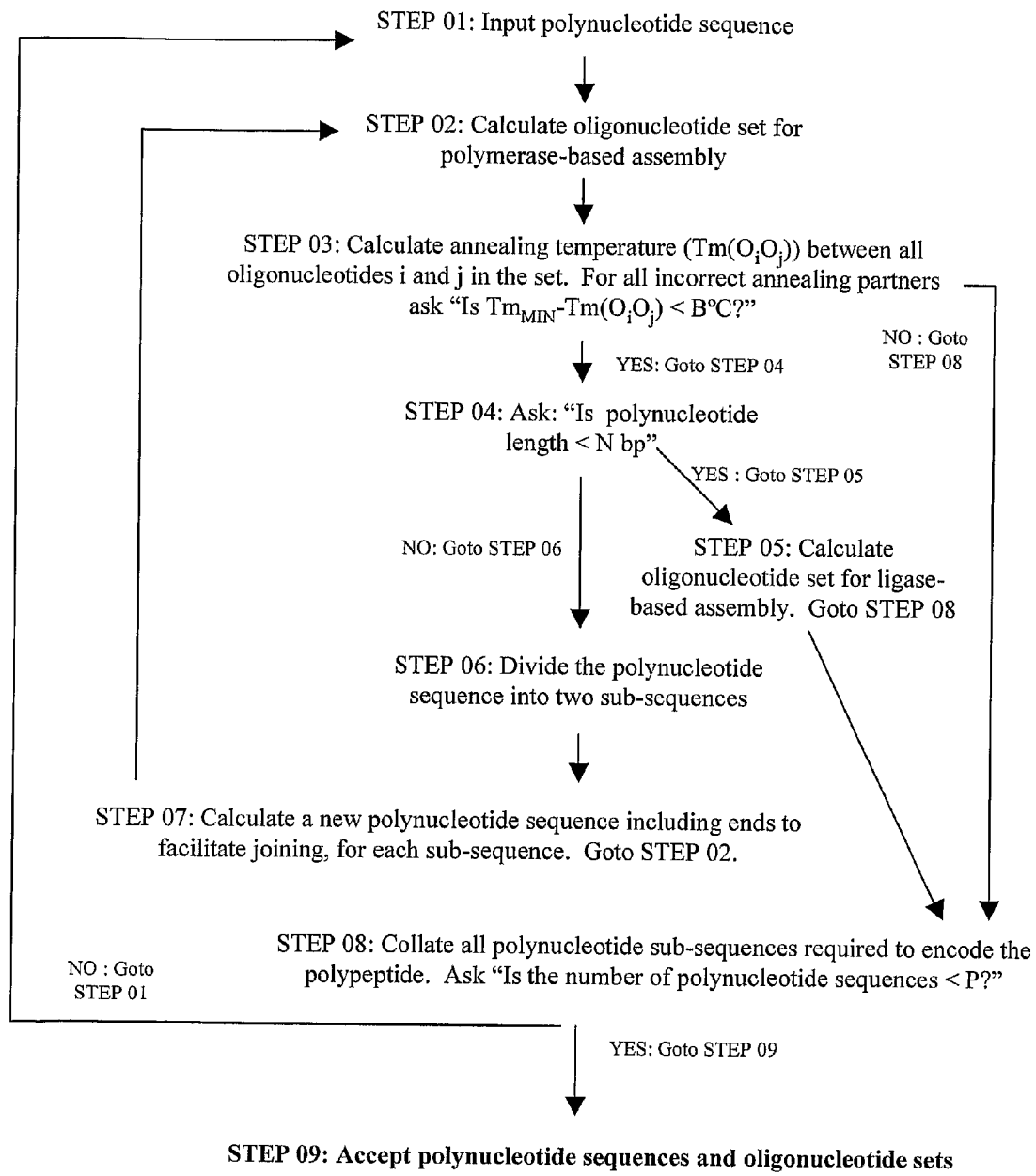

FIG. 45 illustrates an automatable process for designing a polynucleotide in parts. This process can be encoded into a computer program. (01) Input a polynucleotide sequence. (02) Calculate an oligonucleotide set that will assemble into the calculated polynucleotide. Processes such as those shown in FIGS. 29, 30 and 31 are possible ways of calculating the oligonucleotide sets. Varying the parameters within these methods will result in different oligonucleotide sets. (03) Determine whether any pair of incorrect annealing partners have an annealing temperature closer than a defined value (B) to the lowest annealing temperature between correct annealing partners. The aim of this step is to determine whether there are oligonucleotides that are likely to present a problem by annealing to incorrect partners during the assembly process. The value B is a parameter that can be varied in the method. If no, proceed to 08. If yes, proceed to 04. (04) Determine whether the length of the polynucleotide is less than N base pairs long. The value N is a parameter that can be varied in the method. If yes, then further division is undesirable, and the design criteria should be changed to allow ligase-based assembly instead of polymerase-based assembly, so proceed to 06. If no, proceed to 07. (05) Calculate an oligonucleotide set to assemble into the polynucleotide using a ligase-based method. One example of such a method is the process shown in FIG. 26. (06) Divide the polynucleotide into two sub-sequences. There are many different ways to divide the polynucleotide. For example it can be divided between two residues such that the division separates two incorrect annealing partners with high annealing temperatures within the oligonucleotide set. The polynucleotide can also be divided randomly. (08) For each part of the polynucleotide, add overlap sequences or restriction sites that will be useful in joining the polynucleotide segments together; for example the type IIs restriction sites shown in FIG. 25 may be added to the ends of the sequence in order to produce a complementary overlap between polynucleotide segments. In addition a recombinase-recognition sequence may be added to the end of each polynucleotide segment to facilitate independent cloning of each polynucleotide segment by a recombinase-based method. Since steps 03 to 08 are iterative, the original polynucleotide may be divided into more than 2 sub-sequences. It is important to ensure that the resultant polynucleotide segments can be joined, for example by overlap extension or restriction digestion and ligation, to form a single polynucleotide. Return to 02. (09) Count the number of polynucleotides. If the number is <P accept the design. If the number is >P reject the design and return to 01. Because the parameters for oligonucleotide design may be tuned differently, a repeat of the process may yield a different solution that may conform to the design criteria. Variation of the point of polynucleotide division can also give different results. The value P is a parameter that can vary within the method.

FIG. 46 illustrates a sequence of a vector (SEQ ID NO: 39) lacking most common restriction sites, carrying a kanamycin resistance gene and a pUC origin of replication. Inserts may be cloned into the EcoRV site.

FIG. 47 illustrates a sequence of a vector (SEQ ID NO: 40) lacking most common restriction sites, carrying a kanamycin resistance gene and a pUC origin of replication. Inserts carrying the appropriate ends, for example 5'-GGGGA-CAAGTTTGTACAAAAAAGCAGGCT-3' (SEQ ID NO: 41) at the 5' end and 5'-ACCCAGCTTTCTTGTA-CAAAGTGGTCCCC-3' (SEQ ID NO: 42) may be cloned into recombination sites in this vector using a commercially available lambda recombinase.

FIG. 48 illustrates a sequence of a vector (SEQ ID NO: 43) lacking most common restriction sites, carrying a kanamycin resistance gene and a pUC origin of replication. This vector is useful for construction of genes in parts. Digestion of the vector shown in FIG. 48 with the restriction enzyme BsaI excises a stuffer cassette sequence and leaves the vector with a TTTT overhang at one end and a CCCC overhang at the other end: aacggtctcCTTTTNNNNN . . . NNNNNNccccagagaccgtt (SEQ ID NO: 44). Addition of the sequence 5'-GGTCTCCTTTT-3' (SEQ ID NO: 45) to the 5' end of the 5' part of a synthetic polynucleotide synthesized in parts and addition of the sequence 5'-CCCCAGAGACC-3' (SEQ ID NO: 46) to the 3' end of the 3' part of a synthetic polynucleotide synthesized in parts, followed by digestion of the parts with BsaI, will create overhangs complementary to those of the vector.

Figure 49:
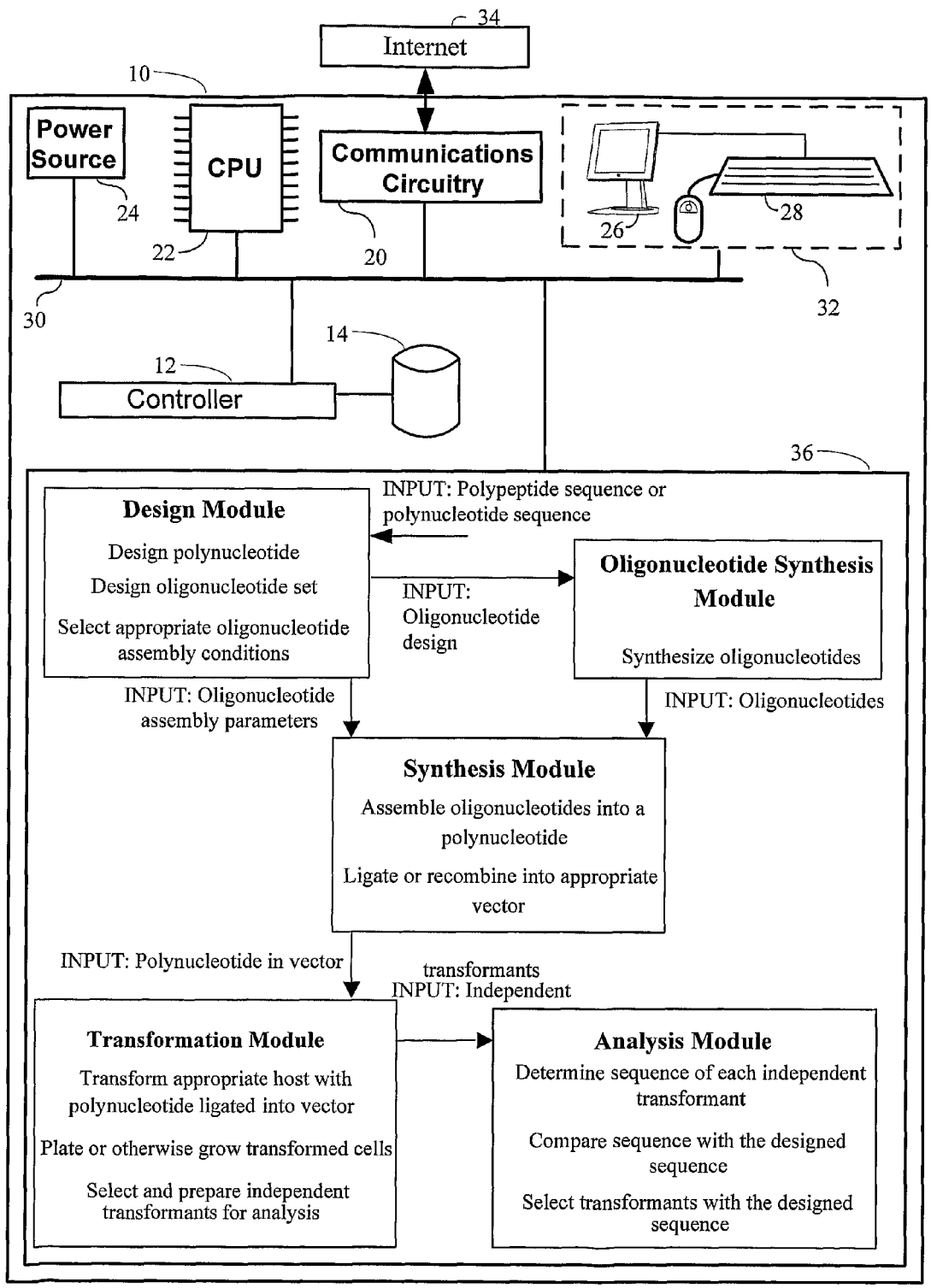

FIG. 49 illustrates components of an integrated device for synthesizing polynucleotides in accordance with the present invention. One or more of these modules may be designed to perform some or all of the processes required to synthesize polynucleotides, thereby resulting in a partially or fully integrated device. The design module is primarily bioinformatic module that performs the following tasks: (1) polynucleotide design, for example design of a polynucleotide to encode a specific polypeptide, reduction or elimination of repeat elements, design of two or more polynucleotides for synthesis and joining to form a single polynucleotide, (2) oligonucleotide design, for example reduction or elimination of annealing regions in incorrect annealing partners, design of a "constant Tm" set, (3) select the assembly conditions appropriate for the designed oligonucleotide set, for example the annealing temperature, the number of cycles and time for each cycle, the use of polymerase or ligase-based assembly conditions. The oligonucleotide synthesis module performs the physical process of oligonucleotide synthesis. The input to this module is a set of oligonucleotide sequences that is provided by the design module. The oligonucleotide synthesis module could be an outside oligonucleotide vendor that receives the sequence information electronically either directly from the design module, or via an intermediary such as an ordering system. The oligonucleotide synthesis module could also be an oligonucleotide synthesis machine that is physically or electronically linked to and instructed by the design module. The oligonucleotide synthesis module could synthesize oligonucleotides using standard phosphoramidite chemistry, or using the modifications described here. The synthesis module performs the physical process of assembling oligonucleotides into a polynucleotide. The synthesis module receives informational input from the design module, to set the parameters and conditions required for successful assembly of the oligonucleotides. It also receives physical input of oligonucleotides from the oligonucleotide synthesis module. The synthesis module is capable of performing variable temperature incubations required by polymerase chain reactions or ligase chain reactions in order to assemble the mixture of oligonucleotides into a polynucleotide. For example the synthesis module can include a thermocycler based on Peltier heating and cooling, or based on microfluidic flow past heating and cooling regions. The synthesis module also performs the tasks of amplifying the polynucleotide, if necessary, from the oligonucleotide assembly reaction. The synthesis module also performs the task of ligating or recombining the polynucleotide into an appropriate cloning vector. The transformation module performs the following tasks: (1) transformation of the appropriate host with the polynucleotide ligated into a vector, (2) separation and growth of individual transformants (e.g. flow-based separations, plating-based separations), (3) selection and preparation of individual transformants for analysis. The analysis module performs the following tasks (1) determination of the sequence of each independent transformant, (2) comparison of the determined sequence with the sequence that was designed, and (3) identification of transformants whose sequence matches the designed sequence.

Figure 50:
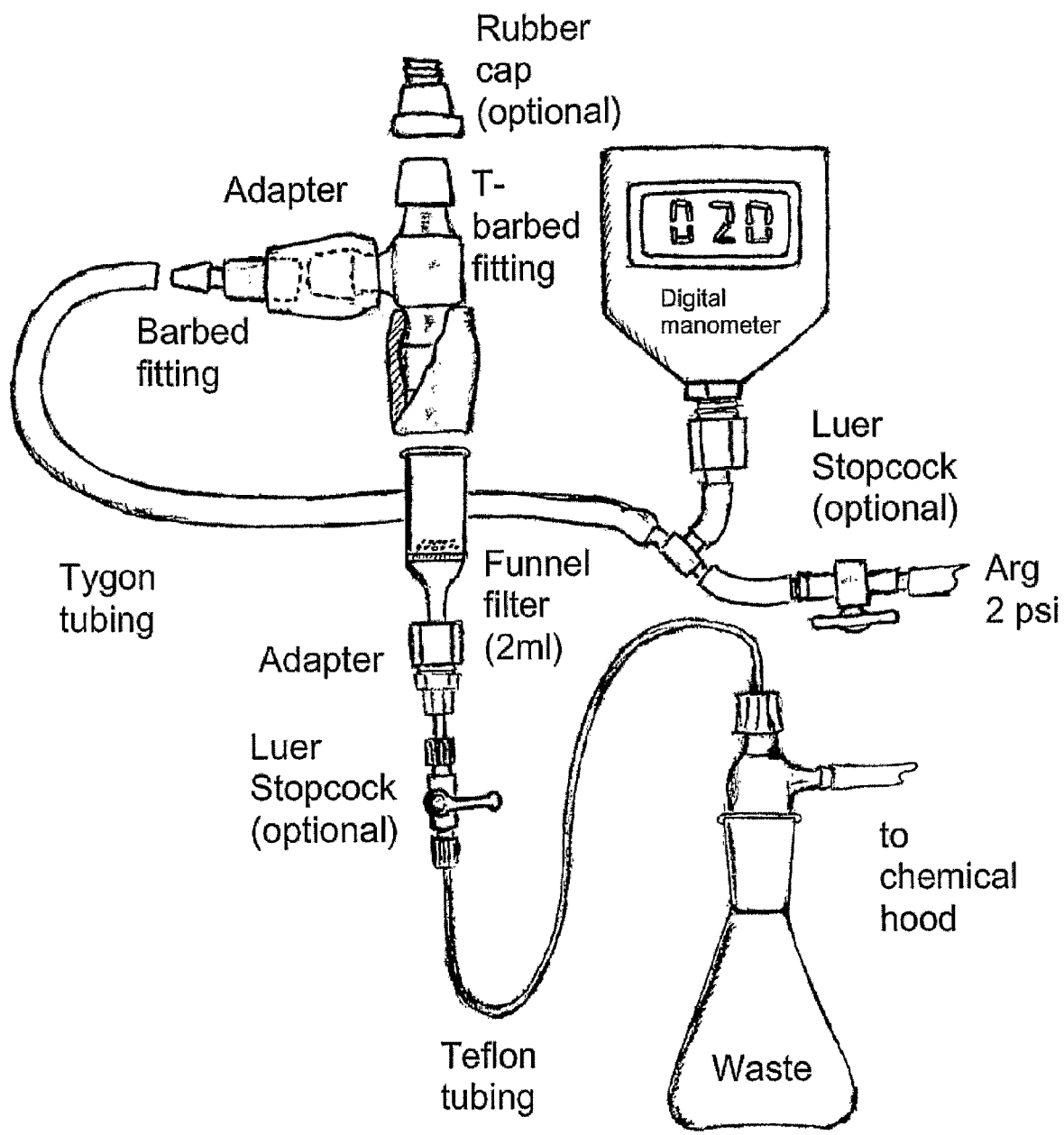

FIG. 50 illustrates the design for an oligonucleotide reaction vessel using argon flow in accordance with the present invention. Vacuum filtration is replaced by an argon purging procedure with pressure regulated using a manometer. An optional stopcock regulates the argon input. Another optional stopcock for closing waste permits steps that require keeping liquid inside the funnel longer then one minute.

Figure 51:
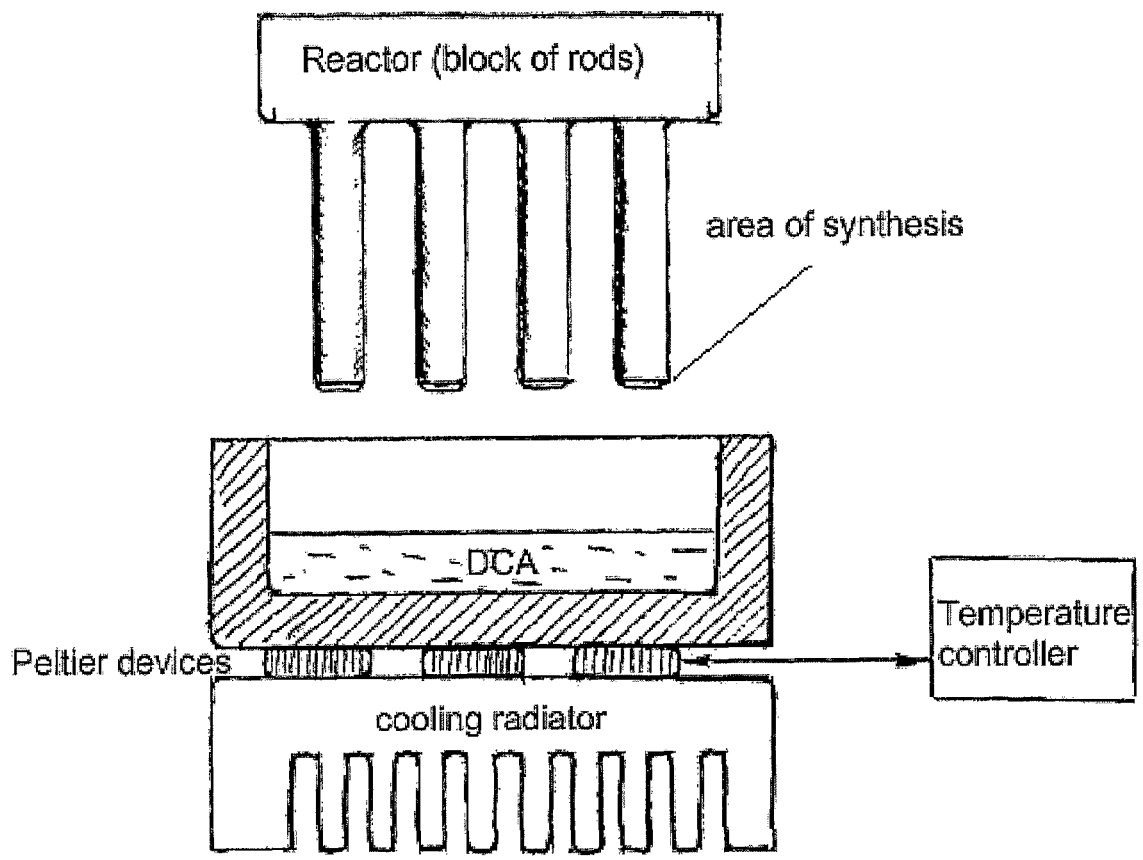

FIG. 51 illustrates the design for a temperature-controlled reaction vessel in accordance with the present invention. A Peltier temperature control block is used to regulate the temperature of the reaction chambers to enhance differentiation in the rates of wanted reactions and unwanted side-reactions.

FIG. 52 illustrates two designed P450 sequences. The first (A) (SEQ ID NO: 47) has an inverted repeat at the beginning. The second (B) (SEQ ID NO: 48) has a removal of that repeat by substitution of two nucleotides (i.e. choice of two alternative codons) increased expression between 5- and 10-fold.

5. DETAILED DESCRIPTION OF THE INVENTION

Before the present invention is described in detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

5.1 Definitions

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, reference to "a variant" includes a plurality of variants, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise herein, all technical and scientific terms used herein have the same meaning as commonly understood by one of ordinary skill in the art to which this invention belongs. Singleton, et al., *Dictionary of Microbiology and Molecular Biology*, 2nd Ed., John Wiley and Sons, New York (1994), and Hale & Marham, *The Harper Collins Dictionary of Biology*, Harper Perennial, NY, 1991, provide one of skill with a general dictionary of many of the terms used in this invention. Although any methods and materials similar or equivalent to those described herein can be used in the practice or testing of the present invention, the preferred methods and materials are described. Unless otherwise indicated, nucleic acids are written left to right in 5' to 3' orientation; amino acid sequences are written left to right in amino to carboxy orientation, respectively. The terms defined immediately below are more fully defined by reference to the specification as a whole.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

Where the polynucleotides are to be used to express encoded proteins, nucleotides that can perform that function or which can be modified (e.g., reverse transcribed) to perform that function are used. Where the polynucleotides are to be used in a scheme that requires that a complementary strand be formed to a given polynucleotide, nucleotides are used which permit such formation.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., where one or more of the hydroxyl groups are replaced with halogen, aliphatic groups, or is functionalized as ethers, amines, or the like.

Standard A-T and G-C base pairs form under conditions which allow the formation of hydrogen bonds between the N3-H and C4-oxy of thymidine and the NI and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-.beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-.beta.-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al., hereby incorporated by reference in its entirety). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al., 1993, J. Am. Chem. Soc. 115:4461-4467 and references cited therein; and isoguanine nucleotides may be prepared using the method described by Switzer et al., 1993, supra, and Mantsch et al., 1993, Biochem. 14:5593-5601, or by the method described in U.S. Pat. No. 5,780,610 to Collins et al., each of which is hereby incorporated by reference in its entirety. Other nonnatural base pairs may be synthesized by the method described in Piccirilli et al., 1990, Nature 343:33-37, hereby incorporated by reference in it entirety, for the synthesis of 2,6-diaminopyrimidine and its complement (1-methylpyrazolo-[4,3]pyrimidine-5,7-(4H,6H)-dione. Other such modified nucleotidic units which form unique base pairs are known, such as those described in Leach et al. (1992) J. Am. Chem. Soc. 114:3675-3683 and Switzer et al., supra.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands or hundreds of thousands of base pairs.

The term "protein" refers to contiguous "amino acids" or amino acid "residues." Typically, proteins have a function. However, for purposes of this invention, proteins also encompass polypeptides and smaller contiguous amino acid sequences that do not have a functional activity. The functional proteins of this invention include, but are not limited to, esterases, dehydrogenases, hydrolases, oxidoreductases, transferases, lyases, ligases, receptors, receptor ligands, cytokines, antibodies, immunomodulatory molecules, signalling molecules, fluorescent proteins and proteins with insecticidal or biocidal activities. Useful general classes of enzymes include, but are not limited to, proteases, cellulases, lipases, hemicellulases, laccases, amylases, glucoamylases, esterases, lactases, polygalacturonases, galactosidases, ligninases, oxidases, peroxidases, glucose isomerases, nitrilases, hydroxylases, polymerases and depolymerases. In addition to enzymes, the encoded proteins which can be used in this invention include, but are not limited to, transcription factors, antibodies, receptors, growth factors (any of the PDGFs, EGFs, FGFs, SCF, HGF, TGFs, TNFs, insulin, IGFs, LIFs, oncostatins, and CSFs), immunomodulators, peptide hormones, cytokines, integrins, interleukins, adhesion molecules, thrombomodulatory molecules, protease inhibitors, angiostatins, defensins, cluster of differentiation antigens, interferons, chemokines, antigens including those from infectious viruses and organisms, oncogene products, thrombopoietin, erythropoietin, tissue plasminogen activator, and any other biologically active protein which is desired for use in a clinical, diagnostic or veterinary setting. All of these proteins are well defined in the literature and are so defined herein. Also included are deletion mutants of such proteins, individual domains of such proteins, fusion proteins made from such proteins, and mixtures of such proteins; particularly useful are those which have increased half-lives and/or increased activity.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing in co- and/or post-translational modifications of the polypeptide made in vivo or in vitro, for example, glycosylations, acetylations, phosphorylations, PEGylations and sulphations. In addition, protein fragments, analogs (including amino acids not encoded by the genetic code, e.g. homocysteine, ornithine, p-acetylphenylalanine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

"Amino acids" or "amino acid residues" may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "codon usage table" or "codon bias table" are used interchangeably to describe a table which correlates each codon that may be used to encode a particular amino acid, with the frequencies with which each codon is used to encode that amino acid in a specific organism, or within a specified class of genes within that organism. A "hybrid codon usage table" or "hybrid codon bias table" can also be constructed by combining two or more codon usage tables according to a variety of possible rules, some of which will be enumerated in more detail elsewhere in this document.

The terms "threshold" or "cutoff" are used interchangeably to refer to the minimum allowable frequency in using a codon bias table. For example if a threshold or cutoff of 10% is set for a codon bias table, then no codons that are used less frequently than 10% of the time are accepted for subsequent polynucleotide design and synthesis. Thresholds may be expressed as percentages (e.g., the percentage of time that an organism or class of genes within an organism uses a specified codon to encode an amino acid) or as frequencies (0.1 would be the frequency of codon usage that could also be expressed as 10%).

The term "splice variant" or "splicing variant" refers to the different possible RNA products that may be produced by a cell that transcribes a segment of DNA to produce an RNA molecule. These different products result from the action of the RNA splicing and transportation machinery, whose specificity of function differs from cell to cell, causing different signals within an RNA sequence to be recognized as intron donor and acceptor sites, and leading to different RNA products.

The term "expression system" refers to any in vivo or in vitro biological system that is used to produce one or more protein encoded by a polynucleotide.

The term "annealing temperature" or "melting temperature" or "transition temperature" refers to the temperature at which a pair of nucleic acids is in a state intermediate between being fully annealed and fully melted. The term refers to the behavior of a population of nucleic acids: the "annealing temperature" or "melting temperature" or "transition temperature" is the temperature at which 50% of the molecules are annealed and 50% are separate. Annealing temperatures can be determined experimentally. There are also methods well know in the art for calculating these temperatures.

The term "constant Tm set" refers to a set of nucleic acid sub-sequences, designed such that the annealing temperature of each member of the set to its reverse complement sequence are within a very narrow range. Typically such a set is created by sequentially adding nucleotides to a sequence until a defined annealing temperature has been reached.

5.2 Synthesis of Oligonucleotides 5.2.1 Removal of Non-Tritylated Truncated Chains Oligonucleotides that are useful for assembly of polynucleotides and other demanding applications must meet different performance criteria from oligonucleotides for standard applications. Frequently for high-quality applications only relatively small amounts of oligonucleotides are required: preferably less than 100 pmol of oligonucleotide, more preferably less than 50 pmol of oligonucleotide, more preferably less than 10 pmol of oligonucleotide and more preferably less than 5 pmol of oligonucleotide. The purity is important, with oligonucleotides containing internal deletions or apurinic residues being particularly harmful to many applications. The following are a list of modifications to the current generally used phosphoramidite-based chemistry for oligonucleotide synthesis. These modifications improve the quality of oligonucleotides for subsequent applications including but not limited to assembly into polynucleotides.

Figure 1:
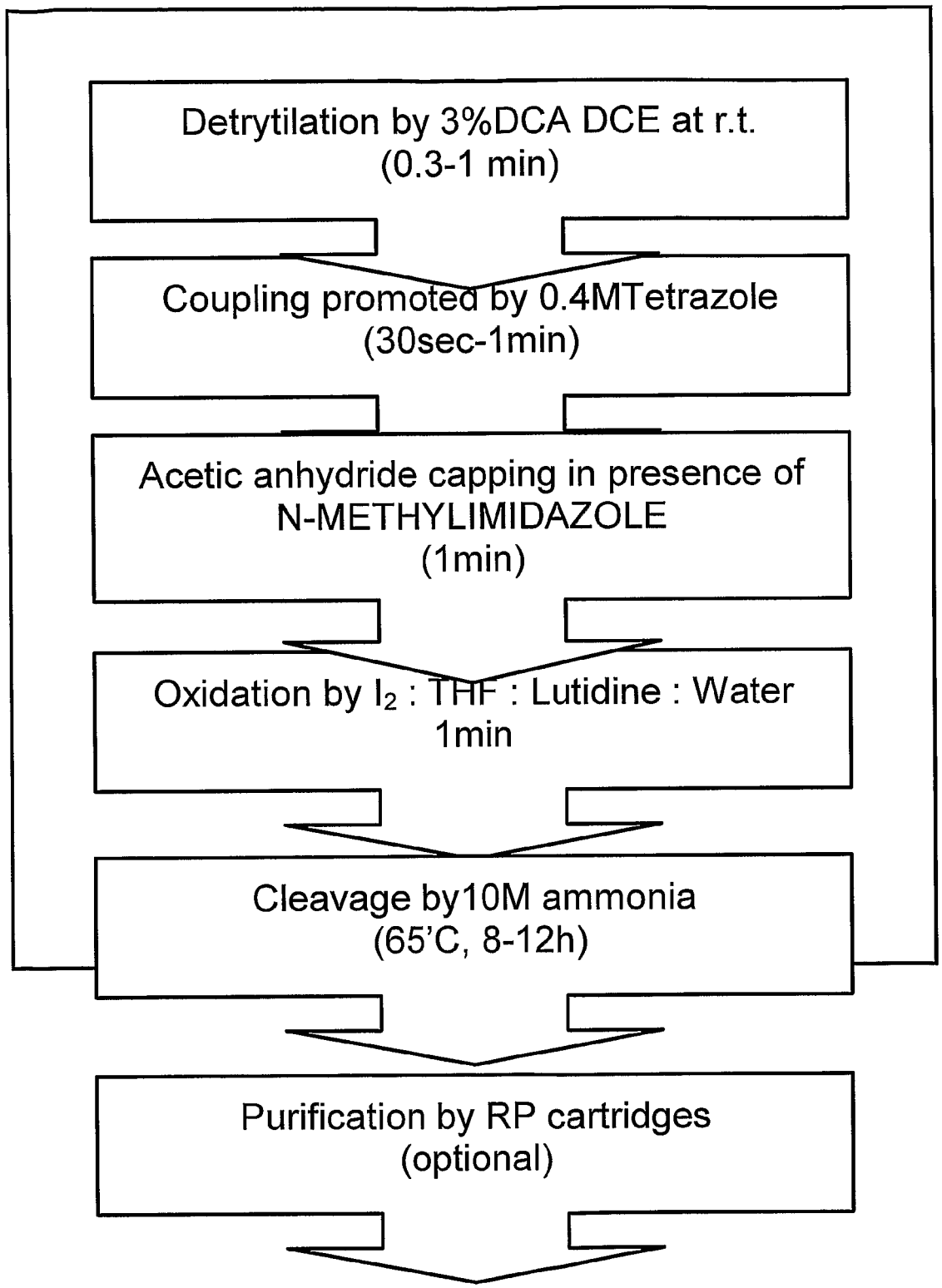
Figure 2A:
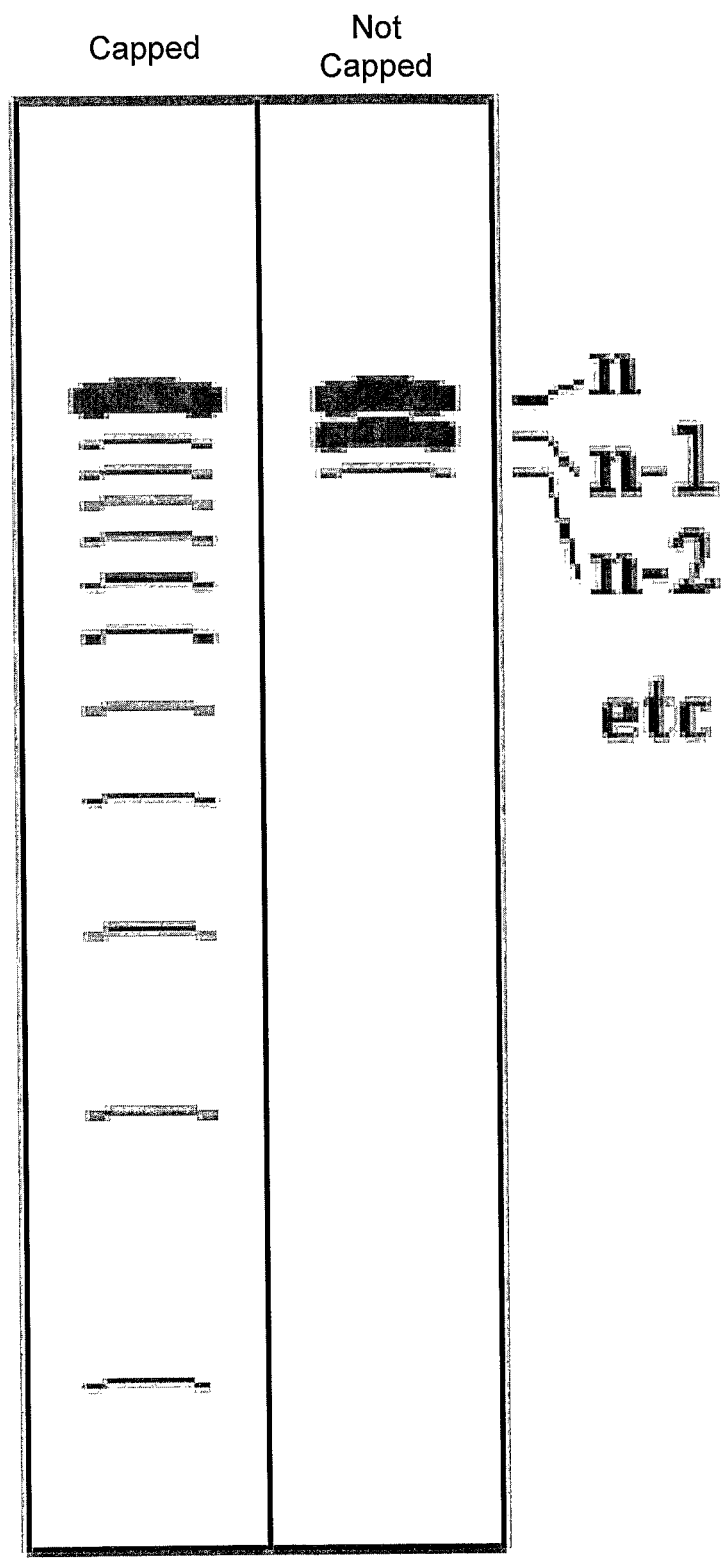
Figure 2B:
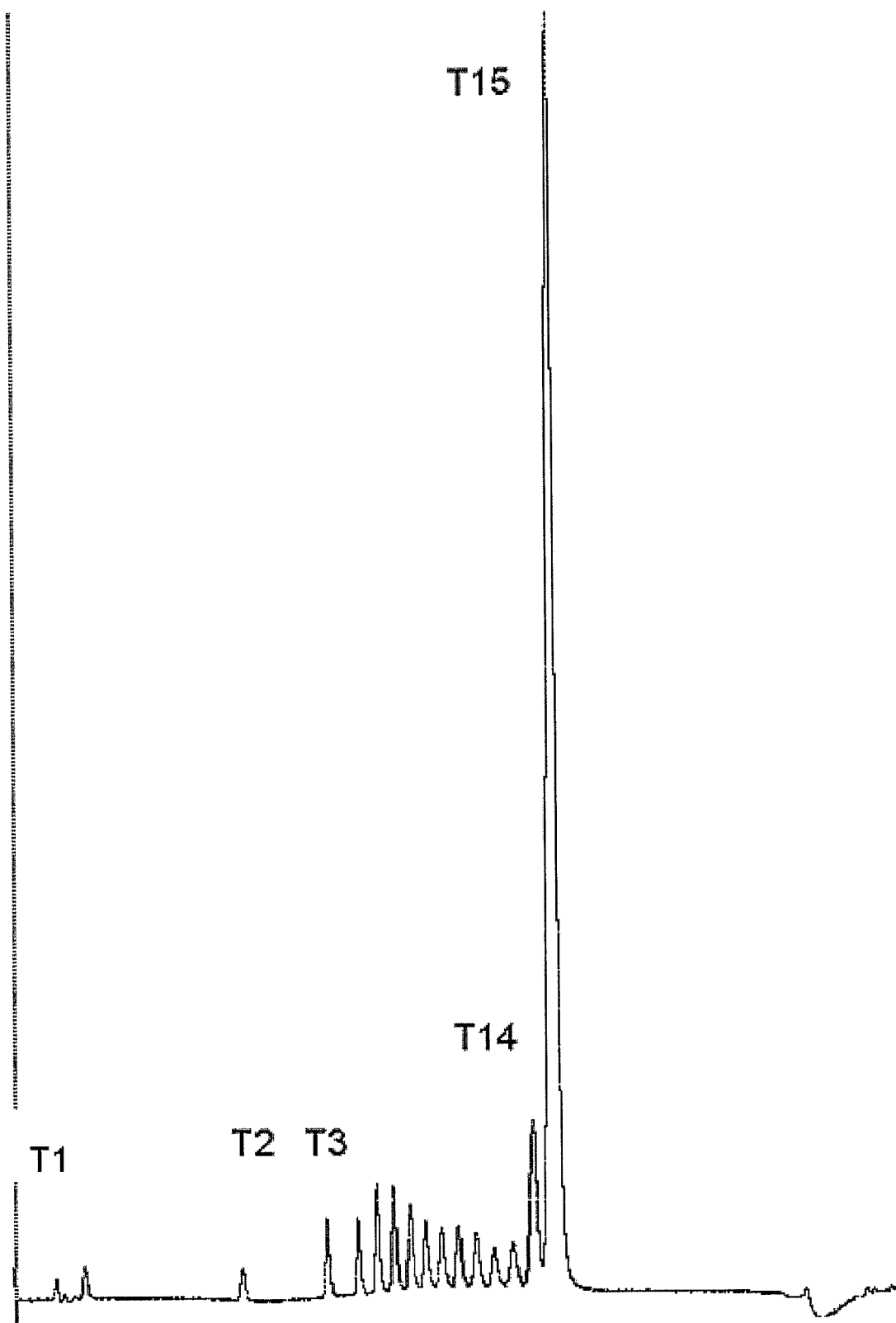

The standard oligonucleotide coupling process described in Gait's practical handbook, Gait, 1984, *Practical approach series*, xiii, 217, hereby incorporated by reference is shown in FIG. 1. Despite the high efficiency of phosphoramidite chemistry, chain elongation is not quantitative. The standard capping process, stepwise acetylation of the unphosphitylated chains, Beaucage and Radhakrishnan, 1992, Tetrahedron, 48, 2223-2311, hereby incorporated by reference in its entirety, using acetic anhydride, 2,6-lutidine and N-methylimidazole in tetrahydrofuran is implemented to prevent further extension of oligonucleotide chains that do not incorporate the last base. Oligonucleotides synthesized with this capping step should thus contain a ladder of products corresponding to the extension failures at each cycle that are then capped. If this capping step is omitted, extension failures in one cycle are expected to extend in the subsequent cycle resulting in a large n−1 peak and much reduced peaks for n−2, n−3 etc. as illustrated in FIG. 2A. In contrast with this expectation, it has been determined that when a 15-mer of polydezoxythymidine is synthesized on CPG-(2000 Å) without capping, there is a ladder of products that more closely resembled the products expected in the presence of capping (FIG. 2B). This shows that the failure of growing oligonucleotide chains to extend quantitatively results in part from a sub-population of chains that become non-reactive. Oligonucleotide packing produces populations that (1) grow as desired, (2) are permanently trapped by neighboring chains or (3) permanently protected by neighboring trityl groups resulting in n−1, n−2, n−3 etc. byproducts, or (4) are nonoxidized and generate n−1 byproducts.

Figure 2C:
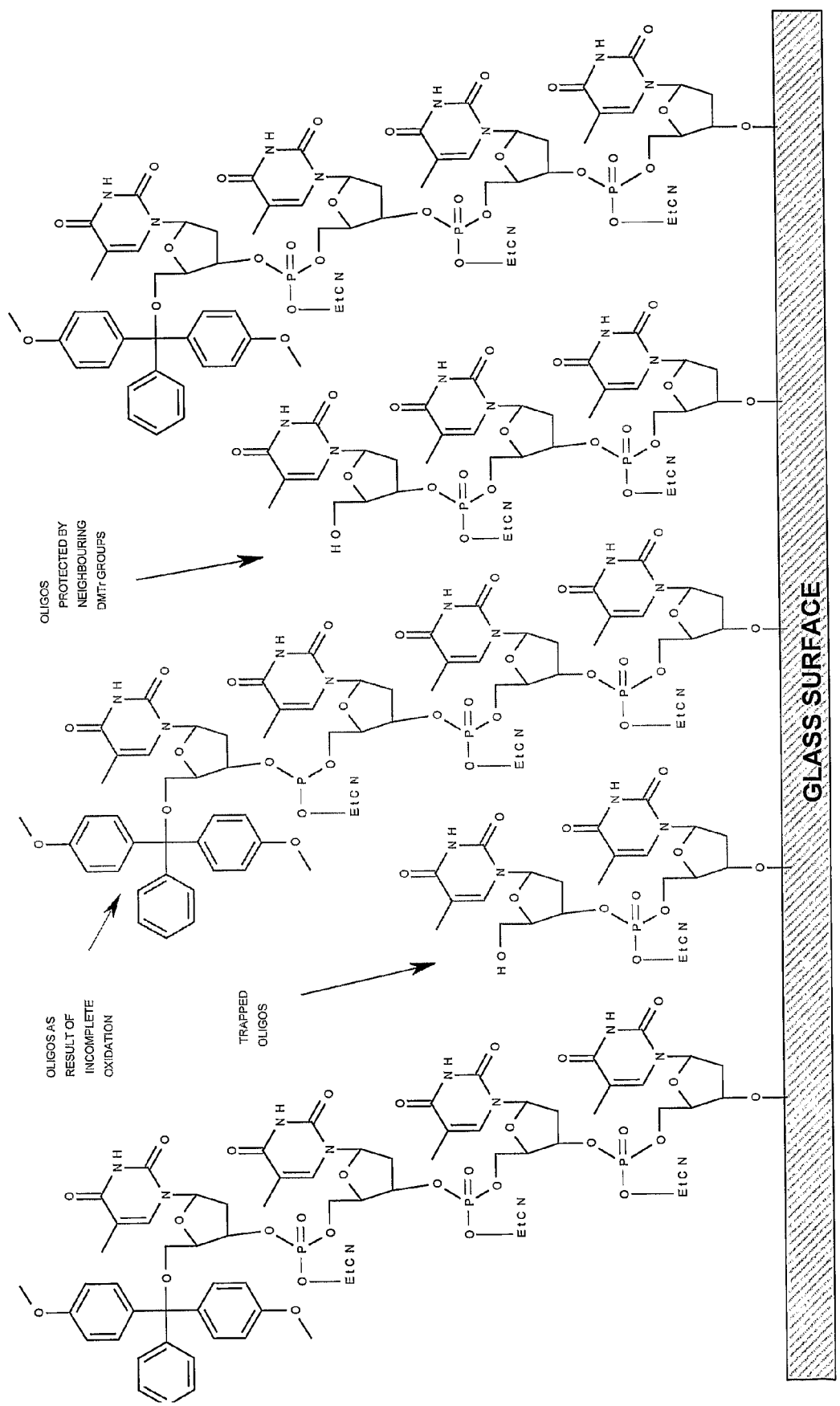

Oligonucleotides that are not extended for one or more cycles, and that then re-enter the active pool are even more deleterious to ultimate function than oligonucleotides that are truncated but otherwise correct in sequence. The former class of oligonucleotides contains internal deletions of one or more base; incorporation of such deletions is a very serious limitation, for example in the assembly of polynucleotides from oligonucleotides. It is therefore important to ensure that an unextended oligonucleotide chain does not re-enter the reactive pool. This is the intention of the capping step, but the experiments summarized in FIG. 2 show that if oligonucleotide chains become unavailable for extension for multiple cycles they may also be unavailable for the capping reaction.

Figure 3A:
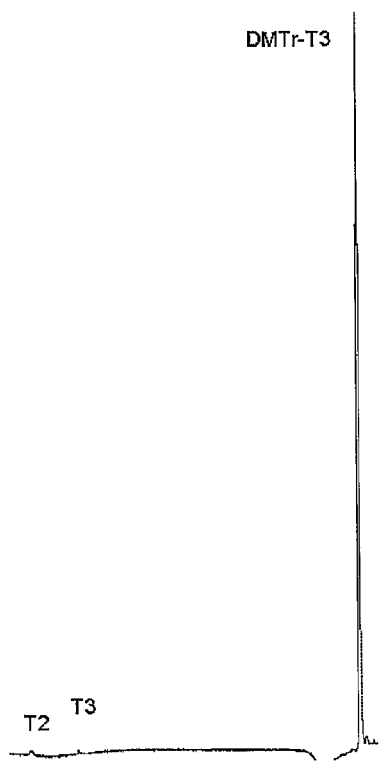
Figure 3B:
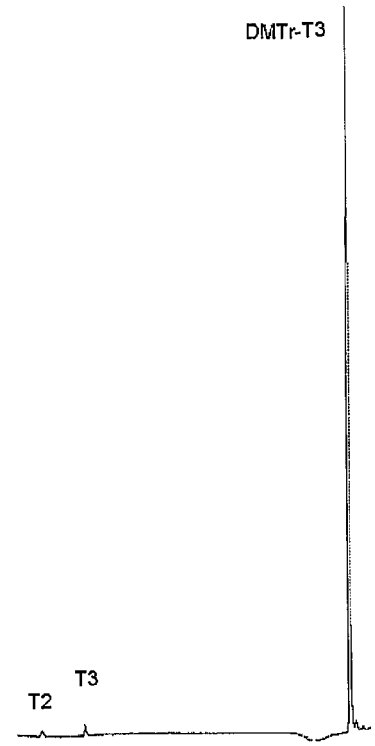
Figure 3C:
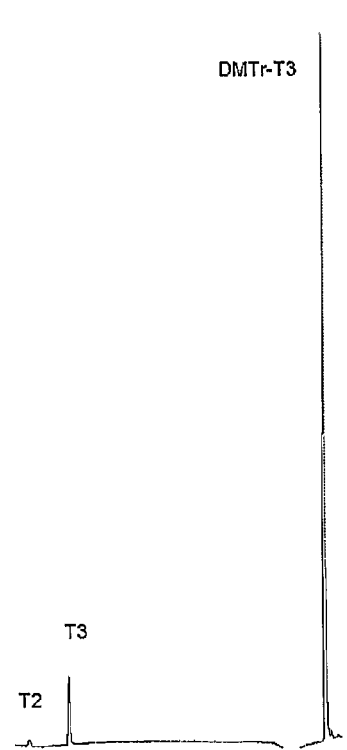
Figure 3D:
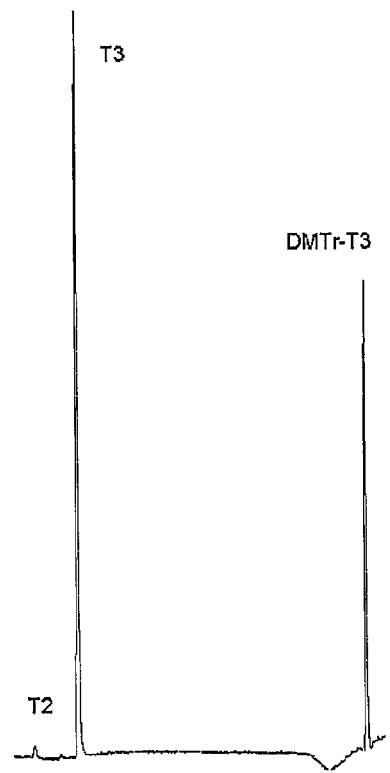
Figure 4A:
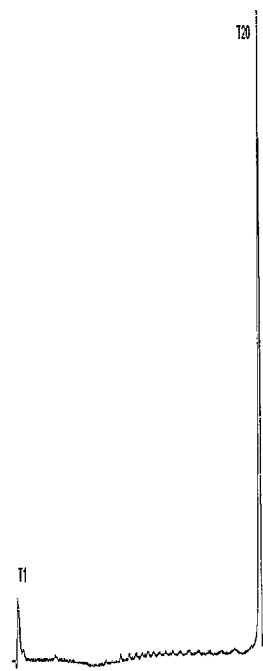
Figure 4B:
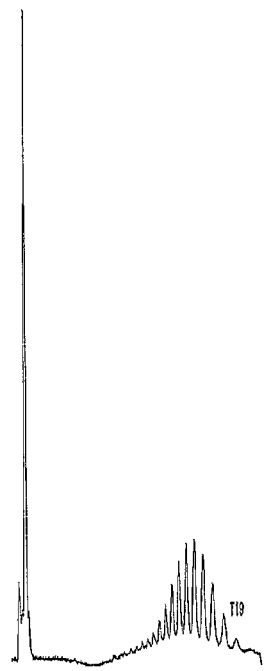
Figure 4C:
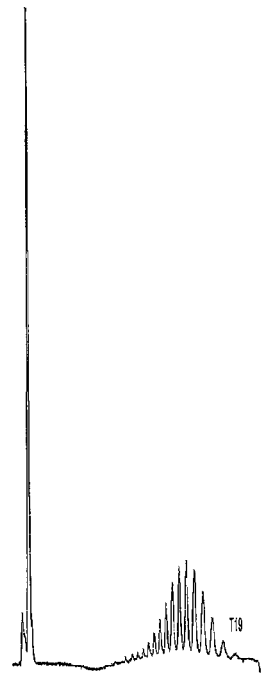
Figure 4D:
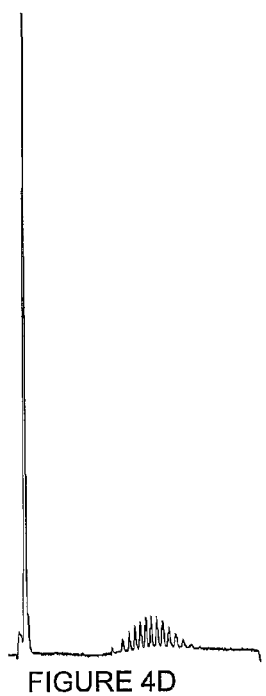
Figure 4E:
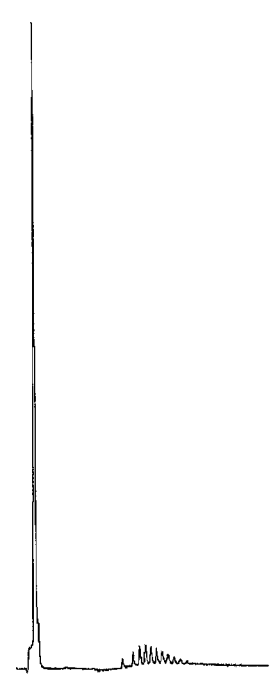
Figure 4F:
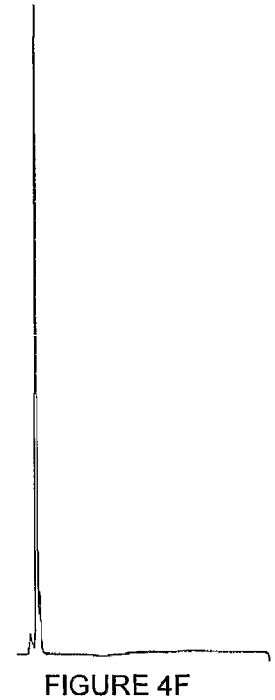

Oligonucleotide packing produces truncated n−1, n−2, n−3 etc. byproducts as a result of trapping by neighboring chains or protected by neighboring trityl groups. These byproducts are not themselves tritylated because the chain extension failure is a failure to extend that follows the detritylation step at the beginning of the cycle. Such permanently terminated chains will be truncated but otherwise correct in sequence. Short truncated oligonucleotides can be problematic. For example, they are problematic when using them to synthesize genes containing repetitive sequences. Short truncated oligonucleotides can, in principle, be removed using the enzyme phosphodiesterase, though it has previously been reported that the DMT-protection is unstable under phosphodiesterase digestion conditions. See, Urdea and Horn, 1986, Tetrahedron Lett 27, 2933-2936, which is hereby incorporated by reference. As illustrated in FIG. 3, it has been determined that the instability of the trityl protection group is primarily a function of pH. The protection is stable for 60 hours at pH 7 (FIG. 3B). Although the oligonucleotide hydrolysis activity of phosphodiesterase decreases at higher pHs (FIG. 4), 1 nmol of 20mer can be completely removed by 0.1 U of enzyme at 25° C. at pH 7.0 (FIG. 4F).

Accordingly, the present invention provides a method of treating a synthetic oligonucleotide product. In the method, synthetic oligonucleotide product is cleaved from a solid support in the absence of a final detritylation step. The cleaved oligonucleotide product is then treated with a phosphodiesterase or a pyrophosphatase at a pH greater than 5.5. In some embodiments the cleaved oligonucleotide product is alternatively treated with a phosphodiesterates or a pyrophosphatase at a pH greater than 5.6, or a pH greater than 5.7, or a pH greater than 5.8, or a pH greater than 5.9, or a pH greater than 6.0, or a pH greater than 6.1, or a pH greater than 6.2, or a pH greater than 6.3, or a pH greater than 6.4, or a pH greater than 6.5. In some embodiments the treating step is performed for between 20 minutes and 24 hours, between 25 minutes and 2 hours, less than 5 hours or between 18 minutes and 24 minutes.

Any pyrophosphatase or phosphodiesterase can be used to accomplish such enzymatic cleavage. For example, any pyrophosphatase or phosphodiesterase described by Bollen et al., 2000, Critical Reviews in Biochemistry and Molecular Biology 35, 393-432, which is hereby incorporated by reference in its entirety, can be used. Nucleotide pyrophosphatases/phosphodiesterases (NPPs) release nucleoside 5'-monophosphates from nucleotides and their derivatives. They exist both as membrane proteins, with an extracellular active site, and as soluble proteins in body fluids. NPPs include, but are not limited to the mammalian ecto-enzymes NPP1 (PC-1), NPP2 (autotaxin) and NPP3 (B10; gp130RB13-6). These are modular proteins consisting of a short N-terminal intracellular domain, a single transmembrane domain, two somatomedin-B-like domains, a catalytic domain, and a C-terminal nuclease-like domain. The catalytic domain of NPPs is conserved from prokaryotes to mammals and shows structural and catalytic similarities with the catalytic domain of other phospho-/sulfo-coordinating enzymes such as alkaline phosphatases. Hydrolysis of pyrophosphate/phosphodiester bonds by NPPs occurs via a nucleotidylated threonine. NPPs are also known to auto(de)phosphorylate this active-site threonine, a process accounted for by an intrinsic phosphatase activity, with the phosphorylated enzyme representing the catalytic intermediate of the phosphatase reaction.

In some embodiments, the method further comprises detritylating a tritylated oligonucleotide in the oligonucleotide product after the treating step. In some embodiments, the method further comprises physically separating a tritylated oligonucleotide from a non-tritylated oligonucleotide in the cleaved oligonucleotide product, where the tritylated oligonucleotide is a full length oligonucleotide; and detritylating the tritylated oligonucleotide.

Phosphodiesterase can selectively remove oligonucleotides lacking a 5'-trityl group. FIG. 5 shows that phosphodiesterase does not cleave fully unprotected oligonucleotides still bound to the CPG support (FIG. 5A). This is not surprising, since the target population of untritylated oligomers is inaccessible even to small chemical reagents. In contrast, when the trityl protected oligomers are cleaved from CPG, phosphodiesterase treatment removes most of truncated byproducts (<n−2) (compare FIGS. 5B and C).

Figure 6C:
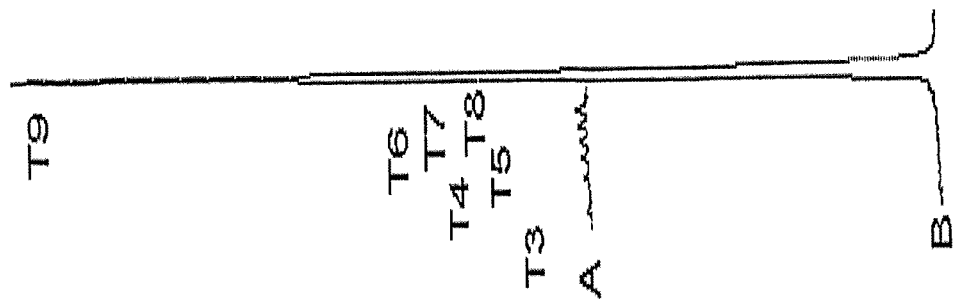
Figure 6B:
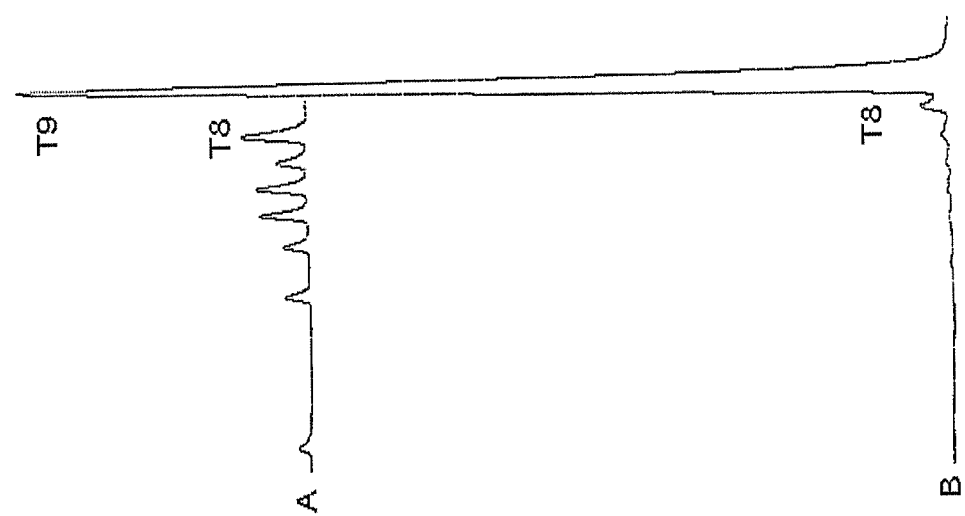
Figure 6A:
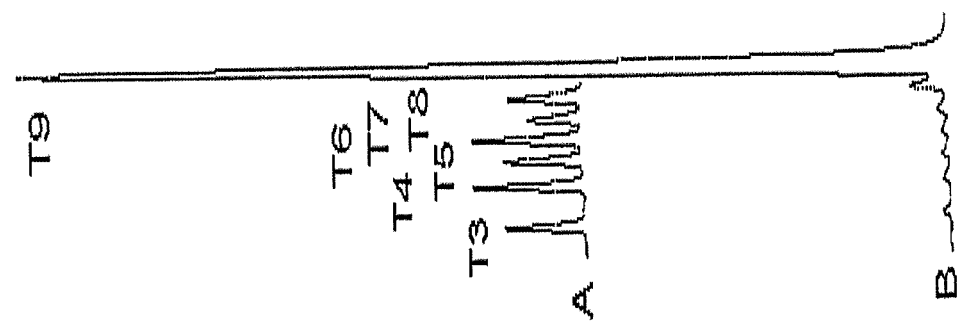
Figure 7A:
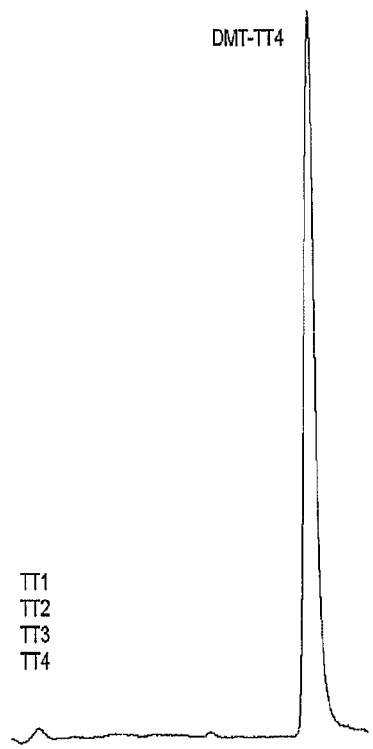
Figure 7B:
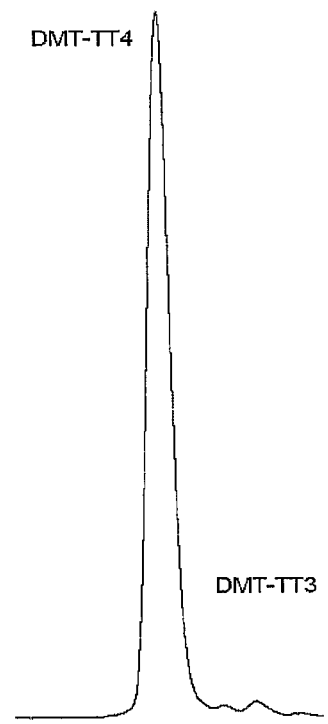
Figure 7C:
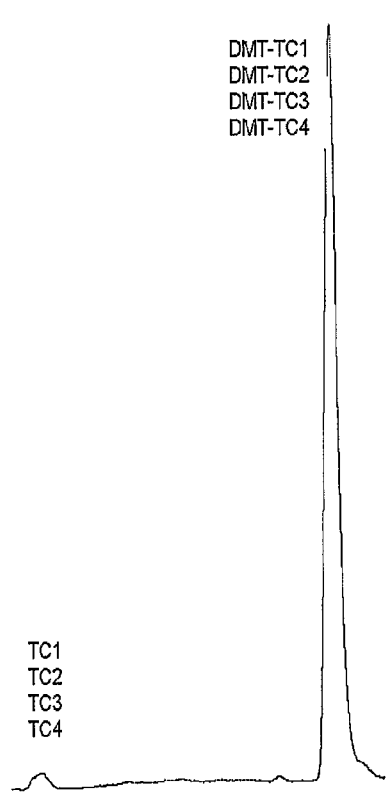
Figure 7D:
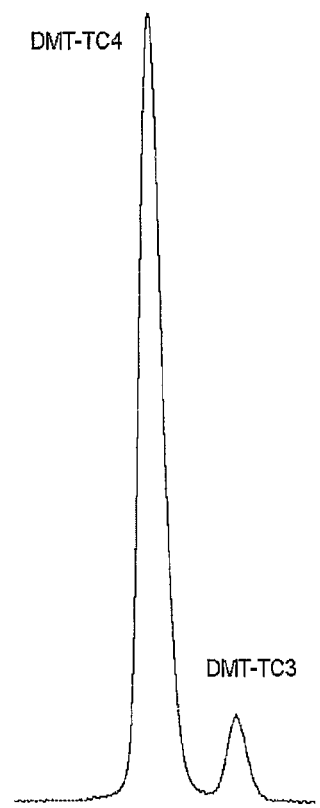
Figure 7E:
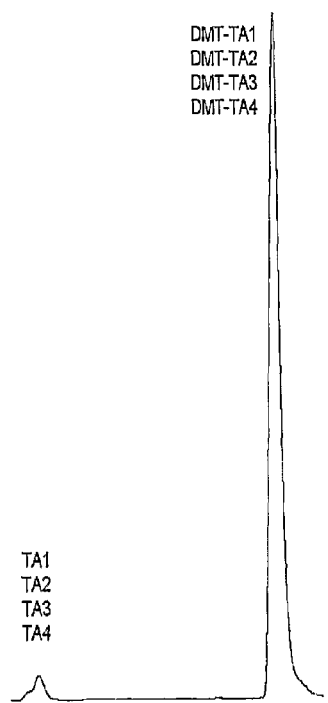
Figure 7F:
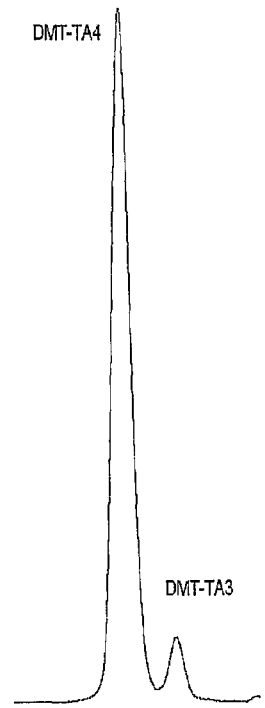
Figure 7G:
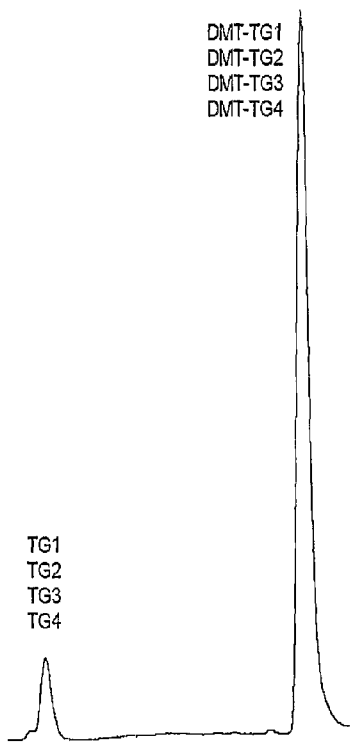
Figure 7H:
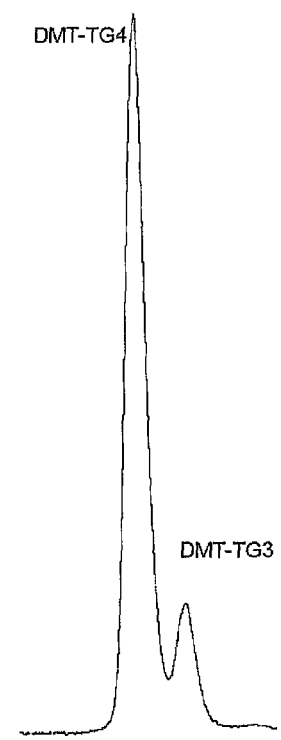

Capped and uncapped oligonucleotides can be separated from the full-length tritylated product by HPLC (compare traces A and B in FIG. 6). Treating tritylated oligonucleotides with phosphodiesterase and then performing a subsequent reverse phase separation to separate the tritylated (full-length) from the non-tritylated (truncated) oligonucleotides allows simultaneous purification of a pool of oligonucleotides. This approach removes the major limitation of subsequent hydrophobic purification by increasing the difference in retention time between fractions of truncated and desired products. This procedure provides a format that is readily amenable to high throughput implementation.

5.2.2 Eliminating Sources of Internally Deleted Chains by Improved Capping

The second class of truncation products shown in FIG. 2 are oligonucleotides that failed to add a base in one or more cycles of elongation, but were then able to re-enter a subsequent cycle and continue extending. These truncated but growing oligonucleotides are tritylated like the full-length oligonucleotides and correspond to the small population of oligomers that are resistant to phosphodiesterase treatment in FIG. 4C. In contrast to the physically trapped truncated oligonucleotides, these chains are active participants in the ongoing synthesis, they will have internal deletions corresponding to the cycle(s) in which they did not participate, and they will also have a 5' trityl group.

The two different classes of extension failures are shown in FIG. 7. Homo-tetramers of each base are synthesized and cleaved from the CPG support without detritylation. Tritylated and non-tritylated oligomers are then separated by HPLC. Consistent with a physical trapping explanation, a larger sub-population of untritylated truncated chains and truncated byproducts is observed for more sterically hindered nucleotides (dC, dA, and dG). Tritylated truncated chains corresponding to oligonucleotides lacking one or more addition but still active participants in the extension cycle are also observed.

While phosphodiesterase is a suitable treatment for removing the physically inaccessible (trapped) chain extension failures, an alternative stratagem can be used to eliminate this second class of chemically available failures. There are two ways to address this population: permanent capping to prevent further extension of unreacted chains (this capping is a standard part of conventional oligonucleotide synthesis), and optimizing the reaction steps to maximize the efficiency of nucleotide addition.

Any unextended chains that are physically accessible should be prevented from undergoing further extension to ensure optimal quality for gene synthesis. Different capping methods have been used to prevent further cycles of oligonucleotide polymerization on unextended chains. See, for example, Matteucci and Caruthers, 1981, J Am Chem Soc, 103, 3185-3191; Eadie and Davidson, 1987, Nucleic Acids Res 15, 8333-49; Chaix et al., 1989, Tetrahedron Lett 30, 71-74; and Yu et al., 1994, Tetrahedron Lett 34, 8565-8568, each of which is hereby incorporated by reference in its entirety. Early protocols used dimethylaminopyridine (DMAP) catalyzed capping after oxidation. These methods were subsequently replaced with capping by acetic anhydride and N-methylimidasole (NMI) in tetrahydrofuran (THF) before the oxidation step. This change was introduced to reduce the oxidation and acetylation of guanidine residues.

Figure 9A:
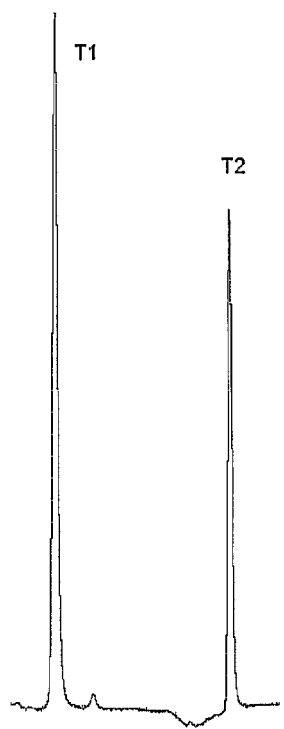
Figure 9B:
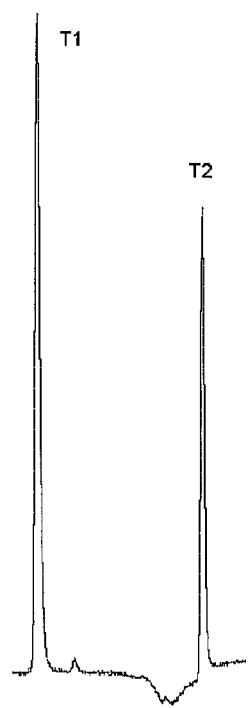
Figure 9C:
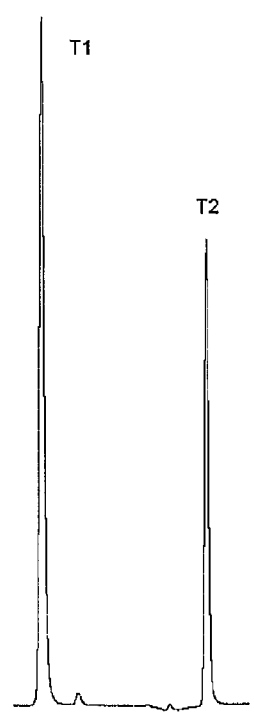
Figure 9D:
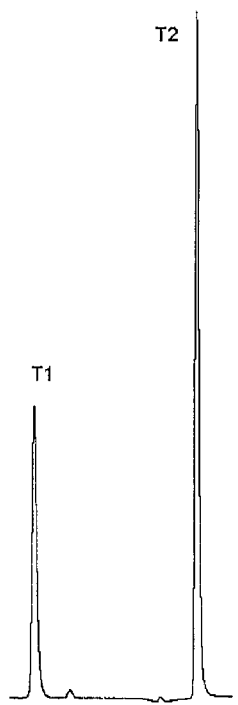
Figure 9E:
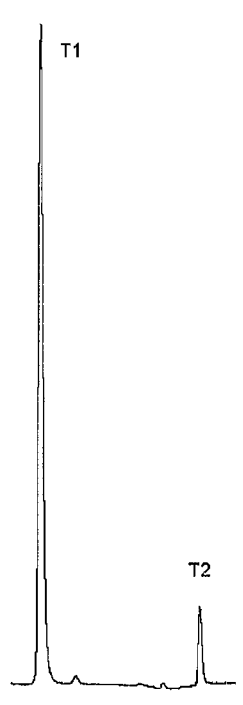
Figure 9F:
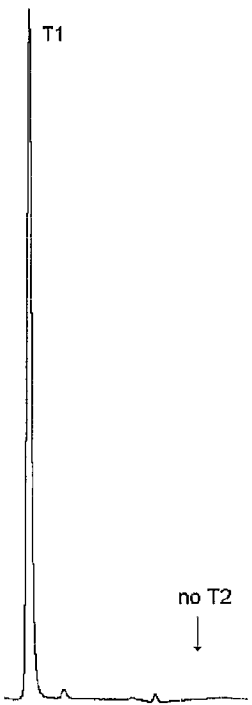
Figure 10A:
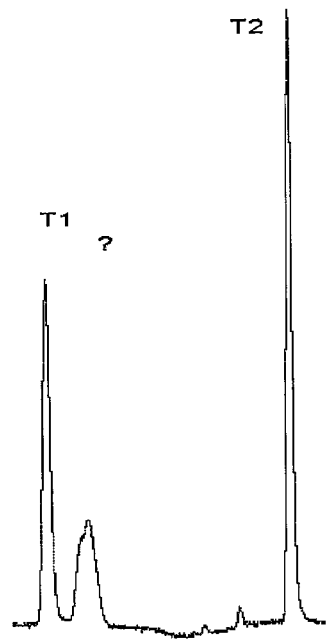
Figure 10B:
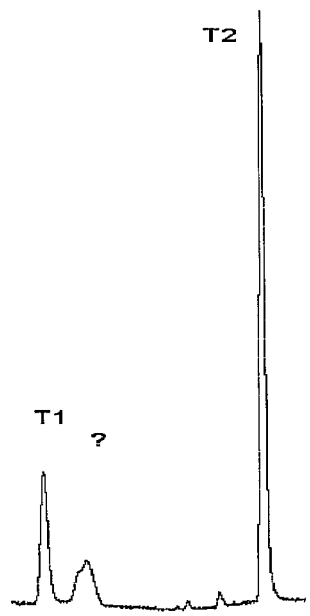
Figure 10C:
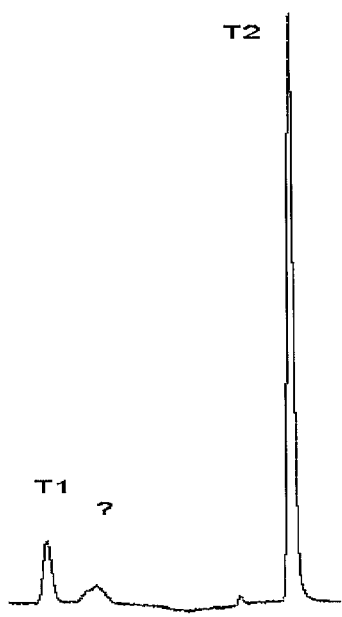
Figure 10D:
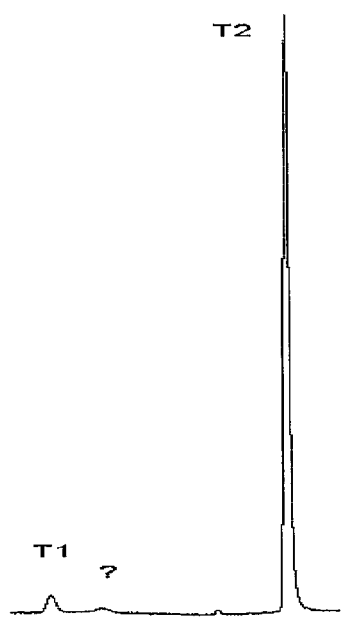
Figure 10E:
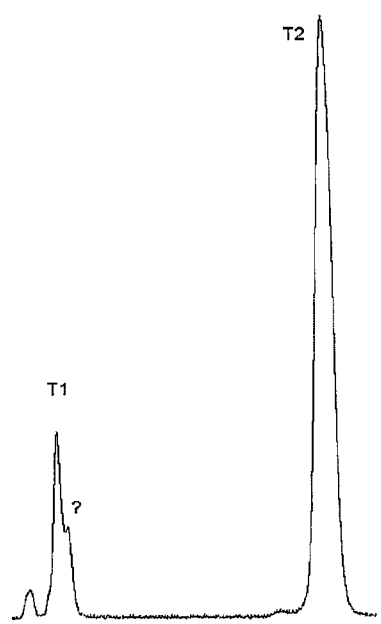
Figure 10F:
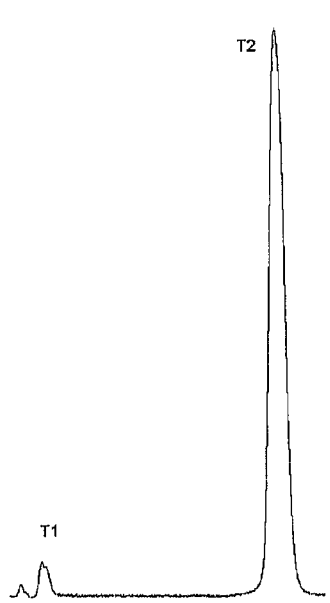

The efficiency of capping using acetic anhydride in presence of N-methylimidazole (NMI), phenoxyacetic anhydride ($Pac_2O$) and dimethoxy N,N-diisopropyl phosphoramidite (DMPA) was compared. It was determined that a capping time of between 1 and 5 minutes is required for quantitative capping using acetic anhydride (FIG. 8A), while capping with $Pac_2O$ was essentially complete after 30 seconds (FIG. 8B) and capping with DMPA took only 15 seconds for completion (FIG. 8C). This result was confirmed by using different capping mixtures for 15 seconds (FIG. 9). Quantitative capping was found only with N,N-dimethylaminopyridine (DMAP) (FIG. 9F) although a 1.5:1.5:7 mixture of N-methylimidazole:2,6-lutidine:toluene gave quantitative capping after a minute (FIG. 9E).

Complete elimination of oligonucleotides that have failed to react in any other cycle from further cycles is important to quality for gene synthesis. Therefore DMAP capping at least for nucleotides A, C and T is proposed. The $O^6$-position of guanidine modification problem caused by this capping reagent can be efficiently avoided by engineering the nucleic acid synthesis instrument with the capability to perform oxidation before or after capping, by applying the full protection strategy, or by combining both approaches $Ac_2O$-NMI capping before oxidation and $Ac_2O$-DMAP capping after oxidation.

From FIGS. 8 and 9 it is clear that DMAP capping after oxidation provides superior capping protection to N-methylimidazole capping before oxidation. FIG. 6 also shows that the standard capping step before oxidation reduces the number of truncated oligonucleotides relative to an uncapped protocol (FIGS. 61A, 2A). Moving the capping step to follow oxidation reduces the levels of truncated oligonucleotides further (FIGS. 62A, 3A), particularly noticeable with the reduced levels of tritylated n−1 product (i.e., T8). Complete elimination from further cycles of oligonucleotides that have failed to react in any other cycle is absolutely critical to oligonucleotide quality. Using DMAP capping at least for nucleotides A, C and T will therefore improve overall oligonucleotide quality. A problem has been reported with modification of the $O^6$-position of guanidine caused by this capping reagent. See Eadie and Davidson, 1987, Nucleic Acids Res 15, 8333-49; Pon et al., 1985, Tetrahedron Lett. 26, 2525-2528; Pon et al., 1985, Nucleic Acids Res 13, 6447-65; and Pon et al., 1986, Nucleic Acids Res 14, 6453-70, each of which is hereby incorporated by reference in its entirety. This can be efficiently avoided by either performing capping before oxidation for addition of dG but after oxidation for A, C and T. Alternatively growing chains may be $Ac_2O$-NMI capped before oxidation and $Ac_2O$-DMAP capped after oxidation.

Accordingly, the present invention provides a method of synthesizing an oligonucleotide comprising an $n^{th}$ nucleotide and an $n+1^{th}$ nucleotide, where the $n^{th}$ nucleotide and the $n+1^{th}$ nucleotide are coupled to each other in the oligonucleotide. In the method, the $n^{th}$ nucleotide is detrylated when the $n^{th}$ nucleotide is a terminal nucleotide of a nucleic acid attached to a solid support. The $n+1^{th}$ nucleotide is coupled to the $n^{th}$ nucleotide. The nucleic acid attached to the solid support is then exposed with a first capping reagent, prior to an oxidation step, when the $n+1^{th}$ nucleotide is deoxyguanosine. The oxidation step is then performed. The nucleic acid is attached to the solid support with a second capping reagent, after the oxidation step, when the $n+1^{th}$ nucleotide is deoxycytosine, deoxythymidine or deoxyadenosine. In some embodiments, the oligonucleotide comprises a plurality of nucleotides and the aforementioned steps are repeated for all or a portion of the nucleotides in the plurality of nucleotides, thereby synthesizing the oligonucleotide. In some embodiments, the method further comprises separating the nucleic acid from the solid support thereby deriving the oligonucleotide and then separating the oligonucleotide from one or more truncated by-products. In some embodiments, the first capping reagent is N-methylimidazole or the like and the second capping reagent is N,N-dimethylaminopyridine or the like. In some embodiments the oligonucleotide comprises between 10 nucleotides and 100 nucleotides, between 5 nucleotides and 50 nucleotides, or between 3 nucleotides and 40 nucleotides. In some embodiments, the nucleic acid attached to the solid has a length of one nucleotide or greater.

Another aspect of the invention provides a method of synthesizing an oligonucleotide comprising an $n^{th}$ nucleotide and an $n+1^{th}$ nucleotide, where the $n^{th}$ nucleotide and the $n+1^{th}$ nucleotide are adjacent to each other in the oligonucleotide. IN the method, the $n^{th}$ nucleotide is detrylated when the $n^{th}$ nucleotide is a terminal nucleotide of a nucleic acid attached to a solid support. The $n+1^{th}$ nucleotide is then coupled with the $n^{th}$ nucleotide. The nucleic acid attached to the solid support is then exposed with a first capping reagent, prior to an oxidation step. Then an oxidation step is performed. After the oxidation step, the nucleic acid attached to the solid support is exposed with a second capping reagent. In some embodiments the oligonucleotide comprises a plurality of nucleotides and the aforementioned steps are repeated for all or a portion of the nucleotides in the plurality of nucleotides. In some embodiments, the method further comprises separating the nucleic acid from the solid support, thereby deriving the oligonucleotide. In some embodiments, the oligonucleotide is separated from one or more truncated by-products. In some embodiments, the first capping reagent is N-methylimidazole and the second capping reagent is N,N-dimethylaminopyridine. In some embodiments, oligonucleotide comprises between 10 and 100 nucleotides, between 5 nucleotides and 50 nucleotides, or between 3 nucleotides and 40 nucleotides. In some embodiments, the nucleic acid attached to the solid has a length of one nucleotide or greater.

5.2.3 Eliminating Sources of Internally Deleted Chains by Improved Oxidation Two strategies are available to prevent extension of oligonucleotide chains that have failed to add a base in one or more cycle. One is to efficiently block further extension of unextended chains. This is why it has been proposed here to switch to the superior capping agent DMAP. The second stratagem is to maximize the coupling of bases.

The data in FIGS. 6, 7, 8 and 9 present a dilemma. Even if coupling and capping were each only 99% efficient, statistically only 1% of 1% of chains (i.e. 1 in 10,000) should fail in both reactions. The resulting internal deletion in an oligonucleotide should therefore be extremely rare. In practice, however, these deletions are seen at a rate about 30-fold higher: synthetic genes made from commercial oligonucleotides frequently contain between 2 and 5 internal deletions per 1,000 bases. Systematic exploration of reaction conditions to optimize coupling efficiency, revealed that the assay for incomplete oxidation was also measuring exactly the kind of error for which avoidance was sought.

Letsinger's method of nucleotidic phosphite triester oxidation has been the standard chemistry for almost thirty years. See, Letsinger et al., 1975, J Am Chem Soc, 3278-3279, which is hereby incorporated by reference. However, there is no clear consensus in the literature for the iodine and/or water ratios, type of base for iodic acid neutralization or duration of reaction. Several different oxidation conditions were tested by synthesizing a dimmer, then detritylating, cleaving and analyzing by HPLC. Incompletely oxidized phosphate bonds were cleaved by the detritylating conditions, resulting in monomer. Dimer stability was used as a measure of the completeness of oxidation (FIG. 10).

Using 0.1M iodine in THF:2,6-lutidine:Water 40:10:1, oxidation was only 82% complete after 1 minute and 98% after 10 minutes (FIG. 10A-D). In comparison a 10-fold increase in water concentration resulted in 93% oxidation in just 15 seconds (compare FIGS. 10E and F).

Figure 12A:
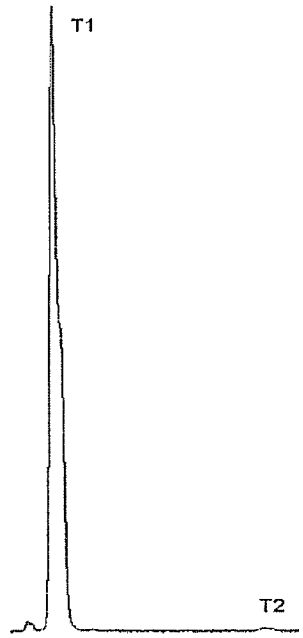
Figure 12B:
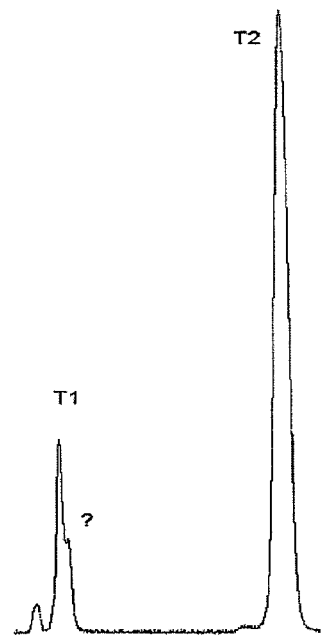
Figure 12C:
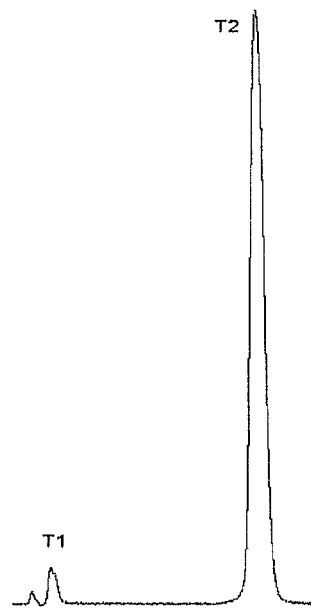
Figure 12D:
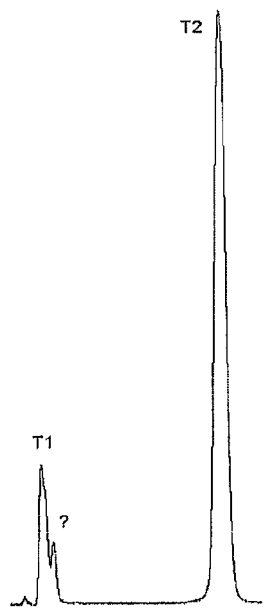
Figure 12E:
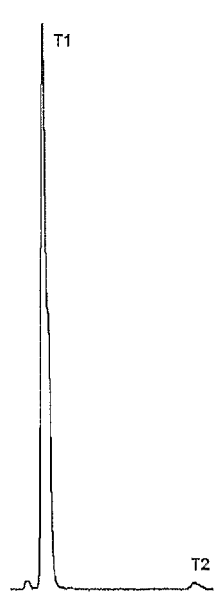
Figure 12F:
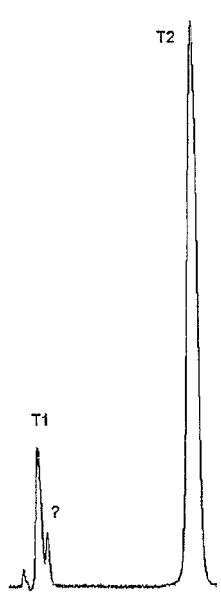
Figure 12G:
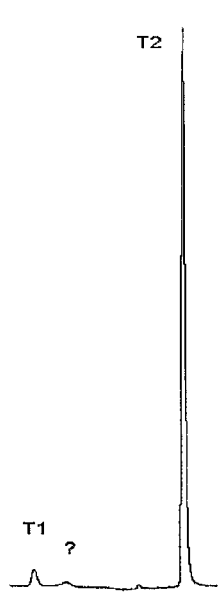

Loss of an incompletely oxidized base at the detritylation step would result in exactly the kind of internal deletions that we wish to avoid in oligonucleotides to be used as building blocks for synthetic genes (see FIG. 11). It is thus important that oxidation be as complete as possible. Several different reagents were evaluated in a 15 second oxidation test (FIG. 12). From these test it was found that the most efficient oxidation reagent was freshly prepared iodine/water oxidizer (FIG. 12C).

An aspect of the invention provides a method of synthesizing an oligonucleotide comprising an $n^{th}$ nucleotide and an $n+1^{th}$ nucleotide, where the $n^{th}$ nucleotide and the $n+1^{th}$ nucleotide are coupled to each other in the oligonucleotide. The method comprises detritylating the $n^{th}$ nucleotide when the $n^{th}$ nucleotide is a terminal nucleotide of a nucleic acid attached to a solid support. Then the $n+1^{th}$ nucleotide is coupled with the $n^{th}$ nucleotide. The nucleic acid is then exposed to a capping reagent prior to an exposing step. The nucleic acid is then exposed to an oxidizing solution comprising a plurality of components, where a first component and a second component in the plurality of components are mixed together less than twelve hours prior to exposing the nucleic acid to the oxidizing solution. In some embodiments, the oligonucleotide comprises a plurality of nucleotides and the aforementioned steps are repeated for all or a portion of the nucleotides in the plurality of nucleotides, thereby synthesizing said oligonucleotide. In some embodiments, the method further comprises separating the nucleic acid from the solid support, thereby deriving the oligonucleotide and then separating the oligonucleotide from one or more truncated by-products. In some embodiments, the first component is iodine. In some embodiments, the iodine concentration in the oxidizing solution is between 0.05M and 0.5M. In some embodiments, the second component is THF:2,6-lutidine:water 4:1:1. In some embodiments, the method further comprise exposing the nucleic acid to a capping reagent after the exposing step.

5.2.4 A Combined Protocol for Improved Oligonucleotide Quality

By combining the modifications to the standard procedure, new oligonucleotide synthesis procedures have been designed as illustrated in FIG. 13. The main features of this protocol are (1) oxidation is performed with freshly prepared iodine in THF:2,6-lutidine:water (4:4:1); (2) a second capping step is performed after oxidation using acetic anhydride and DMAP; (3) oligonucleotides are cleaved and deprotected in gaseous ammonia with the final trityl group in place; (4) truncated and cleaved depurinated oligonucleotides are optionally digested with phosphodiesterase and (5) there is an optional trityl-based HPLC purification prior to detritylation.

5.3 Synthesis of Oligonucleotides on Non-Porous Solid Supports

The major applications for commercially synthesized oligonucleotides are as PCR primers or DNA micro-array probes, neither of which demand the same level of quality as building blocks for synthetic genes. Current commercial synthesizers use controlled-pore glass as a support for oligonucleotide synthesis, the design of such reaction vessels has already reached the minimal reaction volume (~45 μl) at which a two component reaction and resin can still form a homogeneous suspension without sticking to the walls and leaking out from the supported filter. Porous support materials have the disadvantage that they may trap reagents, chemicals may leak during the reaction and there may be unpredictable plugging and unplugging of pores by gases and micro particles. A non-porous glass support will reduce or eliminate these problems, and allow smaller reaction volumes for oligonucleotide synthesis (~5 μl) together with the high quality needed for subsequent polynucleotide assembly.

Non-porous surfaces suitable as substrates on which to perform oligonucleotide synthesis include polished Quartz (100% $SiO_2$) or Pyrex (81% $SiO_2$) discs or plates from Chemglass with an exposed surface area of less than 1000 $mm^2$, preferably less than 300 $mm^2$, more preferably less than 100 $mm^2$.

5.3.1 Surface Preparation

Figure 15A:
Figure 15B:
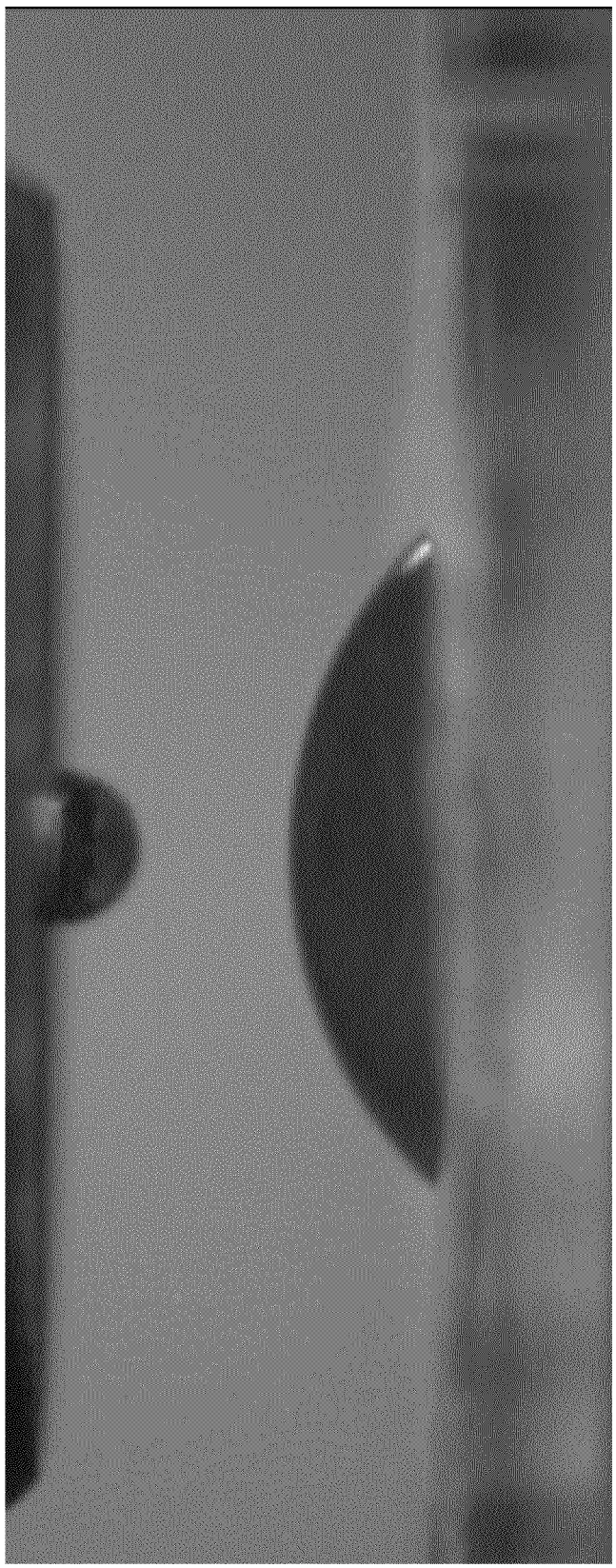
Figure 15C:
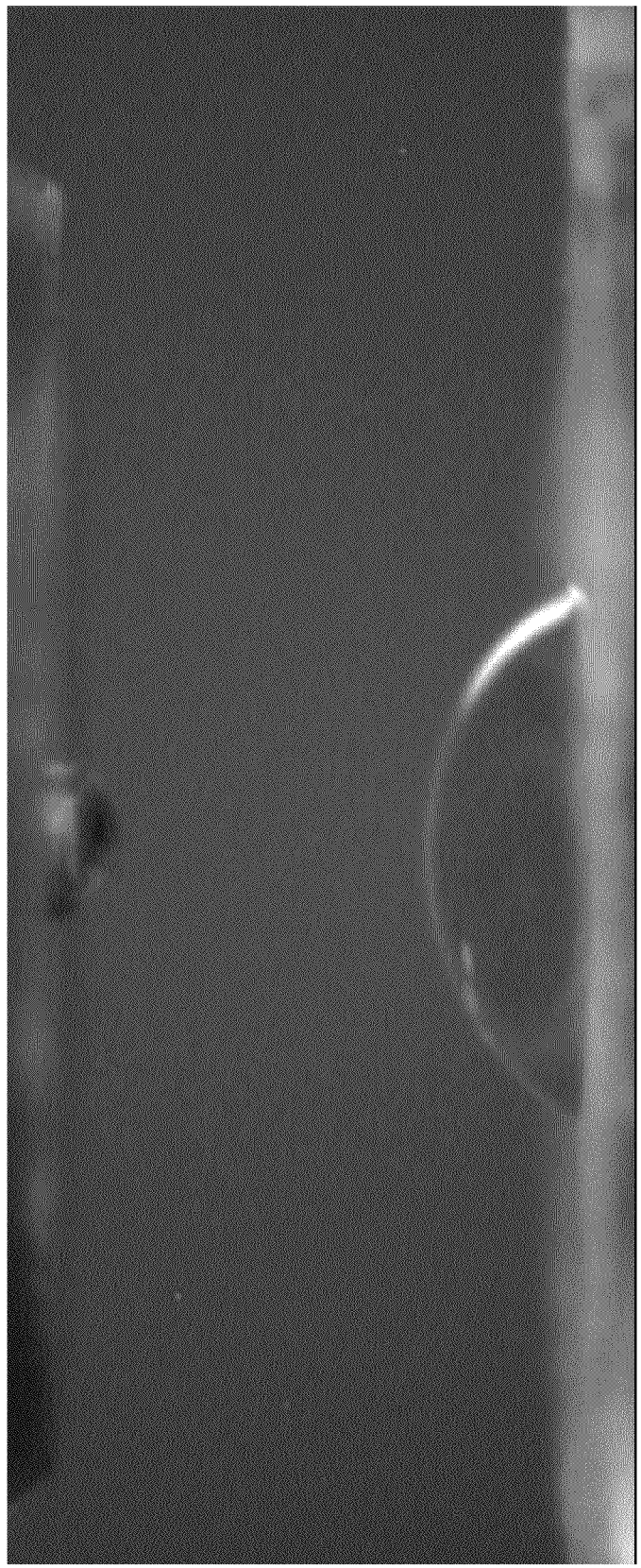
Figure 15D:
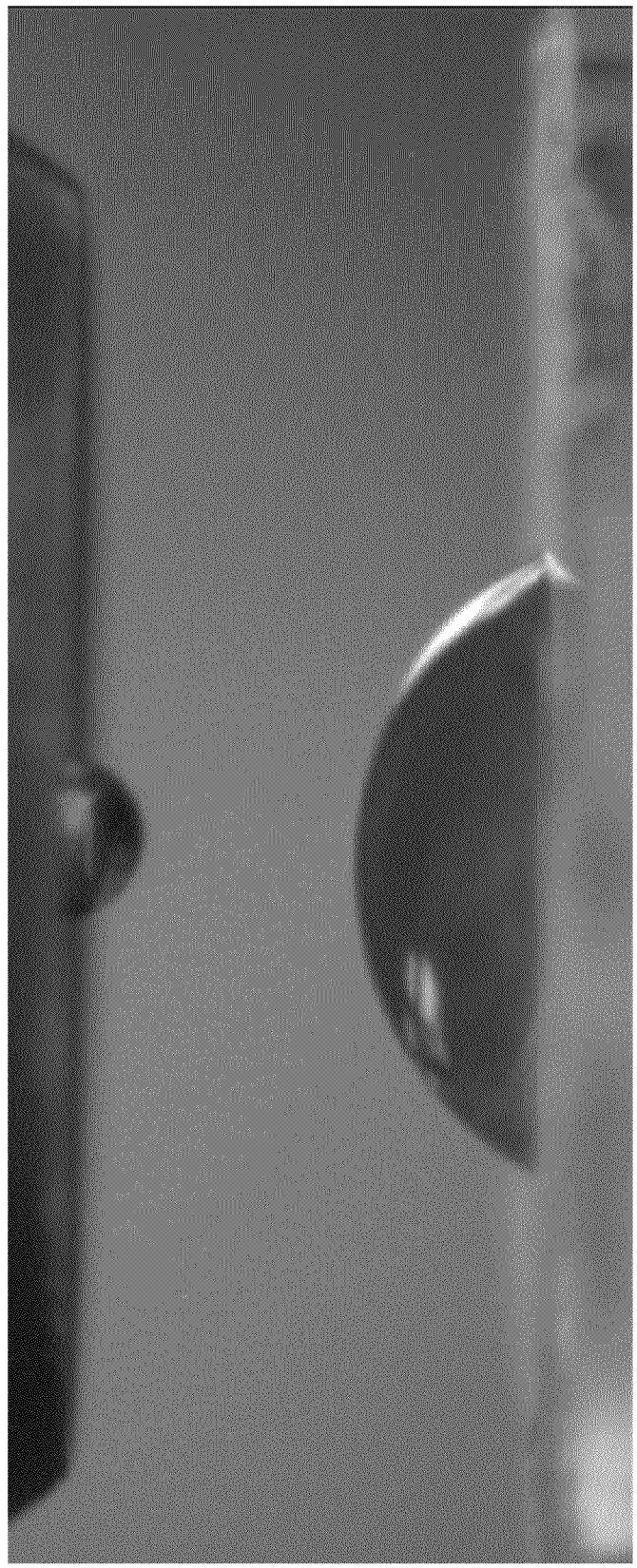
Figure 15E:
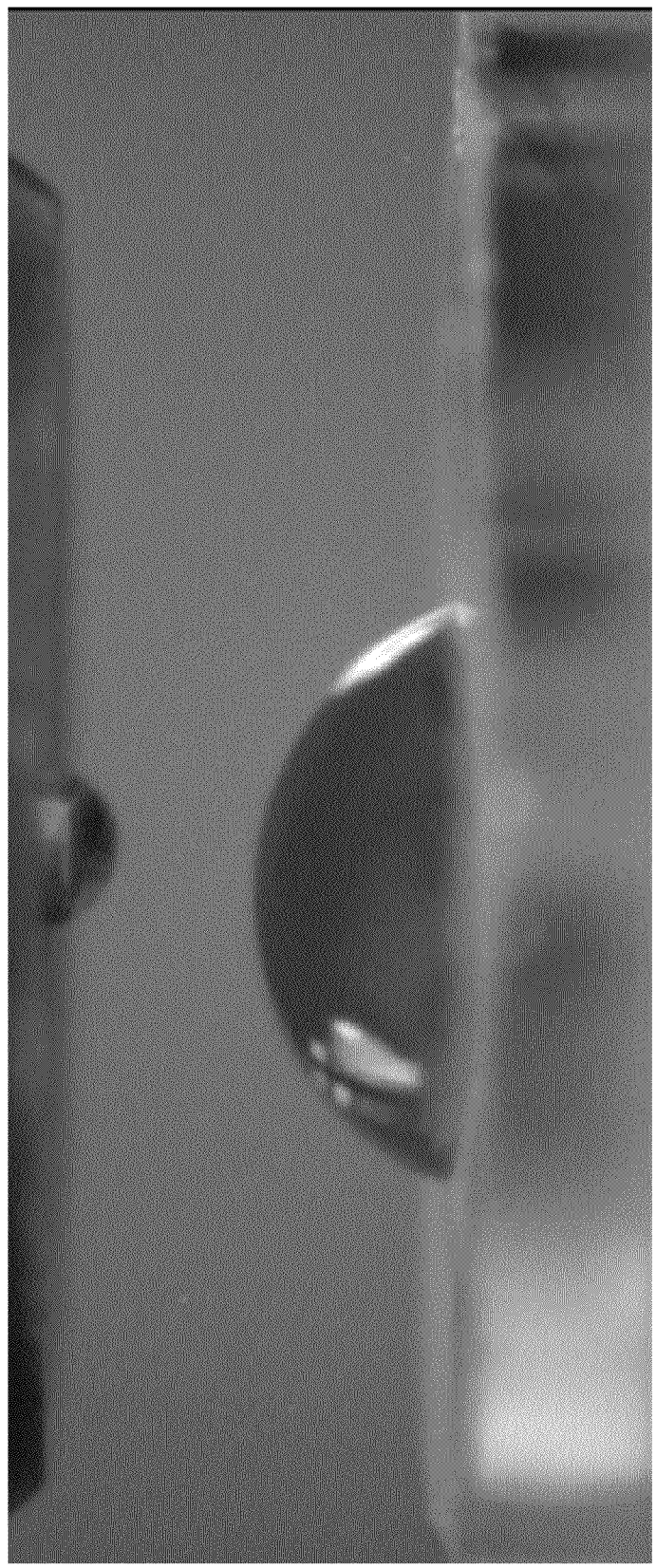
Figure 15F:
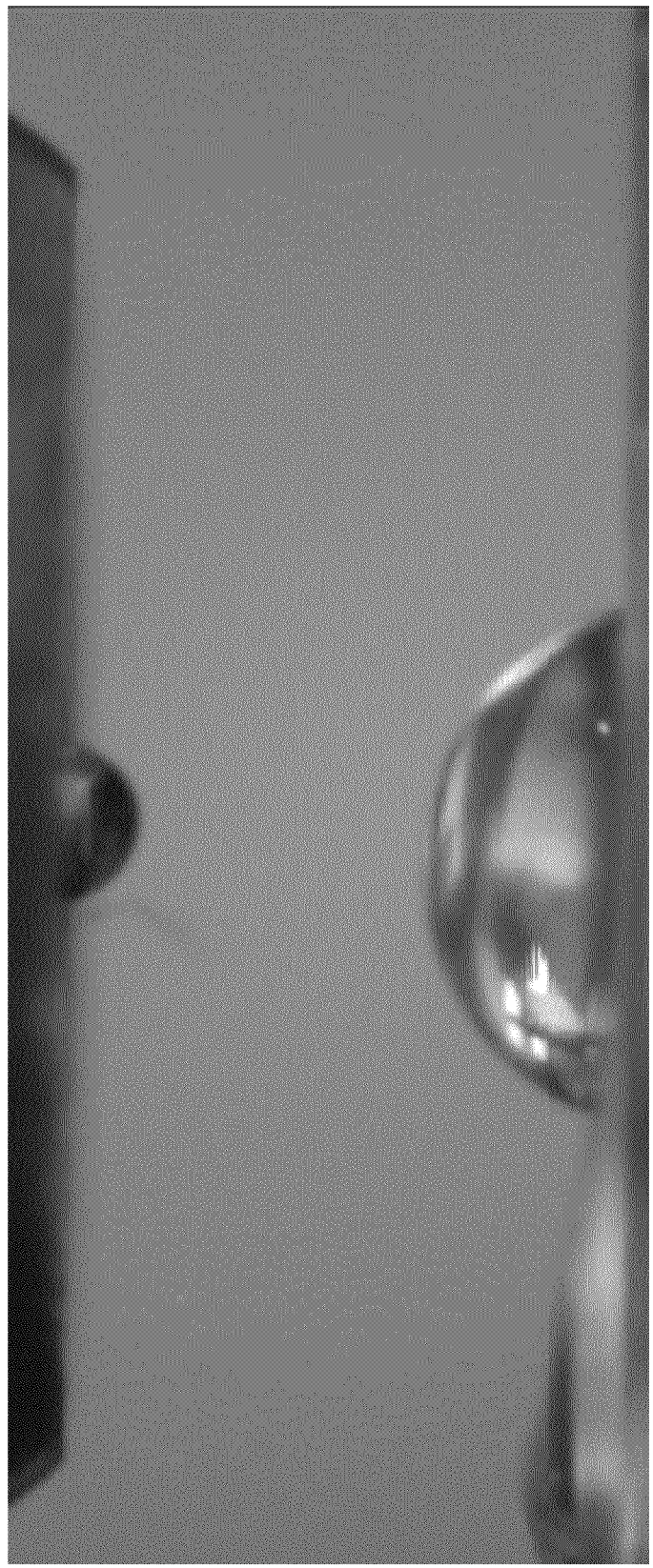
Figure 15G:
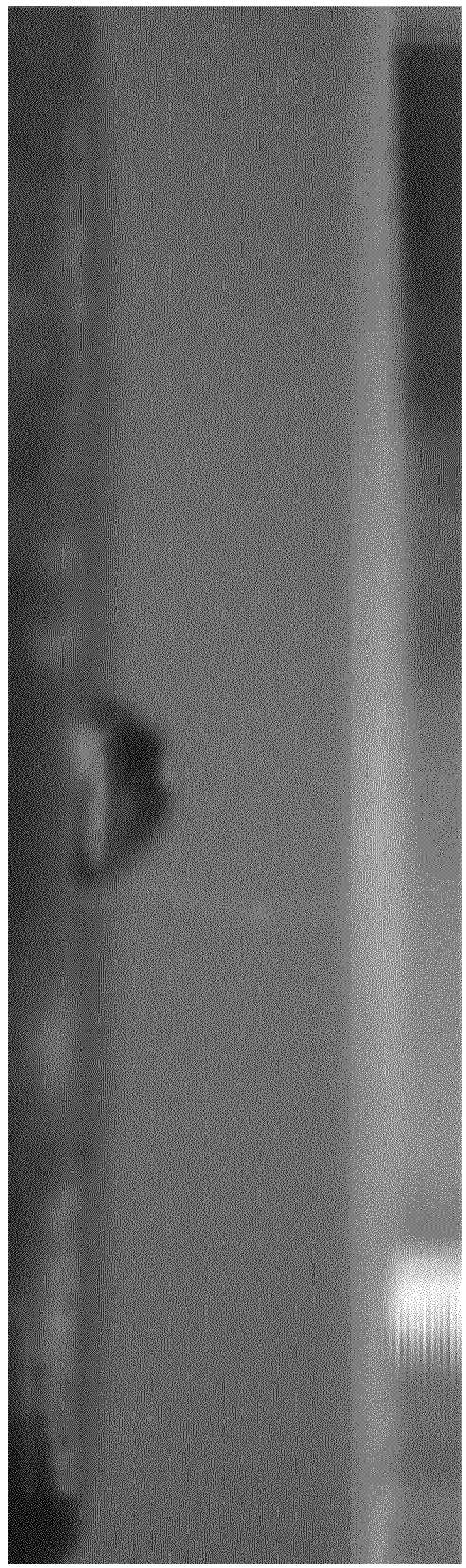
Figure 15H:
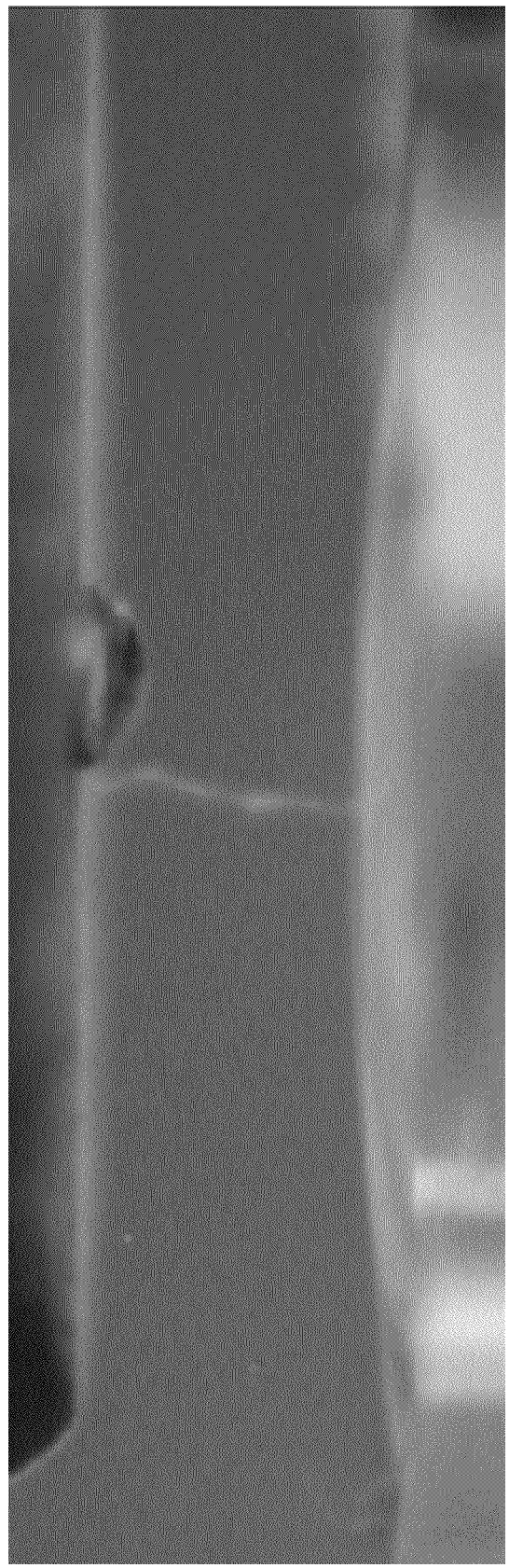
Figure 15I:
Figure 15J:
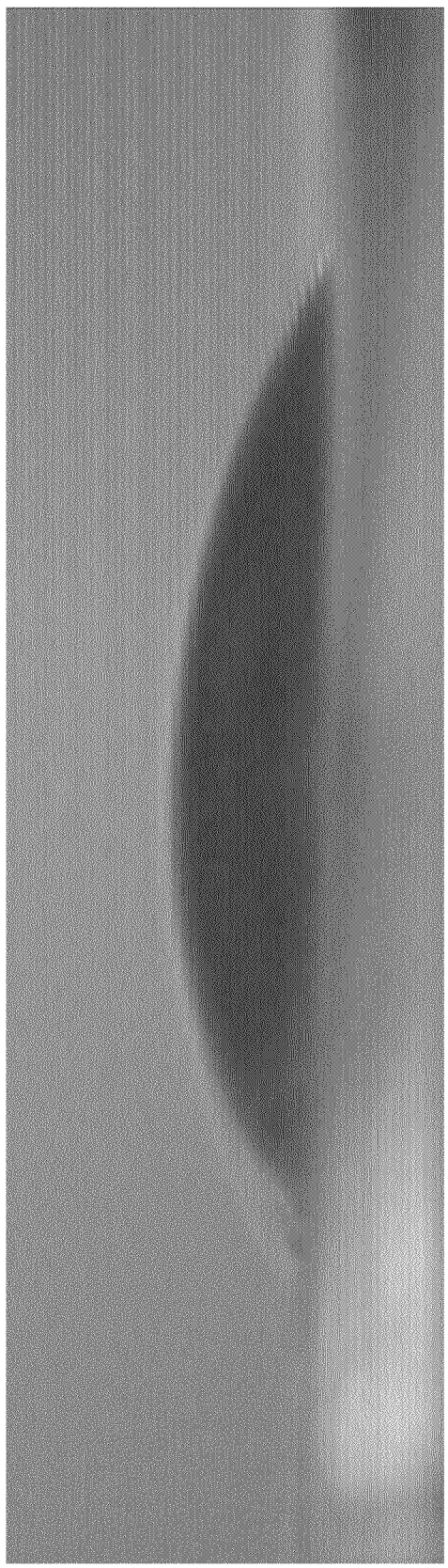
Figure 15K:
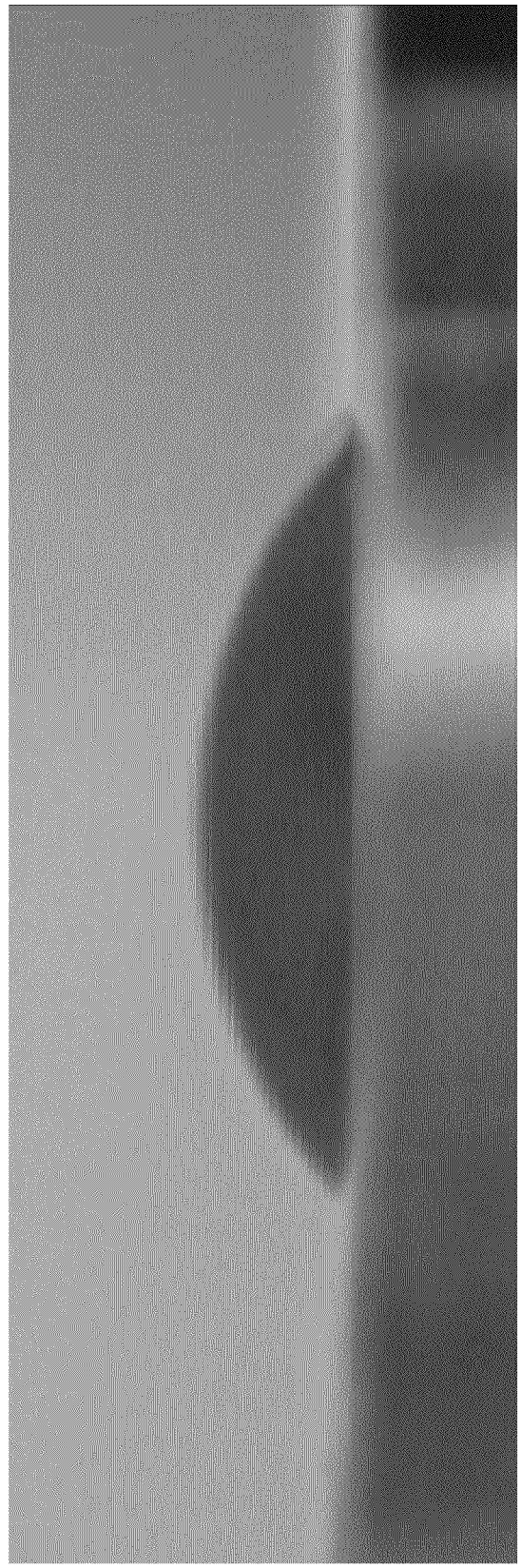
Figure 15L:
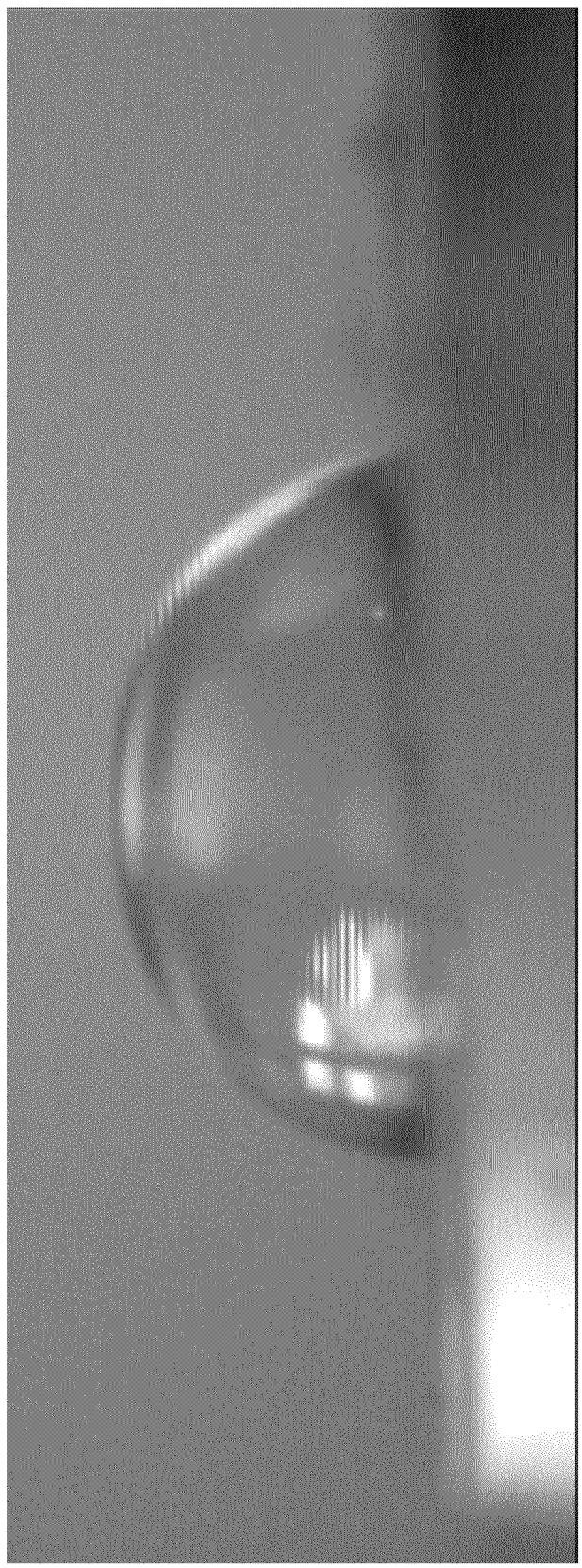
Figure 15M:
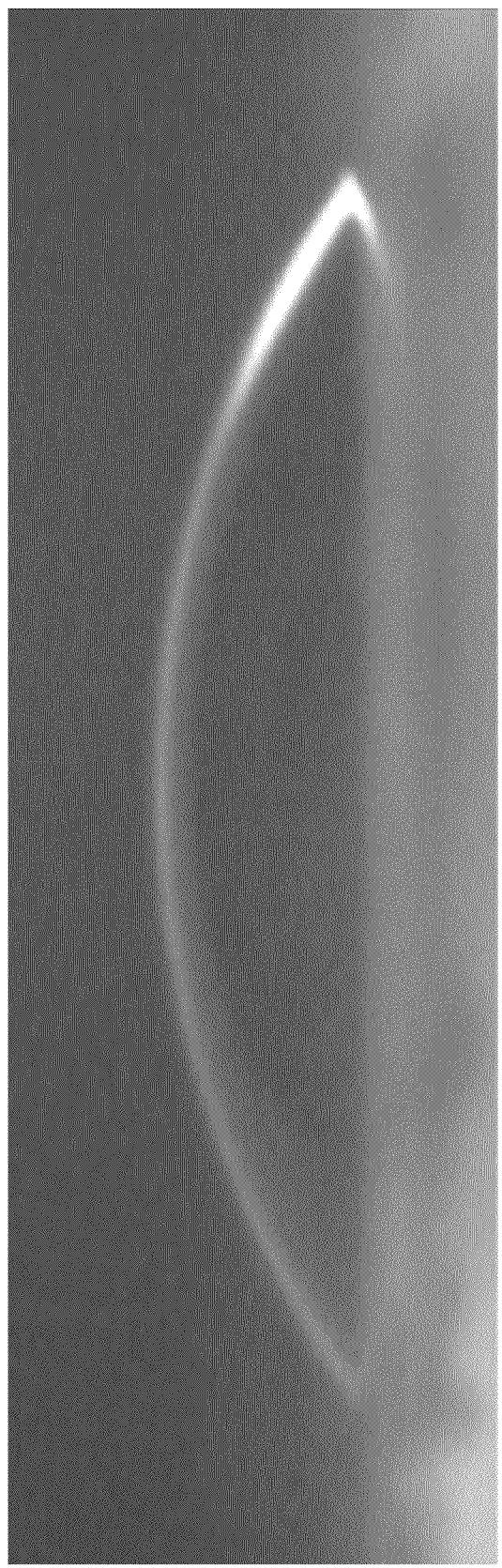
Figure 15N:
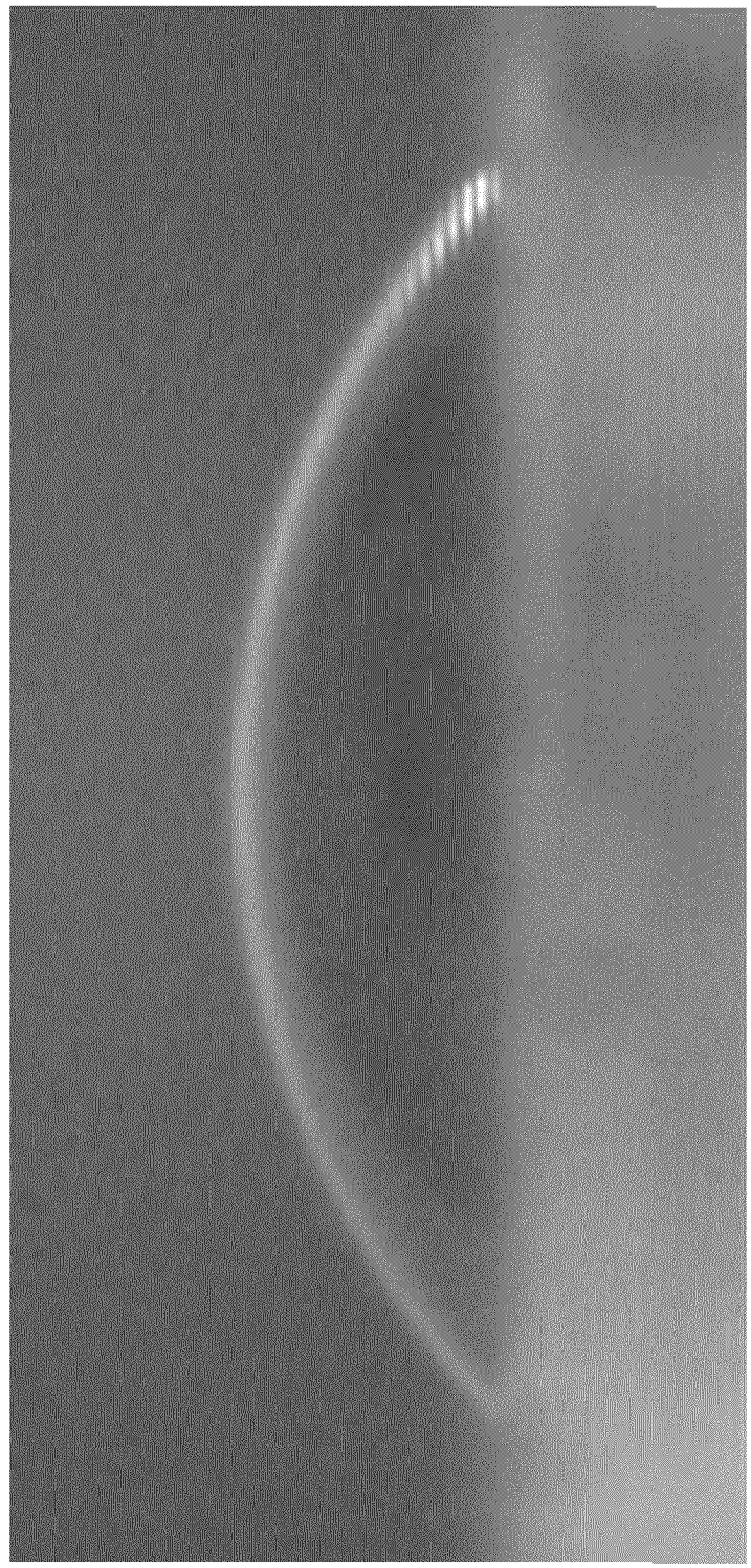
Figure 15O:
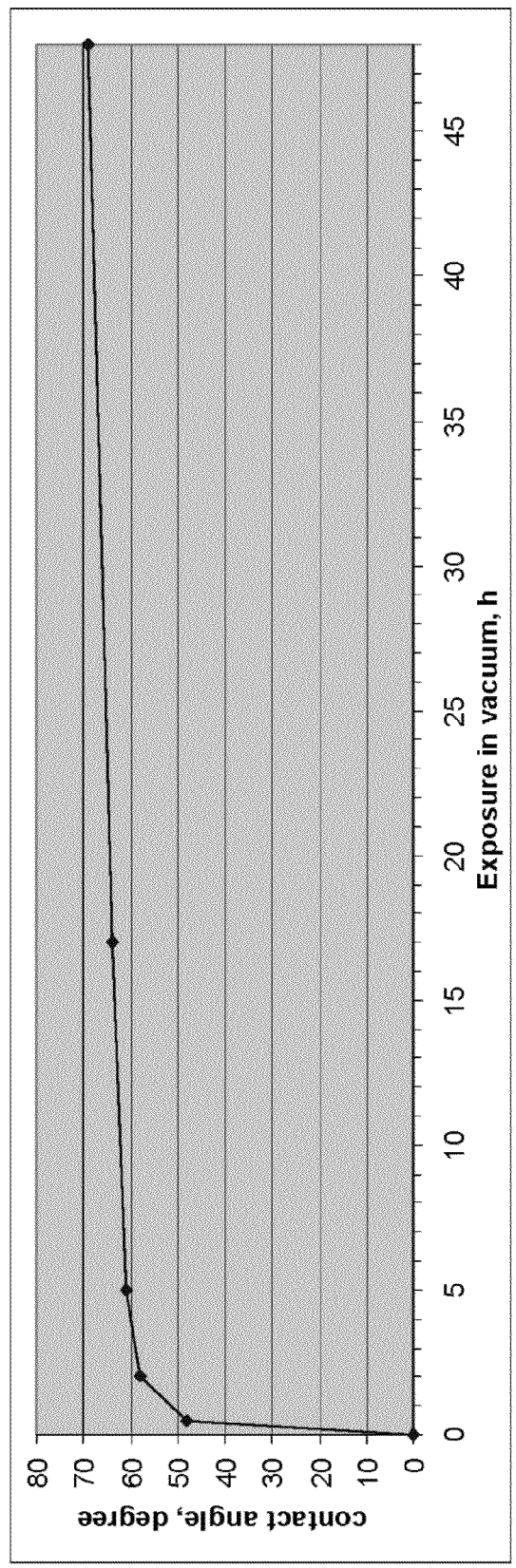

A freshly exposed glass surface is known to rapidly increase in surface hydrophobicity, a tendency that has been ascribed to adsorption of impurities from the air. See Petri et al., 1999, Langmuir 15, 4520-4523, which is hereby incorporated by reference in its entirety. By measuring the contact angle of a freshly broken glass surface with a water drop it was determined that when placed in a vacuum the surface becomes more hydrophobic even more rapidly than in air (FIGS. 15A and B). The most dramatic thermodynamically driven stabilization, by formation of new Si—O—Si bonds, occurs within first hour. Broken bond stabilization by air keeps the surface hydrophilic much longer. Using freshly polished and activated glass surfaces for derivatization will thus minimize reproducibility problems (FIG. 15C).

5.3.2 Surface Activation

Figure 16A:
Figure 16B:
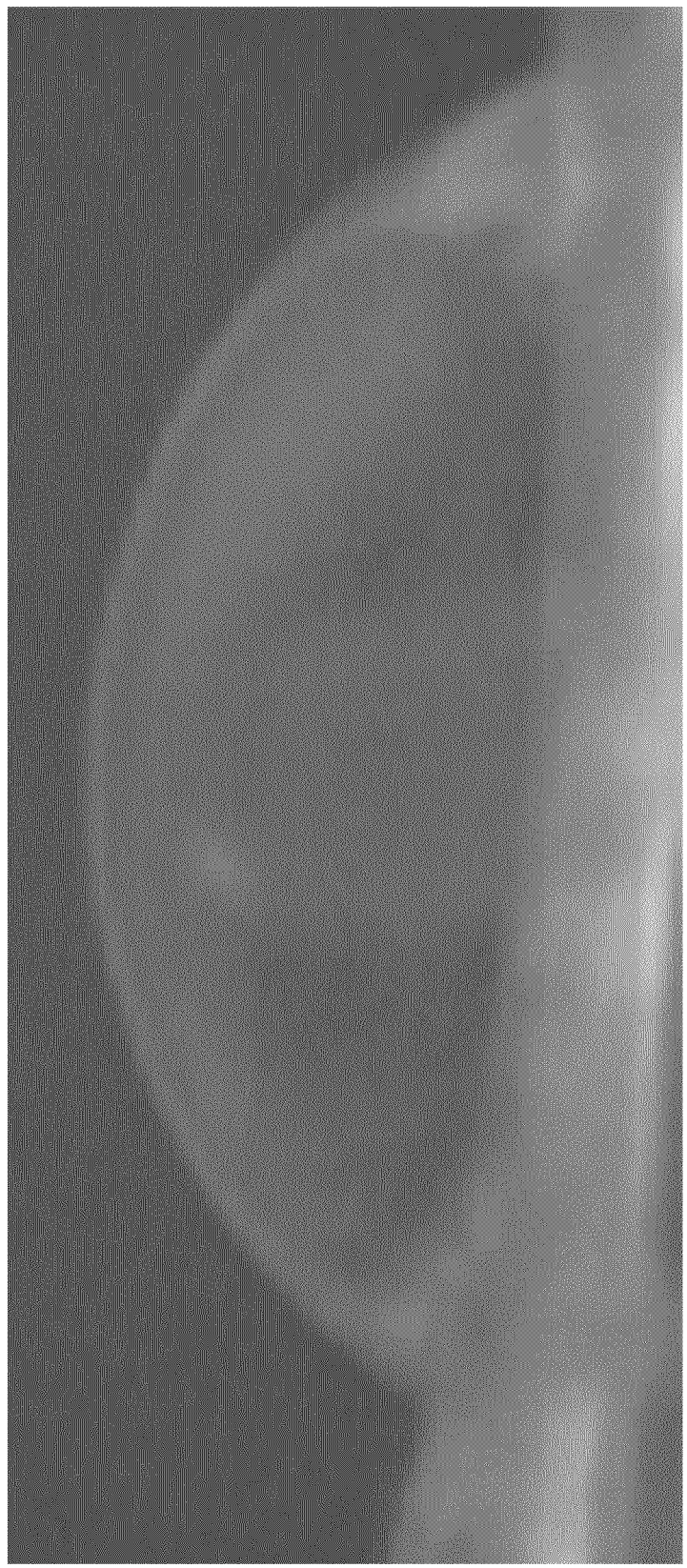
Figure 16C:
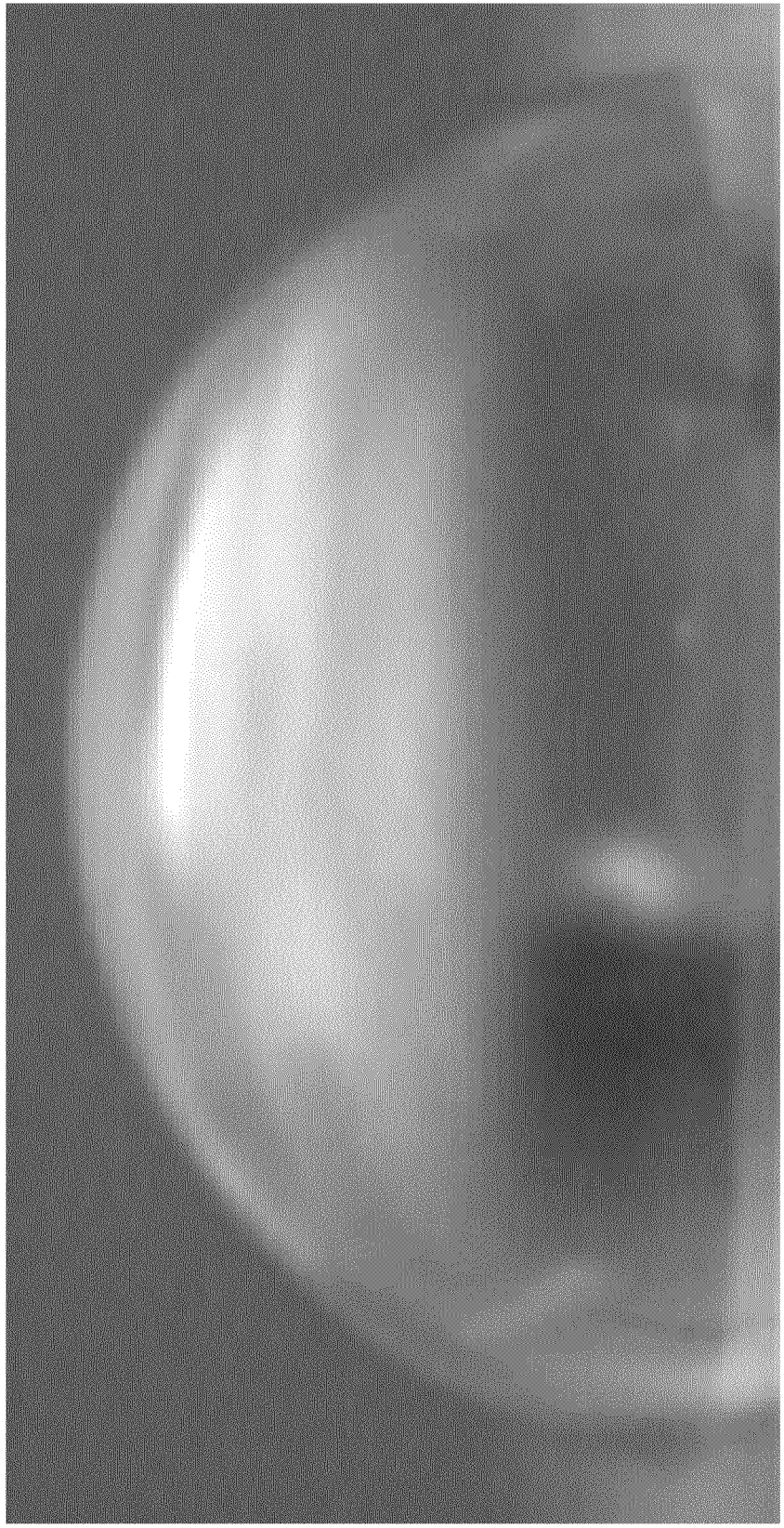
Figure 16D:
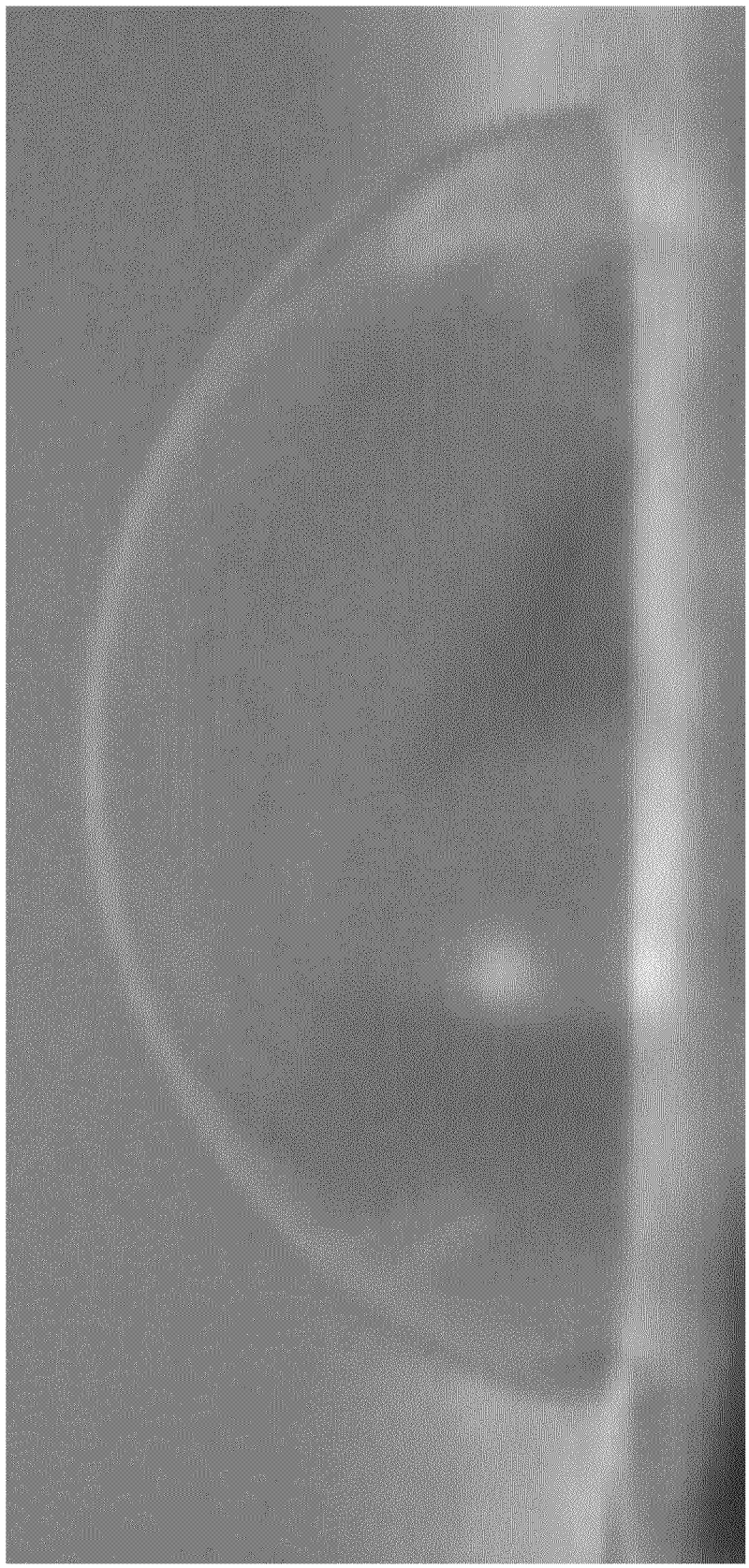
Figure 16E:
Figure 16F:

Glass surfaces are activated by hydrolysis of Si—O—Si bonds, typically by boiling the glass in inorganic acid. See, Allenmark, 1988, Ellis Horwood series in analytical chemistry 224. Such a method is not easy to apply to manufacturing. However, it has been determined herein that treatment of glass with 50% sodium hydroxide works as a suitable alternative (FIG. 16E).

5.3.3 Surface Derivatization and Loading

Figure 17A:
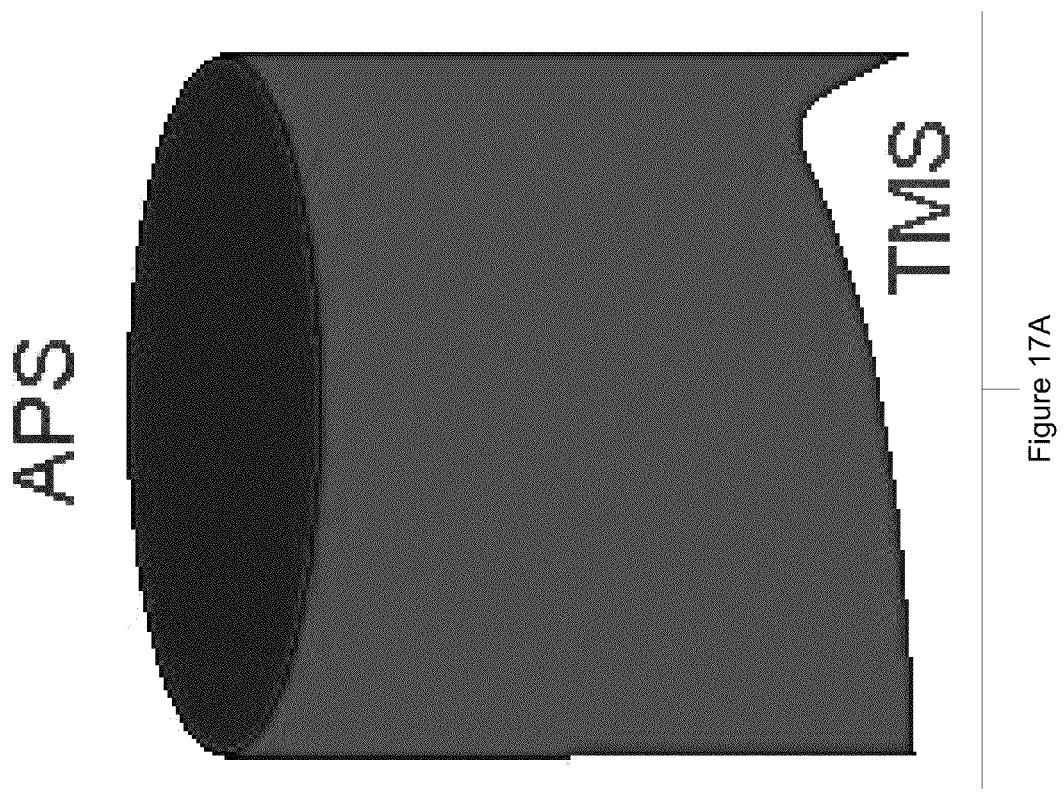
Figure 17B:
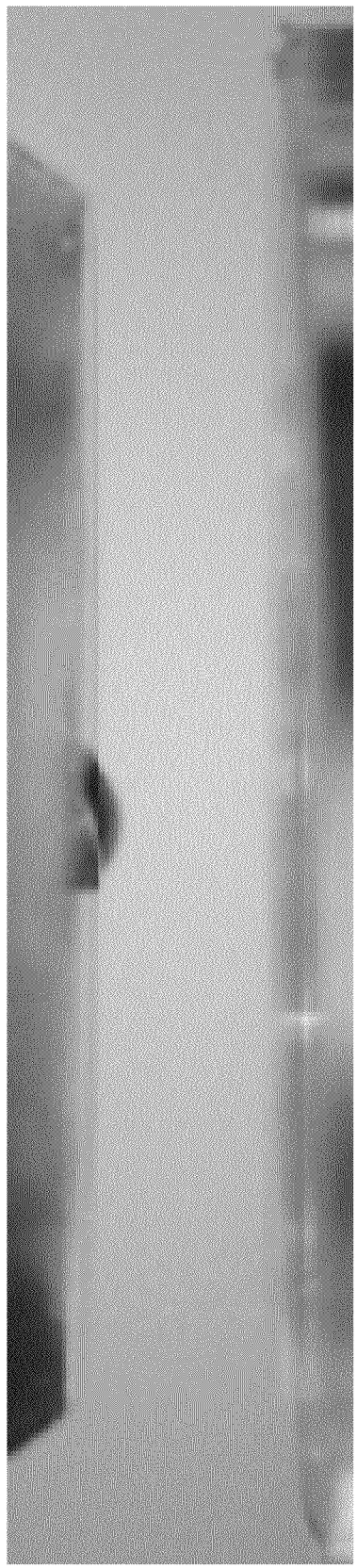
Figure 17C:
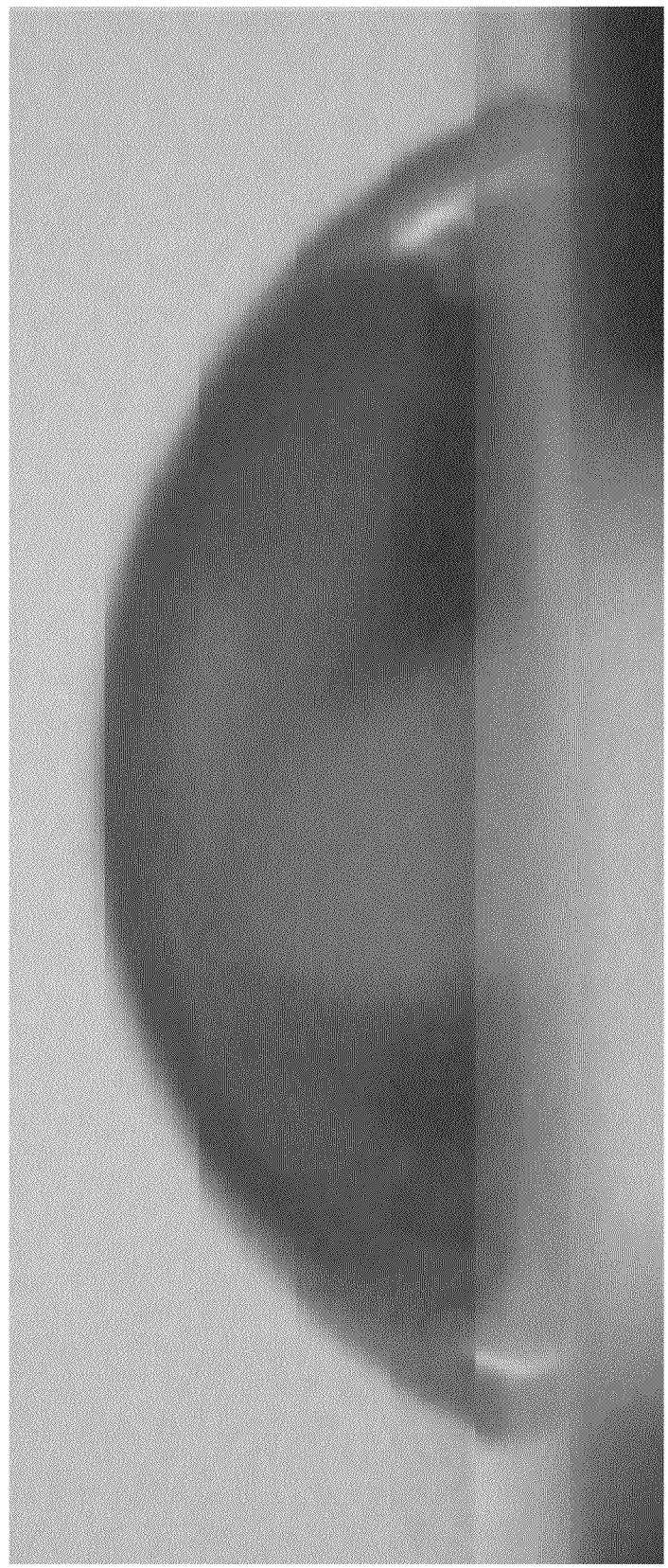
Figure 17D:
Figure 17E:
Figure 17F:
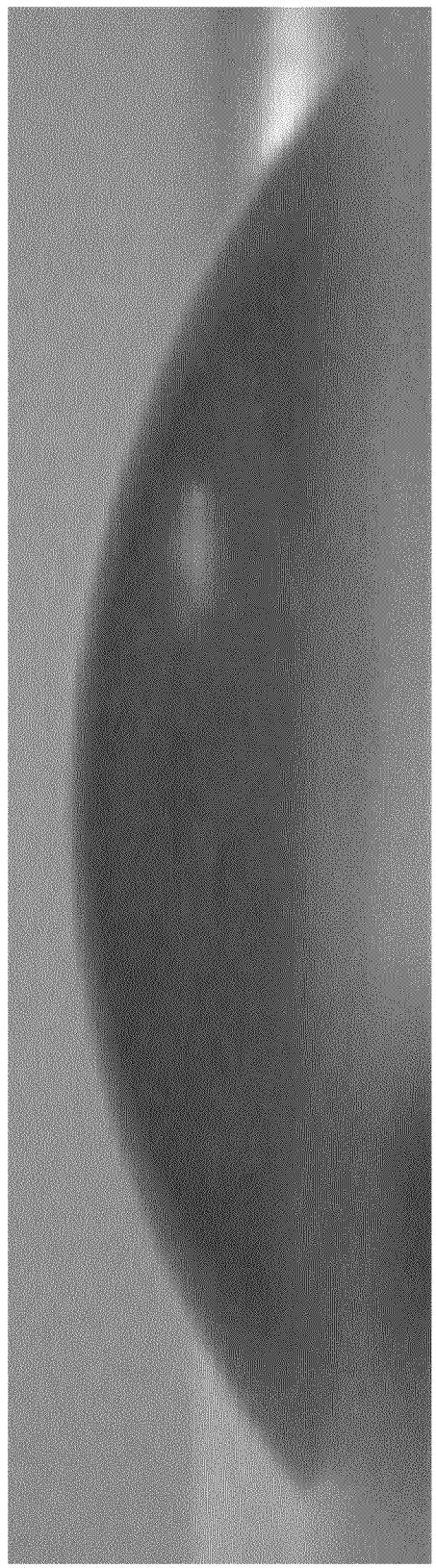
Figure 17G:
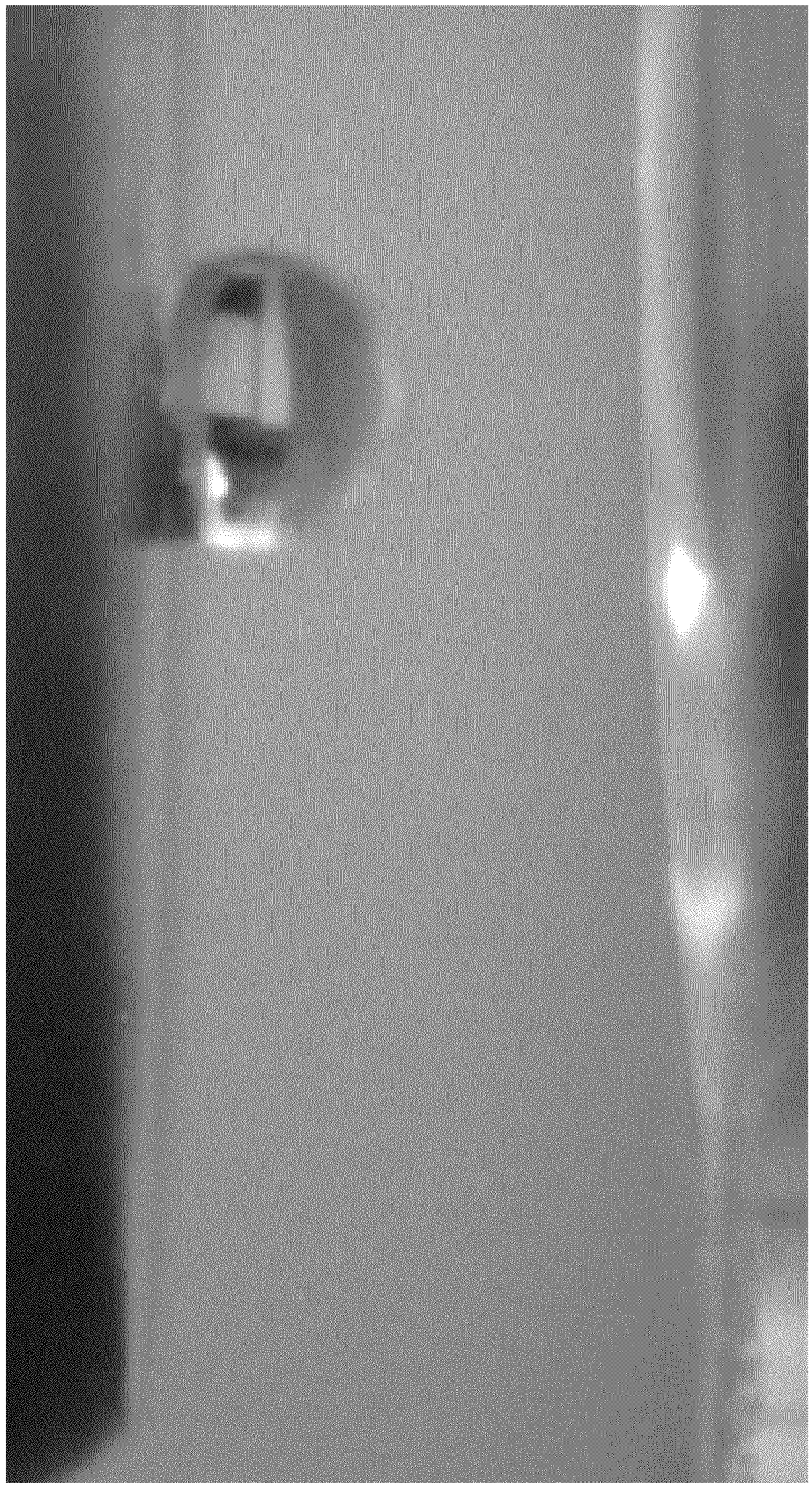
Figure 17H:
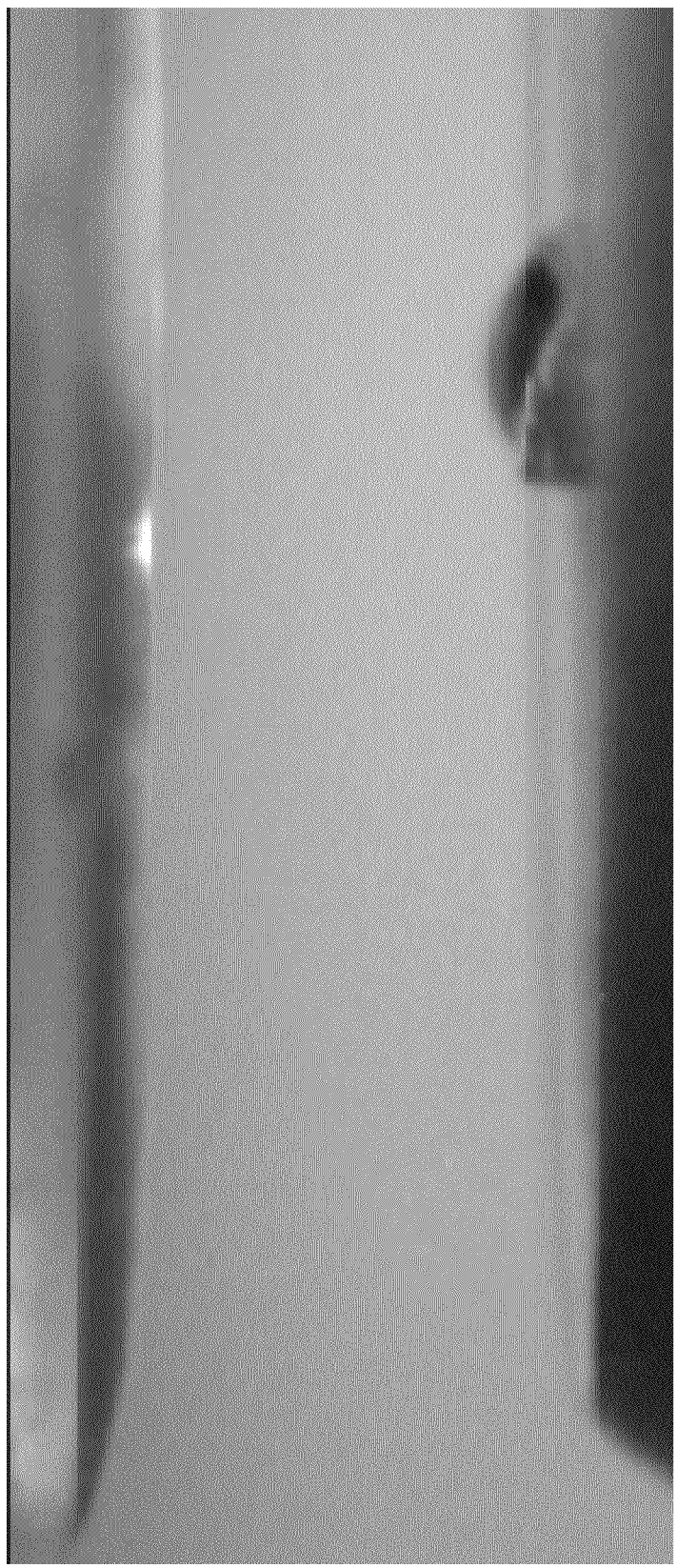
Figure 17I:
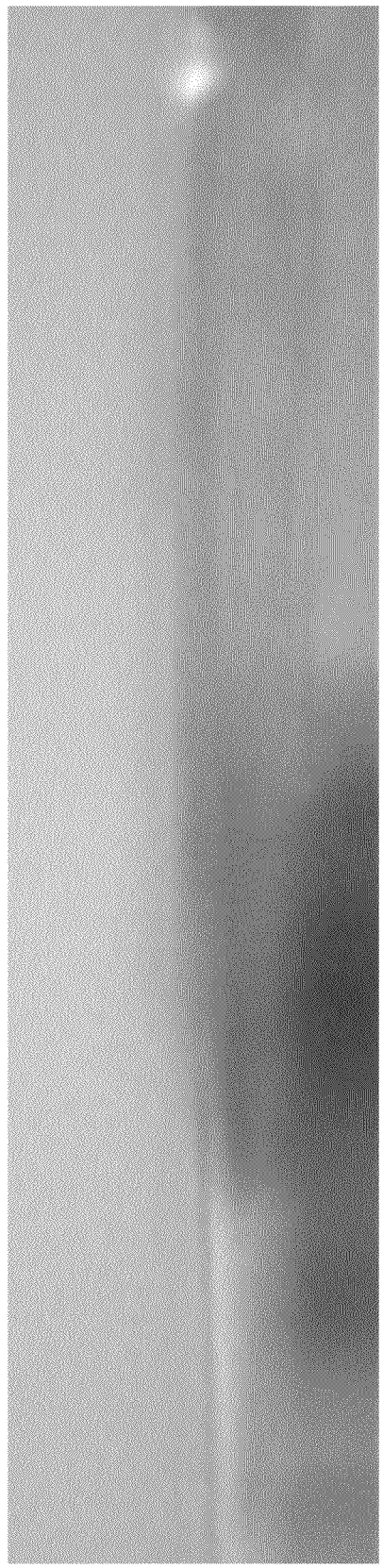
Figure 17J:
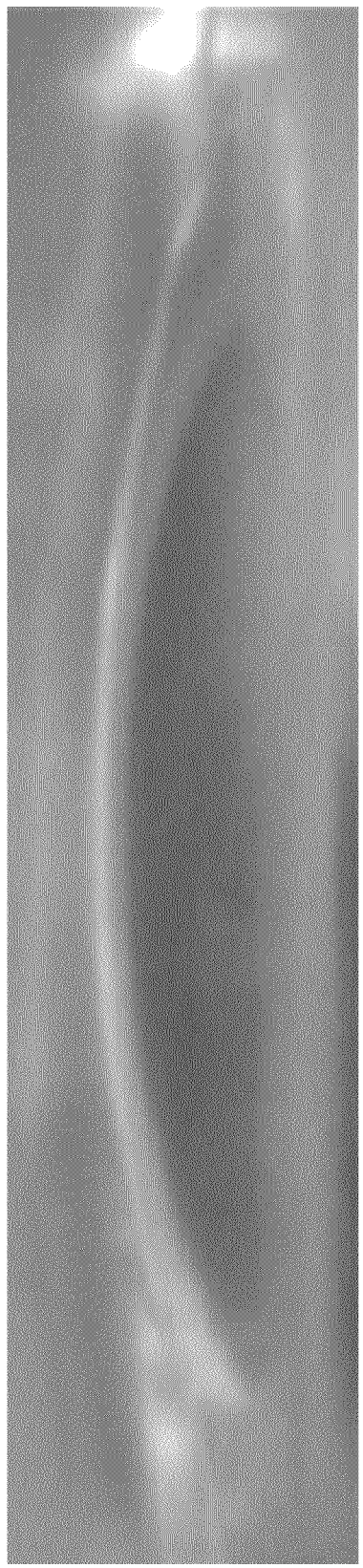
Figure 18A:
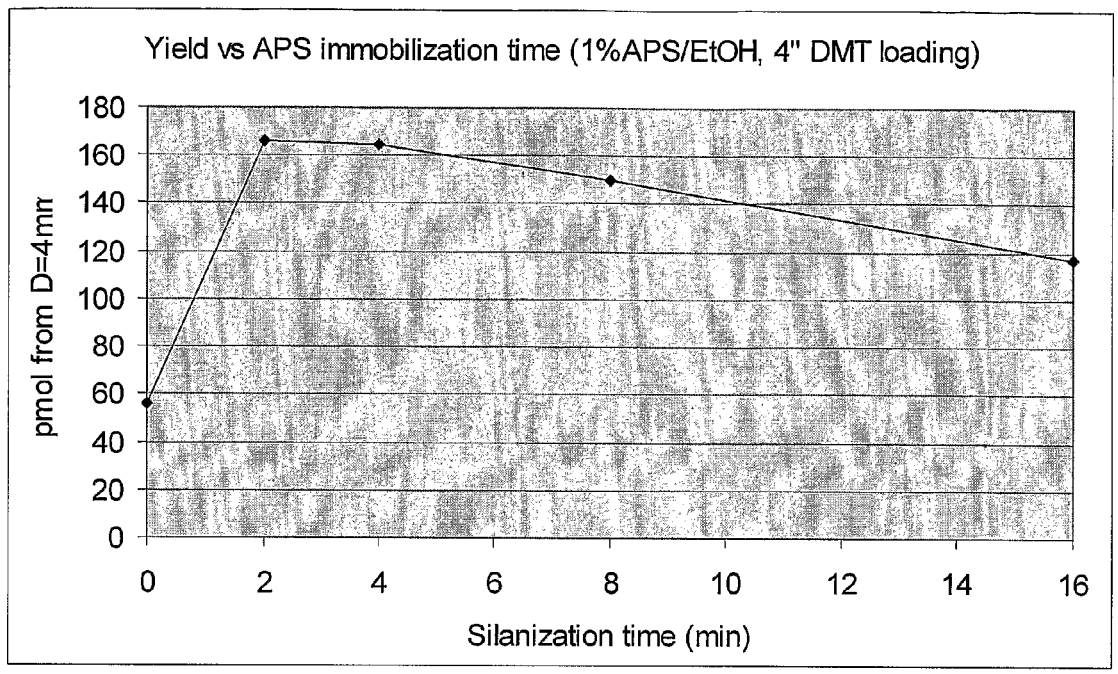

To localize oligonucleotide synthesis to the flat end of the rod the rod sides can be chemically protected, for example with trimethylsilane (FIG. 17A). Silanization can be monitored on a freshly activated glass surface by measuring changes in the contact angle of a 2 µl water drop (FIG. 17B). Once the sides of the rod are silanized, the end can be derivatized, for example with aminopropylsilane. Longer exposure of the surface to aminopropylsilane, or use of aged aminopropylsilane produces a more hydrophobic surface (FIGS. 17C and D) which is less useful. A short derivatization step was selected because incomplete or irreproducible rod derivatization can cause low coupling efficiencies (FIG. 18A).

The derivatized surface can be loaded with functional groups for oligonucleotide synthesis such as dimethoxytritylthymidine succinate to load the first nucleotide onto the surface.

Attachment of the first nucleotide can be performed by 2-(1-H-benzotriazole-1-yl)-1,1,2,2-tetramethyluronium hexafluorophosphate (HBTU), 2000 Novabiochem catalog, for example, by injecting 5-10 µl drops of reagents on top of vertically installed rods (4 mm diameter). Preferably, the rod walls are freshly treated with trimethylchlorosilane to prevent drops from slipping down. Alternatively, the reaction area can be oriented downwards.

Synthesized oligonucleotides can be released from the end of glass reaction pins by gaseous ammonia, which effects a rapid, mild deprotection and cleavage of oligodesoxyribonucleotides from the support. Under these conditions the rate of isobutyril-dG deprotection is comparable with the removal of 4-(tert-butyl)-phenoxyacetyl group by aqueous ammonia at room temperature. See, for example, Boal et al., 1996, Nucleic Acids Res 24, 3115-7, which is hereby incorporated by reference in its entirety.

To reduce or eliminate the fraction of oligonucleotides with low reactivity towards polymerization on non-porous supports, oligonucleotide chains may be supported by glass rods derivatized with polyethylene glycol or polypropylene rods functionalized by ammonium plasma. See, for example, Chu et al., 1992, Electrophoresis 13, 105-14, which is hereby incorporated by reference in its entirety.

5.4 Devices for Oligonucleotide Synthesis

5.4.1 Reactor Design

Oligonucleotides that are useful for assembly of polynucleotides must meet higher performance criteria than oligonucleotides for many other applications. Only relatively small amounts of oligonucleotides are required: preferably less than 10 pmol of oligonucleotide and more preferably less than 5 pmol of oligonucleotide. Purity is important, and oligonucleotides containing internal deletions or apurinic residues are particularly deleterious.

The major applications for commercially synthesized oligonucleotides are as PCR primers or DNA micro-array probes, neither of which demands the same level of quality as building blocks for synthetic genes. Current commercial synthesizers use controlled-pore glass as a support for oligonucleotide synthesis, the design of such reaction vessels has already reached the minimal reaction volume (~45 µl) at which a two component reaction and resin can still form a homogeneous suspension without sticking to the walls and leaking out from the supported filter. Porous support materials have the disadvantage that they may trap reagents, chemicals may leak during the reaction and there may be unpredictable plugging and unplugging of pores by gases and microparticles. A non-porous glass support will reduce or eliminate these problems, and allow smaller reaction volumes for oligonucleotide synthesis (~5 µl) together with the high quality needed for subsequent polynucleotide assembly.

Non-porous surfaces suitable as substrates on which to perform oligonucleotide synthesis include polished quartz (100% $SiO_2$) or Pyrex (81% $SiO_2$) discs or plates from Chemglass with an exposed surface area of less than 1000 $mm^2$, preferably less than 300 $mm^2$, and more preferably less than 100 $mm^2$.

Modifications to the standard reaction vessel for CPG-supported oligonucleotide synthesis (Gait, 1984, Practical approach series, xiii, 217; Ito et al., 1982, Nucleic Acids Res 10, 1755, each of which is hereby incorporated by reference) improve oligonucleotide quality. The punching that frequently causes vortex formation during argon purging and contamination by chemicals stuck to the septa can be reduced or eliminated by using a technique based on positive pressure inert gas flow. Instead of punching through a septum, chemicals are added through an open channel with an argon flow to prevent air entering the reactor. The risk of air bypassing can be removed by using an argon purging procedure instead of vacuum filtration. Only one flow regulator (such as a stopcock) for regulating the argon input is required. All air sensitive solutions can be pressurized with an inert gas such as argon. An example of such a device is shown in FIG. 50.

Accordingly, an aspect of the present invention provides a device for synthesizing oligonucleotides. The apparatus comprises (i) a reaction vessel for containing substrate supported seed nucleotides, (ii) an open channel in fluid communication with the reaction vessel, (iii) and a positive-pressure inert gas flow regulated by a stopcock, where the positive-pressure inert gas flow is configured to add chemicals through said open channel. In some embodiments, the positive-pressure inert gas flow is an argon gas flow.

5.4.2 Combined Synthesizer and Chemistry Improvements

By using a freshly prepared oxidizer with high water content and using a DMAP catalyzed capping step after oxidation instead of (or in addition to) N-methylimidazole catalyzed capping before oxidation there is no need to acylate thymidine, cytosine and adenosine residues before oxidation. The guanidine modification problem (Eadie & Davidson, 1987, Nucleic Acids Res 15, 8333-49, which is hereby incorporated by reference), can be avoided in an oligonucleotide synthesizer, hardware and software, that efficiently performs a double capping protocol.

Depurination occurs at the acidic deprotection step. In commercial synthesizers, depurination is typically minimized by controlling the pH and reaction time. See Septak, 1996, Nucleic Acids Res 24, 3053-3058; and Paul & Royappa, 1996, Nucleic Acids Res, 24, 3048-3052, each of which is hereby incorporated by reference in its entirety. An important parameter for adjusting the relative rates of different reactions is temperature, though this cannot be adjusted with current commercial synthesizer designs. Different dependencies of reaction rates on temperature were empirically described by Arrhenius in 1889 and subsequently theoretically validated by Eyring in 1935. According to transition state theory, the reaction constant (k) depends on temperature (T):

$$k = A \cdot e^{B/T}$$

Arrhenius Equation $$k = \frac{k_B T}{h} \cdot e^{\frac{\Delta S^{\neq}}{R}} \cdot e^{-\frac{\Delta H^{\neq}}{RT}}$$

Eyring Equation where,
A=Arrhenius constant;
B=reaction activation energy;
R=gas constant=[8.314 J/(mol·K)];
$\Delta S^{\#}$=reaction activation entropy [J·mol$^{-1}$·K$^{-1}$];
$\Delta H^{\#}$=reaction activation enthalpy [kJ·mol$^{-1}$];
$k_B$=Boltzmann's constant [1.381·10$^{-23}$ J·K$^{-1}$]; and
h=Plank constant [6.626·10$^{-34}$ J·s].

The efficiency of adenosine detrylation relative to its depurination can be adjusted by altering the reaction temperature. The kinetic parameters $\Delta S^{\#}$ and $\Delta H^{\#}$ for other reactions can be determined by standard methods. An automated instrument with a controlled temperature deprotection block, for example controlled by a Peltier device, will allow control of the relative rates of the critical reactions. One example of such a device design is shown in FIG. 51. One application of such a device is to reduce the formation of depurinated side-products during oligonucleotide detrylation. This reaction is performed below the room temperature. For this purpose, a container with a solution of dichloroacetic acid is cooled down by Peltier devices attached to the reaction chamber.

Accordingly, some embodiments of the present invention provide an oligonucleotide synthesizing apparatus comprising (i) a reaction cell for containing substrate supported seed nucleotides, (ii) a plurality of chemical supply reservoirs for containing certain predetermined bases, reagents and solvents to be used in an oligonucleotide synthesis process, (iii) a dispenser coupled to the plurality of chemical supply reservoirs and to the reaction cell for selectively dispensing one or more of the predetermined bases, reagents, and/or solvents at predetermined times and in predetermined controlled volumes, (iv) a processor for executing a plurality of subroutines corresponding to the sequential steps of an oligonucleotide synthesizing process; and (v) a temperature controller for controlling the temperature of the reaction cell in order to differentially affect the rate of two different reactions that occur in the reaction cell. In some embodiments, the temperature controller is a controlled temperature deprotection block. In some embodiments, this controlled temperature deprotection block is controlled by a Peltier device. In some embodiments, the dispenser comprises an open channel in fluid communication with the reaction cell and the oligonucleotide synthesizing apparatus further comprises a positive-pressure inert gas flow regulated by a stopcock, where the positive-pressure inert gas flow is configured to add chemicals through the open channel. In some embodiments, positive-pressure inert gas flow is an argon gas flow. Details of conventional nucleic acid synthesizers are found in Zelinka et al., U.S. Pat. No. 4,598,049, which is hereby incorporated by reference in its entirety.

5.5 Assembly of Oligonucleotides into Polynucleotides

5.5.1 Combined Synthesizer and Chemistry Improvements

Polynucleotide synthesis typically comprises two steps. First, two or more oligonucleotides are synthesized chemically. These oligonucleotides are preferably between 5 and 200 nucleotides in length, more preferably between 10 and 100 nucleotides in length, even more preferably between 15 and 75 nucleotides in length. Second, these oligonucleotides are assembled in an enzyme-mediated process into polynucleotides. These polynucleotides are preferably longer than 100 nucleotides in length and more preferably longer than 200 nucleotides in length.

5.5.2 Polynucleotide Design

Figure 21:
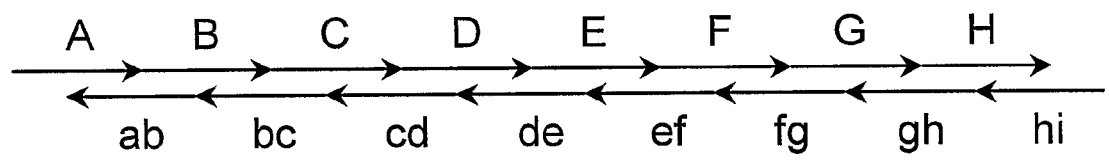

To assemble oligonucleotides into polynucleotides, the oligonucleotides are first annealed to one another, as shown in FIG. 21. The annealing of each oligonucleotide to its two correct partners is important to ensure the subsequent formation of a polynucleotide with the correct sequence. The annealing of each oligonucleotide to its correct partners can be influenced by the design of the polynucleotide itself, the design of the oligonucleotides from which the polynucleotide will be assembled, and the reaction conditions and processes used for polynucleotide assembly. Methods for designing oligonucleotides, polynucleotides and choosing reaction conditions that improve the ease and fidelity of polynucleotide synthesis are aspects of the present invention.

Complementary nucleic acid sequences bind to one another, in part as a result of hydrogen bonding within a complementary base pair: two hydrogen bonds between a thymine and adenine, three hydrogen bonds between a guanine and cytosine. The different number of bonds within the two different complementary base pairs means that a thymine-adenine pair contributes less stability to a DNA duplex than a cytosine-guanine pair. As a result, the sequence of a polynucleotide affects the ease and fidelity with which that polynucleotide may be assembled from oligonucleotides.

Factors involving base composition affect the annealing temperatures of the oligonucleotides that will be used to assemble a polynucleotide. One such factor is the overall representation of each base; that is the fraction of nucleotides that are either cytosine or guanine. This is known as the GC content. A sequence with a higher GC content will tend to have a higher thermal stability than a sequence of the same length with a lower GC content. Another such factor is the uniformity of base representation, in other words, whether a part of the polynucleotide contains a high GC content while another part of the polynucleotide has a low GC content. In this case oligonucleotides for assembly of the part of the polynucleotide containing a high GC content would have a higher thermal stability than oligonucleotides for assembly of the part of the polynucleotide containing a low GC content.

The presence of repeated sequence elements can also affect the degree to which oligonucleotides anneal with one another in the polynucleotide assembly process. For example the set of oligonucleotides that are required to assemble a polynucleotide that contains a sequence of repeated nucleotides may contain two oligonucleotides containing this sequence and 2 oligonucleotides containing the reverse complement of this sequence, one being the correct annealing partner and one being the incorrect annealing partner. The longer this repeat sequence is, the higher its contribution to the stability of annealing of the oligonucleotide and its complement, and the greater the stability of annealing of the oligonucleotide with the incorrect annealing partner. The greater the stability of annealing of an oligonucleotide with an incorrect annealing partner, the greater the chances that it will anneal to this incorrect partner during the polynucleotide synthesis process, resulting in a decrease in fidelity of the polynucleotide synthesis process.

Because of the degeneracy of the genetic code, one polypeptide sequence may be encoded by many different polynucleotides. Some of these polynucleotides will be easier to synthesize in a high fidelity process, while others will be more difficult. When a polynucleotide is being designed and/or synthesized to encode a polypeptide, a polynucleotide sequence may therefore be chosen that facilitates the high fidelity synthesis of that polynucleotide, in addition to ensuring that the polynucleotide will possess the desired functional properties. Methods for choosing a polynucleotide sequence that fulfills functional as well as ease-of-synthesis criteria may be accomplished using computer programs (e.g., software). The methods and the software for performing the methods are aspects of the present invention.

Most organisms use the same genetic code, that is, in general the same triplet of nucleotides (codon) specifies the same amino acid. Different organisms use these codons with different frequencies within their genes, however. For example different codon biases are found in humans, human viruses such as hepatitis A, hepatitis B, hepatitis C, human immunodeficiency virus (HIV), human papilloma virus (HPV), influenza, flaviviruses, lentiviruses, papovaviruses, human pathogens such as *Mycobacteria, Chlamydomonas, Candida, Plasmodium falciparum* (the causative agent of malaria), *Cryptosporidium, Leishmania* and other protozoa, model organisms such as Tetrahymena, and commonly used expression systems such as baculovirus, *Escherichia coli, Bacillus*, filamentous fingi, mammalian cell lines including COS cells and 3T3 cells, yeasts including *Saccharomyces cerevisiae*, plants including maize and cotton and model organisms for the study of disease and tests of the efficacies of DNA vaccines such as macaques, mice and rabbits. This difference in turn affects the ability of an organism to express a polypeptide that is encoded by a particular polynucleotide sequence. A polynucleotide that contains a large number of codons that are used rarely by an organism will generally express more poorly in that organism than one that does not. Polypeptide expression can be enhanced by using a polynucleotide whose distribution of codons matches the distribution found in the intended expression host organism. The distribution of codons used within the genes of an organism can be represented as a codon bias table. Examples of such tables are shown in FIGS. 22, 23 and 25. Such tables represent the average use of codons within many genes in an organism (FIGS. 23 and 25), or the average use of codons within many genes of a specific class (such as highly expressed genes, FIG. 22) in an organism.

A codon bias table may be used in the design of a polynucleotide that encodes a specific polypeptide. The polynucleotide may be designed so that each of the 20 amino acids contained in the polypeptide is encoded in the polynucleotide by codons selected at a frequency represented in the codon bias table. For example, Tyr is encoded by the codons TAT and TAC. In highly expressed *E coli* genes TAT is used 35% of the time (its frequency is 0.35) and TAC is used 65% of the time (its frequency is 0.65), as shown in FIG. 22. In a polynucleotide designed for expression in *E coli*, Tyr may therefore be encoded approximately 35% of the time with TAT and 65% of the time with TAC. Such a polynucleotide would have an *E coli* codon distribution for Tyr. The same process may be used for all of the amino acids in the polypeptide. Because a codon bias table contains average values compiled from information from many genes, it is not necessary to precisely match the values found in the codon bias tables in order to obtain a polypeptide that will express well in a host organism. It may be preferable to use the codon bias table to guide a probabilistic choice of amino acid. For example, in designing a polynucleotide to encode a polypeptide for expression in *E coli*, each time a Tyr is encountered, a selection method or computer program may be used that has a 35% chance of selecting TAT and a 65% chance of selecting TAC. On average, many polypeptides designed by such a method would contain TAT and TAC in the ratio of 0.35:0.65, although any individual polynucleotide may vary from this ratio and may still express well in the host. Similar methods may be used to select codons to encode the other amino acids from the polypeptide.

A second way in which codon bias tables may be used in the design of a polynucleotide that encodes a specific polypeptide is to identify and eliminate codons that are very rarely used in a specific host. For example in FIG. 22 it can be seen that Arg is encoded by six possible codons: CGG, CGA, CGT, CGC, AGG and AGA. Of these, codons CGG, CGA, AGA and AGG each occur only about 1% of the time in highly expressed *E coli* genes, while CGT occurs 64% of the time and CGC 33% of the time. It may be advantageous to eliminate the four rarely used codons from the synthetic polynucleotide entirely. In this case only CGT and CGC would be used to encode Arg in the synthetic polynucleotide. Using a probabilistic selection method, CGT would then be selected $64/97 = 66\%$ of the time, and CGC would be selected $33/97 = 34\%$ of the time.

Threshold values for codons may be selected such that a codon that appears less frequently in a codon bias table than that threshold value are not used in a polynucleotide for expression in that host. Threshold values of 0.1 (10%), 0.09 (9%), 0.08 (8%), 0.07 (7%), 0.06 (6%), 0.05 (5%) and 0.04 (4%) can all be useful. Threshold values can be set using a method in which codons are selected probabilistically based upon a codon bias table, then codons whose frequency is below the threshold are discarded and another codon is chosen, again probabilistically. Alternatively a codon bias table may be pre-calculated with the frequency for a codon that appears below the threshold frequency being set to zero so that it is never selected by a probabilistic selection method.

Hybrid codon bias tables may be constructed for designing a polynucleotide encoding a polypeptide to be expressed in more than one expression system. One method of constructing such hybrid codon bias tables is to combine two or more starting codon bias tables from one or more organism. FIG. 24 shows a hybrid codon bias table constructed from the codon bias tables shown in FIGS. 22 and 23. In one combination method, a threshold frequency is selected and any codons that fall below the threshold are eliminated from all of the starting codon bias tables. For the remaining codons there are several possible methods of processing the frequencies. An average of the frequencies in the starting bias tables may be obtained. Such an example for preparing a codon bias table is shown in FIG. 24. Alternatively the higher of the values may be selected for each of the codons. Another possibility is to select the lower value. In all cases, the frequencies should be normalized so that the sum of the frequencies for all codons that encode one amino acid are equal to 1. By avoiding low frequency codons for multiple organisms, expression in all of those organisms will be improved, thereby increasing the general usefulness of the synthetic polynucleotide.

The incorporation of additional features into a designed polynucleotide may improve the usefulness of that polynucleotide. For example, it may be desirable to reduce the sequence identity between the synthetic polynucleotide and a naturally occurring polynucleotide that encodes a polypeptide or polypeptide fragment of the same amino acid sequence. Such a synthetic polynucleotide may function to produce its encoded polypeptide under conditions where the natural polynucleotide is inhibited by complementary oligonucleotides or polynucleotides, for example by antisense DNA or interfering RNA (RNAi). Conversely, it may be useful to increase the sequence identity between the synthetic polynucleotide and a naturally occurring polynucleotide to increase the frequency of recombination between the two under experimental conditions such as polynucleotide fragmentation and reassembly in vitro or in vivo. Methods and software for designing polynucleotides with maximized or minimized sequence identity to another polynucleotide sequence is an aspect of the invention.

Another feature that may improve the usefulness of a polynucleotide is the elimination or addition of sequences that serve as recognition and/or cleavage sites for restriction endonucleases. Such sequences may be useful for subsequent manipulations of the polynucleotide or subsequences of the polynucleotide such as subcloning or replacement of modules of the polynucleotide. Methods and software for designing polynucleotides with modified restriction endonuclease cleavage sites is an aspect of the invention.

It may also be advantageous to modify the restriction sites within a polynucleotide to effect subsequent recombinations between related polynucleotides. For example a polynucleotide may be designed to contain sites for one or more type IIs restriction endonucleases at every place possible within a sequence, without changing the polypeptide sequence encoded by the polynucleotide. Type IIs restriction endonucleases cut outside their recognition sequence. Examples include AlwI, BbsI, BbvI, BpmI, BsaI, BseRI, BsgI, BsmAI, BsmBI, BsmFI, BspMI, BsrDI, EarI, FokI, HgaI, HphI, MboII, MnlI, PleI, SapI, SfaNI, BstF5I, FauI. It is also possible to modify the polynucleotide sequence, without changing the polypeptide sequence encoded by the polynucleotide, so that each overhang resulting from digestion of the polynucleotide with the one or more type IIs restriction endonuclease is unique. Such sites will preferably be between 10 and 500 bases apart, more preferably between 15 and 200 bases apart, even more preferably between 25 and 100 bases apart. Digestion of a polynucleotide with the one or more type IIs restriction endonucleases, followed by ligation of the fragments will thus result in faithful reassembly of the original polynucleotide sequence. Design of two or more polynucleotide sequences to contain the same sets of unique overhangs following digestion with the one or more type IIs restriction endonuclease will thus permit digestion of the two polynucleotides followed by ligation of all of the fragments to assemble chimeric polynucleotides. Methods and software for designing one or more polynucleotide to contain a frequency of type IIs restriction sites to allow digestion and reassembly of fragments in the original order to create the original polynucleotide or chimeric polynucleotides is an aspect of the invention.

In addition to the functional criteria by which codons may be selected to encode a polypeptide, codons may be selected that contribute to the ease and fidelity of synthesis of the polynucleotide. Two factors of particular importance in designing a polynucleotide that can be easily and accurately assembled from oligonucleotides are an even distribution of GC content, and the reduction or elimination of repeated sequence elements.

A polynucleotide in which the GC content of the polynucleotide is evenly distributed, may be assembled from oligonucleotides with more uniform lengths and annealing temperatures than a polynucleotide in which the GC content is unevenly distributed. Both of these factors improve the ease and fidelity of subsequent assembly of oligonucleotides into polynucleotides. The uniformity of GC content may be assessed by selecting a "window" of contiguous nucleotides within the polynucleotide and determining the fraction of those nucleotides that are either G or C. A window may consist of 50 contiguous nucleotides, more preferably 40 contiguous nucleotides more preferably 35 contiguous nucleotides, more preferably 30 contiguous nucleotides and even more preferably 25 contiguous nucleotides. Within such a window the GC content of a designed polynucleotide is preferably less than 80% but more than 20%, more preferably it is less than 75% but more than 25%, more preferably it is less than 70% but more than 30% and even more preferably it is less than 65% but more than 35%.

The presence of repeated sequence elements within a polynucleotide will result in stretches of sequence identity in incorrect annealing partners. This in turn will result in a decrease in fidelity of assembly of the oligonucleotides and an increase in the frequency of internal deletions within the gene. The elimination or reduction of repeated sequence elements is thus an important component of a polynucleotide design process that seeks to improve speed and accuracy of synthesis. A repeated sequence element may be defined in terms of the length of a sequence of contiguous nucleotides within a polynucleotide, the frequency with which that sequence occurs within the polynucleotide. Preferably any sequence of 20 contiguous nucleotides within a polynucleotide will occur only once, more preferably any sequence of 18 contiguous nucleotides within a polynucleotide will occur only once, more preferably any sequence of 16 contiguous nucleotides within a polynucleotide will occur only once, more preferably any sequence of 14 contiguous nucleotides within a polynucleotide will occur only once, even more preferably any sequence of 12 contiguous nucleotides within a polynucleotide will occur only once.

The occurrence of sequences within a polynucleotide that differ by only a small number of nucleotides occur within the polynucleotide will also result in stretches of sequence identity in incorrect annealing partners. This in turn will result in a decrease in fidelity of assembly of the oligonucleotides and an increase in the frequency of internal deletions within the gene. The elimination or reduction of almost-repeated sequence elements is thus another important component of a polynucleotide design process that seeks to improve speed and accuracy of synthesis. Preferably no sequence of 35 contiguous nucleotides within a polynucleotide will occur a second time with three mismatched nucleotides, no sequence of 26 contiguous nucleotides within a polynucleotide will occur a second time with 2 mismatched nucleotides, no sequence of 16 contiguous nucleotides within a polynucleotide will occur a second time with 1 mismatched nucleotide.

Another method for reducing or eliminating repeated sequence elements that are likely to be problematic in the assembly of oligonucleotides into polynucleotides is to minimize the number of sub-sequences within the polynucleotide that will anneal to any of the other sub-sequences within the polynucleotide under the conditions that are to be used to assemble to polynucleotide. There are many ways to do this that are more or less computationally intensive.

Particularly useful methods for designing polynucleotides are those that integrate functional constraints such as the selection of codons that will express well in one or more chosen host systems, the elimination of unwanted restriction sites and the inclusion of desired restriction sites, with synthesis constraints such as the elimination of repeated sequence elements and the balancing of GC content throughout the sequence. Systematic methods for accomplishing such a design that are readily amenable to automation using computer programs are shown schematically in FIGS. 26, 27 and 28.

The first 50 codons are often the most important for getting good expression. If it is necessary to add codons with low frequencies in one or more of the starting codon bias tables to avoid additional constraints in the synthetic polynucleotide, these codons should preferably occur after the first 50 codons. Nucleotide regions that are likely to form secondary structures such as hairpins are also preferably avoided for 50 bases before the initiating ATG and within the first 50 codons, more preferably for 40 bases before the initiating ATG and within the first 40 codons and most preferably for 30 bases before the initiating ATG and within the first 30 codons.

5.5.3 Oligonucleotide Design

When oligonucleotides are designed for assembly into polynucleotides, one factor that favors the annealing of oligonucleotides with their correct annealing partners is a difference between the annealing temperatures between intended annealing partners and the annealing temperatures between unintended annealing partners. Preferably the highest annealing temperature for any pair of unintended annealing partners will be at least 5° C. lower than the lowest annealing temperature for any pair of correct annealing partners, more preferably this difference will be at least 8° C., more preferably it will be 11° C. and even more preferably it will be at least 14° C. Such a difference helps to ensure that when the intended annealing partners anneal to one another during the assembly process, incorrect annealing partners are unable to anneal to one another. This increases the efficiency and fidelity of the polynucleotide synthesis process.

The annealing temperatures for all intended annealing partners within an oligonucleotide set that is to be assembled into a polynucleotide can affect the fidelity and efficiency of assembly. The optimal annealing temperature may vary as a result of the overall GC content of the polynucleotide. The lowest calculated annealing temperature for any pair of intended annealing partners within an oligonucleotide set to be assembled into a polynucleotide is preferably calculated to be 56° C., more preferably 58° C., more preferably 60° C. and even more preferably 62° C.

The discrimination between intended and unintended annealing partners is further aided when oligonucleotides that are to be assembled into polynucleotides are designed such that the annealing temperatures between all intended oligonucleotide partners are approximately equal. Preferably the annealing temperatures between all of the intended annealing partners in a set of oligonucleotides for assembly into one polynucleotide will be within 10° C. of each other, more preferably within 8° C. of each other, more preferably within 6° C. of each other, more preferably within 4° C. of each other and even more preferably within 3° C. of each other.

When oligonucleotides are designed for assembly into polynucleotides, it is also often desirable to have oligonucleotide lengths that are close to one another, as this helps to reduce the maximum oligonucleotide length required. This may be beneficial because shorter oligonucleotides can in general be synthesized more accurately than longer oligonucleotides. Preferably the maximum length of any oligonucleotide within a set of oligonucleotides designed to assemble into a polynucleotide is 75 bases, more preferably 70 bases, more preferably 65 bases, more preferably 60 bases and even more preferably 55 bases.

Suitable methods for designing oligonucleotides that are to be assembled into polynucleotides are those that consider all of these factors. Such methods are an aspect of the present invention. For example it is advantageous in the synthesis of polynucleotides with GC contents >60%, or polynucleotides containing regions of repeated sequence to increase the annealing temperature for oligonucleotides. Increased annealing temperatures will require greater oligonucleotide lengths One example of a way in which this can be done, intended to illustrate but not to limit the invention, is shown schematically in FIGS. 29 to 31. Oligonucleotides can be designed to have a narrow range of annealing temperatures by dividing the polynucleotide into consecutive sections that are each calculated to have the same annealing temperatures to their complements.

One method for the initial division of a polynucleotide sequence into sub-sequences that are useful for subsequent oligonucleotide design is shown in FIG. 13. First, an annealing temperature is selected. Then a first section of the polynucleotide is selected by sequential addition of consecutive bases until a sub-sequence is obtained whose annealing temperature to its intended complement exceeds the selected annealing temperature. A second section of the polynucleotide is selected by starting at the first nucleotide following the previous section and repeating the process. By continuing this process for the entire length of the polynucleotide, a set of sub-sequences can be obtained with a narrow range of annealing temperatures (a "constant Tm set" of sub-sequences). Other similar methods include those in which the process is initiated at the other end of the polynucleotide using the reverse complement sequence of the polynucleotide to produce a reverse set of "constant Tm" subsequences. In some cases it may also be desirable to create gaps in the polynucleotide sequence used to generate the "forward" or "reverse" set of "constant Tm" subsequences. For example, if a polynucleotide contains repetitive sequence elements, it may be preferable to omit a part or all of one or more of these repeat elements from the polynucleotide sequence used to calculate the "constant Tm set". Different sets of sub-sequences can be obtained by starting the process at different positions along the polynucleotide. Different sets of sub-sequences can be obtained by using different values for the annealing temperature. Even slight differences in annealing temperature can yield different sets of sub-sequences. For example annealing temperatures of 62° C., 62.1° C., 62.2° C., 62.3° C., 62.4° C. and 62.5° C. will yield different sets of sub-sequences. It is often of interest to produce many slightly different "constant Tm sets" of subsequences. These can then be combined to form oligonucleotides and then assessed for other properties that can influence assembly into polynucleotides.

A "constant Tm set" of polynucleotide sub-sequences can be converted into a set of oligonucleotides suitable for polynucleotide assembly in several ways. One method is represented schematically in FIG. 30. In this method, a set of forward oligonucleotides is designed by combining the first and second "constant Tm" sub-sequences, then the next third and fourth and so on. A set of reverse oligonucleotides is designed by combining the second and third "constant Tm" sub-sequences and obtaining the sequence of the reverse complement, then repeating the process with the fourth and fifth "constant Tm" sub-sequence and so on. Variations on this method include using a "constant Tm set" designed from the polynucleotide reverse complement sequence to design the reverse set of oligonucleotides, then associating this with the appropriate set of forward oligonucleotides. In another variation, oligonucleotides may be designed such that both strands of the polynucleotide are not completely covered. This may be particularly useful when the polynucleotide contains repetitive sequence elements, since inappropriate annealing of oligonucleotides to incorrect annealing partners is more likely if incorrect annealing partners contain longer or higher annealing temperature subsequences in common.

The computational resources required to design a "constant Tm set" of oligonucleotides are small. It is thus useful to produce many designs, each differing slightly from one another, but all constrained by the criterion of having a narrow range of annealing temperatures between correct annealing partners. These different sets of oligonucleotides with "constant Tm" can then be screened for other properties that also affect the efficiency and fidelity with which oligonucleotides assemble into polynucleotides. An example of such a set of screening criteria is shown in FIG. 31.

Different criteria will be of different importance depending upon the physical method to be used to assemble the oligonucleotides. For example if the polymerase chain reaction is to be used, it is preferable to avoid an oligonucleotide that ends with a sequence that is repeated in an oligonucleotide other than the correct annealing partner. If ligation is used, it is preferable to ensure that no two oligonucleotides end with the same set of two, three or four bases. A method for designing oligonucleotides that are to be assembled by ligation is shown in FIG. 32.

An aspect of the present invention provides a method of designing a set of oligonucleotides for assembly into a polynucleotide. The method comprises identifying a first plurality of single-stranded oligonucleotides that collectively encode all or a portion of a first strand of the polynucleotide, where each respective single-stranded oligonucleotide in the first plurality of single-stranded oligonucleotides is characterized by an annealing temperature to its exact complement that is in a first predetermined annealing temperature range. A second plurality of single-stranded oligonucleotides is identified from the first plurality of single-stranded oligonucleotides, where a single-stranded oligonucleotide in the second plurality of single-stranded oligonucleotides is formed by joining an adjacent pair of oligonucleotides in the first plurality of single-stranded oligonucleotides. A third plurality of single-stranded oligonucleotides is identified that collectively encode all or a portion of a second strand of the polynucleotide, where each respective single-stranded oligonucleotide in the third plurality of single-stranded oligonucleotides is characterized by an annealing temperature to its exact complement that is in a second predetermined annealing temperature range. A fourth plurality of single-stranded oligonucleotides is identified from the third plurality of single-stranded oligonucleotides, where a single-stranded oligonucleotide in the fourth plurality of single-stranded oligonucleotides is formed by joining an adjacent pair of oligonucleotides in the third plurality of single-stranded oligonucleotides. The set of oligonucleotides comprises the second plurality of oligonucleotides and the fourth plurality of oligonucleotides. Next, a determination is made as to whether the set of oligonucleotides satisfies at least one assembly criterion, where (i) when the set of oligonucleotides satisfies the at least one assembly criterion, the set of oligonucleotides is selected, and (ii) when the set of oligonucleotides does not satisfy said at least one assembly criterion, the set of oligonucleotides is rejected and the aforementioned steps are repeated.

In some embodiments, a different first predetermined annealing temperature range and a different second predetermined annealing temperature range is used when the aforementioned steps are repeated. In some embodiments, the first predetermined annealing temperature range and the second predetermined annealing temperature range are the same. In some embodiments, the first predetermined annealing temperature range and the second predetermined annealing temperature range are different. In some embodiments, the first predetermined annealing temperature range and the second predetermined annealing temperature range is each between 45° C. and 72° C. In some embodiments, the first predetermined annealing temperature range and the second predetermined annealing temperature range is each between 50° C. and 65° C.

In some embodiments, the first predetermined annealing temperature range and the second predetermined annealing temperature range is each between 55° C. and 62° C. In some embodiments, each single-stranded oligonucleotide in the second plurality of single-stranded oligonucleotides is formed by joining an adjacent pair of oligonucleotides in the first plurality of single-stranded oligonucleotides. In some embodiments, each single-stranded oligonucleotide in the fourth plurality of single-stranded oligonucleotides is formed by joining an adjacent pair of oligonucleotides in the third plurality of single-stranded oligonucleotides.

In some embodiments, the method further comprises (f) assembling the set of oligonucleotides by the polymerase chain reaction or ligase chain reaction with an annealing temperature that is a predetermined amount lower than the lowest annealing temperature of the first predetermined annealing temperature range, thereby forming an assembly mixture that comprises the polynucleotide. In some embodiments, the predetermined amount is 1° C. or larger. In some embodiments, the method further comprises cloning the polynucleotide into a vector.

In some embodiments, the assembly mixture comprises a plurality of different polynucleotide molecules, and the method further comprises creating a plurality of heteroduplexes between different individual polynucleotide molecules within the plurality of different polynucleotide molecules in the assembly, treating the plurality of heteroduplexes with an agent that binds preferentially to mismatched sequences within a double-stranded DNA molecule, and using the agent to remove double-stranded DNA molecules containing mismatched sequences from the assembly mixture.

In some embodiments, the method further comprises amplifying the polynucleotide by the polymerase chain reaction. In some embodiments, the method further comprises cloning the polynucleotide into a vector. In some embodiments, the at least one assembly criterion comprises a requirement that the annealing temperature of each intended complementary pair of single-stranded oligonucleotides in the set of oligonucleotides falls within a third predetermined temperature range. In some embodiments, the third predetermined temperature range encompasses a total of 4° C. or less. In some embodiments, the third predetermined temperature range encompasses a total of 3° C. or less.

In some embodiments, the at least one assembly criterion comprises a requirement that the single-stranded oligonucleotide length of each oligonucleotide in the set of oligonucleotides is within a predetermined oligonucleotide length range. In some embodiments, the predetermined oligonucleotide length range is between 20 nucleotides and 70 nucleotides, or between 25 nucleotides and 65 nucleotides.

In some embodiments, the at least one assembly criterion comprises a requirement that the number of single-stranded oligonucleotides in the second plurality of single-stranded oligonucleotides matches the number of single-stranded oligonucleotides in the fourth plurality of single-stranded oligonucleotides. In some embodiments, the at least one assembly criterion comprises a requirement that the annealing temperature of each pair of single-stranded oligonucleotides in the set of oligonucleotides for assembly, whose annealing is not intended for said assembly, is below a predetermined temperature. In some embodiments, the predetermined temperature is the annealing temperature of a pair of oligonucleotides in the set of oligonucleotides whose annealing is intended for assembly of the polynucleotide. In some embodiments, this predetermined temperature is at least 10° C. below, at least 15° C. below, or at least 20° C. below the annealing temperature of a pair of oligonucleotides in the set of oligonucleotides whose annealing is intended for assembly of said polynucleotide.

In some embodiments, the at least one assembly criterion comprises a requirement that a maximum length of a sequence that occurs more than once within the first strand of the polynucleotide and that is found at a terminus of any oligonucleotide in the set of oligonucleotides is less than a predetermined length. In some embodiments, the predetermined length is 10 nucleotides or greater, or 12 nucleotides or greater. In some embodiments, a pair of oligonucleotides in the set of oligonucleotides that are intended to be annealed to form the polynucleotide are not completely overlapping.

In some embodiments, a first single-stranded oligonucleotide has an n-mer overhang relative to a second single-stranded oligonucleotide in the set of oligonucleotides, and annealing of the first single-stranded oligonucleotide and the second oligonucleotide single-stranded oligonucleotide is intended for assembly of the polynucleotide, where n is between 1 and 40. In some embodiments, the at least one assembly criterion comprises a requirement that a predetermined length of a nucleotide sequence at a terminus of an oligonucleotide in the set of oligonucleotides is not found at either terminus of any other oligonucleotide in the set of oligonucleotides. In various embodiments, the predetermined length is 5 nucleotides, 4 nucleotides, or 3 nucleotides.

In some embodiments, the polynucleotide encodes a polypeptide, and the method further comprises (i) selecting, prior to the identifying step, an initial polynucleotide sequence for the polynucleotide that codes for the polypeptide, where a codon frequency in the initial polynucleotide sequence is determined by a codon bias table and (ii) modifying, prior to the identifying step, an initial codon choice in the initial polynucleotide sequence for the polynucleotide in accordance with a design criterion, thereby constructing a final polynucleotide sequence for the polynucleotide that codes for the polypeptide. In some embodiments, the design criterion comprises one or more of:

(i) exclusion of a restriction site sequence in said initial polynucleotide sequence;

(ii) incorporation of a restriction site sequence in said initial polynucleotide sequence;

(iii) a designation of a target G+C content in the initial polynucleotide sequence;

(iv) an allowable length of a sub-sequence that can be exactly repeated within either strand of the initial polynucleotide sequence;

(v) an allowable annealing temperature of any sub-sequence to any other sub-sequence within either strand of the initial polynucleotide sequence;

(vi) exclusion of a hairpin turn in the initial polynucleotide sequence;

(vii) exclusion of a repeat element in the initial polynucleotide sequence;

(viii) exclusion of a ribosome binding site in the initial polynucleotide sequence;

(ix) exclusion of a polyadenylation signal in the initial polynucleotide sequence;

(x) exclusion of a splice site in the initial polynucleotide sequence;

(xi) exclusion of an open reading frame in each possible 5' reading frame in the initial polynucleotide sequence;

(xii) exclusion of a polynucleotide sequence that facilitates RNA degradation in the initial polynucleotide sequence;

(xiii) exclusion of an RNA polymerase termination signal in the initial polynucleotide sequence;

(xiv) exclusion of a transcriptional promoter in the initial polynucleotide sequence;

(xv) exclusion of an immunostimulatory sequence in the initial polynucleotide sequence;

(xvi) incorporation of an immunostimulatory sequence in the initial polynucleotide sequence;

(xvii) exclusion of an RNA methylation signal in the initial polynucleotide sequence;

(xviii) exclusion of a selenocysteine incorporation signal in the initial polynucleotide sequence;

(xix) exclusion of an RNA editing sequence in the initial polynucleotide sequence;

(xx) exclusion of an RNAi-targeted sequence in the initial polynucleotide sequence; and/or (xxi) exclusion of an inverted repeat within the first 45 nucleotides encoding said synthetic polypeptide in the initial polynucleotide sequence.

In some embodiments, the design criterion comprises reduced sequence identity to a reference polynucleotide, and wherein modifying the initial codon choice in the initial polynucleotide in accordance with the design criterion comprises altering a codon choice in the initial polynucleotide sequence to reduce sequence identity to the reference polynucleotide. In some embodiments, the design criterion comprises increased sequence identity (e.g., at least 0.05% or more identical, at least 1% or more identical, at least 2% or more identical, at least 3% or more identical, at least 4% or more identical) and modifying the initial codon choice in the initial polynucleotide in accordance with the design criterion comprises altering a codon choice in said initial polynucleotide sequence to increase sequence identity to the reference polynucleotide.

Another aspect of the present invention provides a computer program product for use in conjunction with a computer system, the computer program product comprising a computer readable storage medium and a computer program mechanism embedded therein. In this aspect of the invention, the computer program mechanism comprises instructions for identifying a first plurality of single-stranded oligonucleotides that collectively encode all or a portion of a first strand of a polynucleotide, where each respective single-stranded oligonucleotide in the first plurality of single-stranded oligonucleotides is characterized by an annealing temperature to its exact complement that is in a first predetermined annealing temperature range. The computer program mechanism further comprises instructions for identifying a second plurality of single-stranded oligonucleotides from the first plurality of single-stranded oligonucleotides, where a single-stranded oligonucleotide in the second plurality of single-stranded oligonucleotides is formed by joining an adjacent pair of oligonucleotides in the first plurality of single-stranded oligonucleotides. The computer program mechanism further comprises instructions for identifying a third plurality of single-stranded oligonucleotides that collectively encode all or a portion of a second strand of the polynucleotide, where each respective single-stranded oligonucleotide in the third plurality of single-stranded oligonucleotides is characterized by an annealing temperature to its exact complement that is in a second predetermined annealing temperature range. The computer program mechanism further comprises instructions for identifying a fourth plurality of single-stranded oligonucleotides from the third plurality of single-stranded oligonucleotides, where a single-stranded oligonucleotide in the fourth plurality of single-stranded oligonucleotides is formed by joining an adjacent pair of oligonucleotides in the third plurality of single-stranded oligonucleotides. A set of oligonucleotides comprises the second plurality of oligonucleotides and the fourth plurality of oligonucleotides. Further, the computer program mechanism comprises instructions for determining whether the set of oligonucleotides satisfies at least one assembly criterion, where (i) when the set of oligonucleotides satisfies said at least one assembly criterion, the set of oligonucleotides is selected and (ii) when the set of oligonucleotides does not satisfy the at least one assembly criterion, the set of oligonucleotides is rejected and the aforementioned steps are repeated. In some embodiments, this process is stored in a computer system comprising a central processing unit and a memory, coupled to the central processing unit

5.5.4 Oligonucleotide Assembly Conditions

Methods for assembling polynucleotides from oligonucleotides include ligation, the polymerase chain reaction, the ligase chain reaction and combinations thereof. These methods may all be used to construct synthetic polynucleotides from oligonucleotides. See, for example, Hayden et al., 1988, DNA 7: 571-7; Ciccarelli et al., 1991, Nucleic Acids Res 19: 6007-13; Jayaraman et al., 1991, Proc Natl Acad Sci USA 88: 4084-8; Jayaraman et al., 1992, Biotechniques 12: 392-8; Graham et al., 1993, Nucleic Acids Res 21: 4923-8; Kobayashi et al., 1997, Biotechniques 23: 500-3; Au et al., 1998, Biochem Biophys Res Commun. 248: 200-203; Hoover et al., 2002, Nucleic Acids Res 30: e43, each of which is hereby incorporated by reference in its entirety. A suitable method for assembling any set of oligonucleotides depends upon the physical properties of the set of oligonucleotides. The optimal reaction conditions used to minimize incorporation of errors during assembly of the oligonucleotides depends upon the precise criteria used to design the oligonucleotides, and this interrelationship is an aspect of the present invention. Assembly methods that are optimized for assembling oligonucleotide sets designed according to the methods described here are another aspect of the invention.

Variables within a method for assembling oligonucleotides into a polynucleotide include the composition of the reaction buffer, the polymerase(s) used, the concentrations of oligonucleotides used and the thermal conditions of the reaction mixture.

The presence of dimethyl sulphoxide (DMSO), betain, trimethyl ammonium chloride and other agents that reduce the annealing temperature of nucleic acids may be included to improve the specificity of oligonucleotide annealing and the polymerization performance of the polymerase. These agents may also decrease the fidelity of the polymerase, however. To balance these activities, DMSO is preferably included in a reaction mix at 5% v/v, more preferably at 3% v/v. However, these agents should be omitted if the annealing temperature of the oligonucleotide set is lower than 60° C., more preferably if it is lower than 58° C., even more preferably if it is below 56° C. They should also be omitted if the GC content of the polynucleotide is below 46%, more preferably if it is below 44% and even more preferably if it is below 42%.

An important factor for correct assembly of oligonucleotides is the concentration of each oligonucleotide, and the total concentration of oligonucleotides. The total oligonucleotide concentration within an assembly reaction is preferably between 5 µM and 0.05 µM, more preferably between 2.5 µM and 0.1 µM, even more preferably between 1.5 µM and 0.25 µM. Within this reaction mixture, each oligonucleotide is preferably represented at an equimolar amount with all of the other oligonucleotides present.

The thermal conditions for the assembly of oligonucleotides into polynucleotides are also a critical factor in efficient and high fidelity polynucleotide synthesis. Of greatest importance is the alignment between the calculated annealing temperature for the correct annealing partners in an oligonucleotide set, and the annealing temperature used in the assembly reaction. Some examples of thermocycler programs of use in assembling polynucleotides form oligonucleotides are shown in FIGS. 32-36. The annealing temperature is preferably between 10° C. below and 5° C. above the lowest calculated annealing temperature between intended annealing partners within the oligonucleotide set, more preferably it is between 8° C. below and 2° C. above the lowest calculated annealing temperature between intended (correct) annealing partners within the oligonucleotide set, and even more preferably it is between 6° C. below and 2° C. below the lowest calculated annealing temperature between intended annealing partners within the oligonucleotide set.

An alternative strategy to the polymerase chain reaction for polynucleotide assembly is the use of thermostable ligases. An example of a thermocycle program for a typical ligation cycle reaction is shown in FIG. 43. For a ligation-based assembly, the polynucleotide is preferably between 100 and 3,000 bases, more preferably between 150 and 2,000 bases, more preferably between 250 and 1,500 bases long.

Following the assembly of oligonucleotides into a polynucleotide, it is possible to amplify the full-length polynucleotide out of the mixture by PCR using a pair of amplification primers. Following the amplification of full-length polynucleotide, it is possible to reduce errors that are present in a subset of the polynucleotide population, for example those that were introduced in the oligonucleotide synthesis step, or in the polymerase chain reaction assembly or amplification steps. This can be done by using enzymes that recognize mismatched bases in double stranded DNA, for example T4 endonuclease VII and T7 endonuclease I (see, for example, Babon et al., 2003, Mol Biotechnol 23: 73-81, which is hereby incorporated by reference in its entirety). To create mismatches the mixture of polynucleotides in an assembly or amplification reaction is heated to a temperature that melts the DNA present (for example, to a temperature above 90° C.), then cooled to a temperature that allows it to anneal at which the endonuclease enzyme is active (for example to a temperature below 50° C.). The enzyme or mixture of enzymes that cleaves DNA at or near the site of a mismatched base, such as T4 endonuclease VII, T7 endonuclease I or a mixture thereof, is then added to the reaction and allowed to incubate and cleave the mismatched DNA.

Two alternative methods for DNA denaturation prior to endonuclease treatment are heat denaturation with ethylene glycol or alkali denaturation. To denature with ethylene glycol, the PCR product (1-5 µg) is added to a denaturation mix consisting of 10 mM Tris-Cl pH 7.5, 1 mM EDTA, 20% glycerol, and 20% ethylene glycol. The sample is heated at 95-100° C. for 5 minutes, and then slowly cooled to room temperature. For alkali denaturation, the pcr product (1-5 µg) is suspended in 200 mM NaOH. The mix is incubated for 10 minutes at 37° C. then placed on ice. 1.0 M HCl is added to a final concentration of 200 mM. A third alternative method for heteroduplex formations uses exonuclease. See, for example, Thomas et al., 2002, Biological Chemistry 383, 1459-1462, which is hereby incorporated by reference in its entirety. Prior to the use of exonuclease, two PCR reactions are performed. In the first, a 5N-phosphorylated primer is used along with a 3N-non-phosphorylated primer. In the second, a 3N-phosphorylated primer is employed along with a 5N-non-phosphorylated primer. Treatment of the resulting PCR products with exonuclease removes the phosphorylated strand. The two single strand polynucleotides are mixed, heat denatured, and annealed by slow cooling. Briefly, a typical reaction mix using exonuclease contains 67 mM glycine-KOH pH 9.4, 2.5 mM $MgCl_2$, 50 mg/ml BSA, 1-5 ug of PCR product, 5-10 U exonuclease. The reaction is incubated for 15 minutes to one hour at 37° C. PCR amplification using equimolar amounts of phosphorylated and non-phosphorylated primers may alternatively be performed to obviate the need for two separate PCR reactions.

Alternative enzymes capable of catalyzing DNA cleavage at mismatches in heteroduplex DNA include, the CEL I nuclease from celery, the *Aspergillus* SI nuclease, Endonuclease V from *E. coli*, and the MutHSL proteins from *E. coli*. See, for example, Smith and Modrich, 1997, Proc Natl Acad Sci 94, 6847-6850, which is hereby incorporated by reference in its entirety. Specificity and reaction rate of all these enzymes can be modulated by temperature of incubation and/or addition of DNA denaturants, such as formamide, ethylene glycol, and dimethyl sulfoxide. Using a mixture of two or more enzymes can additionally broaden specificity of mismatches cleaved.

For MutHSL-mediated removal of mutant sequences, a 20 µl mix consisting of Hepes pH 8.0, 50 mM KCL, 2.5 mM DTT, 125 µg/ml BSA, 5 mM ATP, 10 mM $MgCl_2$, and 1 µg of denatured and reannealed PCR product is incubed for eight minutes at 37° C. The reaction is initiated by adding 30 µl of a mix containing 5 µg of MutS, 12 µg of MutL, and 18 µg of MutH in 20 mM potassium phosphate pH 7.4, 50 mM KCL, 0.1 mM EDTA, 1 mM DTT, 1 mg/ml BSA. The reaction is incubated for 45 minutes at 37° C. The reactions can be supplemented with an additional 30 µl of the MutHSL mix, as well as 3 µl of a solution containing 500 mM Hepes pH 8.0, 200 mM KCL, 10 mM DTT, 20 mM ATP, and 40 mM $MgCl_2$. Incubation is continued at 37° C. for 45 minutes. Supplementation and incubation is repeated. After final incubation, the reaction is stopped with the addition of EDTA to 10 mM. Standard molecular biology methods are used to concentrate, purify, and clone.

Chemical methods for mismatch cleavage can be used instead or in combination with endonucleases for removal of polynucleotides bearing undesirable mutations. These methods rely on the chemical modification of the mismatch by treatment of heteroduplex DNA with hydroxylamine and osmium tetroxide. See, for example, Cotton et al., 1998, Proc Natl Acad Sci 85, 4397-4401, which is hereby incorporated by reference in its entirety) or potassium permanganate and tetraethylammonium chloride. See, for example, Roberts et al., 1997, Nucl Acids Res 25, 3377-3378, which is hereby incorporated by reference in its entirety. This is followed by treatment with piperidine to cleave the DNA at the modified site. For example, 1-5 µg of denatured and reannealed PCR product in 6 µl of distilled water is added to 20 µl of a hydroxylamine solution, which is prepared by dissolving 1.39 g of hydroxylamine hydrochloride in 1.6 ml of distilled water for an ~2.5 M solution. The DNA-hydroxylamine solution is incubated for 2 hours at 37° C. The reaction is stopped by transferring the mixture to ice and adding 200 µl of a stop solution consisting of 0.3 M sodium acetate, 0.1 mM EDTA pH 5.2, and 25 µg/ml tRNA. The DNA is precipitated with ethanol, washed with 70% ethanol and dried. The pellet is suspended in 6 µl of distilled water and treated with 15 µl of 4% osmium tetroxide in a total volume of 24.5 µl containing 1 mM EDTA, 10 mM Tris-Cl pH 7.7, and 1.5% pyridine. The sample is incubated for 20-120 minutes at 37° C. The reaction is stopped and pelleted as described for hydroxylamine step. Chemical cleavage is achieved by incubating the DNA with piperidine. For this, 50 ml of 1 M piperidine is added directly to the pellet and incubated at 90° C. for 30 minutes. The DNA is precipitated with ethanol and suspended in 20 µl Tris-Cl pH 8.8, Rnase A 0.5 mg/ml (70 U/mg) before purification and cloning. Immobilization of the starting DNA (denatured and reannealed) to a solid support, such as a silica solid support (Ultra-bind beads from MO BIO Laboratories, Inc.) allows the chemical methods for mismatch cleavage to be performed without ethanol precipitation between each step. See, for example, Bui et al. 2003, BMC Chemical Biology 3; http://www.biomedcentral.com/content/pdf/1472-6769-3-1.pdf, which is hereby incorporated by reference in its entirety.

Rhodium(III) complexes can be used for high-affinity mismatch recognition and photocleavage. See, for example, Junicke et al. 2003, Proc Natl Acad Sci 100: 3737-3742, which is hereby incorporated by reference in its entirety. Two such complexes are $[Rh(bpy)^2(chrysi)]^{3+}$[chrysene-5,6-quinone diimine (chrysi)] and rac-$[Rh(bpy)_2phzi]^{3+}$(bpy, 2,2'-bipyridine; phzi benzo[a]phenazine-5,6-quinone diimine). Binding is carried out in a mix containing 1-5 µg of heteroduplex DNA, 1-100 µM of the Rhodium(III) complex, 50 mM NaCl, 10 mM Tris-HCl, pH 8.5. The mix is irradiated for 15 minutes to one hour at wavelengths ranging from 300-600 nm.

Denaturing HPLC (dHPLC) on a sample of the amplified synthetic gene that has undergone one of the described treatments to form heteroduplexes can be used to separate heteroduplexes from homoduplexes (correct sequences). An example of a dHPLC system capable of performing this separation is the WAVE® system manufactured and sold by Transgenomic, Inc. (Omaha, Nebr.). Using this system, the sample containing homoduplexes and heteroduplexes (if a mutation is present) is injected into the buffer flow path containing triethylammonium acetate (TEAA) and acetonitrile (ACN). In solution, the TEAA forms the positively charged triethylammonium ion (TEA+) that has both hydrophobic and hydrophilic ends. The DNASep® cartridge is located in the oven and contains beads that are hydrophobic. When the buffer passes through the cartridge the hydrophobic end of the TEA+ is attracted to the beads. The positively charged portion of the TEA+ forms an ionic bond with the negatively charged phosphate backbone of the DNA. The result is that the DNA fragments are held onto the cartridge by these bridging properties of the TEA+ ions. The fragment specific methods created by Navigator™ Software control both the temperature of the oven and the ACN gradient. The concentration of ACN increases over time based on this method. As the ACN concentration increases bridging capabilities of the TEA+ ions decrease and the DNA fragments are released from the cartridge. Heteroduplexes, with mismatched base pairs, elute off of the cartridge first followed by the homoduplexes. The homoduplex fraction is enriched for correct sequences and can be collected and cloned. Denaturing HPLC-mediated separation of heteroduplexes from homoduplexes is preferably performed on synthetic constructs <500 bp in length. Larger genes can be assembled from the collected homoduplexes using PCR SOEing (splicing by overlap extension) or type II restriction digest and ligation.

Following the assembly or amplification or mismatch digestion steps, the polynucleotide can be cloned into an appropriate vector, either by restriction digestion and ligation, TA cloning or recombinase-based cloning. Site-specific recombinase-based cloning is particularly advantageous because it requires a specific sequence to be present at each end of the polynucleotide. This provides a strong selection against partially assembled polynucleotides that lack one or both ends. Thus using recombinases for cloning eliminates any need for gel-purification of the polynucleotide prior to cloning, thus increasing the efficiency and fidelity of the process. Recombinase-based cloning of assembled synthetic oligonucleotides is thus an aspect of the invention. The efficiency of recombinase-based cloning also makes possible the assembly of polynucleotides using a ligation or ligase chain reaction strategy, and to omit the PCR amplification step.

5.5.5 Design of a Polynucleotide for Synthesis in Multiple Parts

In some cases it may not be possible to design and synthesize a polynucleotide in a single step. For example, the sequence may be too large, or it may be too repetitive to synthesize in a single unit. In this case, synthesis of the polynucleotide can be achieved by separately synthesizing two or more smaller polynucleotides and then enzymatically joining these, for example by restriction digestion and ligation, or splicing by overlap extension, Horton et al., 1989, Gene 77: 61-8, to form a single polynucleotide.

The division of the polynucleotide sequence into parts prior to synthesis can be performed manually or automatically using a computer. The most advantageous division of a sequence into parts will separate repeated sequence elements into different synthetic units, to reduce the possibility of incorrect oligonucleotide partner annealing. In one aspect of the invention, division of a polynucleotide into parts can be performed after the oligonucleotides have been designed and synthesized. The polynucleotide can then be assembled as two or more segments that can subsequently be joined for example by overlap extension. In another aspect of the invention, a polynucleotide can be divided into parts in conjunction with the design methods shown in FIGS. 26, 27 and 28. These methods are not computationally intensive, and can therefore be repeated many times using only a small amount of processor time. Examples of such a design process are shown in FIGS. 44 and 45. Processes that iterate polynucleotide design, oligonucleotide design and polypeptide or polynucleotide division allow many possible designs to be tested and one that fulfills multiple design criteria to be selected, thereby increasing the efficiency and fidelity of polynucleotide synthesis. These methods and computer programs that automate these processes are aspects of the invention.

Polynucleotides that are designed in parts must subsequently be joined to produce a single polynucleotide. This may be accomplished by adding sequences to the ends of polynucleotides containing recognition sites for restriction endonucleases. Particularly useful are the type IIs restriction endonucleases that cut outside their recognition sequences. Adding these sites to the end of a polynucleotide sequence can allow two polynucleotides to be joined without the addition of any other sequence to the final polynucleotide. FIG. 41 shows sequences that can be added to the 5' end of one polynucleotide and to the 3' end of another polynucleotide to produce two polynucleotide fragments that will produce a single designed sequence after digestion with the named restriction enzyme and ligation. Two or more fragments can be ligated simultaneously to form a single polynucleotide. The addition of these sequences can be automated. For example a two, three or four base sequence within a polynucleotide can be selected, either manually or automatically, and a computer program can then be used to add the desired ends to the 5' and 3' polynucleotide segments. In addition to adding sequences that facilitate subsequent joining of polynucleotide segments, it can be advantageous to add further sequences that facilitate recombinase-based cloning of the polynucleotides. This can also be accomplished using a computer program. Computer programs that automatically add type IIs restriction sites and recombinase cloning sites to the ends of polynucleotides aid in the efficient and high fidelity synthesis of polynucleotides and are an aspect of the invention.

5.5.6 Vectors for Synthetic Polynucleotides

Vectors that are amenable to the polynucleotide synthesis and joining processes include those that lack type IIs restriction endonuclease sites, and those that allow cloning using recombinases. Examples of such vector sequences are shown in FIGS. 46, 47 and 48. Polynucleotide fragments can be designed, synthesized and cloned into such a vector, then excised with one of many possible type IIs restriction enzymes without cutting the vector. Additional features that can be advantageous are replication origins that produce low copy number plasmids. These increase the stability of large segments of DNA. Such vectors increase the efficiency and fidelity of polynucleotide assembly and are an aspect of the invention.

One aspect of the invention provides a method of designing a single designed polynucleotide having a sequence. In the method, the sequence is divided into a plurality of polynucleotide sub-sequences. A first restriction site is added to a 3' end of a first polynucleotide sub-sequence in the plurality of polynucleotide sub-sequences. A second restriction site is added to a 5' end of a second polynucleotide sub-sequence in the plurality of polynucleotide sub-sequences such that cleavage of the first restriction site and the second restriction site causes a terminal portion of the first polynucleotide sub-sequence to become complementary with a terminal portion of the second polynucleotide sub-sequence. For each respective sub-sequence in the plurality of polynucleotide sub-sequences a series of steps are performed. First, a first plurality of single-stranded oligonucleotides that collectively encode all or a portion of a first strand of the respective sub-sequence are identified, where each respective single-stranded oligonucleotide in the first plurality of single-stranded oligonucleotides is characterized by an annealing temperature to its exact complement that is in a first predetermined annealing temperature range. Second, a second plurality of single-stranded oligonucleotides is identified from the first plurality of single-stranded oligonucleotides, where a single-stranded oligonucleotide in the second plurality of single-stranded oligonucleotides is formed by joining an adjacent pair of oligonucleotides in the first plurality of single-stranded oligonucleotides. Third, a plurality of single-stranded oligonucleotides that collectively encode all or a portion of a second strand of the respective sub-sequence is identified, where each respective single-stranded oligonucleotide in the third plurality of single-stranded oligonucleotides is characterized by an annealing temperature to its exact complement that is in a second predetermined annealing temperature range. Fourth, a plurality of single-stranded oligonucleotides from the third plurality of single-stranded oligonucleotides is identified, where a single-stranded oligonucleotide in the fourth plurality of single-stranded oligonucleotides is formed by joining an adjacent pair of oligonucleotides in the third plurality of single-stranded oligonucleotides. Here, a set of oligonucleotides comprises the second plurality of oligonucleotides and the fourth plurality of oligonucleotides. Fifth, a determination is made as to whether the set of oligonucleotides satisfies at least one assembly criterion, where when the set of oligonucleotides satisfies the at least one assembly criterion, the set of oligonucleotides is selected, when the set of oligonucleotides does not satisfy the at least one assembly criterion, the set of oligonucleotides is rejected and steps one through five are repeated. The process is repeating when a set of oligonucleotides has not been selected for each respective sub-sequence in the plurality of polynucleotide sub-sequences.

In some embodiments, the first restriction site is for a restriction enzyme that cleaves outside its recognition sequence such as a type IIs site. In some embodiments, the second restriction site is for a restriction enzyme that cleaves outside its recognition sequence such as a type IIs site.

In some embodiments, method further comprises assembling the set of oligonucleotides for a respective sub-sequence in the plurality of polynucleotide subsequences using a polymerase chain reaction or a ligase chain reaction with an annealing temperature that is a predetermined amount lower than the lowest annealing temperature of any intended complementary pair of single-stranded oligonucleotides in the set of oligonucleotides, and, repeating this step for each respective sub-sequence in the plurality of polynucleotide sub-sequences.

In some embodiments, the method further comprises cloning each polynucleotide sub-sequence into a vector and obtaining each cloned polynucleotide sub-sequence from its vector and joining the sub-sequences to form the single designed polynucleotide.

Another aspect of the present invention provides a computer program product for use in conjunction with a computer system, the computer program product comprising a computer readable storage medium and a computer program mechanism embedded therein, the computer program mechanism for designing a single designed polynucleotide having a sequence. The computer program mechanism comprises instructions for dividing the sequence into a plurality of polynucleotide sub-sequences and instructions for adding a first restriction site to a 3' end of a first polynucleotide sub-sequence in said plurality of polynucleotide sub-sequences. The computer program mechanism further comprises instructions for adding a second restriction site to a 5' end of a second polynucleotide sub-sequence in the plurality of polynucleotide sub-sequences, such that cleavage of the first restriction site and the second restriction site would cause a terminal portion of the first polynucleotide sub-sequence to become complementary with a terminal portion of the second polynucleotide sub-sequence. For each respective sub-sequence in the plurality of polynucleotide sub-sequences, the computer program product comprises (i) instructions for identifying a first plurality of single-stranded oligonucleotides that collectively encode all or a portion of a first strand of the respective sub-sequence, where each respective single-stranded oligonucleotide in the first plurality of single-stranded oligonucleotides is characterized by an annealing temperature to its exact complement that is in a first predetermined annealing temperature range, (ii) instructions for identifying a second plurality of single-stranded oligonucleotides from the first plurality of single-stranded oligonucleotides, where a single-stranded oligonucleotide in the second plurality of single-stranded oligonucleotides is formed by joining an adjacent pair of oligonucleotides in the first plurality of single-stranded oligonucleotides; (iii) instructions for identifying a third plurality of single-stranded oligonucleotides that collectively encode all or a portion of a second strand of said respective sub-sequence, where each respective single-stranded oligonucleotide in the third plurality of single-stranded oligonucleotides is characterized by an annealing temperature to its exact complement that is in a second predetermined annealing temperature range; (iv) instructions for identifying a fourth plurality of single-stranded oligonucleotides from the third plurality of single-stranded oligonucleotides, where a single-stranded oligonucleotide in the fourth plurality of single-stranded oligonucleotides is formed by joining an adjacent pair of oligonucleotides in the third plurality of single-stranded oligonucleotides; where a set of oligonucleotides comprises the second plurality of oligonucleotides and the fourth plurality of oligonucleotides; and (v) instructions for determining whether the set of oligonucleotides satisfies at least one assembly criterion, where, when the set of oligonucleotides satisfies the at least one assembly criterion, the set of oligonucleotides is selected; and when the set of oligonucleotides does not satisfy the at least one assembly criterion, the set of oligonucleotides is rejected and instructions (i) through (v) are repeated. The computer program product further includes instructions for repeating the aforementioned instructions when a set of oligonucleotides has not been selected for each respective sub-sequence in said plurality of polynucleotide sub-sequences. Some aspect of the present invention comprises a computer system for designing a single designed polynucleotide having a sequence, the computer system comprising a central processing unit and a memory, coupled to the central processing unit, where the memory stores the above identified computer program product.

Another aspect of the present invention provides a method of cloning a polynucleotide, where the polynucleotide comprises i) a desired sequence, ii) a first restriction site at the 3' end of the desired sequence; iii) a second restriction site at the 5' end of the desired sequence; iv) a first recognition site that is recognized by a site-specific recombinase, where the first recognition site is outside the desired sequence and is in a 3' terminal portion of the polynucleotide; and v) a second recognition site sequence that is recognized by said site-specific recombinase, wherein the second recognition site is outside the desired sequence and is in a 5' terminal portion of the polynucleotide. The method comprises a) assembling the polynucleotide from a plurality of component oligonucleotides; and b) cloning the polynucleotide into a vector comprising a plurality of sites recognized by the site-specific recombinase, using a recombinase to effect the cloning.

In some embodiments, the vector does not comprise a recognition sequence for the first restriction site or the second restriction site. In some embodiments, a recognition sequence for the first restriction site is not in the desired sequence. In some embodiments, a recognition sequence for the second restriction site is not in the desired sequence.

In some embodiments, the method further comprises amplifying the nucleotide while the nucleotide is in the vector; and cleaving the polynucleotide from the vector using the first restriction site and the second restriction side, thereby deriving a polynucleotide having the desired sequence.

Another aspect of the present invention provides a method of designing a polynucleotide that has a first oligonucleotide sequence, the method comprising (a) selecting an initial codon sequence that codes for the polypeptide, where a codon frequency in the initial codon sequence is determined by a codon bias table; and (b) modifying an initial codon choice in the initial codon sequence in accordance with a design criterion, thereby constructing a codon sequence that codes for the first oligonucleotide sequence. Then, a set of oligonucleotides is designed for assembly into a second oligonucleotide sequence, where the second oligonucleotide sequence encodes a contiguous portion of the first oligonucleotide sequence. Such a designing step (c) comprises: (i) identifying a first plurality of single-stranded oligonucleotides that collectively encode all or a portion of a first strand of said second oligonucleotide sequence, where each respective single-stranded oligonucleotide in the first plurality of single-stranded oligonucleotides is characterized by an annealing temperature to its exact complement that is in a first predetermined annealing temperature range; (ii) identifying a second plurality of single-stranded oligonucleotides from the first plurality of single-stranded oligonucleotides, where a single-stranded oligonucleotide in the second plurality of single-stranded oligonucleotides is formed by joining an adjacent pair of oligonucleotides in the first plurality of single-stranded oligonucleotides; and (iii) identifying a third plurality of single-stranded oligonucleotides that collectively encode all or a portion of a second strand of the second oligonucleotide sequence, where each respective single-stranded oligonucleotide in the third plurality of single-stranded oligonucleotides is characterized by an annealing temperature to its exact complement that is in a second predetermined annealing temperature range; (iv) identifying a fourth plurality of single-stranded oligonucleotides from the third plurality of single-stranded oligonucleotides, where a single-stranded oligonucleotide in the fourth plurality of single-stranded oligonucleotides is formed by joining an adjacent pair of oligonucleotides in the third plurality of single-stranded oligonucleotides. In the method, a set of oligonucleotides comprises the second plurality of oligonucleotides and the fourth plurality of oligonucleotides. A determination is made as to whether the set of oligonucleotides satisfies at least one assembly criterion, where when the set of oligonucleotides satisfies the at least one assembly criterion, the set of oligonucleotides is selected, and when the set of oligonucleotides does not satisfy the at least one assembly criterion, the set of oligonucleotides is rejected and the aforementioned steps are repeated.

In some embodiments a different first predetermined annealing temperature range and a different second predetermined annealing temperature range is used when steps i) through v) are repeated. In some embodiments the first predetermined annealing temperature range and the second predetermined annealing temperature range are the same. In some embodiments, the first predetermined annealing temperature range and the second predetermined annealing temperature range are different. In some embodiments, the first predetermined annealing temperature range and the second predetermined annealing temperature range is each between 45° C. and 72° C., between 50° C. and 65° C., or between 55° C. and 62° C.

In some embodiments, each single-stranded oligonucleotide in the second plurality of single-stranded oligonucleotides is formed by joining an adjacent pair of oligonucleotides in the first plurality of single-stranded oligonucleotides. In some embodiments, each single-stranded oligonucleotide in the fourth plurality of single-stranded oligonucleotides is formed by joining an adjacent pair of oligonucleotides in the third plurality of single-stranded oligonucleotides.

In some embodiments, the method further comprises assembling the set of oligonucleotides by the polymerase chain reaction or ligase chain reaction with an annealing temperature that is a predetermined amount lower than the lowest annealing temperature of the first predetermined annealing temperature range, thereby forming an assembly mixture that comprises the polynucleotide. In some embodiments, the predetermined amount is 1° C. or larger.

In some embodiments, the method further comprises cloning the polynucleotide into a vector. In some embodiments, the assembly mixture comprises a plurality of different polynucleotide molecules, the method further comprising creating a plurality of heteroduplexes between different individual polynucleotide molecules within the plurality of different polynucleotide molecules in the assembly and then treating the plurality of heteroduplexes with an agent that binds preferentially to mismatched sequences within a double-stranded DNA molecule. In some embodiments, the agent is used to remove double-stranded DNA molecules containing mismatched sequences from the assembly mixture.

In some embodiments, the method further comprises amplifying the polynucleotide by the polymerase chain reaction. In some embodiments, the method further comprises cloning the polynucleotide into a vector. In some embodiments, the at least one assembly criterion comprises a requirement that the annealing temperature of each intended complementary pair of single-stranded oligonucleotides in the set of oligonucleotides falls within a third predetermined temperature range. In some embodiments, the third predetermined temperature range encompasses a total of 4° C. or less. In some embodiments, the third predetermined temperature range encompasses a total of 3° C. or less. In some embodiments, the at least one assembly criterion comprises a requirement that the single-stranded oligonucleotide length of each oligonucleotide in the set of oligonucleotides is within a predetermined oligonucleotide length range. In some embodiments, the predetermined oligonucleotide length range is between 20 nucleotides and 70 nucleotides, or between 25 nucleotides and 65 nucleotides.

In some embodiments, the at least one assembly criterion comprises a requirement that the number of single-stranded oligonucleotides in the second plurality of single-stranded oligonucleotides matches the number of single-stranded oligonucleotides in the fourth plurality of single-stranded oligonucleotides. In some embodiments, the at least one assembly criterion comprises a requirement that the annealing temperature of each pair of single-stranded oligonucleotides in the set of oligonucleotides for assembly, whose annealing is not intended for said assembly, is below a predetermined temperature. In some embodiments, the predetermined temperature is the annealing temperature of a pair of oligonucleotides in the set of oligonucleotides whose annealing is intended for assembly of the polynucleotide. In some embodiments, the predetermined temperature is 10° C. below, 15° C. below, or 20° C. below the annealing temperature of a pair of oligonucleotides in the set of oligonucleotides whose annealing is intended for assembly of the polynucleotide. In some embodiments, the at least one assembly criterion comprises a requirement that a maximum length of a sequence that occurs more than once within the first strand of the polynucleotide and that is found at a terminus of any oligonucleotide in the set of oligonucleotides is less than a predetermined length. In some embodiments, the predetermined length is 10 nucleotides or greater, or 12 nucleotides or greater. In some embodiments, a pair of oligonucleotides in the set of oligonucleotides that are intended to be annealed to form the polynucleotide are not completely overlapping. In some embodiments, a first single-stranded oligonucleotide has an n-mer overhang relative to a second single-stranded oligonucleotide in the set of oligonucleotides, and annealing of the first single-stranded oligonucleotide and the second oligonucleotide single-stranded oligonucleotide is intended for assembly of the polynucleotide, where n is between 1 and 40.

In some embodiments, the at least one assembly criterion comprises a requirement that a predetermined length of a nucleotide sequence at a terminus of an oligonucleotide in the set of oligonucleotides is not found at either terminus of any other oligonucleotide in the set of oligonucleotides. In some embodiments, the predetermined length is 5 nucleotides, 4 nucleotides, or 3 nucleotides.

In some embodiments, the design criterion comprises one or more of:

(i) exclusion of a restriction site sequence in said initial polynucleotide sequence;

(ii) incorporation of a restriction site sequence in said initial polynucleotide sequence;

(iii) a designation of a target G+C content in the initial polynucleotide sequence;

(iv) an allowable length of a sub-sequence that can be exactly repeated within either strand of the initial polynucleotide sequence;

(v) an allowable annealing temperature of any sub-sequence to any other sub-sequence within either strand of the initial polynucleotide sequence;

(vi) exclusion of a hairpin turn in the initial polynucleotide sequence;

(vii) exclusion of a repeat element in the initial polynucleotide sequence;

(viii) exclusion of a ribosome binding site in the initial polynucleotide sequence;

(ix) exclusion of a polyadenylation signal in the initial polynucleotide sequence;

(x) exclusion of a splice site in the initial polynucleotide sequence;

(xi) exclusion of an open reading frame in each possible 5' reading frame in the initial polynucleotide sequence;

(xii) exclusion of a polynucleotide sequence that facilitates RNA degradation in the initial polynucleotide sequence;

(xiii) exclusion of an RNA polymerase termination signal in the initial polynucleotide sequence;

(xiv) exclusion of a transcriptional promoter in the initial polynucleotide sequence;

(xv) exclusion of an immunostimulatory sequence in the initial polynucleotide sequence;

(xvi) incorporation of an immunostimulatory sequence in the initial polynucleotide sequence;

(xvii) exclusion of an RNA methylation signal in the initial polynucleotide sequence;

(xviii) exclusion of a selenocysteine incorporation signal in the initial polynucleotide sequence;

(xix) exclusion of an RNA editing sequence in the initial polynucleotide sequence;

(xx) exclusion of an RNAi-targeted sequence in the initial polynucleotide sequence; and (xxi) exclusion of an inverted repeat within the first 45 nucleotides encoding said polypeptide in the initial polynucleotide sequence.

In some embodiments, the design criterion comprises reduced sequence identity to a reference polynucleotide, and modifying the initial codon choice in the initial polynucleotide in accordance with the design criterion comprises altering a codon choice in the initial polynucleotide sequence to reduce sequence identity to the reference polynucleotide.

In some embodiments, the design criterion comprises increased sequence identity to a reference polynucleotide, and modifying the initial codon choice in the initial polynucleotide in accordance with the design criterion comprises altering a codon choice in the initial polynucleotide sequence to increase sequence identity to the reference polynucleotide.

In some embodiments, the method further comprise assembling the set of oligonucleotides by the polymerase chain reaction or ligase chain reaction with an annealing temperature that is a predetermined amount lower than the lowest annealing temperature of the first predetermined annealing temperature range, thereby forming an assembly mixture that comprises an oligonucleotide with the second oligonucleotide sequence. In some embodiments, the predetermined amount is 1° C. or larger. In some embodiments, the method further comprises cloning the oligonucleotide with the second oligonucleotide sequence into a vector. In some embodiments, the assembly mixture comprises a plurality of different polynucleotide molecules, and the method further comprises creating a plurality of heteroduplexes between different individual polynucleotide molecules within the plurality of different polynucleotide molecules in the assembly and treating the plurality of heteroduplexes with an agent that binds preferentially to mismatched sequences within a double-stranded DNA molecule; and using the agent to remove double-stranded DNA molecules containing mismatched sequences from the assembly mixture. In some embodiments, the method further comprises amplifying the oligonucleotide with the second oligonucleotide sequence by the polymerase chain reaction.

In some embodiments, the method further comprises cloning the oligonucleotide with the second oligonucleotide sequence into a vector. The method further comprises repeating the selecting, modifying, and designing when repetition of steps i) through v) fails to identify a set of oligonucleotides that satisfies said at least one assembly criterion.

Still another aspect of the present invention provides a computer program product for use in conjunction with a computer system, the computer program product comprising a computer readable storage medium and a computer program mechanism embedded therein, the computer program mechanism for designing a polynucleotide that has a first oligonucleotide sequence. The computer program mechanism comprises a) instructions for selecting an initial codon sequence that codes for the polypeptide, where a codon frequency in the initial codon sequence is determined by a codon bias table; b) instructions for modifying an initial codon choice in the initial codon sequence in accordance with a design criterion, thereby constructing a codon sequence that codes for said first oligonucleotide sequence; c) instructions for designing a set of oligonucleotides for assembly into a second oligonucleotide sequence, where the second oligonucleotide sequence encodes a contiguous portion of the first oligonucleotide sequence, the designing step c) comprising: (i) instructions for identifying a first plurality of single-stranded oligonucleotides that collectively encode all or a portion of a first strand of the second oligonucleotide sequence, where each respective single-stranded oligonucleotide in the first plurality of single-stranded oligonucleotides is characterized by an annealing temperature to its exact complement that is in a first predetermined annealing temperature range; (ii) instructions for identifying a second plurality of single-stranded oligonucleotides from the first plurality of single-stranded oligonucleotides, where a single-stranded oligonucleotide in the second plurality of single-stranded oligonucleotides is formed by joining an adjacent pair of oligonucleotides in the first plurality of single-stranded oligonucleotides; (iii) instructions for identifying a third plurality of single-stranded oligonucleotides that collectively encode all or a portion of a second strand of the second oligonucleotide sequence, where each respective single-stranded oligonucleotide in the third plurality of single-stranded oligonucleotides is characterized by an annealing temperature to its exact complement that is in a second predetermined annealing temperature range; (iv) instructions for identifying a fourth plurality of single-stranded oligonucleotides from the third plurality of single-stranded oligonucleotides, where a single-stranded oligonucleotide in the fourth plurality of single-stranded oligonucleotides is formed by joining an adjacent pair of oligonucleotides in the third plurality of single-stranded oligonucleotides; where a set of oligonucleotides comprises the second plurality of oligonucleotides and the fourth plurality of oligonucleotides; and (v) instructions for determining whether the set of oligonucleotides satisfies at least one assembly criterion, where when the set of oligonucleotides satisfies the at least one assembly criterion, the set of oligonucleotides is selected; and when the set of oligonucleotides does not satisfy the at least one assembly criterion, the set of oligonucleotides is rejected and the aforementioned instructions are repeated. Still another aspect of the present invention provides a computer system Still another aspect of the present invention provides a computer system for designing a polynucleotide that has a first oligonucleotide sequence, the computer system comprising a central processing unit and a memory, coupled to the central processing unit, the memory storing the aforementioned computer program product.

5.6 Integrated Devices for Polynucleotide Synthesis

The methods described here may be conveniently performed using a single device capable of performing one or more of the functions required for synthesis of a polynucleotide. A schematic representation of the functions performed by different modules of a polynucleotide synthesizing device is shown in FIG. 49. In particular, FIG. 49 illustrates a system 10 that is operated in accordance with one embodiment of the present invention. System 10 comprises standard components including a central processing unit 22, and memory 36 for storing program modules and data structures, user input/output device 32, a network interface 20 for coupling computer 10 to other computers via a communication network 34, and one or more busses 30 that interconnect these components. User input/output device 32 comprises one or more user input/output components such as a mouse, display 26, and keyboard 28. In some embodiments, some of the program modules and data structures are stored in a permanent storage device 14 that is controlled by controller 12. In some embodiments, device 14 is a hard disk. System 10 further includes a power source 24 to power the aforementioned components.

Memory 36 comprises a number of modules and data structures that are used in accordance with the present invention. It will be appreciated that, at any one time during operation of the system, a portion of the modules and/or data structures stored in memory 36 is stored in random access memory while another portion of the modules and/or data structures is stored in non-volatile storage 14. In a typical embodiment, memory 36 comprises an operating system. The operating system comprises procedures for handling various basic system services and for performing hardware dependent tasks. Memory 36 further comprises a file system for file management. In some embodiments, the file system is a component of the operating system. Memory 36 and/or 14 also comprises the modules described below.

Design Module.

This is a primarily bioinformatic module that performs the following tasks. 1. Polynucleotide design (for example design of a polynucleotide to encode a specific polypeptide, reduction or elimination of repeat elements, design of two or more polynucleotides for synthesis and joining to form a single polynucleotide. Examples include computer programs that perform the processes shown in FIGS. 26, 27, 28, 44 and 45). 2. Oligonucleotide design (for example reduction or elimination of annealing regions in incorrect annealing partners, design of a "constant Tm" set. Examples include computer programs that perform the processes shown in FIGS. 29, 30, 31 and 42). 3. Select the assembly conditions appropriate for the designed oligonucleotide set (for example the annealing temperature, the number of cycles and time for each cycle, the use of polymerase or ligase-based assembly conditions. Examples include the conditions shown in FIGS. 32, 33, 34, 35, 36 and 43).

Oligonucleotide Synthesis Module.

This module performs the physical process of oligonucleotide synthesis. The input to this module is a set of oligonucleotide sequences that is provided by the design module. The oligonucleotide synthesis module could be an outside oligonucleotide vendor that receives the sequence information electronically either directly form the design module, or via an intermediary such as an ordering system. The oligonucleotide synthesis module could also be an oligonucleotide synthesis machine that is physically or electronically linked to and instructed by the design module. The oligonucleotide synthesis module could synthesize oligonucleotides using standard phosphoramidite chemistry, or using the modifications described here.

Synthesis Module.

This module performs the physical process of assembling oligonucleotides into a polynucleotide. The synthesis module receives informational input from the design module, to set the parameters and conditions required for successful assembly of the oligonucleotides. It also receives physical input of oligonucleotides from the oligonucleotide synthesis module. The synthesis module is capable of performing variable temperature incubations required by polymerase chain reactions or ligase chain reactions in order to assemble the mixture of oligonucleotides into a polynucleotide. For example the synthesis module can include a thermocycler based on Peltier heating and cooling, or based on microfluidic flow past heating and cooling regions. The synthesis module also performs the tasks of amplifying the polynucleotide, if necessary, from the oligonucleotide assembly reaction. The synthesis module also performs the task of ligating or recombining the polynucleotide into an appropriate cloning vector.

Transformation Module.

This module performs the following tasks. 1. Transformation of the appropriate host with the polynucleotide ligated into a vector. 2. Separation and growth of individual transformants (e.g. flow-based separations, plating-based separations). 3. Selection and preparation of individual transformants for analysis.

Analysis Module.

This module performs the following tasks. 1. Determination of the sequence of each independent transformant. This can be done using a conventional sequencer using extension and termination reactions e.g. with dye terminators such as those recognized by Applied Biosystems Machines 3100, 3130 etc. Alternatively use of sequencing technologies developed for determining the sequence of polynucleotides whose sequence is already approximately known ("re-sequencing technologies") can also be used to more cheaply identify errors incorporated during polynucleotide synthesis. These include hybridization-based technologies. 2. Comparison of the determined sequence with the sequence that was designed. 3. Identification of transformants whose sequence matches the designed sequence.

The modules described above and depicted in FIG. 49 can be physically distinct or combined into five or fewer devices. Computer programs to effect communication between the modules, as well as to perform the functions of each module, are an aspect of the invention.

6. EXAMPLES

The following examples are set forth so as to provide those of ordinary skill in the art with a complete description of how to make and use embodiments of the present invention, and are not intended to limit the scope of what is regarded as the invention.

6.1 Increased Coupling Efficiency on a Controlled Pore Glass Support

Figure 14A:
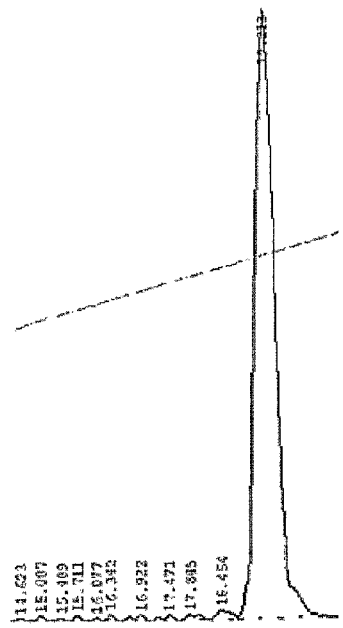
Figure 14B:
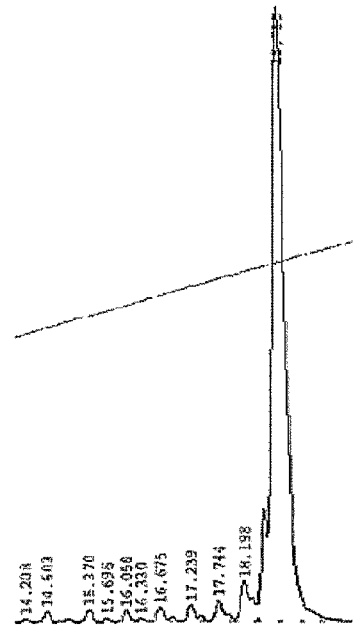
Figure 14C:
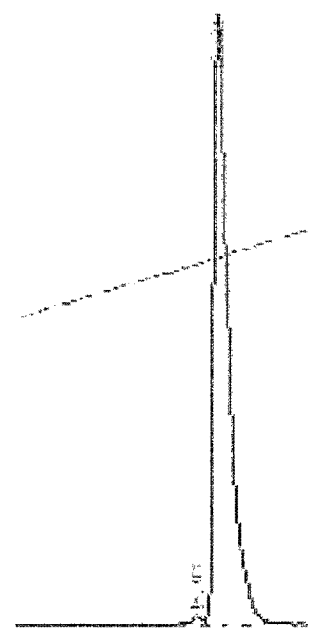
Figure 14D:
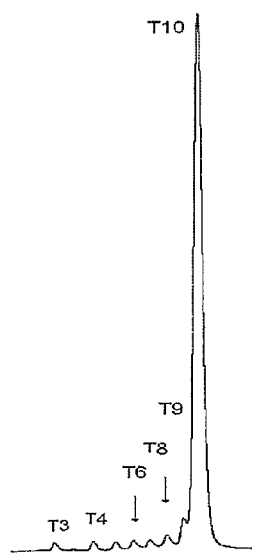
Figure 14E:
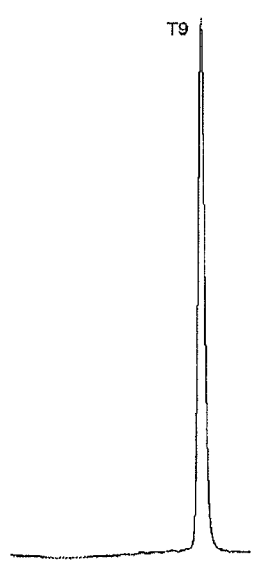
Figure 14F:
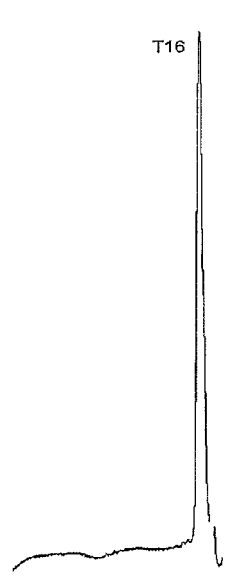

The coupling efficiency of the modified protocol of FIG. 13 is shown by a comparison between literature descriptions of high quality, low quality and gel purified oligonucleotides (FIG. 14A-C), a commercially purchased oligonucleotide (FIG. 14D) and oligonucleotides synthesized by the modified procedure (FIGS. 14E and F). The modified procedure described herein showed a coupling efficiency of 99.9%.

To measure the coupling efficiency the capping step was eliminated and multiple coupling cycles were performed as described in, for example, Matteucci and Caruthers, 1981, J Am Chem Soc 103, 3185-3191; Pon et al., 1985, Tetrahedron Lett. 26, 2525-2528; Adams et al., 1983, J Am Chem Soc 105, 661-663; McBride et al., 1986, J Am Chem Soc 108, 2040-2048; Letsinger et al., 1984, Tetrahedron 40, 137-143; Hayakawa et al., 1990, J Am Chem Soc 112, 1691-1696; and Hayakawa & Kataoka, 1998, J Am Chem Soc 120, 12395-12401, which are hereby incorporated by reference in their entireties. The oligonucleotide synthesis products were analyzed by HPLC. Comparisons of the amounts of full-length and truncated products were used to calculate the coupling efficiencies of standard and modified procedures.

Protocols for Oligonucleotide Synthesis on CPG and Quartz Rods: Chain Propagation Steps A desoxythymidine modified quartz rod (4 mm diameter) and/or 5 mg of dT-CPG 500 (Glen Research) were placed inside a 2 mm filter funnel attached at the top to an argon line (2-3 psi) and at the bottom to a waste line. When both rod and CPG were used, the rod was installed with its derivatized surface 0.5 mm above the CPG layer. CPG particles stuck to the wall were washed down with acetonitrile (1 ml). After sedimentation of all glass particles, the system was purged with argon for one minute before addition of 200 ul of capping reagent, prepared by mixing the equal amounts of stock solution A (1 ml $Ac_2O$, 9 ml DMA) and stock solution B (1.2 g DMAP, 7.3 ml DMA, 1.5 ml 2,6-lutidine, was added to block all untritylated reactive groups for one minute followed by washes with acetonitrile (500 µl), methanol (2×500 µl), acetonitrile (2×500 µl) and drying under argon flow for 1 minute. Detritylation with 15% dichloroacetic acid in methylene chloride (200 µl) was performed for one minute. This reagent was removed by applying positive argon pressure, solid supports were washed with methyl cyanide (HPLC grade, 4×500 µl) and dried for two minutes under argon flow. During this time 0.1M dimethoxytritylthymidine phosphoramidite solution in dry acetonitrile (100 µl) was pre-activated by mixing inside the Hamilton syringe (500 µl) with 0.4M tetrazole solution in acetonitrile (100 µl) with an argon bubble as an air-free mixer. After approximately 1.5 minutes of activation period, the phosphoramidite solution (200 µl) was added to the dry solid support under argon: inert gas continued to flow on the top of the filter to prevent air from entering. After a one minute coupling step, reagents were washed away by acetonitrile (4×500 µl) and argon was purged through the filter funnel for one minute. Oxidation was performed for one minute by addition of an aliquot (200 µl) of 0.12M aqueous iodine stock solution that was prepared the same day. After completion of oxidation the supports were washed with acetonitrile (4×500 µl), dried under argon for one minute and capped as described at the beginning of this paragraph. Following capping either the next synthesis cycle was repeated or the cleavage step was initiated.

Protocols for Oligonucleotide Synthesis on CPG: Cleavage of Oligos from CPG

Dried CPG was treated with 10M ammonia (100 µl, N.F. grade, Baker) for two hours at room temperature. Ammonia solution was transferred into 1.5 ml Eppendorf vial and solvents evaporated on SpeedVac SVC 1000 (Savant). Diluted (1:100) aliquot (2 ul) was analyzed by HPLC.

Protocols for Oligonucleotide Synthesis on CPG and Quartz Rods: Determination of Coupling Efficiency Samples obtained from CPG or rod (with or without PDE-II digestion in solution) were analyzed on an XTerra MS C18 column (3.5 µm, 2.1×100 mm, Waters) on a Waters HPLC. Four mobile phases were used for separation. Mobile phase A was 0.05M triethylamine acetate at pH=7, mobile phase B was mixture 12% of mobile phase D and 88% of mobile phase A, mobile phase C was 0.1% trifluoroacetic acid and mobile phase D was acetonitrile. The temperature was set at 60° C. to prevent hybridization and increase mass-transaction between solid and mobile phases. Flow was 0.4 ml/min for optimal separation on 2.1 mm column. Several gradients were followed one after another. During ten minutes of analysis of 5N—O unprotected oligos pool the mobile phase was change by curve #2 (Waters gradient curve specification) from 70% A and 30% B to 18% A and 82% B. After this column was stabilized for seven minutes by flushing with 100% A, dimethoxytrityl group was removed by solvent C for eight minutes and column was prepared for analysis of "Trityl-OFF" fraction by stabilization washing with 70% A and 30%

B for 10 min. The quality of sample adsorbed at the beginning of column was determined by ten minute gradient elution according to curve #2 until 18% A and 82% B was reached. Column was regenerated by streaming of acetonitrile for one minute and stabilized by 70% A and 30% B for twelve minutes to be prepared for the next injection.

6.2 Oligonucleotide Synthesis on a Non-Porous Glass Support

Protocols for Oligonucleotide Synthesis on Quartz Rods: Rod Derivatization

The end of a broken quartz rod (L=4 cm, D=4 mm, Chemglass) was flattened by polishing on 220 mesh silicone carbide paper. After treatment with 50% w/v sodium hydroxide for ten minutes followed by concentrated nitric acid for five minutes rods were vacuum dried for five minutes, immersed in pyridine:trimethylchlorosilane (2:1) for one minute, washed with methanol and vacuum dried for one minute. The trimethylsilane layer was removed from the end of rod by polishing with 220 mesh carbide paper. Particles formed during the polishing process were blown out using dry air. The rod was inserted into a solution of 1% triethoxyaminopropylsilane in ethanol for one minute. Excess reagent was removed by washing with methanol. The rod was vacuum dried for one minute and treated with a mixture of 0.2 M 3'-succinyl protected nucleotide: 0.8M diisopropylethylamine (DIEA): 0.4M HBTU=1:1:1 for 10 minutes. After washing with methanol and vacuum drying, the rod with immobilized nucleotide was ready for the nucleotide coupling procedure.

Figure 16G:
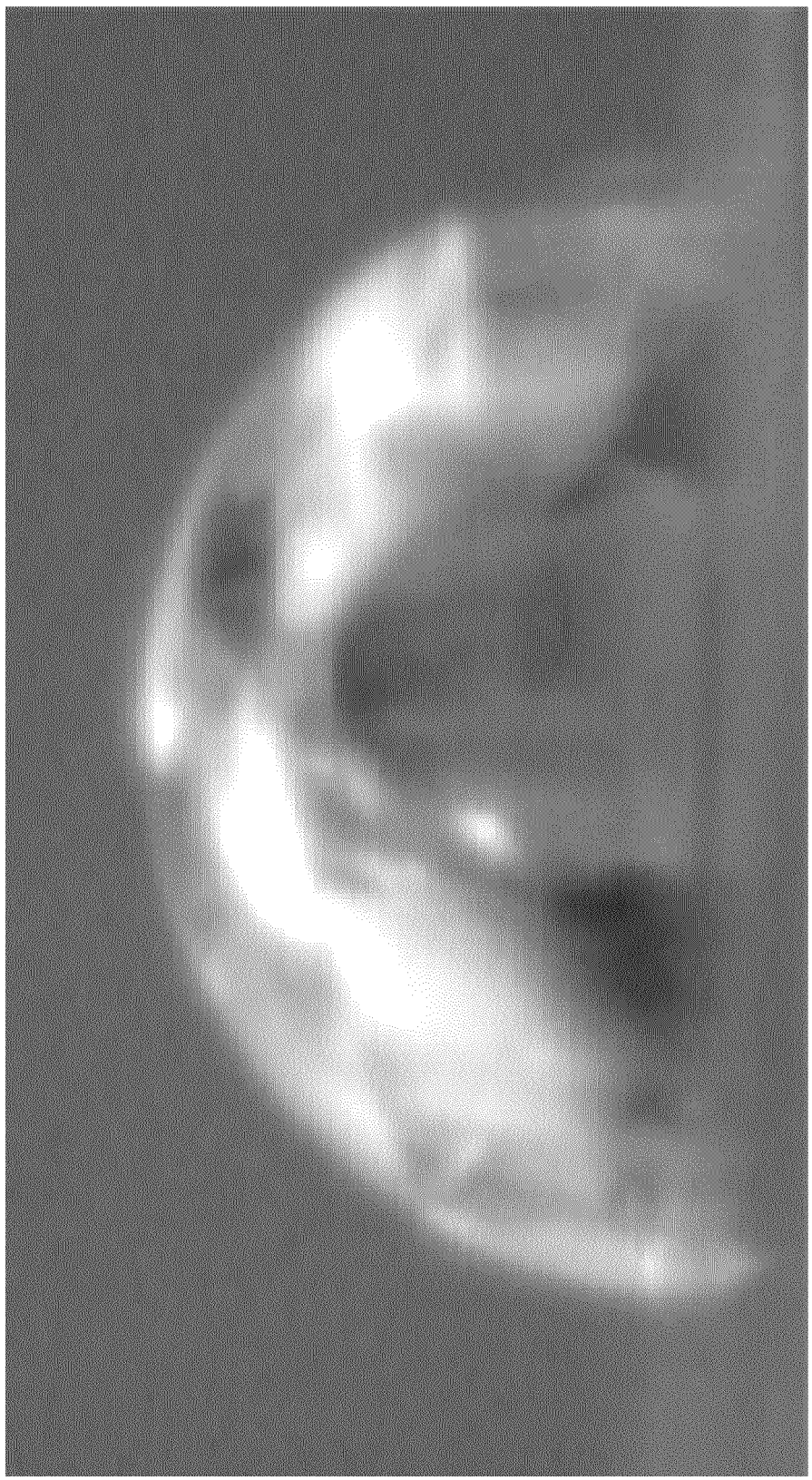
Figure 16H:
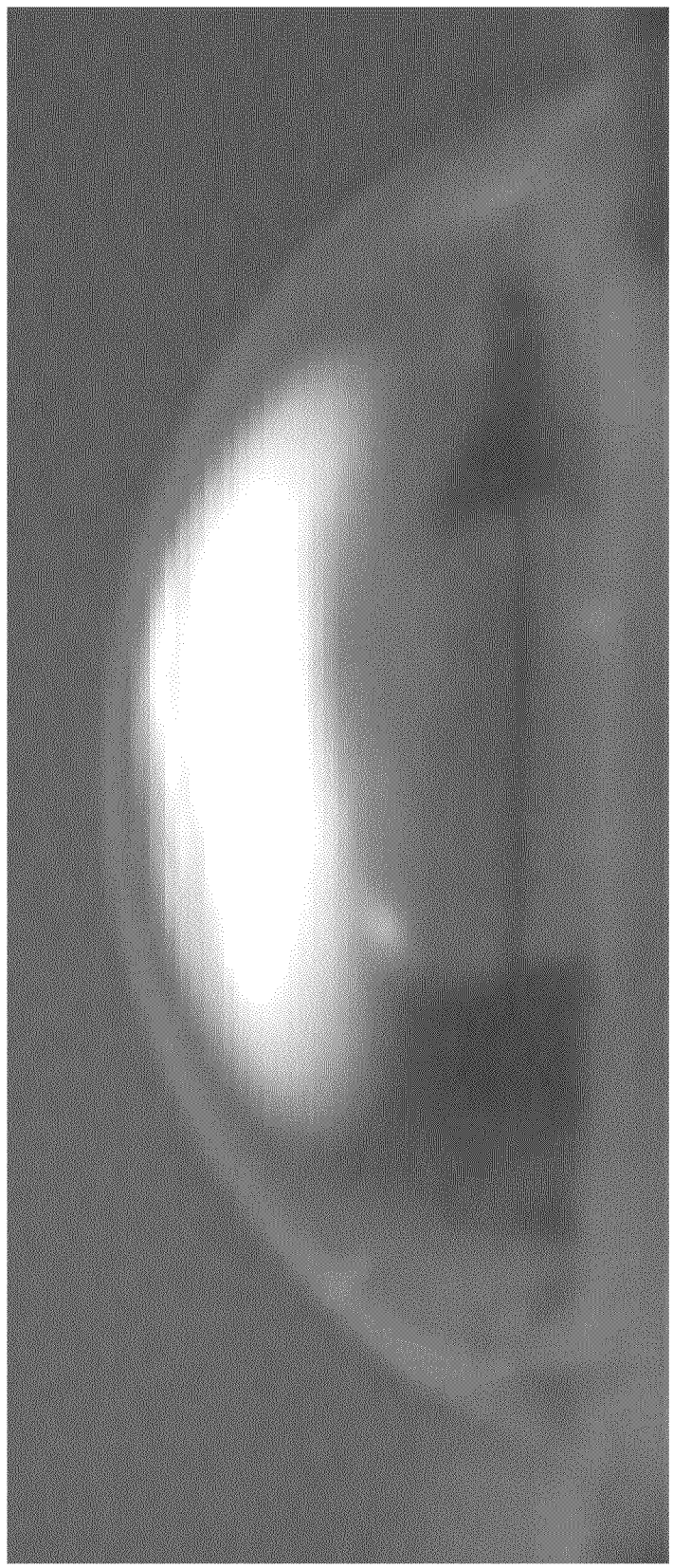
Figure 16I:
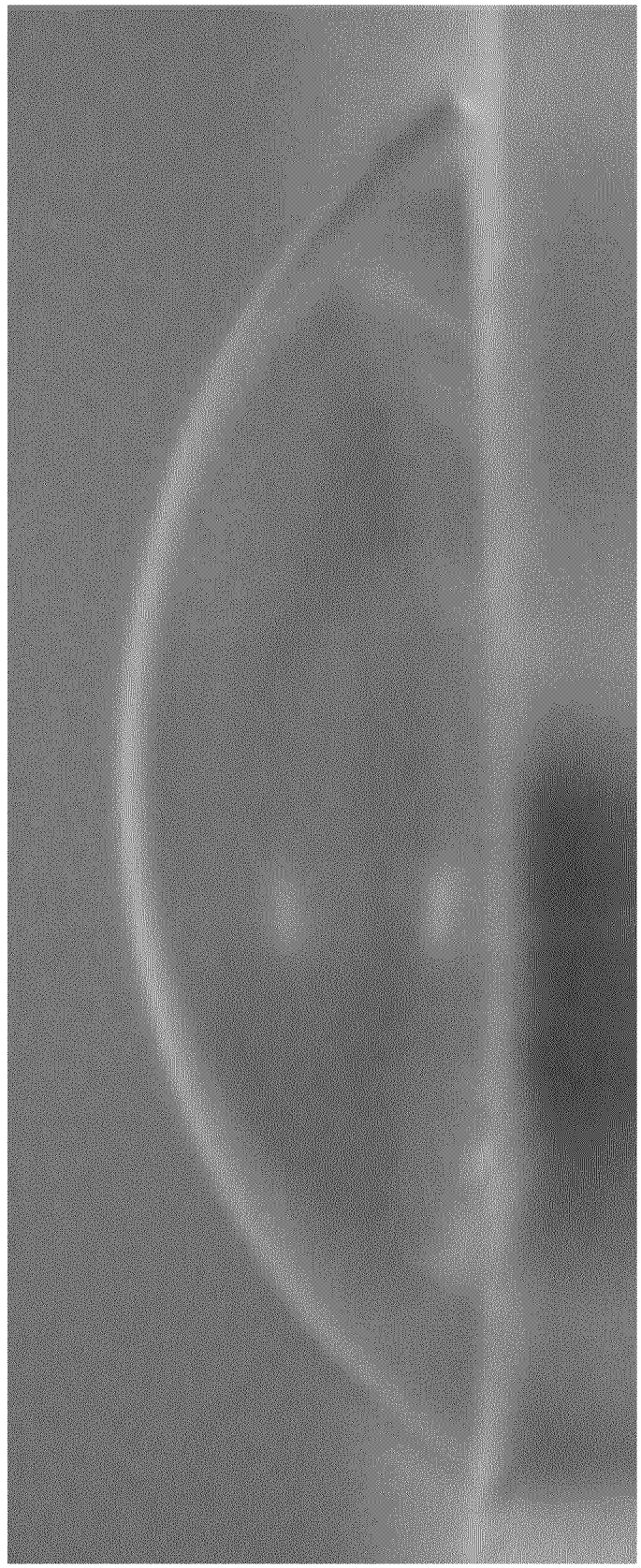
Figure 16J:
Figure 16K:
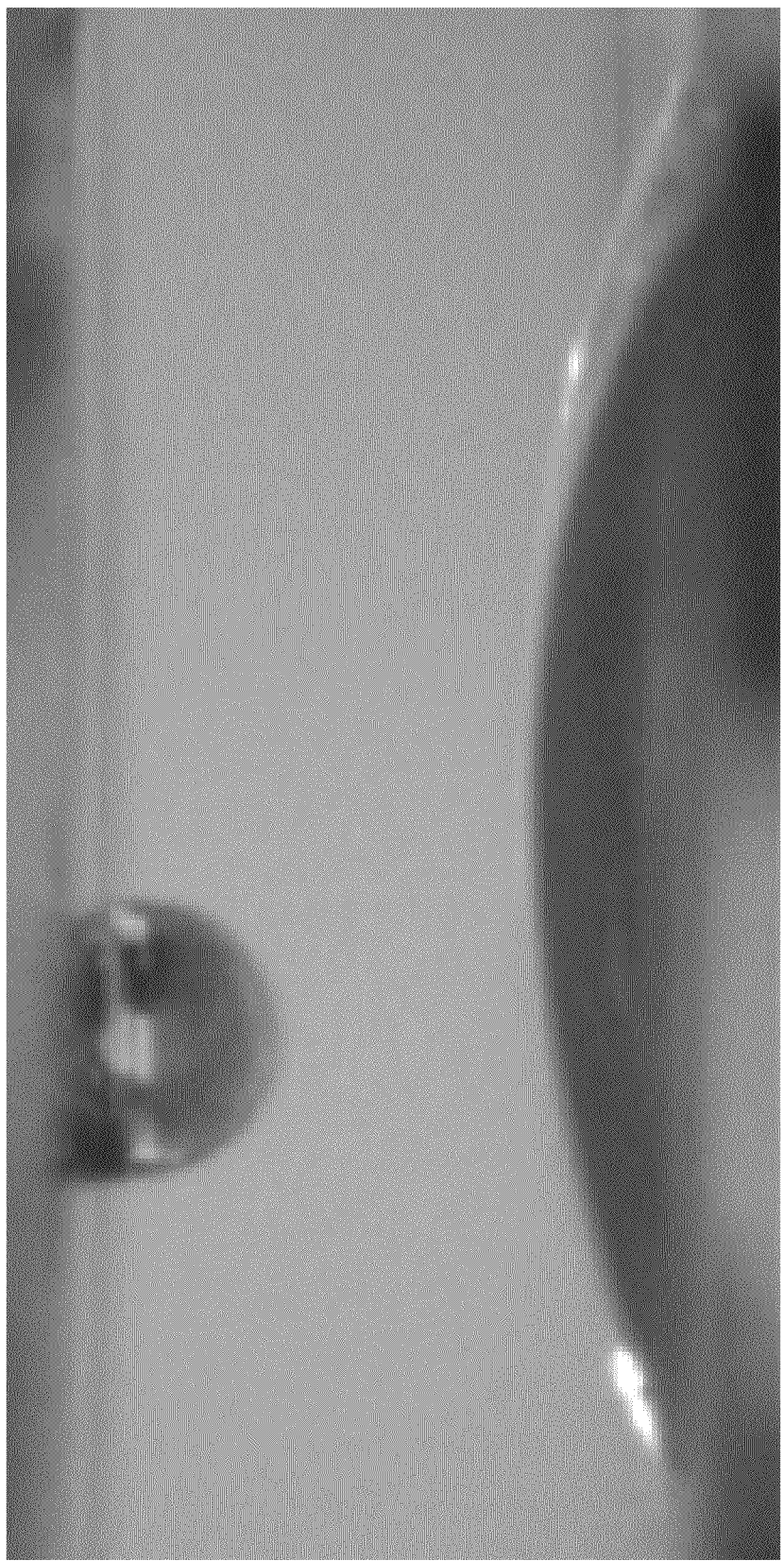
Figure 16L:
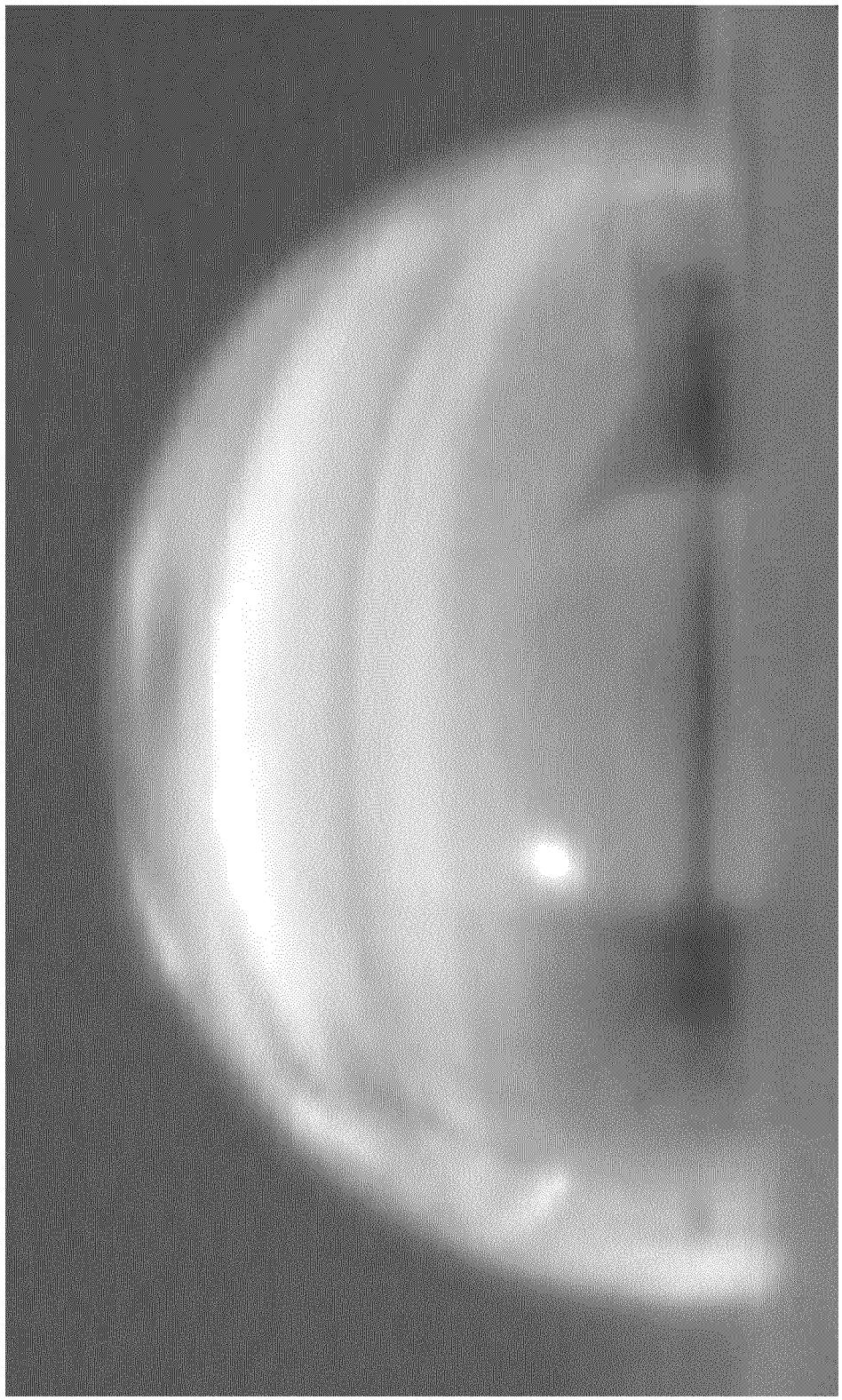
Figure 16M:
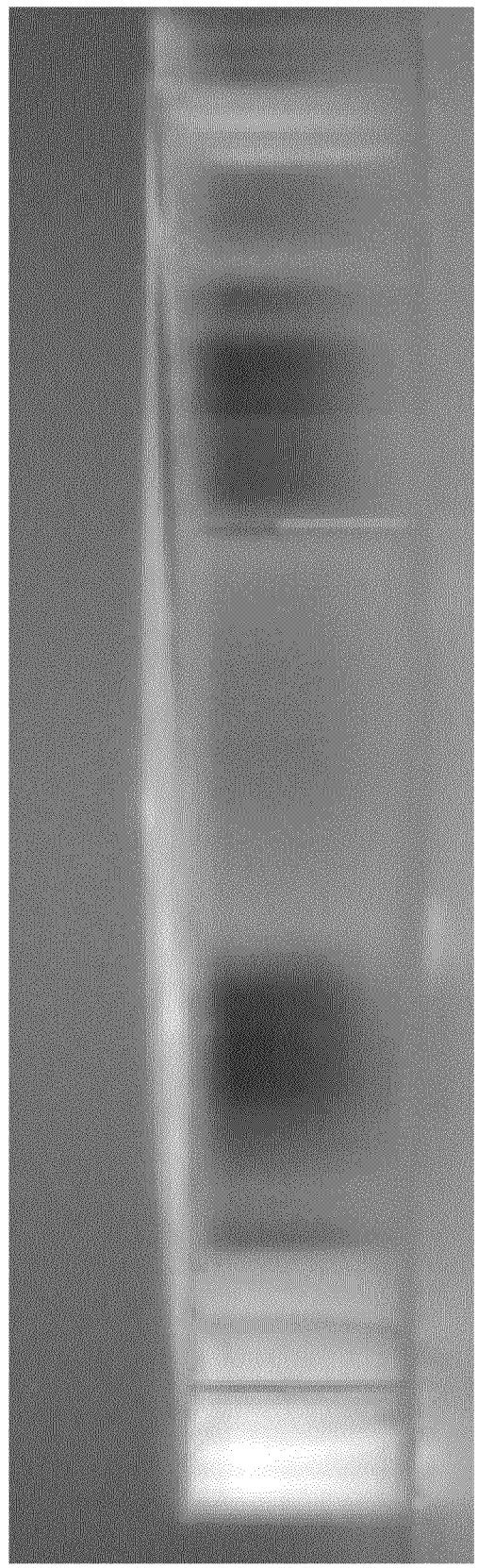
Figure 16N:
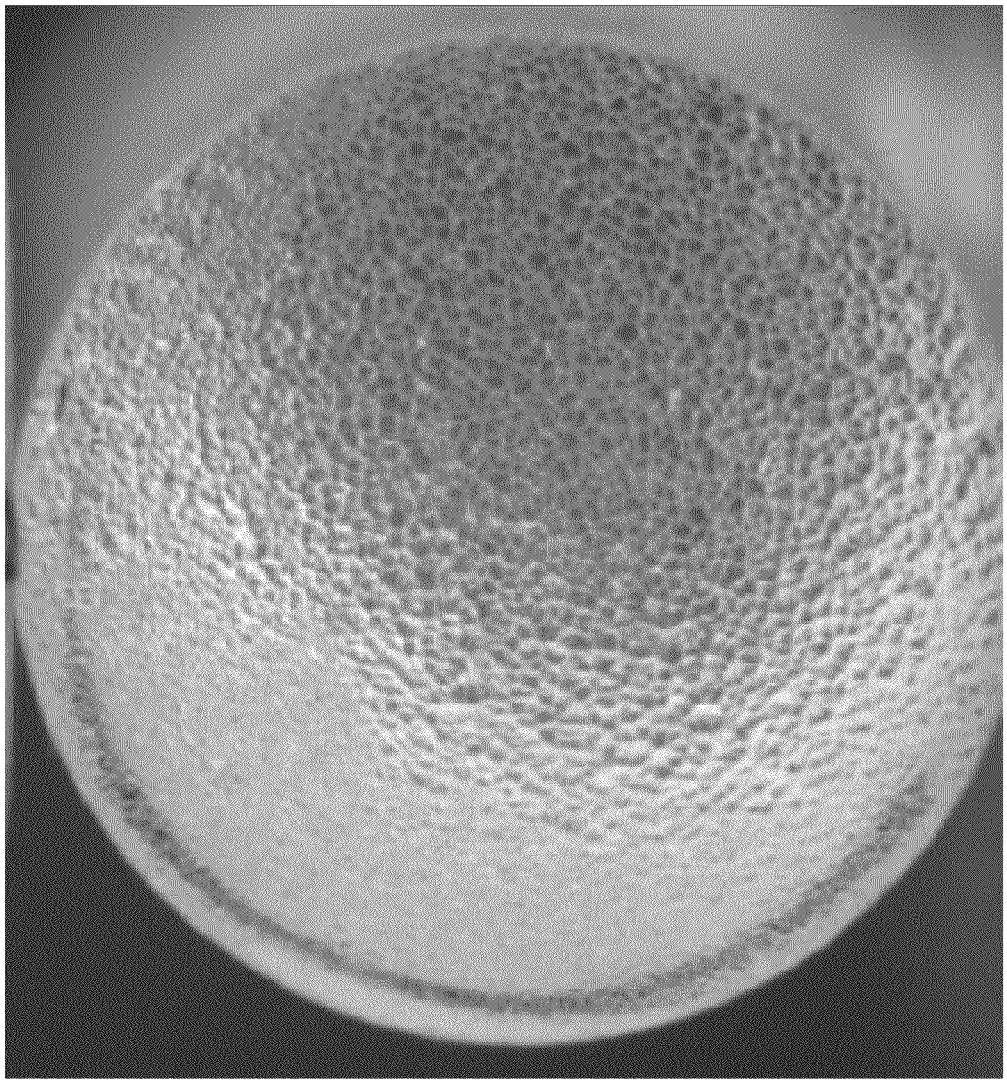
Figure 16O:
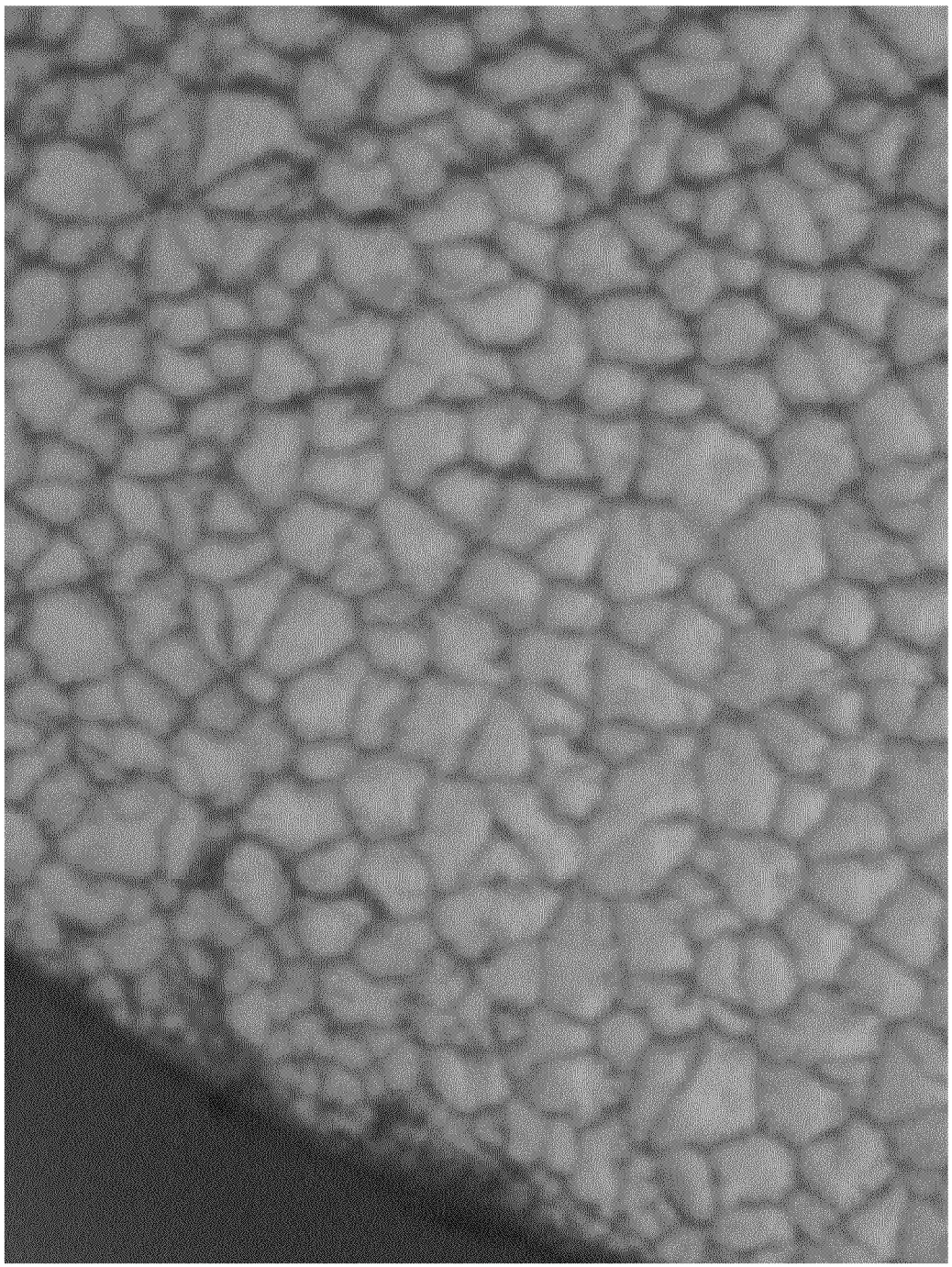
Figure 18B:
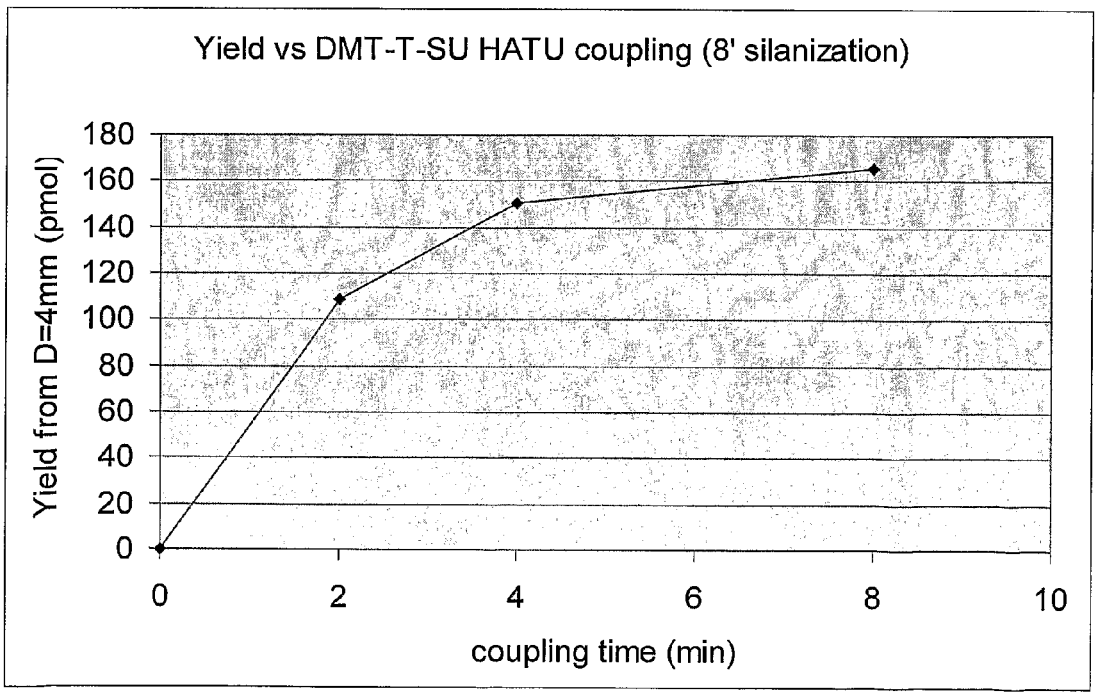

Maximal loading of approximately 1.3 nmol/cm$^2$ was achieved on surfaces derivatized for 1-2 minutes (FIG. 18A) and coupled for eight to ten minutes (FIG. 18B). This loading density is almost ten times higher than previously reported for a glass support but almost ten times lower then described for plasma-activated polystyrene. See, Pon, 2000, Current protocols, UNIT 3.1 and 3.2, which is hereby incorporated by reference in its entirety. Without intending to be limited any particular theory, high loading capacity is attributed to rough micro-surface formed as a result of sandpaper polishing and 50% sodium hydroxide treatment (FIG. 16G). Chain propagation steps were performed as for Example 6.1.

Protocols for Oligonucleotide Synthesis on Quartz Rods: Cleavage of Oligos from Quartz Rod The dried rod was placed inside an autoclave (1 gal 316SS Pressure Dispenser 130 psi, 4355T68 McMaster) containing 50 ml of 28% ammonia (technical grade, Lancaster). The temperature inside cleavage chamber was raised to 55° C. and the pressure to 35 psi by heating on the water bath to 95° C. After one hour the ammonia gas was let out, the rod removed, and cleaved oligos collected into a Hamilton syringe (10 µl) after applying drop of 0.05M phosphate buffer (10 µl) to the end of the vertically positioned rod. The entire sample was analyzed by HPLC on narrow bore reverse phase column (2.1 mm) with standard UV flow cell (8 mm, 12 µl). Determination of coupling efficiency was performed as for Example 6.1.

Figure 20A:
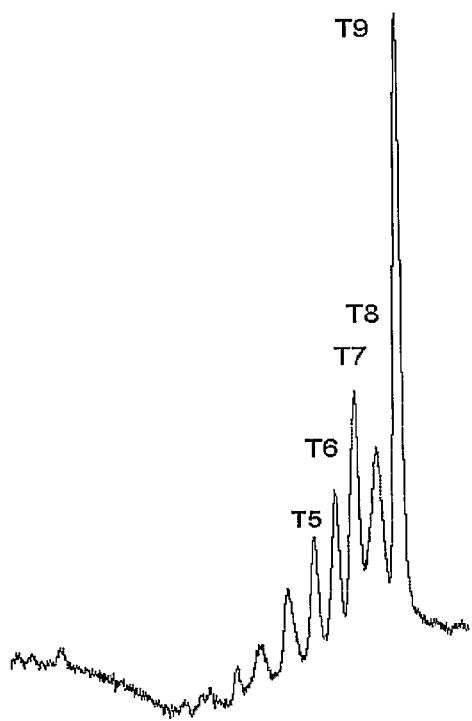
Figure 20B:
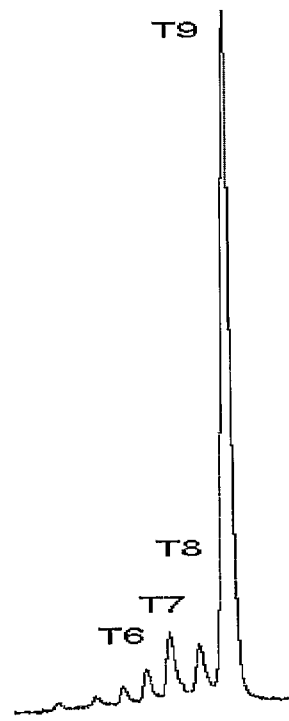
Figure 20C:
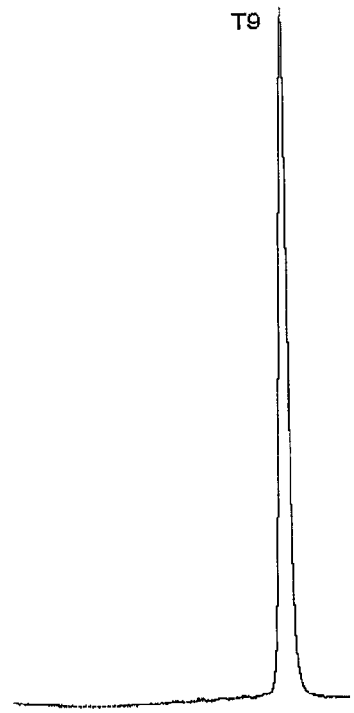

An initial test was performed of the quartz rod support by synthesizing a polythymidine 9mer following the standard procedure. The result was similar to those described by Seliger et al., 1989, J Chromatogr 476, 49-57; LeProust et al., 2001, Nucleic Acids Res 29, 2171-80, each of which is hereby incorporated by reference in its entirety (FIG. 20A). When the modified procedure was used, a significant improvement in coupling efficiency, 98.9%, was obtained (FIG. 20B), though the 99.9% efficiency obtained using CPG (FIG. 20C) was not obtained. Grafted gelatinous polymer support on quartz rods will probably improve coupling efficiency further. See Pon, 2000, Current protocols, UNIT 3.1 and 3.2, which is hereby incorporated by reference in its entirety.

6.3 Oligonucleotide Synthesis Using a New Synthesizer Design

The apparatus design shown in FIG. 19 produced controlled synthetic conditions, suitable reproducibility of experiments and low chemical consumption. To compare the effectiveness of synthesis on CPG and non-porous glass supports an internal adapter was constructed that for the performance of both syntheses simultaneously under identical conditions.

Figure 19A:
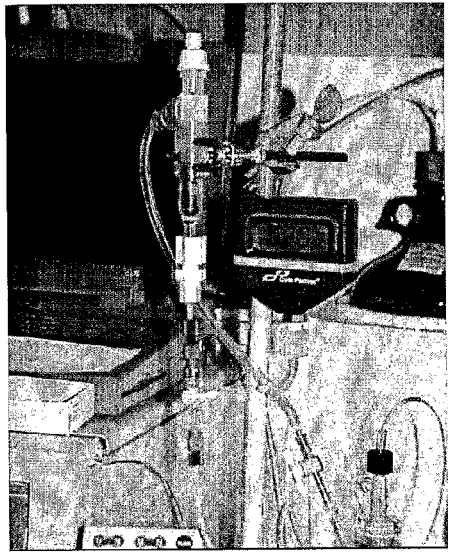
Figure 19B:
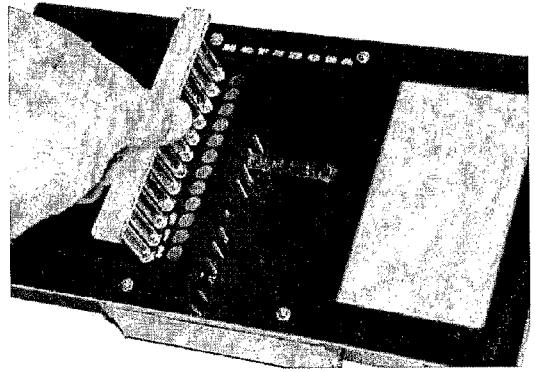
Figure 19C:
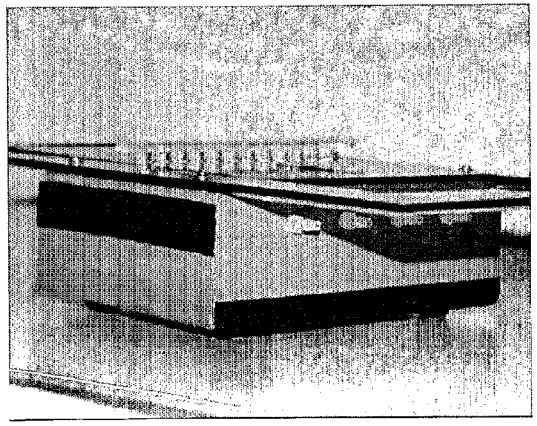
Figure 19D:
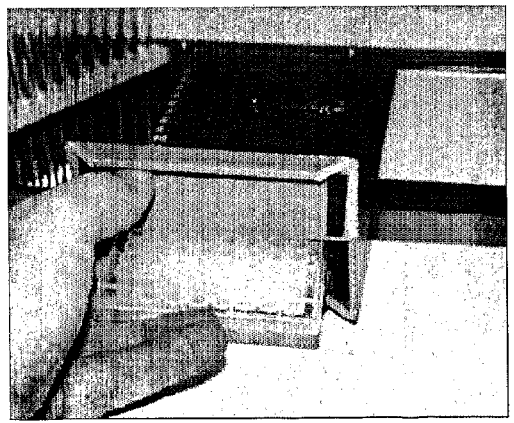
Figure 19E:
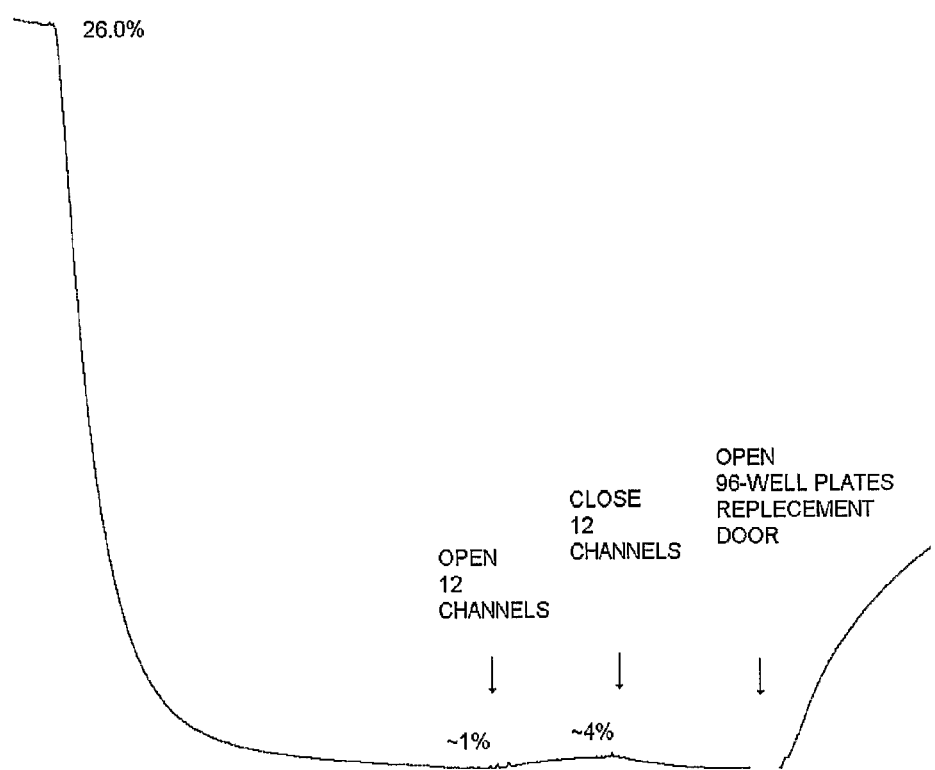
Figure 19F:
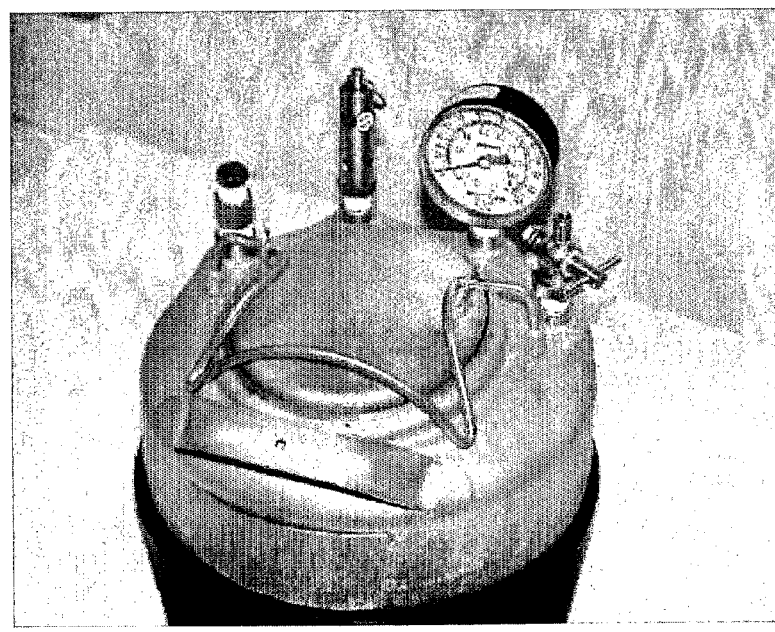

The positive flow technique was used when designing a twelve-pin prototype (FIGS. 19B-D). A twelve-channel prototype of a 96-well synthesizer was built based on a round bottom 96-well reaction plate. Positive argon pressure created an acceptable level of inert atmosphere during reagent delivery and coupling steps (FIG. 19E).

6.4 Synthesis of a 1574 BP Gene

In this example a 1574 BP gene was synthesize. The sequence was initially analyzed for GC content and the presence of repeats using a computer program:

```
Name = G00277/Length = 1574
                                           (SEQ ID NO: 49)
Seq = TGCTGGGGAAAAGTAAACACACACAGGCGCACTCGAGAACAGAT

GAGTTCTTTGGACGAGGATGAAGAGGACTTCGAAATGCTGGACACGGAGA

ACCTCCAGTTTATGGGGAAGAAGATGTTTGGCAAACAGGCCGGCGAAGAC

GAGAGTGATGATTTTGCTATAGGGGGTAGCACCCCGACCAATAAACTGAA

ATTTTATCCATATGCGAACAACAAATTGACAAGAGCTACGGGGACCTTGA

ACCTGTCATTAAGTAATGCAGCTTTGTCAGAGGCTAACTCCAAATTTCTT

GGGAAAATTGAAGAAGAGGAAGAAGAGGAGGAAGAAGGCAAGGATGAGGA

AAGCGTGGATGCTCGTATTAAAAGGTGGTCTCCGTTCCATGAAAATGAAA

GTGTTACTACTCCTATTGCAAAAAGAGCTGCGGAAAAAACGAACAGTCCT

ATTGCTCTCAAACAATGGAACCAGCGATGGTTTCCGAAAAATGATGCTCG

CACTGAAAATACATCCTCATCCTCTTCATATAGCGTCGCTAAACCTAACC

AATCAGCCTTTACGTCTTCGGGCCTCGTATCTAAAATGTCTATGGACACT

TCGTTATACCCTGCGAAATTGAGGATACCAGAAACACCAGTGAAAAAATC

ACCCTTAGTGGAGGGAAGAGACCATAAGCATGTCCACCTTTCGAGTTCGA

AAAATGCATCGTCTTCTCTAAGTGTTTCCCCTTTAAATTTTGTTGAAGAC

AATAATTTACAAGAAGACCTTTTATTTTCAGATTCTCCGTCTTCGAAAGC

TTTACCTTCCATCCATGTACCAACCATAGACGCATCCCCACTGAGCGAGG

CAAAATATCATGCACATGATCGTCACAATAACCAGACAAACATCCTGTCT

CCCACTAATAGCTTGGTTACCAACAGCTCTCCACAAACATTGCATTCTAA

CAAGTTCAAAAAAATCAAAAGAGCAAGGAATTCGGTTATTTTGAAAAATA

GAGAGCTAACAAACAGTTTACAACAATTCAAAGATGATTTATACGGCACG

GACGAGAATTTCCCACCTCCAATCATAATATCAAGTCATCATTCAACTAG
```

-continued

```
AAAGAACCCTCAACCTTATCAATTTCGTGGACGCTATGACAATGACGCTG

ACGAAGAGATCTCCACTCCAACAAGACGAAAATCTATTATTGGGGCAGCA

TCTCAAACACATAGAGAAAGCAGACCATTGTCACTCTCCTCTGCCATCGT

GACAAACACAACAAGTGCAGAGACGCATTCCATATCTTCCACCGATTCTT

CGCCGTTAAATTCCAAAAGGCGTCTAATCTCTTCAAATAAGTTATCAGCA

AATCCAGATTCCCATCTTTTCGAAAAATTTACGAATGTGCATTCCATTGG

TAAAGGCCAGTTTTCCACGGTCTACCAGGTTACGTTTGCCCAAACAAACA

AAAAGTATGCAATCAAAGCCATTAAACCAAACAAATATAATTCCTTGAAA

CGCATATTACTGGAAATTAAAATACTAAACGAGGTAACAAACCAAATTAC

CATGGATCAAGAAGGGAAGGAATACATCAT

A = 550 T = 376 G = 296 C = 352 GC% = 0.41169

MAX REPEAT 11

MAX COMPLEMENT REPEAT 10
```

ALMOST REPEATS (SEQ ID NO: 50)
304 17 GAAGAAGAGGAAGAAGA (SEQ ID NO: 51)
313 17 GAAGAAGAGGAGGAAGA (SEQ ID NO: 52)
316 16 GAAGAGGAGGAAGAAG

One hundred and twenty different sets of "constant Tm" oligonucleotides were then designed using a process similar to that shown in FIG. 30. Different sets were designed by starting at different positions within the polynucleotide, and by using different design annealing temperatures (Z was increased in 0.05° C. increments from 60° C. to 63° C.). For each of these oligonucleotide sets the number of oligonucleotides (#), the lengths of amplification oligonucleotides at each end (Amp), the minimum and maximum annealing temperature of correct annealing pairs within the set (Tm), the minimum and maximum oligonucleotide length (Len), the maximum length of repeat sequence at the end of an oligonucleotide (MaxRep@Ends) and the initial set annealing temperature (TmCUT) were reported as follows.

| | | | | | | | |
|---|---|---|---|---|---|---|---|
| set1.txt | #Ol = 73 | Amp[23,27] | ENDS[22-12] | Tm[60.0108-63.2891] | Len[35-55] | MaxRep@Ends: 12 | TmCUT: 60 |
| set2.txt | #Ol = 73 | Amp[23,27] | ENDS[21-12] | Tm[60.0108-63.2891] | Len[35-55] | MaxRep@Ends: 12 | TmCUT: 60 |
| set3.txt | #Ol = 73 | Amp[23,27] | ENDS[20-12] | Tm[60.0089-63.2891] | Len[35-55] | MaxRep@Ends: 12 | TmCUT: 60 |
| set4.txt | #Ol = 73 | Amp[23,27] | ENDS[19-12] | Tm[60.0089-63.2891] | Len[36-55] | MaxRep@Ends: 12 | TmCUT: 60 |
| set5.txt | #Ol = 73 | Amp[23,27] | ENDS[18-12] | Tm[60.0089-63.2891] | Len[36-55] | MaxRep@Ends: 12 | TmCUT: 60 |
| set6.txt | #Ol = 73 | Amp[23,27] | ENDS[17-12] | Tm[60.0089-63.2891] | Len[36-55] | MaxRep@Ends: 12 | TmCUT: 60 |
| set7.txt | #Ol = 73 | Amp[23,27] | ENDS[16-12] | Tm[60.0089-63.2891] | Len[36-55] | MaxRep@Ends: 12 | TmCUT: 60 |
| set8.txt | #Ol = 73 | Amp[23,27] | ENDS[15-12] | Tm[60.0089-63.2891] | Len[36-55] | MaxRep@Ends: 12 | TmCUT: 60 |
| set9.txt | #Ol = 73 | Amp[23,27] | ENDS[14-12] | Tm[60.0923-63.2891] | Len[36-55] | MaxRep@Ends: 12 | TmCUT: 60 |
| set10.txt | #Ol = 73 | Amp[23,27] | ENDS[13-12] | Tm[60.0089-63.2891] | Len[36-55] | MaxRep@Ends: 12 | TmCUT: 60 |
| set11.txt | #Ol = 73 | Amp[23,27] | ENDS[12-12] | Tm[60.0923-63.2891] | Len[36-55] | MaxRep@Ends: 12 | TmCUT: 60 |
| set12.txt | #Ol = 73 | Amp[23,27] | ENDS[11-12] | Tm[60.0923-63.2891] | Len[36-55] | MaxRep@Ends: 12 | TmCUT: 60 |
| set13.txt | #Ol = 73 | Amp[23,27] | ENDS[10-12] | Tm[60.0923-63.2891] | Len[36-55] | MaxRep@Ends: 12 | TmCUT: 60 |
| set14.txt | #Ol = 73 | Amp[23,27] | ENDS[9-12] | Tm[60.0923-63.2891] | Len[36-55] | MaxRep@Ends: 12 | TmCUT: 60 |
| set15.txt | #Ol = 73 | Amp[23,27] | ENDS[8-12] | Tm[60.0923-63.2891] | Len[36-55] | MaxRep@Ends: 12 | TmCUT: 60 |
| set16.txt | #Ol = 74 | Amp[23,27] | ENDS[1-15] | Tm[60.0108-63.2891] | Len[35-55] | MaxRep@Ends: 12 | TmCUT: 60 |
| set17.txt | #Ol = 74 | Amp[23,27] | ENDS[0-15] | Tm[60.0089-63.2891] | Len[36-55] | MaxRep@Ends: 12 | TmCUT: 60 |
| set18.txt | #Ol = 72 | Amp[23,27] | ENDS[24-15] | Tm[60.0572-63.1624] | Len[35-57] | MaxRep@Ends: 12 | TmCUT: 60.05 |
| set19.txt | #Ol = 72 | Amp[23,27] | ENDS[23-15] | Tm[60.0572-63.1624] | Len[35-57] | MaxRep@Ends: 12 | TmCUT: 60.05 |
| set20.txt | #Ol = 73 | Amp[23,27] | ENDS[22-12] | Tm[60.0771-63.2891] | Len[35-55] | MaxRep@Ends: 12 | TmCUT: 60.05 |
| set21.txt | #Ol = 73 | Amp[23,27] | ENDS[21-12] | Tm[60.0771-63.2891] | Len[35-55] | MaxRep@Ends: 12 | TmCUT: 60.05 |
| set22.txt | #Ol = 73 | Amp[23,27] | ENDS[20-12] | Tm[60.0771-63.2891] | Len[36-55] | MaxRep@Ends: 12 | TmCUT: 60.05 |
| set23.txt | #Ol = 73 | Amp[23,27] | ENDS[19-12] | Tm[60.0771-63.2891] | Len[36-55] | MaxRep@Ends: 12 | TmCUT: 60.05 |
| set24.txt | #Ol = 73 | Amp[23,27] | ENDS[18-12] | Tm[60.0923-63.2891] | Len[36-55] | MaxRep@Ends: 12 | TmCUT: 60.05 |
| set25.txt | #Ol = 73 | Amp[23,27] | ENDS[17-12] | Tm[60.0923-63.2891] | Len[36-55] | MaxRep@Ends: 12 | TmCUT: 60.05 |
| set26.txt | #Ol = 73 | Amp[23,27] | ENDS[16-12] | Tm[60.0923-63.2891] | Len[36-55] | MaxRep@Ends: 12 | TmCUT: 60.05 |
| set27.txt | #Ol = 73 | Amp[23,27] | ENDS[15-12] | Tm[60.0923-63.2891] | Len[36-55] | MaxRep@Ends: 12 | TmCUT: 60.05 |
| set28.txt | #Ol = 73 | Amp[23,27] | ENDS[14-12] | Tm[60.0923-63.2891] | Len[36-55] | MaxRep@Ends: 12 | TmCUT: 60.05 |
| set29.txt | #Ol = 73 | Amp[23,27] | ENDS[13-12] | Tm[60.0923-63.2891] | Len[36-55] | MaxRep@Ends: 12 | TmCUT: 60.05 |
| set30.txt | #Ol = 73 | Amp[23,27] | ENDS[12-12] | Tm[60.0923-63.2891] | Len[36-55] | MaxRep@Ends: 12 | TmCUT: 60.05 |
| set31.txt | #Ol = 73 | Amp[23,27] | ENDS[11-12] | Tm[60.0923-63.2891] | Len[36-55] | MaxRep@Ends: 12 | TmCUT: 60.05 |
| set32.txt | #Ol = 73 | Amp[23,27] | ENDS[10-12] | Tm[60.0923-63.2891] | Len[36-55] | MaxRep@Ends: 12 | TmCUT: 60.05 |
| set33.txt | #Ol = 73 | Amp[23,27] | ENDS[9-12] | Tm[60.0923-63.2891] | Len[36-55] | MaxRep@Ends: 12 | TmCUT: 60.05 |
| set34.txt | #Ol = 73 | Amp[23,27] | ENDS[8-12] | Tm[60.0923-63.2891] | Len[36-55] | MaxRep@Ends: 12 | TmCUT: 60.05 |
| set35.txt | #Ol = 74 | Amp[23,27] | ENDS[0-15] | Tm[60.0771-63.2891] | Len[36-55] | MaxRep@Ends: 12 | TmCUT: 60.05 |
| set36.txt | #Ol = 72 | Amp[23,27] | ENDS[24-9] | Tm[60.1225-63.3229] | Len[35-58] | MaxRep@Ends: 12 | TmCUT: 60.1 |
| set37.txt | #Ol = 72 | Amp[23,27] | ENDS[23-9] | Tm[60.1225-63.3229] | Len[35-58] | MaxRep@Ends: 12 | TmCUT: 60.1 |
| set38.txt | #Ol = 73 | Amp[23,27] | ENDS[22-18] | Tm[60.1894-63.3229] | Len[35-58] | MaxRep@Ends: 12 | TmCUT: 60.1 |
| set39.txt | #Ol = 73 | Amp[23,27] | ENDS[21-18] | Tm[60.1894-63.3229] | Len[35-58] | MaxRep@Ends: 12 | TmCUT: 60.1 |
| set40.txt | #Ol = 73 | Amp[23,27] | ENDS[20-18] | Tm[60.1894-63.3229] | Len[35-58] | MaxRep@Ends: 12 | TmCUT: 60.1 |
| set41.txt | #Ol = 73 | Amp[23,27] | ENDS[19-18] | Tm[60.1894-63.3229] | Len[35-58] | MaxRep@Ends: 12 | TmCUT: 60.1 |
| set42.txt | #Ol = 73 | Amp[23,27] | ENDS[18-18] | Tm[60.1143-63.3229] | Len[36-58] | MaxRep@Ends: 12 | TmCUT: 60.1 |
| set43.txt | #Ol = 73 | Amp[23,27] | ENDS[17-18] | Tm[60.1143-63.3229] | Len[36-58] | MaxRep@Ends: 12 | TmCUT: 60.1 |
| set44.txt | #Ol = 73 | Amp[23,27] | ENDS[16-18] | Tm[60.1143-63.3229] | Len[36-58] | MaxRep@Ends: 12 | TmCUT: 60.1 |
| set45.txt | #Ol = 73 | Amp[23,27] | ENDS[15-18] | Tm[60.1143-63.3229] | Len[36-58] | MaxRep@Ends: 12 | TmCUT: 60.1 |
| set46.txt | #Ol = 73 | Amp[23,27] | ENDS[14-18] | Tm[60.1143-63.3229] | Len[36-58] | MaxRep@Ends: 12 | TmCUT: 60.1 |
| set47.txt | #Ol = 73 | Amp[23,27] | ENDS[13-18] | Tm[60.1143-63.3229] | Len[36-58] | MaxRep@Ends: 12 | TmCUT: 60.1 |
| set48.txt | #Ol = 73 | Amp[23,27] | ENDS[12-18] | Tm[60.1894-63.3229] | Len[36-58] | MaxRep@Ends: 12 | TmCUT: 60.1 |
| set49.txt | #Ol = 73 | Amp[23,27] | ENDS[11-18] | Tm[60.1894-63.3229] | Len[36-58] | MaxRep@Ends: 12 | TmCUT: 60.1 |
| set50.txt | #Ol = 73 | Amp[23,27] | ENDS[10-18] | Tm[60.1894-63.3229] | Len[36-58] | MaxRep@Ends: 12 | TmCUT: 60.1 |
| set51.txt | #Ol = 73 | Amp[23,27] | ENDS[9-18] | Tm[60.1894-63.3229] | Len[36-58] | MaxRep@Ends: 12 | TmCUT: 60.1 |

-continued

| | | | | | | | |
|---|---|---|---|---|---|---|---|
| set52.txt | #Ol = 73 | Amp[23,27] | ENDS[8-18] | Tm[60.1894-63.3229] | Len[36-58] | MaxRep@Ends: 12 | TmCUT: 60.1 |
| set53.txt | #Ol = 72 | Amp[23,27] | ENDS[24-9] | Tm[60.2038-63.3229] | Len[35-58] | MaxRep@Ends: 12 | TmCUT: 60.15 |
| set54.txt | #Ol = 72 | Amp[23,27] | ENDS[23-9] | Tm[60.2038-63.3229] | Len[35-58] | MaxRep@Ends: 12 | TmCUT: 60.15 |
| set55.txt | #Ol = 73 | Amp[23,27] | ENDS[22-18] | Tm[60.1894-63.3229] | Len[35-58] | MaxRep@Ends: 12 | TmCUT: 60.15 |
| set56.txt | #Ol = 73 | Amp[23,27] | ENDS[21-18] | Tm[60.1894-63.3229] | Len[35-58] | MaxRep@Ends: 12 | TmCUT: 60.15 |
| set57.txt | #Ol = 73 | Amp[23,27] | ENDS[20-18] | Tm[60.1894-63.3229] | Len[35-58] | MaxRep@Ends: 12 | TmCUT: 60.15 |
| set58.txt | #Ol = 73 | Amp[23,27] | ENDS[19-18] | Tm[60.1894-63.3229] | Len[35-58] | MaxRep@Ends: 12 | TmCUT: 60.15 |
| set59.txt | #Ol = 73 | Amp[23,27] | ENDS[18-18] | Tm[60.1894-63.3229] | Len[35-58] | MaxRep@Ends: 12 | TmCUT: 60.15 |
| set60.txt | #Ol = 73 | Amp[23,27] | ENDS[17-18] | Tm[60.1894-63.3229] | Len[36-58] | MaxRep@Ends: 12 | TmCUT: 60.15 |
| set61.txt | #Ol = 73 | Amp[23,27] | ENDS[16-18] | Tm[60.1894-63.3229] | Len[36-58] | MaxRep@Ends: 12 | TmCUT: 60.15 |
| set62.txt | #Ol = 73 | Amp[23,27] | ENDS[15-18] | Tm[60.1894-63.3229] | Len[36-58] | MaxRep@Ends: 12 | TmCUT: 60.15 |
| set63.txt | #Ol = 73 | Amp[23,27] | ENDS[14-18] | Tm[60.1894-63.3229] | Len[36-58] | MaxRep@Ends: 12 | TmCUT: 60.15 |
| set64.txt | #Ol = 73 | Amp[23,27] | ENDS[13-18] | Tm[60.1894-63.3229] | Len[36-58] | MaxRep@Ends: 12 | TmCUT: 60.15 |
| set65.txt | #Ol = 73 | Amp[23,27] | ENDS[12-18] | Tm[60.1894-63.3229] | Len[36-58] | MaxRep@Ends: 12 | TmCUT: 60.15 |
| set66.txt | #Ol = 73 | Amp[23,27] | ENDS[11-18] | Tm[60.1894-63.3229] | Len[36-58] | MaxRep@Ends: 12 | TmCUT: 60.15 |
| set67.txt | #Ol = 73 | Amp[23,27] | ENDS[10-18] | Tm[60.1894-63.3229] | Len[36-58] | MaxRep@Ends: 12 | TmCUT: 60.15 |
| set68.txt | #Ol = 73 | Amp[23,27] | ENDS[9-18] | Tm[60.1894-63.3229] | Len[36-58] | MaxRep@Ends: 12 | TmCUT: 60.15 |
| set69.txt | #Ol = 73 | Amp[23,27] | ENDS[8-18] | Tm[60.1894-63.3229] | Len[36-58] | MaxRep@Ends: 12 | TmCUT: 60.15 |
| set70.txt | #Ol = 72 | Amp[23,27] | ENDS[24-9] | Tm[60.2038-63.3229] | Len[35-58] | MaxRep@Ends: 12 | TmCUT: 60.2 |
| set71.txt | #Ol = 72 | Amp[23,27] | ENDS[23-9] | Tm[60.2038-63.3229] | Len[35-58] | MaxRep@Ends: 12 | TmCUT: 60.2 |
| set72.txt | #Ol = 73 | Amp[23,27] | ENDS[22-18] | Tm[60.2038-63.2891] | Len[35-58] | MaxRep@Ends: 12 | TmCUT: 60.2 |
| set73.txt | #Ol = 73 | Amp[23,27] | ENDS[21-18] | Tm[60.2038-63.2891] | Len[35-58] | MaxRep@Ends: 12 | TmCUT: 60.2 |
| set74.txt | #Ol = 73 | Amp[23,27] | ENDS[20-18] | Tm[60.2038-63.2891] | Len[35-58] | MaxRep@Ends: 12 | TmCUT: 60.2 |
| set75.txt | #Ol = 73 | Amp[23,27] | ENDS[19-18] | Tm[60.2038-63.2891] | Len[35-58] | MaxRep@Ends: 12 | TmCUT: 60.2 |
| set76.txt | #Ol = 73 | Amp[23,27] | ENDS[18-18] | Tm[60.2038-63.2891] | Len[35-58] | MaxRep@Ends: 12 | TmCUT: 60.2 |
| set77.txt | #Ol = 73 | Amp[23,27] | ENDS[17-18] | Tm[60.2038-63.2891] | Len[35-58] | MaxRep@Ends: 12 | TmCUT: 60.2 |
| set78.txt | #Ol = 73 | Amp[23,27] | ENDS[16-18] | Tm[60.2038-63.2891] | Len[35-58] | MaxRep@Ends: 12 | TmCUT: 60.2 |
| set79.txt | #Ol = 73 | Amp[23,27] | ENDS[15-18] | Tm[60.2038-63.2891] | Len[35-58] | MaxRep@Ends: 12 | TmCUT: 60.2 |
| set80.txt | #Ol = 73 | Amp[23,27] | ENDS[14-18] | Tm[60.2038-63.2891] | Len[35-58] | MaxRep@Ends: 12 | TmCUT: 60.2 |
| set81.txt | #Ol = 73 | Amp[23,27] | ENDS[13-18] | Tm[60.2038-63.2891] | Len[35-58] | MaxRep@Ends: 12 | TmCUT: 60.2 |
| set82.txt | #Ol = 73 | Amp[23,27] | ENDS[12-18] | Tm[60.2038-63.2891] | Len[35-58] | MaxRep@Ends: 12 | TmCUT: 60.2 |
| set83.txt | #Ol = 73 | Amp[23,27] | ENDS[11-18] | Tm[60.2038-63.2891] | Len[35-58] | MaxRep@Ends: 12 | TmCUT: 60.2 |
| set84.txt | #Ol = 73 | Amp[23,27] | ENDS[10-18] | Tm[60.2038-63.2891] | Len[35-58] | MaxRep@Ends: 12 | TmCUT: 60.2 |
| set85.txt | #Ol = 73 | Amp[23,27] | ENDS[9-18] | Tm[60.2038-63.2891] | Len[35-58] | MaxRep@Ends: 12 | TmCUT: 60.2 |
| set86.txt | #Ol = 73 | Amp[23,27] | ENDS[8-18] | Tm[60.2038-63.2891] | Len[35-58] | MaxRep@Ends: 12 | TmCUT: 60.2 |
| set87.txt | #Ol = 71 | Amp[23,27] | ENDS[24-2] | Tm[60.2825-63.3229] | Len[37-58] | MaxRep@Ends: 12 | TmCUT: 60.25 |
| set88.txt | #Ol = 71 | Amp[23,27] | ENDS[23-2] | Tm[60.2825-63.3229] | Len[37-58] | MaxRep@Ends: 12 | TmCUT: 60.25 |
| set89.txt | #Ol = 72 | Amp[23,27] | ENDS[22-22] | Tm[60.3016-63.2891] | Len[35-58] | MaxRep@Ends: 12 | TmCUT: 60.25 |
| set90.txt | #Ol = 72 | Amp[23,27] | ENDS[21-22] | Tm[60.3016-63.2891] | Len[35-58] | MaxRep@Ends: 12 | TmCUT: 60.25 |
| set91.txt | #Ol = 72 | Amp[23,27] | ENDS[20-22] | Tm[60.2574-63.2891] | Len[35-58] | MaxRep@Ends: 12 | TmCUT: 60.25 |
| set92.txt | #Ol = 72 | Amp[23,27] | ENDS[19-22] | Tm[60.2574-63.2891] | Len[35-58] | MaxRep@Ends: 12 | TmCUT: 60.25 |
| set93.txt | #Ol = 72 | Amp[23,27] | ENDS[18-22] | Tm[60.2574-63.2891] | Len[35-58] | MaxRep@Ends: 12 | TmCUT: 60.25 |
| set94.txt | #Ol = 72 | Amp[23,27] | ENDS[17-22] | Tm[60.2574-63.2891] | Len[35-58] | MaxRep@Ends: 12 | TmCUT: 60.25 |
| set95.txt | #Ol = 72 | Amp[23,27] | ENDS[16-22] | Tm[60.3016-63.2891] | Len[37-58] | MaxRep@Ends: 12 | TmCUT: 60.25 |
| set96.txt | #Ol = 72 | Amp[23,27] | ENDS[15-22] | Tm[60.3016-63.2891] | Len[37-58] | MaxRep@Ends: 12 | TmCUT: 60.25 |
| set97.txt | #Ol = 72 | Amp[23,27] | ENDS[14-22] | Tm[60.3016-63.2891] | Len[37-58] | MaxRep@Ends: 12 | TmCUT: 60.25 |
| set98.txt | #Ol = 72 | Amp[23,27] | ENDS[13-22] | Tm[60.3016-63.2891] | Len[37-58] | MaxRep@Ends: 12 | TmCUT: 60.25 |
| set99.txt | #Ol = 72 | Amp[23,27] | ENDS[12-22] | Tm[60.3016-63.4716] | Len[37-58] | MaxRep@Ends: 12 | TmCUT: 60.25 |
| set100.txt | #Ol = 72 | Amp[23,27] | ENDS[11-22] | Tm[60.3016-63.4716] | Len[37-58] | MaxRep@Ends: 12 | TmCUT: 60.25 |
| set101.txt | #Ol = 72 | Amp[23,27] | ENDS[10-22] | Tm[60.3016-63.4716] | Len[37-58] | MaxRep@Ends: 12 | TmCUT: 60.25 |
| set102.txt | #Ol = 72 | Amp[23,27] | ENDS[9-22] | Tm[60.3016-63.4716] | Len[37-58] | MaxRep@Ends: 12 | TmCUT: 60.25 |
| set103.txt | #Ol = 72 | Amp[23,27] | ENDS[8-22] | Tm[60.3016-63.4716] | Len[37-58] | MaxRep@Ends: 12 | TmCUT: 60.25 |
| set104.txt | #Ol = 71 | Amp[23,27] | ENDS[24-2] | Tm[60.3055-63.1624] | Len[37-58] | MaxRep@Ends: 12 | TmCUT: 60.3 |
| set105.txt | #Ol = 71 | Amp[23,27] | ENDS[23-2] | Tm[60.3055-63.1624] | Len[37-58] | MaxRep@Ends: 12 | TmCUT: 60.3 |
| set106.txt | #Ol = 72 | Amp[23,27] | ENDS[22-22] | Tm[60.3016-63.2891] | Len[35-58] | MaxRep@Ends: 12 | TmCUT: 60.3 |
| set107.txt | #Ol = 72 | Amp[23,27] | ENDS[21-22] | Tm[60.3016-63.2891] | Len[35-58] | MaxRep@Ends: 12 | TmCUT: 60.3 |
| set108.txt | #Ol = 72 | Amp[23,27] | ENDS[20-22] | Tm[60.3016-63.2891] | Len[35-58] | MaxRep@Ends: 12 | TmCUT: 60.3 |
| set109.txt | #Ol = 72 | Amp[23,27] | ENDS[19-22] | Tm[60.3016-63.2891] | Len[35-58] | MaxRep@Ends: 12 | TmCUT: 60.3 |
| set110.txt | #Ol = 72 | Amp[23,27] | ENDS[18-22] | Tm[60.3016-63.2891] | Len[35-58] | MaxRep@Ends: 12 | TmCUT: 60.3 |
| set111.txt | #Ol = 72 | Amp[23,27] | ENDS[17-22] | Tm[60.3016-63.2891] | Len[35-58] | MaxRep@Ends: 12 | TmCUT: 60.3 |
| set112.txt | #Ol = 72 | Amp[23,27] | ENDS[16-22] | Tm[60.3016-63.2891] | Len[37-58] | MaxRep@Ends: 12 | TmCUT: 60.3 |
| set113.txt | #Ol = 72 | Amp[23,27] | ENDS[15-22] | Tm[60.3016-63.2891] | Len[37-58] | MaxRep@Ends: 12 | TmCUT: 60.3 |
| set114.txt | #Ol = 72 | Amp[23,27] | ENDS[14-22] | Tm[60.3016-63.2891] | Len[37-58] | MaxRep@Ends: 12 | TmCUT: 60.3 |
| set115.txt | #Ol = 72 | Amp[23,27] | ENDS[13-22] | Tm[60.3016-63.2891] | Len[37-58] | MaxRep@Ends: 12 | TmCUT: 60.3 |
| set116.txt | #Ol = 72 | Amp[23,27] | ENDS[12-22] | Tm[60.3016-63.4716] | Len[37-58] | MaxRep@Ends: 12 | TmCUT: 60.3 |
| set117.txt | #Ol = 72 | Amp[23,27] | ENDS[11-22] | Tm[60.3016-63.4716] | Len[37-58] | MaxRep@Ends: 12 | TmCUT: 60.3 |
| set118.txt | #Ol = 72 | Amp[23,27] | ENDS[10-22] | Tm[60.3016-63.4716] | Len[37-58] | MaxRep@Ends: 12 | TmCUT: 60.3 |
| set119.txt | #Ol = 72 | Amp[23,27] | ENDS[9-22] | Tm[60.3016-63.4716] | Len[37-58] | MaxRep@Ends: 12 | TmCUT: 60.3 |
| set120.txt | #Ol = 72 | Amp[23,27] | ENDS[8-22] | Tm[60.3016-63.4716] | Len[37-58] | MaxRep@Ends: 12 | TmCUT: 60.3 |

The oligonucleotide sets were then screened for an appropriate set using criteria similar to those shown in FIG. 31. Set 107 was selected as having an even number of oligonucleotides (72), a narrow range of calculated annealing temperatures (60.301 to 63.289) and an acceptable maximum repeat at the end of any oligonucleotide (12).

For each oligonucleotide in set 107, the computer program reported its name, with F indicating an oligonucleotide in the forward (5' to 3') direction and R indicating a reverse complement oligonucleotide that runs in the 3' to 5' direction on the polynucleotide. The program also reported the bases or complementary bases, in the case of reverse oligonucleotides, of the polynucleotide that are represented by the oligonucleotide. The oligonucleotide set was also designed with a pair of amplification oligonucleotides, AF1 and AR1, which are to amplify the final product following synthesis.

All oligonucleotides except for AF1 and AR1 were adjusted to a concentration of 10 μM and an equal volume of each were mixed together to provide an oligonucleotide pool with a total oligonucleotide concentration of 10 μM. This pool was diluted 10-fold by adding 5 μl into a mixture of 5 μl 10× Herculase buffer (from Stratagene), 2.5 μl dNTPs (6 mM each of dATP, dCTP, dGTP and dTTP: the final concentration in the mixture is 300 μM each), 2.5 μl MgSO$_4$ (40 mM: the final concentration in the mix is 2 mM), 35 μl water and 0.5 μl Herculase polymerase (a mixture of Taq and Pfu thermostable DNA polymerases from Stratagene). A polynucleotide was synthesized from the mixture of oligonucleotides using the polymerase chain reaction by subjecting the mixture to the temperature steps shown in FIG. 35, using an annealing temperature of 56° C.

After the synthesis step, the polynucleotide was amplified using a mix containing 1× Herculase reaction buffer (supplied by Stratagene), 300 μM each of dATP, dCTP, dGTP and dTTP, 2 mM MgSO$_4$, 0.5 μM oligonucleotide AF1, 0.5 μM oligonucleotide AR1, a 1/10 dilution (ie 5 μl in a 50 μl reaction) of the product of the synthesis reaction from the previous step and a 1/100 dilution of Herculase polymerase (a mixture of Taq and Pfu thermostable DNA polymerases from Stratagene). The product was amplified by subjecting the mixture to the following conditions: 96° C. for 2 minutes, then 20 cycles of (96° C. for 30 seconds, 56° C. for 30 seconds, 72° C. for 90 seconds). Finally an additional 1 μl of Taq DNA polymerase was added, and the mixture was heated to 72° C. for 10 minutes. This step added an A residue to the 3' end of each strand of the polynucleotide, thereby facilitating its cloning into a TA cloning vector.

The gene was cloned by mixing 1 μl from the amplification reaction, 1 μl of water, 0.5 μl of pDRIVE vector (from Qiagen) and 2.5 μl of 2× ligation mix. After a 2 hour ligation, 1 μl of ligation mix was transformed into chemically competent E. coli TOP10 cells and plated onto LB agar plates supplemented with ampicillin and grown for 24 hours at 37° C. Four transformed colonies were picked into 3 ml liquid LB medium and grown for 24 hours at 37° C. before plasmid was prepared from them. The sequences of the inserts cloned into the plasmids were determined by sequencing using an ABI 3730. One of the four plasmids contained an insert whose sequence was identical to the sequence designed.

6.5 Designing a Polynucleotide to Encode a Polypeptide

Many possible sequences encode any one polypeptide. It is thus often desirable to design more than one polynucleotide and then filter these sequences by discarding those that do not meet additional criteria.

In this example a polynucleotide was desired to encode the following polypeptide:

```
                                           (SEQ ID NO: 52)
APAVEQRSEAAPLIEARGEMVANKYIVKFKEGSALSALDAAMEKISGKPD

HVYKNVFSGFAATLDENMVRVLRAHPDVEYIEQDAVVTINAAQTNAPWGL

ARISSTSPGTSTYYYDESAGQGSCVYVIDTGIEASHPEFEGRAQMVKTYY

YSSRDGNGHGTHCAGTVGSRTYGVAKKTQLFGVKVLDDNGSGQYSTIIAG

MDFVASDKNNRNCPKGVVASLSLGGGYSSSVNSAAARLQSSGVMVAVAAG

NNNADARNYSPASEPSVCTVGASDRYDRRSSFSNYGSVLDIFGPGTSILS

TWIGGSTRSISGTSMATPHVAGLAAYLMTLGKTTAASACRYIADTANKGD

LSNIPFGTVNLLAYNNYQA
```

Polynucleotide sequences were designed using a computer program that selected codons based on their frequencies in an E. coli class II codon usage table shown in FIG. 22. Any codon with a frequency of less than 0.1, the threshold frequency, was rejected.

The first polynucleotide design was as follows:

```
                                           (SEQ ID NO: 54)
GCTCCGGCAGTTGAACAGCGTTCTGAAGCGGCGCCGCTGATCGAGGCGCG

TGGTGAGATGGTTGCTAACAAATACATTGTGAAATTCAAGGAGGGCTCTG

CTCTGTCTGCACTGGACGCCGCAATGGAAAAGATCAGCGGCAAGCCGGAC

CACGTGTACAAAAACGTGTTTTCCGGTTTCGCCGCTACTCTGGATGAAAA

TATGGTTCGTGTTCTGCGTGCGCACCCGGATGTAGAATATATCGAACAGG

ATGCAGTCGTAACCATCAATGCTGCTCAGACCAATGCGCCGTGGGGTCTG

GCACGTATTTCTTCTACCTCCCCGGGTACCAGCACCTATTATTACGACGA

AAGCGCCGGCCAGGGCTCTTGCGTTTACGTTATTGACACCGGCATCGAAG

CTTCTCATCCAGAATTCGAGGGTCGTGCGCAGATGGTGAAAACCTACTAC

TACTCCTCTCGCGATGGCAACGGTCATGGCACGCATTGCGCAGGCACGGT

AGGCTCCCGTACGTACGGTGTTGCAAAAAAAACCCAGCTGTTCGGCGTTA

AAGTGCTGGACGATAACGGTTCTGGTCAGTACTCCACCATCATCGCAGGT

ATGGACTTCGTAGCGTCCGACAAAAACAACCGTAACTGTCCGAAAGGCGT

CGTTGCGAGCCTGAGCCTGGGTGGTGGCTATTCTTCCTCCGTGAACTCTG

CGGCGGCCCGCCTGCAGAGCTCTGGTGTAATGGTTGCAGTAGCCGCAGGC

AACAACAACGCTGATGCACGTAACTACTCTCCGGCTTCCGAACCATCTGT

GTGTACCGTGGGTGCATCCGATCGTTACGACCGCCGTAGCTCTTTTTCTA

ACTACGGCTCCGTGCTGGACATTTTCGGCCCGGGTACTTCTATTCTGTCT

ACTTGGATCGGCGGTTCTACCCGCAGCATCAGCGGTACTTCTATGGCGAC

CCCGCACGTGGCAGGCCTGGCGGCTTATCTGATGACTCTGGGTAAAACCA

CCGCGGCGAGCGCGTGTCGTTACATCGCGGATACTGCTAACAAAGGTGAC

CTGTCTAACATCCCTTTCGGTACCGTCAACCTGCTGGCATACAACAACTA

CCAAGCG
```

The computer program also reported the following statistics for the polynucleotide:
Total bp=1107
GC=55.01%
A: 239 T: 259 G: 299 C: 310 Codon Usage Report:

| | | |
|---|---|---|
| A | GCG | 17 |
| A | GCA | 14 |
| A | GCT | 11 |
| A | GCC | 5 |
| R | AGG | 0 |
| R | AGA | 0 |
| R | CGG | 0 |
| R | CGA | 0 |
| R | CGT | 12 |
| R | CGC | 4 |
| N | AAT | 3 |
| N | AAC | 18 |
| D | GAT | 8 |
| D | GAC | 10 |
| C | TGT | 3 |
| C | TGC | 2 |
| Q | CAG | 8 |
| Q | CAA | 1 |
| E | GAG | 4 |
| E | GAA | 10 |
| G | GGG | 0 |
| G | GGA | 0 |
| G | GGT | 20 |
| G | GGC | 17 |
| H | CAT | 3 |
| H | CAC | 3 |
| I | ATA | 0 |
| I | ATT | 5 |
| I | ATC | 11 |
| L | TTG | 0 |
| L | TTA | 0 |
| L | CTG | 19 |
| L | CTA | 0 |
| L | CTT | 0 |
| L | CTC | 0 |
| K | AAG | 3 |
| K | AAA | 11 |
| M | ATG | 8 |
| F | TTT | 2 |
| F | TTC | 7 |
| P | CCG | 10 |
| P | CCA | 2 |
| P | CCT | 1 |
| P | CCC | 0 |
| S | TCT | 21 |
| S | TCC | 11 |
| S | TCA | 0 |
| S | TCG | 0 |
| S | AGT | 0 |
| S | AGC | 10 |
| T | ACG | 3 |
| T | ACA | 0 |
| T | ACT | 6 |
| T | ACC | 15 |
| W | TGG | 2 |
| Y | TAT | 5 |
| Y | TAC | 15 |
| V | GTG | 10 |
| V | GTA | 6 |
| V | GTT | 10 |
| V | GTC | 3 |
| * | TGA | 0 |
| * | TAG | 0 |
| * | TAA | 0 |

Repeats: None
Complementary Repeats (position1 position2 length sequence)

27, R38    12    AGCGGCGCCGCT    (SEQ ID NO: 55)

507, R518  12    CCGTACGTACGG    (SEQ ID NO: 56)

The first polynucleotide was rejected because it contained complementary repeats that could interfere with the assembly of oligonucleotides into a polynucleotide. A second polynucleotide was thus designed using the same probabilistic process. The second polynucleotide design was as follows:

```
                                            (SEQ ID NO: 57)
GCTCCAGCGGTTGAACAGCGCAGCGAGGCCGCACCGCTGATCGAAGCCCG

TGGTGAAATGGTGGCAAACAAATACATTGTCAAGTTCAAAGAAGGTTCCG

CGCTGAGCGCTCTGGATGCTGCAATGGAAAAAATCTCCGGTAAACCGGAC

CACGTATATAAAAATGTCTTTTCTGGCTTCGCGGCTACTCTGGATGAGAA

CATGGTTCGTGTGCTGCGTGCGCATCCGGATGTTGAATACATTGAACAGG

ACGCAGTTGTAACGATTAACGCTGCCCAAACTAACGCGCCATGGGCCTG

GCCCGCATTAGCTCCACCTCCCCAGGTACTTCCACTTATTACTACGACGA

ATCCGCAGGTCAGGGTTCCTGCGTATATGTTATCGACACCGGTATCGAAG

CGTCCCACCCGGAATTTGAGGGTCGTGCGCAAATGGTGAAGACCTACTAC

TACTCTTCCCGTGACGGTAACGGTCACGGTACCCACTGTGCGGGTACTGT

AGGTAGCCGTACCTATGGTGTTGCCAAAAAAACCCAGCTGTTTGGCGTTA

AAGTGCTGGATGATAATGGCTCCGGTCAGTACTCCACCATCATCGCTGGC

ATGGACTTTGTCGCAAGCGACAAAAACAACCGCAACTGCCCGAAAGGTGT

TGTGGCTTCTCTGTCCCTGGGTGGTGGCTATAGCTCCTCTGTGAACTCTG

CGGCAGCGCGTCTGCAATCCTCCGGCGTGATGGTCGCGGTTGCCGCAGGT

AACAACAACGCGGATGCGCGCAACTACTCTCCTGCATCCGAACCGTCCGT

TTGTACTGTTGGTGCGTCTGACCGTTACGACCGTCGTTCTTCTTTCTCCA

ACTACGGTTCTGTACTGGACATCTTCGGTCCTGGCACCTCCATCCTGTCT

ACGTGGATTGGCGGTAGCACCCGTAGCATCTCTGGTACTAGCATGGCTAC

CCCGCACGTAGCAGGCCTGGCGGCATATCTGATGACGCTGGGCAAGACTA

CCGCGGCTAGCGCTTGCCGTTACATCGCGGATACCGCGAACAAAGGCGAC

CTGTCTAACATCCCGTTCGGCACCGTGAACCTGCTGGCATACAACAACTA

TCAGGCG
```

The computer program also reported the following statistics for the second polynucleotide:
Total bp=1107
GC=55.01%
A: 241 T: 257 G: 294 C: 315
Codon Usage Report:

| | | |
|---|---|---|
| A | GCG | 19 |
| A | GCA | 12 |
| A | GCT | 10 |
| A | GCC | 6 |
| R | AGG | 0 |
| R | AGA | 0 |
| R | CGG | 0 |
| R | CGA | 0 |
| R | CGT | 12 |
| R | CGC | 4 |
| N | AAT | 2 |
| N | AAC | 19 |
| D | GAT | 7 |
| D | GAC | 11 |
| C | TGT | 2 |
| C | TGC | 3 |
| Q | CAG | 6 |

-continued

| | | |
|---|---|---|
| Q | CAA | 3 |
| E | GAG | 3 |
| E | GAA | 11 |
| G | GGG | 0 |
| G | GGA | 0 |
| G | GGT | 24 |
| G | GGC | 13 |
| H | CAT | 1 |
| H | CAC | 5 |
| I | ATA | 0 |
| I | ATT | 5 |
| I | ATC | 11 |
| L | TTG | 0 |
| L | TTA | 0 |
| L | CTG | 19 |
| L | CTA | 0 |
| L | CTT | 0 |
| L | CTC | 0 |
| K | AAG | 3 |
| K | AAA | 11 |
| M | ATG | 8 |
| F | TTT | 4 |
| F | TTC | 5 |
| P | CCG | 8 |
| P | CCA | 3 |
| P | CCT | 2 |
| P | CCC | 0 |
| S | TCT | 13 |
| S | TCC | 19 |
| S | TCA | 0 |
| S | TCG | 0 |
| S | AGT | 0 |
| S | AGC | 10 |
| T | ACG | 3 |
| T | ACA | 0 |
| T | ACT | 8 |
| T | ACC | 13 |
| W | TGG | 2 |
| Y | TAT | 7 |
| Y | TAC | 13 |
| V | GTG | 8 |
| V | GTA | 6 |
| V | GTT | 11 |
| V | GTC | 4 |
| * | TGA | 0 |
| * | TAG | 0 |
| * | TAA | 0 |

Repeats: None
Possible RNA stem loop structures:

459 (weak): CCGTGACggtaacgGTCACGG    (SEQ ID NO: 57)

607 (weak): TTTGTCGcaagCGACAAA     (SEQ ID NO: 58)

The second polynucleotide was rejected because it contained possible RNA stem-loop structures that could interfere with the expression of the polynucleotide. A third polynucleotide was thus designed using the same probabilistic process. The third polynucleotide design was as follows:

(SEQ ID NO: 59)
GCGCCGGCAGTAGAACAGCGTTCTGAAGCAGCACCGCTGATCGAAGCTCG

CGGCGAAATGGTAGCGAACAAATATATTGTAAAATTCAAAGAAGGCTCTG

CACTGTCTGCGCTGGATGCTGCGATGGAGAAAATCTCTGGTAAACCGGAT

CACGTATACAAGAACGTTTTTTCTGGCTTCGCTGCAACGCTGGATGAAAA

CATGGTGCGTGTACTGCGTGCGCACCCGGATGTGGAGTACATCGAACAGG

ACGCAGTTGTGACCATCAACGCGGCGCAGACTAACGCTCCGTGGGGCCTG

GCTCGCATCTCTTCCACCTCCCCGGGCACTTCCACCTACTACTATGATGA

GTCTGCTGGTCAGGGTAGCTGTGTTTACGTTATCGATACGGGCATCGAAG

CTTCCCACCCGGAATTCGAAGGCCGTGCGCAGATGGTGAAAACCTATTAC

TATTCTTCTCGTGATGGCAATGGCCACGGCACCCACTGCGCCGGCACCGT

TGGTTCTCGCACCTACGGTGTGGCAAAGAAAACCCAGCTGTTCGGTGTGA

AGGTTCTGGACGATAACGGTTCCGGCCAGTACTCCACTATCATCGCCGGC

ATGGACTTCGTTGCCTCCGACAAAAATAACCGTAATTGCCCGAAAGGTGT

TGTTGCTTCCCTGAGCCTGGGTGGCGGTTATTCCAGCTCTGTGAACTCTG

CAGCCGCTCGCCTGCAGTCCTCTGGCGTTATGGTAGCCGTCGCGGCTGGT

AACAACAACGCGGATGCACGCAATTACTCCCCGGCCTCCGAACCTTCTGT

CTGTACCGTTGGCGCTAGCGACCGTTATGATCGTCGCTCTAGCTTCTCTA

ACTATGGTTCCGTACTGGATATCTTCGGCCCGGGTACCTCTATTCTGTCC

ACTTGGATTGGCGGCTCTACCCGCTCTATCTCCGGTACCTCTATGGCCAC

GCCGCATGTCGCAGGCCTGGCAGCTTACCTGATGACTCTGGGTAAAACTA

CCGCGGCCTCCGCTTGCCGCTACATTGCCGACACTGCTAACAAAGGCGAC

CTGAGCAACATTCCATTCGGCACCGTTAACCTGCTGGCCTACAACAATTA

CCAGGCA

The computer program also reported the following statistics for the third polynucleotide:
Total bp=1107
GC=55.28%
A: 233 T: 262 G: 287 C: 325
Codon Usage Report:

| | | |
|---|---|---|
| A | GCG | 11 |
| A | GCA | 12 |
| A | GCT | 14 |
| A | GCC | 10 |
| R | AGG | 0 |
| R | AGA | 0 |
| R | CGG | 0 |
| R | CGA | 0 |
| R | CGT | 8 |
| R | CGC | 8 |
| N | AAT | 5 |
| N | AAC | 16 |
| D | GAT | 11 |
| D | GAC | 7 |
| C | TGT | 2 |
| C | TGC | 3 |
| Q | CAG | 9 |
| Q | CAA | 0 |
| E | GAG | 3 |
| E | GAA | 11 |
| G | GGG | 0 |
| G | GGA | 0 |
| G | GGT | 15 |
| G | GGC | 22 |
| H | CAT | 1 |
| H | CAC | 5 |
| I | ATA | 0 |
| I | ATT | 5 |
| I | ATC | 11 |
| L | TTG | 0 |
| L | TTA | 0 |
| L | CTG | 19 |
| L | CTA | 0 |
| L | CTT | 0 |
| L | CTC | 0 |
| K | AAG | 3 |
| K | AAA | 11 |

| | | |
|---|---|---|
| M | ATG | 8 |
| F | TTT | 1 |
| F | TTC | 8 |
| P | CCG | 11 |
| P | CCA | 1 |
| P | CCT | 1 |
| P | CCC | 0 |
| S | TCT | 20 |
| S | TCC | 16 |
| S | TCA | 0 |
| S | TCG | 0 |
| S | AGT | 0 |
| S | AGC | 6 |
| T | ACG | 3 |
| T | ACA | 0 |
| T | ACT | 7 |
| T | ACC | 14 |
| W | TGG | 2 |
| Y | TAT | 7 |
| Y | TAC | 13 |
| V | GTG | 7 |
| V | GTA | 7 |
| V | GTT | 12 |
| V | GTC | 3 |
| * | TGA | 0 |
| * | TAG | 0 |
| * | TAA | 0 |

Repeats: None
Complementary Repeats None
Possible RNA stem loop structures: None The third polynucleotide design had no repeat sequence elements and no possible RNA secondary structure elements, so it was selected for synthesis. Three constant Tm sets of oligonucleotides were designed one for each of the three possible polynucleotide designs, using a calculated annealing temperature of 64.5° C. The computer program reported the following statistics for the three sets of oligonucleotides:

set 1 Tm[64.5335-67.6137] Len[33-55] MaxRep@Ends: 11 set 2 Tm[64.5335-67.6137] Len[33-53] MaxRep@Ends: 11 set 3 Tm[64.5312-66.8185] Len[32-51] MaxRep@Ends: 11

Three criteria were then used to select the best design. The first criterion was whether there was less than a 3° C. difference between the maximum and minimum calculated annealing temperatures for correct annealing partners within the set of oligonucleotides corresponding to the design. Only design three fulfilled this criterion. The second criterion was whether the maximum oligonucleotide length less than 55 bp. Designs two and three fulfilled this criterion. The third criterion was whether there were repeats greater than 12 bp at the ends of any oligonucleotides. Designs one, two and three fulfilled this criterion. From this calculation, design one was selected.

All oligonucleotides except for AF1 and AR1 were adjusted to a concentration of 10 µM and an equal volume of each were mixed together to provide an oligonucleotide pool with a total oligonucleotide concentration of 10 µM. This pool was diluted 10-fold by adding 5 µl into a mixture of 5 µl 10× Herculase buffer (from Stratagene), 2.5 µl DMSO, 2.5 µl dNTPs (6 mM each of dATP, dCTP, dGTP and dTTP: the final concentration in the mixture is 300 µM each), 2.5 µl MgSO₄ (40 mM: the final concentration in the mix is 2 mM), 32 µl water and 0.5 µl Herculase polymerase (a mixture of Taq and Pfu thermostable DNA polymerases from Stratagene). A polynucleotide was synthesized from the mixture of oligo-nucleotides using the polymerase chain reaction by subjecting the mixture to the temperature steps shown in FIG. 35 using an annealing temperature of 58° C.

After the synthesis step, the polynucleotide was amplified using a mix containing 1× Herculase reaction buffer, supplied by Stratagene, 300 µM each of dATP, dCTP, dGTP and dTTP, 2 mM MgSO₄, 0.5 µM oligonucleotide AF1, 0.5 µM oligonucleotide AR1, a ⅒ dilution (i.e. 5 µl in a 50 µl reaction) of the product of the synthesis reaction from the previous step and a ¹⁄₁₀₀ dilution of Herculase polymerase (a mixture of Taq and Pfu thermostable DNA polymerases from Stratagene). The product was amplified by subjecting the mixture to the following conditions: 96° C. for two minutes, then 20 cycles of (96° C. for 30 seconds, 58° C. for 30 seconds, 72° C. for 90 seconds). The 1100 bp DNA product was then purified using a Qiagen PCR cleanup kit. The ends of the DNA were cleaved using NcoI and SalI restriction enzymes, the DNA was purified again using a Qiagen PCR cleanup kit and ligated into a vector that had been previously digested with NcoI and SalI. After a 4 hour ligation, 1 µl of ligation mix was transformed into chemically competent E coli TOP10 cells and plated onto LB agar plates supplemented with ampicillin and grown for 24 hours at 37° C. Four transformed colonies were picked into 3 ml liquid LB medium and grown for 24 hours at 37° C. before plasmid was prepared from them. The sequences of the inserts cloned into the plasmids were determined by sequencing using an ABI 3730. Two of the four plasmids contained an insert whose sequence was identical to the sequence designed.

6.6 Design and Synthesis of a Polynucleotide Encoding a Repetitive Polypeptide Sometimes it may be impossible to completely avoid repetitive polynucleotide sequences when encoding a polypeptide and meeting codon bias criteria that are important for the function of the polypeptide. In such cases it may be desirable to divide the polynucleotide into two or more parts, or even to synthesize different parts of the polynucleotide by different methods.

In this example a polynucleotide was desired to encode the following polypeptide:

(SEQ ID NO: 60)
MAQHDEAQQNAFYQVLNMPNLNADQRNGFIQSLKDDPSQSANVLGEAQKL

NDSQAPKADAqQNNFNKDQQSAFYEILNMPNLNEAQRNGFIQSLKDDPSQ

STNVLGEAKKLNESQAPKaDNNFNKEQQNAFYEILNMPNLNEEQRNGFIQ

SLKDDPSQSANLLSEAKKLNESQAPKaDNFNKEQQNAFYEILHLPNLNEE

QRNGFIQSLKDDPSQSANLLAEAKKLNDAQAPKaDNKFNKEQQNAFYEIL

HLPNLTEEQRNGFIQSLKDDPSVSKEILAEAKKLNDAQAPKEEDNNKPGK

EDNNKPGKEDNNKPGKEDNNKPGKEDNNKPGKEDNNKPGKEDGNKPGKED

NKKPGKEDGNKPGKEDNKKPGKEDGNKPGKEDGNKPGKEDGNGVHVVKPG

DTVNDIAKANGTTADKIAADNK

This polynucleotide is repetitive. Such repetitions can be best visualized using a dot-plot. A dot-plot of this polypeptide sequence is shown in FIG. 37. This dot-plot shows that the polypeptide consists of five repeats of approximately 58 amino acids, followed by a non-repeat stretch, fourteen repeats of eight amino acids and a second non-repeat stretch. Many polynucleotides were designed according to the process shown in FIG. 27. However, none of these polynucleotides were free of repeated sequence elements. The sequence was thus broken down into 3 segments; part 1 contained the first three 58 amino acid repeats, part 2 contained the fourth and fifth 58 amino acid repeats, the first non-repeat stretch and the first two 8 amino acid repeats, and part 3 contained the remaining twelve 8 amino acid repeats and the second non-repeat region.

Part 1.
(SEQ ID NO: 61)
MAQHDEAQQNAFYQVLNMPNLNADQRNGFIQSLKDDPSQSANVLGEAQKL

NDSQAPKADAqQNNFNKDQQSAFYEILNMPNLNEAQRNGFIQSLKDDPSQ

STNVLGEAKKLNESQAPKADNNFNKEQQNAFYEILNMPNLNEEQRNGFIQ

SLKDDPSQSANLLSEAKKLNESQAPK

Part 2.
(SEQ ID NO: 62)
ADNKFNKEQQNAFYEILHLPNLNEEQRNGFIQSLKDDPSQSANLLAEAKK

LNDAQAPKaDNKFNKEQQNAFYEILHLPNLTEEQRNGFIQSLKDDPSVSK

EILAEAKKLNDAQAPKEEDNNKPGKEDNNKPGKEDNN

Part 3.
(SEQ ID NO: 63)
KPGKEDNNKPGKEDNNKPGKEDNNKPGKEDGNKPGKEDNKKPGKEDGNKP

GKEDNKKPGKEDGNKPGKEDGNKPGKEDGNGVHVVKPGDTVNDIAKANGT

TADKIAADNK

Separate polynucleotides were then designed to encode each segment using a computer program to execute the scheme shown in FIG. 26 with adjustable parameters set as follows. Step 02, the codon bias table selected was for *E. coli* classII codons, as shown in FIG. 22. Step 03, a threshold frequency of 0.1 was selected. Step 07, N was set to 30, GC content limits were set between 30 and 70%. Step 08, M was set to 12, forbidden restriction sites were set to recognition sequences for BsaI, HindIII, KpnI, MluI, BamHI. Step 09, disallowed repeats were defined as a 14 base pair of sequence identical to a 14 base pair of sequence anywhere else in the polynucleotide. Step 11, X was set to 50. Step 12, Z was set to 7.

The resulting polynucleotides still contained repeated sequence elements, so the sequences were further modified using a computer program to execute the scheme shown in FIG. 28 with adjustable parameters set as follows. Step 02, the codon bias table selected was for *E coli* classII codons, as shown in FIG. 6. Step 03 a threshold frequency of 0.1 was selected. Step 04, the initial design was taken as the result of the sequence designed using the scheme of FIG. 26. Step 05, N was set to 30, GC content limits were set between 30 and 70%. Step 06, forbidden restriction sites were set to recognition sequences for BsaI, HindIII, KpnI, MluI, BamHI. Step 07, P was set to 16, Y was set to 50° C. Step 09, X was set to 1,000.

Following this sequence modification process, polynucleotides for parts 1 and 2 were obtained that lacked repeats, as shown in FIGS. 38 and 39. However no polynucleotide lacking repeats was obtained for part 3, as shown in FIG. 40, because of the extreme nature of the repeats, which were primarily composed of amino acids encoded by only two possible codons. Thus, while it was possible to synthesize polynucleotides for parts 1 and 2 using the polymerase chain reaction, such an assembly protocol was anticipated to be unsuccessful for part 3. An oligonucleotide set for the synthesis of part 3 was thus designed for a ligation-based assembly. To do this an iterative process was performed using the schemes shown in FIGS. 26, 28, 29, 30 and 42. First, a polynucleotide sequence was designed as for parts 1 and 2 using the processes shown in FIGS. 26 and 28 as described above. Second, a set of half-oligonucleotides was designed using the process shown in FIGS. 29 and 30 with adjustable parameters set as follows. Step 02, Z was set to 65° C. Third, the oligonucleotide boundaries were adjusted using the process shown in FIG. 42 with adjustable parameters set as follows. Step 03, N was set to 3. Step 06, A was set to 60° C. Step 07, C was set to 20, D was set to 65. This sequence of design process steps was repeated until a polynucleotide sequence that could be encoded by oligonucleotides fulfilling the design criteria of minimum Tm>60° C., maximum oligonucleotide length <65 bp, all oligonucleotides with unique trimers at their ends was obtained.

The sequences of the three polynucleotide sequences encoding the three parts of the polypeptide are shown below. The lower case sequence has been added to the 5' end of part 1 to add a KpnI and MluI site and to the 3' end of part 2 to add a BamHI and HindIII site for future manipulations of the sequence.

Part 1.
(SEQ ID NO: 64)
ggtacccggtaacgcgtATGGCGCAACATGACGAAGCTCAGCAGAACGC

TTTTTACCAGGTACTGAACATGCCGAACCTGAACGCGGATCAGCGCAACG

GTTTCATCCAGAGCCTGAAAGACGACCCTTCTCAGTCCGCAAACGTTCTG

GGCGAGGCTCAGAAACTGAACGACAGCCAGGCCCCAAAAGCAGATGCTCA

GCAAAATAACTTCAACAAGGACCAGCAGAGCGCATTCTACGAAATCCTGA

ACATGCCAAATCTGAACGAAGCTCAACGCAACGGCTTCATTCAGTCTCTG

AAAGACGATCCGTCCCAGTCCACTAACGTTCTGGGTGAAGCTAAGAAGCT

GAACGAATCCCAGGCACCAAAAGCAGACAACAACTTCAACAAAGAGCAGC

AGAACGCTTTCTATGAAATCTTGAACATGCCTAACCTGAATGAAGAACAG

CGTAACGGCTTCATCCAGTCTCTGAAGGACGACCCTAGCCAGTCTGCTAA

CCTGCTGTCCGAAGCAAAAAAACTGAACGAGTCCCAGGCTCCAAAAGC

Part 2.
(SEQ ID NO: 65)
GGATAACAAATTCAACAAGGAGCAGCAGAACGCATTCTACGAAATCCTGC

ACCTGCCGAACCTGAACGAAGAACAGCGTAACGGTTTCATCCAATCCCTG

AAAGACGATCCTTCCCAGTCCGCAAATCTGCTGGCAGAAGCAAAGAAACT

GAACGACGCACAGGCACCGAAGGCTGACAACAAGTTCAACAAAGAGCAGC

AGAATGCCTTCTACGAGATTCTGCATCTGCCAAACCTGACTGAGGAGCAG

CGCAACGGTTTCATTCAGTCCCTGAAGGACGACCCAAGCGTCAGCAAGGA

AATCCTGGCTGAGGCGAAAAAACTGAACGATGCACAGGCTCCGAAGGAAG

AAGACAACAATAAACCTGGTAAAGAAGATAATAATAAGCCTGGCAAGGAA

GATAACA.

Part 3
(SEQ ID NO: 66)
ACAAGCCGGGCAAGGAGGACAACAATAAACCGGGCAAAGAGGATAATAAC

AAGCCTGGTAAGGAAGACAACAACAAACCAGGCAAAGAAGATGGCAACAA

GCCGGGTAAGGAGGATAATAAAAAACCAGGCAAGGAAGACGGCAACAAAC

CTGGCAAGGAGGATAACAAAAAGCCAGGCAAGGAGGATGGTAATAAACCG

-continued
```
GGCAAAGAAGACGGCAACAAGCCTGGTAAAGAAGACGGTAACGGTGTACA

CGTCGTTAAACCTGGTGACACCGTGAACGACATCGCTAAGGCTAATGGCA

CCACGGCAGACAAGATTGCAGCGGACAATAAATTAGCTGATAAATAAgga tccgcggaagctt
```

These three segments were then designed to be independently cloned using recombinase-based cloning. To do this, restriction sites were added to the ends of the segments. A KpnI site (GGTACC) was added at the 5' end of the first segment. A HindIII site (AAGCTT) was added to the 3' end of the third segment. The joins between the first and second and second and third fragments were designed to use type IIs restriction endonucleases; these enzymes cut outside their recognition sites, and can therefore be used to join sequences without introducing any changes or restriction sites into the final sequence. Type IIs restriction sites can be added to a sequence to create a "sticky" overhang for ligation as shown in FIG. 41. In this example, a BsaI site was added to the 3' end of Part 1, the 5' and 3' ends of part 2 and the 5' end of part 3. The sites are underlined in the sequences shown below. The positioning of these sites, calculated using the scheme shown in FIG. 41, creates a 4 bp overhang GCGG at the 3' end of part 1 and the 5' end of part 2 and a 4 bp overhang CAAC at the 3' end of part 2 and at the 5' end of part 3. After addition of the Type IIs restriction site, an additional sequence was added to each end of each sequence to enable recombinase-based cloning into the vector pDONR221 (Invitrogen). The sequence GGGGACAAGTTTGTACAAAAAAGCAGGCT (SEQ ID NO: 67) was added to the 5' end of each segment, and the sequence ACCCAGCTTTCTTGTACAAAGTGGTCCCC (SEQ ID NO: 68) was added to the 3' end of each segment. These sequences are shown in italics on the sequences below.

```
Part 1.
                                           (SEQ ID NO: 69)
GGGGACAAGTTTGTACAAAAAAGCAGGCTGGTACCCCGGTAACGCGTATG

GCGCAACATGACGAAGCTCAGCAGAACGCTTTTTACCAGGTACTGAACAT

GCCGAACCTGAACGCGGATCAGCGCAACGGTTTCATCCAGAGCCTGAAAG

ACGACCCTTCTCAGTCCGCAAACGTTCTGGGCGAGGCTCAGAAACTGAAC

GACAGCCAGGCCCCAAAAGCAGATGCTCAGCAAAATAACTTCAACAAGGA

CCAGCAGAGCGCATTCTACGAAATCCTGAACATGCCAAATCTGAACGAAG

CTCAACGCAACGGCTTCATTCAGTCTCTGAAAGACGATCCGTCCCAGTCC

ACTAACGTTCTGGGTGAAGCTAAGAAGCTGAACGAATCCCAGGCACCAAA

AGCAGACAACAACTTCAACAAAGAGCAGCAGAACGCTTTCTATGAAATCT

TGAACATGCCTAACCTGAATGAAGAACAGCGTAACGGCTTCATCCAGTCT

CTGAAGGACGACCCTAGCCAGTCTGCTAACCTGCTGTCCGAAGCAAAAA

ACTGAACGAGTCCCAGGCTCCAAAAGCGGAGAGACCACCCAGCTTTCTTG

TACAAAGTGGTCCCC

Part 2.
                                           (SEQ ID NO: 70)
GGGGACAAGTTTGTACAAAAAAGCAGGCTGGTCTCAGCGGATAACAAATT

CAACAAGGAGCAGCAGAACGCATTCTACGAAATCCTGCACCTGCCGAACC

TGAACGAAGAACAGCGTAACGGTTTCATCCAATCCCTGAAAGACGATCCT
```

-continued
```
TCCCAGTCCGCAAATCTGCTGGCAGAAGCAAAGAAACTGAACGACGCACA

GGCACCGAAGGCTGACAACAAGTTCAACAAAGAGCAGCAGAATGCCTTCT

ACGAGATTCTGCATCTGCCAAACCTGACTGAGGAGCAGCGCAACGGTTTC

ATTCAGTCCCTGAAGGACGACCCAAGCGTCAGCAAGGAAATCCTGGCTGA

GGCGAAAAAACTGAACGATGCACAGGCTCCGAAGGAAGAAGACAACAATA

AACCTGGTAAAGAAGATAATAATAAGCCTGGCAAGGAAGATAACAACAGA

GACCACCCAGCTTTCTTGTACAAAGTGGTCCCC

Part 3.
                                           (SEQ ID NO: 71)
GGGGACAAGTTTGTACAAAAAAGCAGGCTGGTCTCACAACAAGCCGGGCA

AGGAGGACAACAATAAACCGGGCAAAGAGGATAATAACAAGCCTGGTAAG

GAAGACAACAACAAACCAGGCAAAGAAGATGGCAACAAGCCGGGTAAGGA

GGATAATAAAAAACCAGGCAAGGAAGACGGCAACAAACCTGGCAAGGAGG

ATAACAAAAAGCCAGGCAAGGAGGATGGTAATAAACCGGGCAAAGAAGAC

GGCAACAAGCCTGGTAAAGAAGACGGTAACGGTGTACACGTCGTTAAACC

TGGTGACACCGTGAACGACATCGCTAAGGCTAATGGCACCACGGCAGACA

AGATTGCAGCGGACAATAAATTAGCTGATAAATAAGGATCCGCGGAAGCT

TACCCAGCTTTCTTGTACAAAGTGGTCCCC
```

Constant Tm sets of oligonucleotides were then designed for the assembly of segments 1 and 2 using a computer program to execute the scheme shown in FIGS. 29-31. The adjustable parameters were set as follows. FIGS. 29 and 30. Step 02, Z was set to 62° C. FIG. 31. Step 02 Y was set to 50° C., R was set to 14 bases. Step 06, A was set to 4° C. Step 07, C was set to 30 bases, D was set to 65 bases. Step 10, B was set to 15° C. Several oligonucleotides were assembled for each part (30 for part 1 and 24 for part 2).

Two separate synthesis reactions were used to assemble part 1 polynucleotide and the part 2 polynucleotide. For each segment, all oligonucleotides except for AF1 and AR1 were adjusted to a concentration of 10 μM and an equal volume of each were mixed together to provide an oligonucleotide pool with a total oligonucleotide concentration of 10 μM. This pool was diluted 10-fold by adding 5 μl into a mixture of 5 μl 10× Herculase buffer (from Stratagene), 2.5 μl dimethyl sulphoxide (DMSO), 2.5 μl dNTPs (6 mM each of dATP, dCTP, dGTP and dTTP: the final concentration in the mixture is 300 μM each), 2.5 μl MgSO$_4$ (40 mM: the final concentration in the mix is 2 mM), 32 μl water and 0.5 μl Herculase polymerase (a mixture of Taq and Pfu thermostable DNA polymerases from Stratagene). A polynucleotide was synthesized from the mixture of oligonucleotides using the polymerase chain reaction by subjecting the mixture to the temperature steps shown in FIG. 32.

After the synthesis step, each polynucleotide segment was amplified using a mix containing 1× Herculase reaction buffer (supplied by Stratagene), 300 μM each of dATP, dCTP, dGTP and dTTP, 2 mM MgSO$_4$, 0.5 μM oligonucleotide AF1, 0.5 μM oligonucleotide AR1, a 1/10 dilution (ie 5 μl in a 50 μl reaction) of the product of the synthesis reaction from the previous step and a 1/100 dilution of Herculase polymerase (a mixture of Taq and Pfu thermostable DNA polymerases from Stratagene). The product was amplified by subjecting the mixture to the following conditions: 96° C. for two minutes, then 20 cycles of: 96° C. for 30 seconds, 56° C. for 30 seconds, and 72° C. for 30 seconds. The PCR product was then cloned into Invitrogen vector pDONR221 by mixing 2 µl of PCR product, 2 µl (300 ng) of pDONR221 vector DNA, 4 µl of 5× clonase reaction buffer, 8 µl TE (10 mM Tris-Cl pH 7.5, 1 mM EDTA) and incubating for 60 minutes at 25° C. The reaction was stopped by addition of 2 µl proteinase K solution (2 mg/ml) and incubation at 37° C. for ten minutes. Following this recombination, 1 µl of ligation mix was transformed into chemically competent *E coli* TOP10 cells and plated onto LB agar plates supplemented with ampicillin and grown for 24 hours at 37° C. Four transformed colonies were picked into 3 ml liquid LB medium and grown for 24 hours at 37° C. before plasmid was prepared from them. The sequences of the inserts cloned into the plasmids were determined by sequencing using an ABI 3730. Three of the four plasmids for Part 1 and two of the four plasmids for part 2 contained an insert whose sequence was identical to the sequence designed.

The set of oligonucleotides for assembly of part 3 were as follows:

```
>G00371C-F1 (with NO 5' phosphate) rescue
                                      (SEQ ID NO: 72)
GGGGACAAGTTTGTACAAAAAAGCAGGCTGGTCTCACAACAAG >G00371C-F2 (with NO 5' phosphate)
                                      (SEQ ID NO: 73)
GACAACAATAAACCGGGCAAAGAGGATAATAACAAGCCTGGTAAGGAAG >G00371C-F3 (with a 5' phosphate)
                                      (SEQ ID NO: 74)
ACAACAACAAACCAGGCAAAGAAGATGGCAACAAGCCGGGTAAGGAGGAT

AATAAAAA

>G00371C-F4 (with a 5' phosphate)
                                      (SEQ ID NO: 75)
ACCAGGCAAGGAAGACGGCAACAAACCTGGCAAGGAGGATAACAAAAAGC >G00371C-F5 (with a 5' phosphate)
                                      (SEQ ID NO: 76)
CAGGCAAGGAGGATGGTAATAAACCGGGCAAAGAAGACGGCAACAAGCCT

GGTA

>G00371C-F6 (with a 5' phosphate)
                                      (SEQ ID NO: 77)
AAGAAGACGGTAACGGTGTACACGTCGTTAAACCTGGTGACACCGTGAA >G00371C-F7 (with a 5' phosphate)
                                      (SEQ ID NO: 78)
CGACATCGCTAAGGCTAATGGCACCACGGCAGACAAGATTGCAGCGGACA

ATAAATTAGCTG

>G00371C-F8 (with a 5' phosphate)
                                      (SEQ ID NO: 79)
ATAAATAAGGATCCGCGGAAGCTTACCCAGCTTTCTTGTACAAAGTGGTC

CCC

>G00371C-R1 (with a 5' phosphate)
                                      (SEQ ID NO: 80)
TTTGCCCGGTTTATTGTTGTCCTCCTTGCCCGGCTTGTTGTGAGACCAGC

CTGCTTTTTTG

>G00371C-R2 (with a 5' phosphate)
                                      (SEQ ID NO: 81)
CTTCTTTGCCTGGTTTGTTGTTGTCTTCCTTACCAGGCTTGTTATTATCC

TC

>G00371C-R3 (with a 5' phosphate)
                                      (SEQ ID NO: 82)
GGTTTGTTGCCGTCTTCCTTGCCTGGTTTTTTATTATCCTCCTTACCCGG

CTTGTTGCCAT

>G00371C-R4 (with a 5' phosphate)
                                      (SEQ ID NO: 83)
TACCATCCTCCTTGCCTGGCTTTTTGTTATCCTCCTTGCCA >G00371C-R5 (with a 5' phosphate)
                                      (SEQ ID NO: 84)
GTACACCGTTACCGTCTTCTTTACCAGGCTTGTTGCCGTCTTCTTTGCCC

GGTTTAT

>G00371C-R6 (with a 5' phosphate)
                                      (SEQ ID NO: 85)
GTGGTGCCATTAGCCTTAGCGATGTCGTTCACGGTGTCACCAGGTTTAAC

GACGT

>G00371C-R7 (with NO 5' phosphate)
                                      (SEQ ID NO: 86)
TAAGCTTCCGCGGATCCTTATTTATCAGCTAATTTATTGTCCGCTGCAAT

CTTGTCTGCC

>G00371C-R8 (with NO 5' phosphate) rescue
                                      (SEQ ID NO: 87)
GGGGACCACTTTGTACAAGAAAGCTGGG
```

All oligonucleotides except for F1 and R8 were adjusted to a concentration of 10 µM and an equal volume of each were mixed together to provide an oligonucleotide pool with a total oligonucleotide concentration of 10 µM. A mixture of 12 µl oligo pool, 32 µl water, 5 µl 10× buffer and 1 µl of thermostable DNA ligase (either Pfu ligase or Ampligase) was prepared. A polynucleotide was synthesized from the mixture of oligonucleotides using the polymerase chain reaction by subjecting the mixture to the temperature steps shown in FIG. 43.

After the synthesis step, the polynucleotide segment was amplified using a mix containing 1× Herculase reaction buffer (supplied by Stratagene), 300 µM each of dATP, dCTP, dGTP and dTTP, 2 mM $MgSO_4$, 0.5 µM oligonucleotide AF1, 0.5 µM oligonucleotide AR1, a 1/10 dilution (ie 5 µl in a 50 µl reaction) of the product of the synthesis reaction from the previous step and a 1/100 dilution of Herculase polymerase (a mixture of Taq and Pfu thermostable DNA polymerases from Stratagene). The product was amplified by subjecting the mixture to the following conditions: 96° C. for 2 minutes, then 20 cycles of (96° C. for 30 seconds, 56° C. for 30 seconds, 72° C. for 30 seconds). The PCR product was then cloned into Invitrogen vector pDONR221 by mixing 2 µl of PCR product, 2 µl (300 ng) of pDONR221 vector DNA, 4 µl of 5× clonase reaction buffer, 8 µl TE (10 mM Tris-Cl pH 7.5, 1 mM EDTA) and incubating for 60 minutes at 25° C. The reaction was stopped by the addition of 2 µl proteinase K solution (2 mg/ml) and incubation at 37° C. for ten minutes. Following this recombination, 1 µl of ligation mix was transformed into chemically competent *E. coli* TOP10 cells and plated onto LB agar plates supplemented with ampicillin and grown for 24 hours at 37° C. Four transformed colonies were picked into 3 ml liquid LB medium and grown for 24 hours at 37° C. before plasmid was prepared from them. The sequences of the inserts cloned into the plasmids were determined by sequencing using an ABI 3730. One of the four plasmids for Part 3 contained an insert whose sequence was identical to the sequence designed.

The inserts for the three parts were excised from pDONR221. Part 1 was excised by digestion with KpnI and BsaI. Part 2 was excised by digestion with BsaI. Part 3 was excised by digestion with BsaI and HindIII. Each fragment was purified on an agarose gel and equimolar amounts were combined with a vector (pDRIVE) that had been digested with HindIII and KpnI. After a two hour ligation, 1 µl of ligation mix was transformed into chemically competent *E coli* TOP10 cells and plated onto LB agar plates supplemented with ampicillin and grown for 24 hours at 37° C. Four transformed colonies were picked into 3 ml liquid LB medium and grown for 24 hours at 37° C. before plasmid was prepared from them. The sequences of the inserts cloned into the plasmids were determined by sequencing using an ABI 3730. Four of the plasmids contained an insert whose sequence was identical to the sequence designed as shown below:

(SEQ ID NO: 88)
ccggtaacgcgtATGGCGCAACATGACGAAGCTCAGCAGAACGCTTTTTA
CCAGGTACTGAACATGCCGAACCTGAACGCGGATCAGCGCAACGGTTTCA
TCCAGAGCCTGAAAGACGACCCTTCTCAGTCCGCAAACGTTCTGGGCGAG
GCTCAGAAACTGAACGACAGCCAGGCCCCAAAAGCAGATGCTCAGCAAAA
TAACTTCAACAAGGACCAGCAGAGCGCATTCTACGAAATCCTGAACATGC
CAAATCTGAACGAAGCTCAACGCAACGGCTTCATTCAGTCTCTGAAAGAC
GATCCGTCCCAGTCCACTAACGTTCTGGGTGAAGCTAAGAAGCTGAACGA
ATCCCAGGCACCAAAAGCAGACAACAACTTCAACAAAGAGCAGCAGAACG
CTTTCTATGAAATCTTGAACATGCCTAACCTGAATGAAGAACAGCGTAAC
GGCTTCATCCAGTCTCTGAAGGACGACCCTAGCCAGTCTGCTAACCTGCT
GTCCGAAGCAAAAAAACTGAACGAGTCCCAGGCTCCAAAAGCGGATAACA
AATTCAACAAGGAGCAGCAGAACGCATTCTACGAAATCCTGCACCTGCCG
AACCTGAACGAAGAACAGCGTAACGGTTTCATCCAATCCCTGAAAGACGA
TCCTTCCCAGTCCGCAAATCTGCTGGCAGAAGCAAAGAAACTGAACGACG
CACAGGCACCGAAGGCTGACAACAAGTTCAACAAAGAGCAGCAGAATGCC
TTCTACGAGATTCTGCATCTGCCAAACCTGACTGAGGAGCAGCGCAACGG
TTTCATTCAGTCCCTGAAGGACGACCCAAGCGTCAGCAAGGAAATCCTGG CTGAGGCGAAAAAACTGAACGATGCACAGGCTCCGAAGGAAGAAGACAAC
AATAAACCTGGTAAAGAAGATAATAATAAGCCTGGCAAGGAAGATAACAA
CAAGCCGGGCAAGGAGGACAACAATAAACCGGGCAAAGAGGATAATAACA
AGCCTGGTAAGGAAGACAACAACAAACCAGGCAAAGAAGATGGCAACAAG
CCGGGTAAGGAGGATAATAAAAAACCAGGCAAGGAAGACGGCAACAAACC
TGGCAAGGAGGATAACAAAAAGCCAGGCAAGGAGGATGGTAATAAACCGG
GCAAAGAAGACGGCAACAAGCCTGGTAAACAAGACGGTAACGGTGTACAC
GTCGTTAAACCTGGTGACACCGTGAACGACATCGCTAAGGCTAATGGCAC
CACGGCAGACAAGATTGCAGCGGACAATAAATTAGCTGATAAAtaaggat
ccgcgg

6.7 Improving Polynucleotide Synthesis Fidelity Using T7 Endonuclease

In this example a polynucleotide was desired to encode the following polypeptide:

(SEQ ID NO: 89)
APAVEQRSEAAPLIEARGEMVANKYIVKFKEGSALSALDAAMEKISGKPD
HVYKNVFSGFAATLDENMVRVLRAHPDVEYIEQDAVVTINAAQTNAPWGL
ARISSTSPGTSTYYYDESAGQGSCVYVIDTGIEASHPEFEGRAQMVKTYY
YSSRDGNGHGTHCAGTVGSRTYGVAKKTQLFGVKVLDDNGSGQYSTIIAG
MDFVASDKNNRNCPKGVVASLSLGGGYSSSVNSAAARLQSSGVMVAVAAG
NNNADARNYSPASEPSVCTVGASDRYDRRSSFSNYGSVLDIFAPGTSILS
TWIGGSTRSISGTSMATPHVAGLAAYLMTLGKTTAASACRYIADTANKGD
LSNIPFGTVNLLAYNNYQA

The polynucleotide was designed as described in Example 6.2:

(SEQ ID NO: 90)
GCACCGGCCGTTGAACAGCGTTCTGAAGCAGCTCCTCTGATTGAGGCACGTGGTGAAATGGTAGCAAACAAG
TACATCGTGAAGTTCAAGGAGGGTTCTGCTCTGTCTGCTCTGGATGCTGCTATGGAAAAGATCTCTGGCAAG
CCTGATCACGTCTATAAGAACGTGTTCAGCGGTTTCGCAGCAACTCTGGACGAGAACATGGTCCGTGTACTG
CGTGCTCATCCAGACGTTGAATACATCGAACAGGACGCTGTGGTTACTATCAACGCGGCACAGACTAACGCA
CCTTGGGGTCTGGCACGTATTTCTTCTACTTCCCCGGGTACGTCTACTTACTACTACGACGAGTCTGCCGGT
CAAGGTTCTTGCGTTTACGTGATCGATACGGGCATCGAGGCTTCTCATCCTGAGTTTGAAGGCCGTGCACAA
ATGGTGAAGACCTACTACTACTCTTCCCGTGACGGTAATGGTCACGGTACTCATTGCGCAGGTACTGTTGGT
AGCCGTACCTACGGTGTTGCTAAGAAAACGCAACTGTTCGGCGTTAAAGTGCTGGACGACAACGGTTCTGGT
CAGTACTCCACCATTATCGCGGGTATGGATTTCGTAGCGAGCGATAAAAACAACCGCAACTGCCCGAAAGGT
GTTGTGGCTTCTCTGTCTCTGGGTGGTGGTTACTCCTCTTCTGTTAACAGCGCAGCTGCACGTCTGCAATCT
TCCGGTGTCATGGTCGCAGTAGCAGCTGGTAACAATAACGCTGATGCACGCAACTACTCTCCTGCTAGCGAG
CCTTCTGTTTGCACCGTGGGTGCATCTGATCGTTATGATCGTCGTAGCTCCTTCAGCAACTATGGTTCCGTC
CTGGATATCTTCGCGCCTGGTACTTCTATCCTGTCTACCTGGATTGGCGGTAGCACTCGTTCCATTTCCGGT
ACGAGCATGGCTACTCCACATGTTGCTGGTCTGGCAGCATACCTGATGACCCTGGGTAAGACCACTGCTGCA

-continued

```
TCCGCTTGTCGTTACATCGCGGATACTGCGAACAAAGGCGATCTGTCTAACATCCCGTTCGGCACCGTTAAT

CTGCTGGCATACAACAACTATCAGGCT
```

An oligonucleotide set was designed as described in Example 6.2:
Oligo Name Sequence (5' to 3')

| Oligo | Sequence | SEQ ID NO |
|---|---|---|
| E189-AF1 | TAACAGGAGGAATTAACCATGAAAAAACTG | (SEQ ID NO: 91) |
| E189-AR1 | TAATCTGTATCAGGCTGAAAATCTTCTCT | (SEQ ID NO: 92) |
| E189-F1 | TAACAGGAGGAATTAACCATGAAAAAACTGCTGTTC | (SEQ ID NO: 93) |
| E189-F5 | AAGTACATCGTGAAGTTCAAGGAGGGTTCTGCTCTGTCTGC | (SEQ ID NO: 94) |
| E189-F9 | CGTTGAATACATCGAACAGGACGCTGTGGTTACTATCAACGCG | (SEQ ID NO: 95) |
| E189-F13 | GGCATCGAGGCTTCTCATCCTGAGTTTGAAGGCCGTGC | (SEQ ID NO: 96) |
| E189-F17 | TTAAAGTGCTGGACGACAACGGTTCTGGTCAGTACTCCACC | (SEQ ID NO: 97) |
| E189-F21 | CGTCTGCAATCTTCCGGTGTCATGGTCGCAGTAGCAG | (SEQ ID NO: 98) |
| E189-F29 | CGTTACATCGCGGATACTGCGAACAAAGGCGATCTGTCTAACA | (SEQ ID NO: 99) |
| E189-R1 | CCACCAGCGGAATCGCGAACAGCAGTTTTTTCATGGTTAATT | (SEQ ID NO: 100) |
| E189-R5 | TTTTCCATAGCAGCATCCAGAGCAGACAGAGCAGAACCC | (SEQ ID NO: 101) |
| E189-R9 | AGGTGCGTTAGTCTGTGCCGCGTTGATAGTAACCACAGC | (SEQ ID NO: 102) |
| E189-R13 | GTAGTAGTAGGTCTTCACCATTTGTGCACGGCCTTCAAACTCAG | (SEQ ID NO: 103) |
| E189-R17 | CGAAATCCATACCCGCGATAATGGTGGAGTACTGACCAGAAC | (SEQ ID NO: 104) |
| E189-R21 | GCATCAGCGTTATTGTTACCAGCTGCTACTGCGACCATGAC | (SEQ ID NO: 105) |
| E189-R25 | ACGAGTGCTACCGCCAATCCAGGTAGACAGGATAGAAGTACC | (SEQ ID NO: 106) |
| E189-R29 | CGGTGCCGAACGGGATGTTAGACAGATCGCCTTTGTTC | (SEQ ID NO: 107) |
| E189-F2 | GCGATTCCGCTGGTGGTGCCGTTCTATAGCCATAGC | (SEQ ID NO: 108) |
| E189-F6 | TCTGGATGCTGCTATGGAAAAGATCTCTGGCAAGCCTGATC | (SEQ ID NO: 109) |
| E189-F10 | GCACAGACTAACGCACCTTGGGGTCTGGCACGTAT | (SEQ ID NO: 110) |
| E189-F14 | ACAAATGGTGAAGACCTACTACTACTCTTCCCGTGACGGTAATGG | (SEQ ID NO: 111) |
| E189-F18 | ATTATCGCGGGTATGGATTTCGTAGCGAGCGATAAAAACAACCG | (SEQ ID NO: 112) |
| E189-F22 | CTGGTAACAATAACGCTGATGCACGCAACTACTCTCCTGCT | (SEQ ID NO: 113) |
| E189-F26 | ATTGGCGGTAGCACTCGTTCCATTTCCGGTACGAGCA | (SEQ ID NO: 114) |
| E189-F30 | TCCCGTTCGGCACCGTTAATCTGCTGGCATACAACAAC | (SEQ ID NO: 115) |
| E189-R2 | GGCCGGTGCCATGGTGCTATGGCTATAGAACGGCA | (SEQ ID NO: 116) |
| E189-R6 | GCTGAACACGTTCTTATAGACGTGATCAGGCTTGCCAGAGATC | (SEQ ID NO: 117) |
| E189-R10 | ACCCGGGGAAGTAGAAGAAATACGTGCCAGACCCCA | (SEQ ID NO: 118) |
| E189-R14 | GCGCAATGAGTACCGTGACCATTACCGTCACGGGAAGA | (SEQ ID NO: 119) |
| E189-R18 | ACACCTTTCGGGCAGTTGCGGTTGTTTTATCGCTCGCTA | (SEQ ID NO: 120) |
| E189-R22 | GCAAACAGAAGGCTCGCTAGCAGGAGAGTAGTTGCGT | (SEQ ID NO: 121) |
| E189-R26 | GCAACATGTGGAGTAGCCATGCTCGTACCGGAAATGGA | (SEQ ID NO: 122) |
| E189-R30 | TGATGGTCGACAGCCTGATAGTTGTTGTATGCCAGCAGATTAA | (SEQ ID NO: 123) |
| E189-F3 | ACCATGGCACCGGCCGTTGAACAGCGTTCTGAAGC | (SEQ ID NO: 124) |
| E189-F7 | ACGTCTATAAGAACGTGTTCAGCGGTTTCGCAGCAACTCTGG | (SEQ ID NO: 125) |
| E189-F11 | TTCTTCTACTTCCCCGGGTACGTCTACTTACTACTACGACGA | (SEQ ID NO: 126) |
| E189-F15 | TCACGGTACTCATTGCGCAGGTACTGTTGGTAGCCGT | (SEQ ID NO: 127) |
| E189-F19 | CAACTGCCCGAAAGGTGTTGTGGCTTCTCTGTCTCTGG | (SEQ ID NO: 128) |

-continued

```
E189-F23  AGCGAGCCTTCTGTTTGCACCGTGGGTGCATCTGA              (SEQ ID NO: 129)

E189-F27  TGGCTACTCCACATGTTGCTGGTCTGGCAGCATACCT            (SEQ ID NO: 130)

E189-F31  TATCAGGCTGTCGACCATCATCATCATCATTGAGTTTAAACGG      (SEQ ID NO: 131)

E189-R3   TGCCTCAATCAGAGGAGCTGCTTCAGAACGCTGTTCAAC          (SEQ ID NO: 132)

E189-R7   ACACGGACCATGTTCTCGTCCAGAGTTGCTGCGAAACC           (SEQ ID NO: 133)

E189-R11  GAACCTTGACCGGCAGACTCGTCGTAGTAGTAAGTAGACGT        (SEQ ID NO: 134)

E189-R15  TTTCTTAGCAACACCGTAGGTACGGCTACCAACAGTACCT         (SEQ ID NO: 135)

E189-R19  CAGAAGAGGAGTAACCACCACCCAGAGACAGAGAAGCCACA        (SEQ ID NO: 136)

E189-R23  GAGCTAGGACGATCATAACGATCAGATGCACCCACGGT           (SEQ ID NO: 137)

E189-R27  TGGTCTTACCCAGGGTCATCAGCTATGCTGCCAGACCA           (SEQ ID NO: 138)

E189-R31  AAAACAGCCAAGCTGGAGACCGTTTAAACTCAATGATGATGATGA    (SEQ ID NO: 139)

E189-F4   AGCTCCTCTGATTGAGGCACGTGGTGAAATGGTAGCAAAC         (SEQ ID NO: 140)

E189-F8   ACGAGAACATGGTCCGTGTACTGCGTGCTCATCCAGA            (SEQ ID NO: 141)

E189-F12  GTCTGCCGGTCAAGGTTCTTGCGTTTACGTGATCGATACG         (SEQ ID NO: 142)

E189-F16  ACCTACGGTGTTGCTAAGAAAACGCAACTGTTCGGCG            (SEQ ID NO: 143)

E189-F20  GTGGTGGTTACTCCTCTTCTGTTAACAGCGCAGCTGCA           (SEQ ID NO: 144)

E189-F24  TCGTTATGATCGTCGTAGCTCCTTCAGCAACTATGGTTCCGT       (SEQ ID NO: 145)

E189-F28  GATGACCCTGGGTAAGACCACTGCTGCATCCGCTTGT            (SEQ ID NO: 146)

E189-F32  TCTCCAGCTTGGCTGTTTTGGCGGATGAGAGAAGATTTTCA        (SEQ ID NO: 147)

E189-F25  CCTGGATATCTTCGCGCCTGGTACTTCTATCCTGTCTACCTGG      (SEQ ID NO: 148)

E189-R4   TCCTTGAACTTCACGATGTACTTGTTTGCTACCATTTCACCACG     (SEQ ID NO: 149)

E189-R8   GTCCTGTTCGATGTATTCAACGTCTGGATGAGCACGCAGT         (SEQ ID NO: 150)

E189-R12  GATGAGAAGCCTCGATGCCCGTATCGATCACGTAAACGCAA        (SEQ ID NO: 151)

E189-R16  CGTTGTCGTCCAGCACTTTAACGCCGAACAGTTGCGT            (SEQ ID NO: 152)

E189-R20  ACCGGAAGATTGCAGACGTGCAGCTGCGCTGTTAA              (SEQ ID NO: 153)

E189-R28  GCAGTATCCGCGATGTAACGACAAGCGGATGCAGCAG            (SEQ ID NO: 154)

E189-R32  TAATCTGTATCAGGCTGAAAATCTTCTCTCATCCGCC            (SEQ ID NO: 155)

E189-R24  AGGCGCGAAGATATCCAGGACGGAACCATAGTTGCTGAAG         (SEQ ID NO: 156)
```

All oligonucleotides except for AF1 and AR1 were adjusted to a concentration of 10 μM and an equal volume of each were mixed together to provide an oligonucleotide pool with a total oligonucleotide concentration of 10 μM. This pool was diluted 10-fold by adding 5 μl into a mixture of 5 μl 10× Herculase buffer (from Stratagene), 2.5 μl DMSO, 2.5 μl dNTPs (6 mM each of dATP, dCTP, dGTP and dTTP: the final concentration in the mixture is 300 μM each), 2.5 μl MgSO$_4$ (40 mM: the final concentration in the mix is 2 mM), 32 μl water and 0.5 μl Herculase polymerase (a mixture of Taq and Pfu thermostable DNA polymerases from Stratagene). A polynucleotide was synthesized from the mixture of oligonucleotides using the polymerase chain reaction by subjecting the mixture to the temperature steps shown in FIG. 34 using an annealing temperature of 58° C.

After the synthesis step, the polynucleotide was amplified using a mix containing 1× Herculase reaction buffer (supplied by Stratagene), 300 μM each of dATP, dCTP, dGTP and dTTP, 2 mM MgSO$_4$, 0.5 μM oligonucleotide AF1, 0.5 μM oligonucleotide AR1, a 1/10 dilution (ie 5 μl in a 50 μl reaction) of the product of the synthesis reaction from the previous step and a 1/100 dilution of Herculase polymerase (a mixture of Taq and Pfu thermostable DNA polymerases from Stratagene). The product was amplified by subjecting the mixture to the following conditions: 96° C. for two minutes, then 20 cycles of (96° C. for 30 seconds, 58° C. for 30 seconds, 72° C. for 90 seconds). The 1100 bp DNA product was then purified using a Qiagen PCR cleanup kit.

After purification, 2.5 μl of DNA was placed into a 100 μl reaction in 50 mM potassium acetate, 20 mM Tris-acetate, 10 mM magnesium acetate, 1 mM dithiothreitol pH 7.9. This mixture was heated to 94° C. for three minutes, and then cooled to 75° C. for five minutes. The tube was then cooled to 37° C., 3 μl of T7 endonuclease I (10 U/μl) was added, and the tube incubated at 37° C. for 1 hour and 55° C. for 1 hour. A control sample was treated in the same way, but the endonuclease was omitted. Following endonuclease digestion, the DNA was ethanol precipitated and resuspended before the ends of the DNA were cleaved using NcoI and SalI restriction enzymes. The DNA was purified again using a Qiagen PCR cleanup kit and ligated into a vector that had been previously digested with NcoI and SalI. After a 4-hour ligation, 1 μl of ligation mix was transformed into chemically competent *E. coli* TOP10 cells and plated onto LB agar plates supplemented with ampicillin and grown for 24 hours at 37° C. A total of 48 colonies from the treated and untreated samples were subsequently analyzed for protease function. Twenty-four out of forty eight colonies from the treated sample were incorrect (50%), compared with thirty three of the forty eight colonies from the untreated sample (69%).

6.8 Improving Synthetic Polynucleotide Cloning Fidelity Using Recombinase

In this example it was desired to synthesize the following polynucleotide:

(SEQ ID NO: 157)
CGGGGACAAGTTTGTACAAAAAAGCAGGCTGCTCTTCGCCTGCTGGCTGG

TAATCGCCAGCAGGCCTTTTTATTTGGGGGAGAGGGAAGTCATGAAAAAA

CTAACCTTTGAAATTCGATCTCCACCACATCAGCTCTGAAGCAACGTAAA

AAAACCCGCCCCGGCGGGTTTTTTTATACCCGTAGTATCCCCACTTATCT

ACAATAGCTGTCCTTAATTAAGGTTGAATAAATAAAAACAGCCGTTGCCA

GAAAGAGGCACGGCTGTTTTTATTTTCTAGTGAGACCGGGACCAGTTTAT

TAAGCGCCAGTGCTATGACGACCTTCTGCGCGCTCGTACTGTTCGACAAT

GGTGTAATCTTCGTTGTGAGAAGTGATGTCCAGCTTGATGTCAGTTTTGT

AAGCGCCCGGCAGTTGCACAGGTTTTTTGCCATGTACGTAGTTTTTACC

TCTGCGTCGTAGTGACCACCGTCCTTCAGCTTCAGGCGCATTTTAATTTC

GCCCTTCAGGGCACCATCTTCCGGGTACATACGCTCAGTGGACGCTTCCC

AACCCATCGTCTTTTTCTGCATTACAGGACCGTCAGACGGGAAGTTAGTA

CCGCGCAGCTTCACTTTGTAGATGAACTCGCCGTCTTGCAGGCTAGAGTC

TTGGGTCACAGTCACCACACCACCGTCCTCGAAGTTCATAACACGTTCCC

ATTTGAAACCTTCCGGGAAAGACAGTTTCAGGTAATCCGGAATATCCGCC

GGGTGTTTAACGTACGCCTTAGAGCCATACTGGAACTGAGGGCTCAGAAT

ATCCCATGCAAAAGGCAGTGGGCCACCTTTGGTCACTTTCAGTTTCGCGG

TCTGAGTACCCTCGTAAGGACGGCCTTCACCTTCACCCTCGATTTCAAAT

TCGTGGCCATTTACAGAGCCCTCCATACGCACTTTGAAGCGCATGAACTC

CTTGATTACATCTTCAGAGGAGGCCATTTTTTTTCCTCCTTATTTTCTC

AAGCCTAGGTCTGTGTGAAATTGTTATCCGCTCACAATTGAATCTATCAT

AATTGTGAGCGCTCACAATTGTAAAGGTTAGATCCGCTAATCTTATGGAT

AAAAATGCTATGTTCCCCCCCGGGGGATATCAACAGGAGTCCAAGCGACC

GGTGGTTGCATGTCTAGCTAGCTAGAACAGGACTAGTCCTGAGTAATAGT

CAAAAGCCTCCGGTCGGAGGCTTTTGACTTTCTGAAATGTAATCACACTG

GCTCACCTTCGGGTGGGCCTTTCTGCGTTTATAAGAAGGAAAAAAGCGGC

CGCAAAAGGAAAAAATTATTCGTATAGCATACATTATACGAAGTTATAAG

CTTACCCAGCTTTCTTGTACAAAGTGGTCCCC

A total of 64 oligonucleotides were designed and synthesized. No polynucleotide product was obtained when all oligonucleotides except for AF1 and AR1 were assembled in a single reaction. Instead the polynucleotide was divided into four segments, each consisting of sixteen oligonucleotides: segment 1 from 1-370, segment 2 from 347-691, segment 3 from 671-1028, segment 4 from 1004-1367. Each oligonucleotide was adjusted to a concentration of 10 μM and an equal volume of each was mixed together to provide four oligonucleotide pools, each with a total oligonucleotide concentration of 10 μM. The pools were oligonucleotides F1 to R8 (segment 1), F9 to R16 (segment 2), F17 to R24 (segment 3) and F25 to R32 (segment 4). The pools were diluted tenfold by adding 5 μl into a mixture of 5 μl 10× Herculase buffer (from Stratagene), 2.5 μl DMSO, 2.5 μl dNTPs (6 mM each of dATP, dCTP, dGTP and dTTP: the final concentration in the mixture is 300 μM each), 2.5 μl MgSO$_4$ (40 mM: the final concentration in the mix is 2 mM), 32 μl water and 0.5 μl Herculase polymerase (a mixture of Taq and Pfu thermostable DNA polymerases from Stratagene). Polynucleotides were synthesized from the mixture of oligonucleotides using the polymerase chain reaction by subjecting the mixture to the temperature steps shown in FIG. 32 using an annealing temperature of 58° C.

After the synthesis step, the polynucleotide fragments were joined by overlap extension: 2 μl of each assembly reaction were mixed into an amplification reaction containing 1× Herculase reaction buffer (supplied by Stratagene), 300 μM each of dATP, dCTP, dGTP and dTTP, 2 mM MgSO$_4$, 0.5 μM oligonucleotide AF1, 0.5 μM oligonucleotide AR1 and a 1/100 dilution of Herculase polymerase (a mixture of Taq and Pfu thermostable DNA polymerases from Stratagene). The product was amplified by subjecting the mixture to the following conditions: 96° C. for two minutes, then 20 cycles of (96° C. for thirty seconds, 58° C. for thirty seconds, and 72° C. for ninety seconds). Agarose gel analysis of the PCR product showed a ladder of sub-fragments and partially joined fragments.

The PCR product was cloned without purification into Invitrogen vector pDONR221 by mixing 2 μl of PCR product, 2 μl (300 ng) of pDONR221 vector DNA, four μl of 5× clonase reaction buffer, 8 μl TE (10 mM Tris-Cl pH 7.5, 1 mM EDTA) and incubating for sixty minutes at 25° C. The reaction was stopped by the addition of 2 μl proteinase K solution (2 mg/ml) and incubation at 37° C. for ten minutes. Following this recombination, 1 μl of ligation mix was transformed into chemically competent *E coli* TOP10 cells and plated onto LB agar plates supplemented with ampicillin and grown for twenty-four hours at 37° C. Eight transformed colonies were picked into 3 ml liquid LB medium and grown for 24 hours at 37° C. before plasmid was prepared from them. Eight out of eight of the inserts cloned into the plasmids were determined by restriction digestion to be the correct size. This efficiency in cloning full-length product resulted from the requirement of recombinase-based cloning for a specific sequence at each end. Thus only DNA fragments with the recombinase sites provided in primers AF1 and AR1 can be cloned. This is in contrast to TA or restriction cloning where smaller fragments containing the appropriate ends for cloning will be present in the mixture. Such small fragments tend to dominate cloning products, and can be reduced or eliminated only by gel purification. The recombinase cloning step can thus eliminate the requirement for gel purification, thereby increasing the efficiency and fidelity of polynucleotide synthesis.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

What is claimed is:

1. A method of designing a polynucleotide, the method comprising:
   a) selecting an initial polynucleotide sequence that codes for a polypeptide, wherein a codon frequency in said initial polynucleotide sequence is determined by a codon bias table; and
   b) modifying an initial codon choice in said initial polynucleotide sequence in accordance with a design criterion, thereby constructing a final polynucleotide sequence that codes for said polypeptide; wherein the design criterion comprises:
   minimized sequence identity to a reference polynucleotide, and wherein
   modifying said initial codon choice in said initial polynucleotide sequence in accordance with said design criterion comprises altering a plurality of codons in said initial polynucleotide sequence to minimize sequence identity to said reference polynucleotide; and
   synthesizing said final polynucleotide sequence.

2. The method of claim 1, wherein the design criterion further comprises one or more of:
   (i) exclusion of a restriction site sequence in said initial polynucleotide sequence;
   (ii) incorporation of a restriction site sequence in said initial polynucleotide sequence;
   (iii) a designation of a target G+C content in the initial polynucleotide sequence;
   (iv) an allowable length of a sub-sequence that can be exactly repeated within either a 5'-3' or a 3'-5' strand of the initial polynucleotide sequence;
   (v) an allowable annealing temperature of any sub-sequence to any other sub-sequence within either the 5'-3' or the 3'-5' strand of the initial polynucleotide sequence;
   (vi) exclusion of a hairpin turn in the initial polynucleotide sequence;
   (vii) exclusion of a repeat element in the initial polynucleotide sequence;
   (viii) exclusion of a ribosome binding site in the initial polynucleotide sequence;
   (ix) exclusion of a polyadenylation signal in the initial polynucleotide sequence;
   (x) exclusion of a splice site in the initial polynucleotide sequence;
   (xi) exclusion of an open reading frame in each possible 5' reading frame in the initial polynucleotide sequence;
   (xii) exclusion of a polynucleotide sequence that facilitates RNA degradation in the initial polynucleotide sequence;
   (xiii) exclusion of an RNA polymerase termination signal in the initial polynucleotide sequence;
   (xiv) exclusion of a transcriptional promoter in the initial polynucleotide sequence;
   (xv) exclusion of an immunostimulatory sequence in the initial polynucleotide sequence;
   (xvi) incorporation of an immunostimulatory sequence in the initial polynucleotide sequence;
   (xvii) exclusion of an RNA methylation signal in the initial polynucleotide sequence;
   (xviii) exclusion of a selenocysteine incorporation signal in the initial polynucleotide sequence;
   (xix) exclusion of an RNA editing sequence in the initial polynucleotide sequence;
   (xx) exclusion of an RNAi-targeted sequence in the initial polynucleotide sequence; and
   (xxi) exclusion of an inverted repeat within the first 45 nucleotides encoding said polypeptide in the initial polynucleotide sequence.

3. The method of claim 1, wherein the reference polynucleotide is naturally occurring.

4. The method of claim 1, wherein the modifying eliminates a sequence that is a target for an antisense DNA in the initial polynucleotide sequence.

5. The method of claim 1, wherein the modifying eliminates a sequence that is a target for an interfering RNA in the initial polynucleotide sequence.

6. The method of claim 1, wherein the reference polynucleotide encodes the polypeptide or a fragment of the polypeptide.

7. A computer program product for use in conjunction with a computer system, the computer program product comprising a non-transitory computer readable storage medium and a computer program mechanism embedded therein, the computer program mechanism comprising instructions for:
   a) selecting an initial polynucleotide sequence that codes for a polypeptide, wherein a codon frequency in said initial polynucleotide sequence is determined by a codon bias table;
   b) modifying an initial codon choice in said initial polynucleotide sequence in accordance with a design criterion, thereby constructing a final polynucleotide sequence that codes for said polypeptide wherein the design criterion comprises minimized sequence identity to a reference polynucleotide, and wherein said modifying said initial codon choice in said initial polynucleotide sequence in accordance with said design criterion comprises altering a plurality of codons in said initial polynucleotide sequence to minimize sequence identity to said reference polynucleotide; and
   c) outputting or displaying said final polynucleotide sequence.

8. The computer program product of claim 7, wherein the design criterion further comprises one or more of:
   (i) exclusion of a restriction site sequence in said initial polynucleotide sequence;
   (ii) incorporation of a restriction site sequence in said initial polynucleotide sequence;
   (iii) a designation of a target G+C content in the initial polynucleotide sequence;
   (iv) an allowable length of a sub-sequence that can be exactly repeated within either a 5'-3' or a 3'-5' strand of the initial polynucleotide sequence;
   (v) an allowable annealing temperature of any sub-sequence to any other sub-sequence within either the 5'-3' or the 3'-5' strand of the initial polynucleotide sequence;
   (vi) exclusion of a hairpin turn in the initial polynucleotide sequence;
   (vii) exclusion of a repeat element in the initial polynucleotide sequence;
   (viii) exclusion of a ribosome binding site in the initial polynucleotide sequence;
   (ix) exclusion of a polyadenylation signal in the initial polynucleotide sequence;
   (x) exclusion of a splice site in the initial polynucleotide sequence;
   (xi) exclusion of an open reading frame in each possible 5' reading frame in the initial polynucleotide sequence;
   (xii) exclusion of a polynucleotide sequence that facilitates RNA degradation in the initial polynucleotide sequence;
   (xiii) exclusion of an RNA polymerase termination signal in the initial polynucleotide sequence;
   (xiv) exclusion of a transcriptional promoter in the initial polynucleotide sequence;
   (xv) exclusion of an immunostimulatory sequence in the initial polynucleotide sequence;

(xvi) incorporation of an immunostimulatory sequence in the initial polynucleotide sequence;
(xvii) exclusion of an RNA methylation signal in the initial polynucleotide sequence;
(xviii) exclusion of a selenocysteine incorporation signal in the initial polynucleotide sequence;
(xix) exclusion of an RNA editing sequence in the initial polynucleotide sequence;
(xx) exclusion of an RNAi-targeted sequence in the initial polynucleotide sequence; and
(xxi) exclusion of an inverted repeat within the first 45 nucleotides encoding said polypeptide in the initial polynucleotide sequence.

9. The computer program product of claim 7, wherein the reference polynucleotide is naturally occurring.

10. The computer program product of claim 7, wherein the modifying eliminates a sequence that a target for an antisense DNA in the initial polynucleotide sequence.

11. The computer program product of claim 7, wherein the modifying eliminates a sequence that is a target for an interfering RNA in the initial polynucleotide sequence.

12. The computer program product of claim 7, wherein the reference polynucleotide encodes the polypeptide or a fragment of the polypeptide.

13. A computer system comprising:
a physical central processing unit;
a physical memory, electrically coupled to the central processing unit, the memory storing instructions executed by the physical central processing unit for:
a) selecting an initial polynucleotide sequence that codes for a polypeptide, wherein a codon frequency in said initial polynucleotide sequence is determined by a codon bias table;
b) modifying an initial codon choice in said initial polynucleotide sequence in accordance with a design criterion, thereby constructing a final polynucleotide sequence that codes for said polypeptide wherein the design criterion comprises minimized sequence identity to a reference polynucleotide, and wherein said modifying said initial codon choice in said initial polynucleotide sequence in accordance with said design criterion comprises altering a plurality of codons in said initial polynucleotide sequence to minimize sequence identity to said reference polynucleotide; and
c) outputting or displaying said final polynucleotide sequence.

14. The computer system of claim 13, wherein the design criterion further comprises one or more of:
(i) exclusion of a restriction site sequence in said initial polynucleotide sequence;
(ii) incorporation of a restriction site sequence in said initial polynucleotide sequence;
(iii) a designation of a target G+C content in the initial polynucleotide sequence;
(iv) an allowable length of a sub-sequence that can be exactly repeated within either a 5'-3' or a 3'-5' strand of the initial polynucleotide sequence;
(v) an allowable annealing temperature of any sub-sequence to any other sub-sequence within either the 5'-3' or the 3'-5' strand of the initial polynucleotide sequence;
(vi) exclusion of a hairpin turn in the initial polynucleotide sequence;
(vii) exclusion of a repeat element in the initial polynucleotide sequence;
(viii) exclusion of a ribosome binding site in the initial polynucleotide sequence;
(ix) exclusion of a polyadenylation signal in the initial polynucleotide sequence;
(x) exclusion of a splice site in the initial polynucleotide sequence;
(xi) exclusion of an open reading frame in each possible 5' reading frame in the initial polynucleotide sequence;
(xii) exclusion of a polynucleotide sequence that facilitates RNA degradation in the initial polynucleotide sequence;
(xiii) exclusion of an RNA polymerase termination signal in the initial polynucleotide sequence;
(xiv) exclusion of a transcriptional promoter in the initial polynucleotide sequence;
(xv) exclusion of an immunostimulatory sequence in the initial polynucleotide sequence;
(xvi) incorporation of an immunostimulatory sequence in the initial polynucleotide sequence;
(xvii) exclusion of an RNA methylation signal in the initial polynucleotide sequence;
(xviii) exclusion of a selenocysteine incorporation signal in the initial polynucleotide sequence;
(xix) exclusion of an RNA editing sequence in the initial polynucleotide sequence;
(xx) exclusion of an RNAi-targeted sequence in the initial polynucleotide sequence; and
(xxi) exclusion of an inverted repeat within the first 45 nucleotides encoding said polypeptide in the initial polynucleotide sequence.

15. The computer system of claim 13, wherein the reference polynucleotide is naturally occurring.

16. The computer system of claim 13, wherein the modifying eliminates a sequence that is a target for an antisense DNA in the initial polynucleotide sequence.

17. The computer system of claim 13, wherein the modifying eliminates a sequence that is a target for an interfering RNA in the initial polynucleotide sequence.

18. The computer system of claim 13, wherein the reference polynucleotide encodes the polypeptide or a fragment of the polypeptide.

19. A method of designing a polynucleotide, the method comprising:
a) selecting an initial polynucleotide sequence that codes for a polypeptide, wherein a codon frequency in said initial polynucleotide sequence is determined by a codon bias table; and
b) modifying an initial codon choice in said initial polynucleotide sequence in accordance with a design criterion, thereby constructing a final polynucleotide sequence that codes for said polypeptide; wherein the design criterion comprises:
maximized sequence identity to a reference polynucleotide, and wherein
modifying said initial codon choice in said initial polynucleotide in accordance with said design criterion comprises altering a plurality of codons in said initial polynucleotide sequence to maximize sequence identity to said reference polynucleotide; and
c) synthesizing said final polynucleotide sequence.

20. The method of claim 19, wherein the design criterion further comprises one or more of:
(i) exclusion of a restriction site sequence in said initial polynucleotide sequence;
(ii) incorporation of a restriction site sequence in said initial polynucleotide sequence;
(iii) a designation of a target G+C content in the initial polynucleotide sequence;

(iv) an allowable length of a sub-sequence that can be exactly repeated within either a 5'-3' or a 3'-5' strand of the initial polynucleotide sequence;

(v) an allowable annealing temperature of any sub-sequence to any other sub-sequence within either the 5'-3' or the 3'-5' strand of the initial polynucleotide sequence;

(vi) exclusion of a hairpin turn in the initial polynucleotide sequence;

(vii) exclusion of a repeat element in the initial polynucleotide sequence;

(viii) exclusion of a ribosome binding site in the initial polynucleotide sequence;

(ix) exclusion of a polyadenylation signal in the initial polynucleotide sequence;

(x) exclusion of a splice site in the initial polynucleotide sequence;

(xi) exclusion of an open reading frame in each possible 5' reading frame in the initial polynucleotide sequence;

(xii) exclusion of a polynucleotide sequence that facilitates RNA degradation in the initial polynucleotide sequence;

(xiii) exclusion of an RNA polymerase termination signal in the initial polynucleotide sequence;

(xiv) exclusion of a transcriptional promoter in the initial polynucleotide sequence;

(xv) exclusion of an immunostimulatory sequence in the initial polynucleotide sequence;

(xvi) incorporation of an immunostimulatory sequence in the initial polynucleotide sequence;

(xvii) exclusion of an RNA methylation signal in the initial polynucleotide sequence;

(xviii) exclusion of a selenocysteine incorporation signal in the initial polynucleotide sequence;

(xix) exclusion of an RNA editing sequence in the initial polynucleotide sequence;

(xx) exclusion of an RNAi-targeted sequence in the initial polynucleotide sequence; and (xxi) exclusion of an inverted repeat within the first 45 nucleotides encoding said polypeptide in the initial polynucleotide sequence.

21. The method of claim 19, wherein the reference polynucleotide is naturally occurring.

22. The method of claim 19, wherein the modifying eliminates a sequence that is a target for antisense DNA in the initial polynucleotide sequence.

23. The method of claim 19, wherein the modifying eliminates a sequence that is a target for an interfering RNA in the initial polynucleotide sequence.

24. A method of designing a polynucleotide, the method comprising:
a) selecting an initial polynucleotide sequence in a plurality of polynucleotide sequences, wherein each polynucleotide sequence in the plurality of polynucleotide sequences codes for the same polypeptide, wherein said initial polynucleotide sequence is selected from the plurality of polynucleotide sequences on the basis that it has, relative to all other polynucleotide sequences in the plurality of polynucleotide sequences, a maximized or minimized sequence identity to a reference polynucleotide sequence, wherein the reference polynucleotide sequence is other than the initial polynucleotide sequence;
b) modifying an initial codon choice in said initial polynucleotide sequence in accordance with a design criterion, thereby constructing a final polynucleotide sequence that codes for said polypeptide; and
c) synthesizing the final polynucleotide sequence.

25. The method of claim 24, wherein the design criterion comprises one or more of:
(i) exclusion of a restriction site sequence in said initial polynucleotide sequence;

(ii) incorporation of a restriction site sequence in said initial polynucleotide sequence;

(iii) a designation of a target G+C content in the initial polynucleotide sequence;

(iv) an allowable length of a sub-sequence that can be exactly repeated within either a 5'-3' or a 3'-5' strand of the initial polynucleotide sequence;

(v) an allowable annealing temperature of any sub-sequence to any other sub-sequence within either the 5'-3' or the 3'-5' strand of the initial polynucleotide sequence;

(vi) exclusion of a hairpin turn in the initial polynucleotide sequence;

(vii) exclusion of a repeat element in the initial polynucleotide sequence;

(viii) exclusion of a ribosome binding site in the initial polynucleotide sequence;

(ix) exclusion of a polyadenylation signal in the initial polynucleotide sequence;

(x) exclusion of a splice site in the initial polynucleotide sequence;

(xi) exclusion of an open reading frame in each possible 5' reading frame in the initial polynucleotide sequence;

(xii) exclusion of a polynucleotide sequence that facilitates RNA degradation in the initial polynucleotide sequence;

(xiii) exclusion of an RNA polymerase termination signal in the initial polynucleotide sequence;

(xiv) exclusion of a transcriptional promoter in the initial polynucleotide sequence;

(xv) exclusion of an immunostimulatory sequence in the initial polynucleotide sequence;

(xvi) incorporation of an immunostimulatory sequence in the initial polynucleotide sequence;

(xvii) exclusion of an RNA methylation signal in the initial polynucleotide sequence;

(xviii) exclusion of a selenocysteine incorporation signal in the initial polynucleotide sequence;

(xix) exclusion of an RNA editing sequence in the initial polynucleotide sequence;

(xx) exclusion of an RNAi-targeted sequence in the initial polynucleotide sequence; and (xxi) exclusion of an inverted repeat within the first 45 nucleotides encoding said polypeptide in the initial polynucleotide sequence.

26. The method of claim 24, wherein the reference polynucleotide is naturally occurring.

27. A computer program product for use in conjunction with a computer system, the computer program product comprising a non-transitory computer readable storage medium and a computer program mechanism embedded therein, the computer program mechanism comprising instructions for:
a) selecting an initial polynucleotide sequence that codes for a polypeptide, wherein a codon frequency in said initial polynucleotide sequence is determined by a codon bias table;
b) modifying an initial codon choice in said initial polynucleotide sequence in accordance with a design criterion, thereby constructing a final polynucleotide sequence that codes for said polypeptide wherein the design criterion comprises maximized sequence identity to a reference polynucleotide, and wherein said modifying said initial codon choice in said initial polynucleotide in accordance with said design criterion comprises altering a plurality of codons in said initial polynucleotide sequence to maximize sequence identity to said reference polynucleotide; and c) outputting or displaying said final polynucleotide sequence.

28. The computer program product of claim 27, wherein the design criterion further comprises one or more of:
   (i) exclusion of a restriction site sequence in said initial polynucleotide sequence;
   (ii) incorporation of a restriction site sequence in said initial polynucleotide sequence;
   (iii) a designation of a target G+C content in the initial polynucleotide sequence;
   (iv) an allowable length of a sub-sequence that can be exactly repeated within either a 5'-3' or a 3'-5' strand of the initial polynucleotide sequence;
   (v) an allowable annealing temperature of any sub-sequence to any other sub-sequence within either the 5'-3' or the 3'-5' strand of the initial polynucleotide sequence;
   (vi) exclusion of a hairpin turn in the initial polynucleotide sequence;
   (vii) exclusion of a repeat element in the initial polynucleotide sequence;
   (viii) exclusion of a ribosome binding site in the initial polynucleotide sequence;
   (ix) exclusion of a polyadenylation signal in the initial polynucleotide sequence;
   (x) exclusion of a splice site in the initial polynucleotide sequence;
   (xi) exclusion of an open reading frame in each possible 5' reading frame in the initial polynucleotide sequence;
   (xii) exclusion of a polynucleotide sequence that facilitates RNA degradation in the initial polynucleotide sequence;
   (xiii) exclusion of an RNA polymerase termination signal in the initial polynucleotide sequence;
   (xiv) exclusion of a transcriptional promoter in the initial polynucleotide sequence;
   (xv) exclusion of an immunostimulatory sequence in the initial polynucleotide sequence;
   (xvi) incorporation of an immunostimulatory sequence in the initial polynucleotide sequence;
   (xvii) exclusion of an RNA methylation signal in the initial polynucleotide sequence;
   (xviii) exclusion of a selenocysteine incorporation signal in the initial polynucleotide sequence;
   (xix) exclusion of an RNA editing sequence in the initial polynucleotide sequence;
   (xx) exclusion of an RNAi-targeted sequence in the initial polynucleotide sequence; and
   (xxi) exclusion of an inverted repeat within the first 45 nucleotides encoding said polypeptide in the initial polynucleotide sequence.

29. The computer program product of claim 27, wherein the reference polynucleotide is naturally occurring.

30. The computer program product of claim 27, wherein the modifying eliminates a sequence that is a target for an antisense DNA in the initial polynucleotide sequence.

31. The computer program product of claim 27, wherein the modifying eliminates a sequence that is a target for an interfering RNA in the initial polynucleotide sequence.

32. A computer system comprising:
a physical central processing unit;
a physical memory, electrically coupled to the physical central processing unit, the memory storing instructions executed by the central processing unit for:

a) selecting an initial polynucleotide sequence that codes for a polypeptide, wherein a codon frequency in said initial polynucleotide sequence is determined by a codon bias table;

b) modifying an initial codon choice in said initial polynucleotide sequence in accordance with a design criterion, thereby constructing a final polynucleotide sequence that codes for said polypeptide wherein the design criterion comprises maximized sequence identity to a reference polynucleotide, and wherein said modifying said initial codon choice in said initial polynucleotide in accordance with said design criterion comprises altering a codon choice in said initial polynucleotide sequence to maximize sequence identity to said reference polynucleotide; and c) outputting or displaying said final polynucleotide sequence.

33. The computer system of claim 32, wherein the design criterion further comprises one or more of:
   (i) exclusion of a restriction siteسلسلة sequence in said initial polynucleotide sequence;
   (ii) incorporation of a restriction site sequence in said initial polynucleotide sequence;
   (iii) a designation of a target G+C content in the initial polynucleotide sequence;
   (iv) an allowable length of a sub-sequence that can be exactly repeated within either a 5'-3' or a 3'-5' strand of the initial polynucleotide sequence;
   (v) an allowable annealing temperature of any sub-sequence to any other sub-sequence within either the 5'-3' or the 3'-5' strand of the initial polynucleotide sequence;
   (vi) exclusion of a hairpin turn in the initial polynucleotide sequence;
   (vii) exclusion of a repeat element in the initial polynucleotide sequence;
   (viii) exclusion of a ribosome binding site in the initial polynucleotide sequence;
   (ix) exclusion of a polyadenylation signal in the initial polynucleotide sequence;
   (x) exclusion of a splice site in the initial polynucleotide sequence;
   (xi) exclusion of an open reading frame in each possible 5' reading frame in the initial polynucleotide sequence;
   (xii) exclusion of a polynucleotide sequence that facilitates RNA degradation in the initial polynucleotide sequence;
   (xiii) exclusion of an RNA polymerase termination signal in the initial polynucleotide sequence;
   (xiv) exclusion of a transcriptional promoter in the initial polynucleotide sequence;
   (xv) exclusion of an immunostimulatory sequence in the initial polynucleotide sequence;
   (xvi) incorporation of an immunostimulatory sequence in the initial polynucleotide sequence;
   (xvii) exclusion of an RNA methylation signal in the initial polynucleotide sequence;
   (xviii) exclusion of a selenocysteine incorporation signal in the initial polynucleotide sequence;
   (xix) exclusion of an RNA editing sequence in the initial polynucleotide sequence;
   (xx) exclusion of an RNAi-targeted sequence in the initial polynucleotide sequence; and
   (xxi) exclusion of an inverted repeat within the first 45 nucleotides encoding said polypeptide in the initial polynucleotide sequence.

34. The computer system of claim 32, wherein the reference polynucleotide is naturally occurring.

35. The computer system of claim 32, wherein the modifying eliminates a sequence that is a target for antisense DNA in the initial polynucleotide sequence.

36. The computer system of claim 32, wherein the modifying eliminates a sequence that is a target sequence for an interfering RNA in the initial polynucleotide sequence.

* * * * *